(12) United States Patent
Engelberg et al.

(10) Patent No.: US 8,597,093 B2
(45) Date of Patent: Dec. 3, 2013

(54) METHODS AND SYSTEMS FOR ENCOURAGING ATHLETIC ACTIVITY

(75) Inventors: Richard J Engelberg, Portland, OR (US); Michael B Hailey, Forest Grove, OR (US); Stefan F Olander, Portland, OR (US); Michael L Orenstein, Portland, OR (US); Kristen L White, Portland, OR (US); Reshma T Pendleton, Dallas, TX (US)

(73) Assignee: Nike, Inc., Beaverton, OR (US)

( * ) Notice: Subject to any disclaimer, the term of this patent is extended or adjusted under 35 U.S.C. 154(b) by 0 days.

(21) Appl. No.: 13/328,531

(22) Filed: Dec. 16, 2011

(65) Prior Publication Data
US 2012/0290109 A1 Nov. 15, 2012

Related U.S. Application Data

(60) Provisional application No. 61/423,723, filed on Dec. 16, 2010.

(51) Int. Cl.
*A63F 9/00* (2006.01)

(52) U.S. Cl.
USPC ............. 463/1; 463/6; 463/7; 700/91; 700/92

(58) Field of Classification Search
USPC .................................. 463/1, 6–7; 700/91–92
See application file for complete search history.

(56) References Cited

U.S. PATENT DOCUMENTS

| | | | |
|---|---|---|---|
| 2004/0102931 A1 | 5/2004 | Ellis et al. | |
| 2006/0205569 A1 | 9/2006 | Watterson et al. | |
| 2008/0200312 A1* | 8/2008 | Tagliabue | 482/9 |
| 2009/0149299 A1* | 6/2009 | Tchao et al. | 482/9 |
| 2010/0332243 A1* | 12/2010 | Weigman et al. | 705/1.1 |
| 2011/0229864 A1* | 9/2011 | Short et al. | 434/219 |
| 2012/0034971 A1* | 2/2012 | Harp et al. | 463/23 |
| 2012/0130886 A1* | 5/2012 | Shergill et al. | 705/39 |

FOREIGN PATENT DOCUMENTS

| | | | | |
|---|---|---|---|---|
| WO | WO 2009043024 A1 * | 4/2009 | | G06Q 30/00 |
| WO | 2009/111472 | 9/2009 | | |

OTHER PUBLICATIONS

Scripple021. Loser Chooser. Urban Dictionary [online], May 6, 2004 [retrieved Mar. 13, 2013]. Retrieved from the Internet: <URL:http://www.urbandictionary.com/define.php?term=loser+chooser>.*
International Search Report and Written Opinion for corresponding International Application No. PCT/US2011/065511 mailed Apr. 5, 2011.

* cited by examiner

*Primary Examiner* — Dmitry Suhol
*Assistant Examiner* — David Duffy
(74) *Attorney, Agent, or Firm* — Banner & Witcoff, Ltd.

(57) ABSTRACT

Individuals may be encouraged to perform athletic activity based on punishments or adverse effects that may be applied if the individual loses an athletic activity competition. For example, a user's device may be adversely affected by visual or functional effects configured to obscure or obstruct one or more functions of the user's device. The punishment or adverse effect might not be removed or deactivated until a user has completed a new competition without losing. In some arrangements, the user may be required to win in order to have the adverse effect removed.

19 Claims, 190 Drawing Sheets

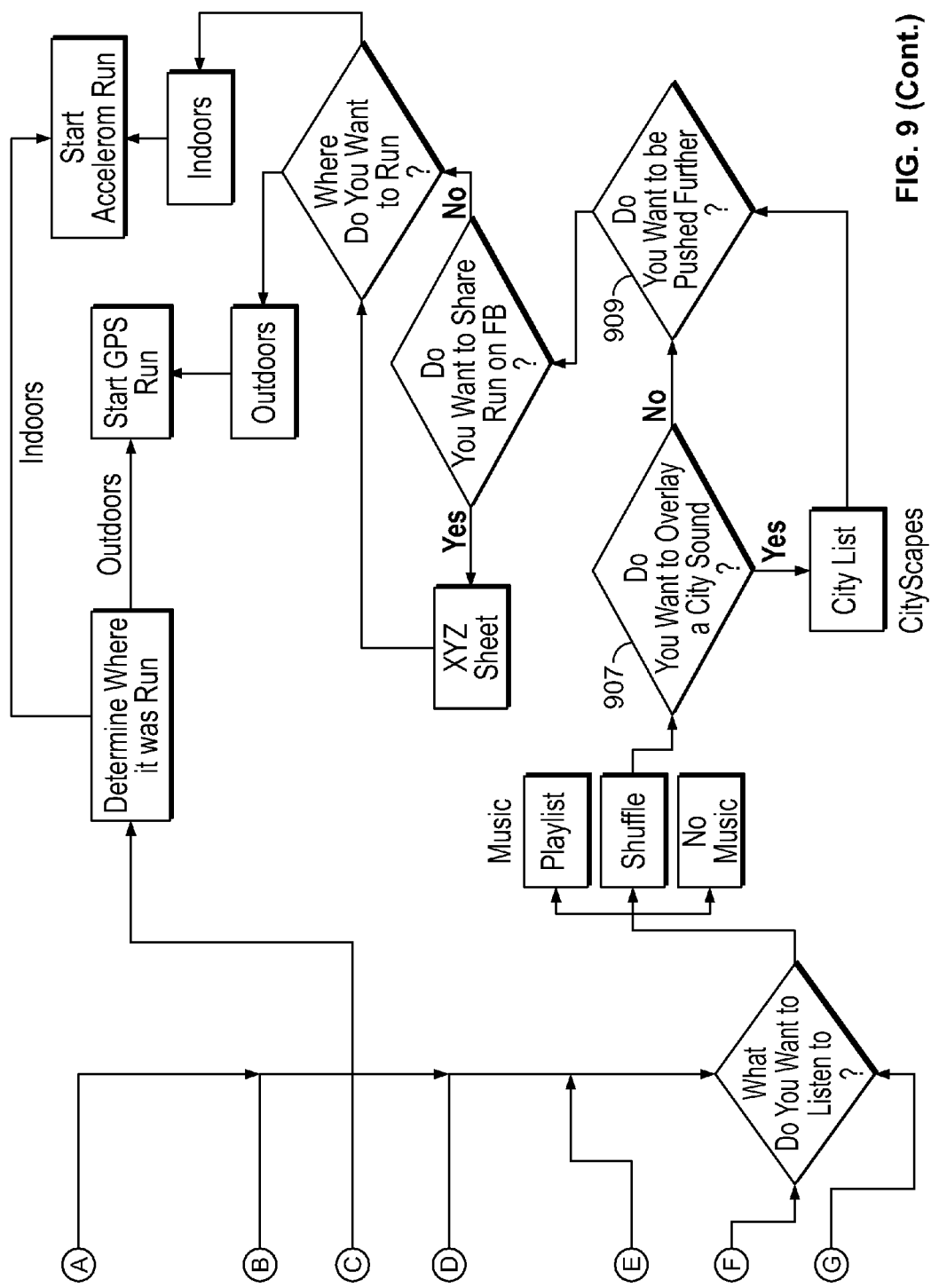

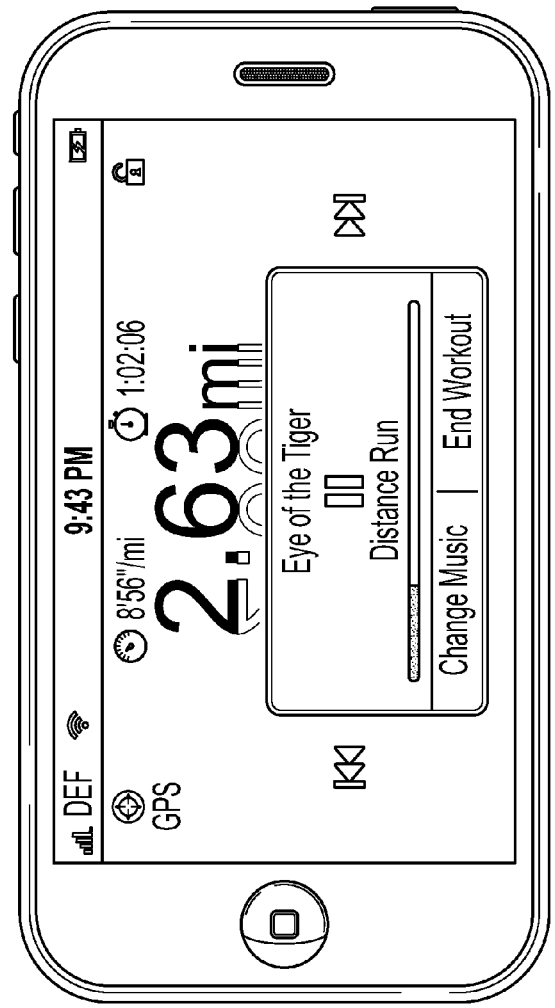
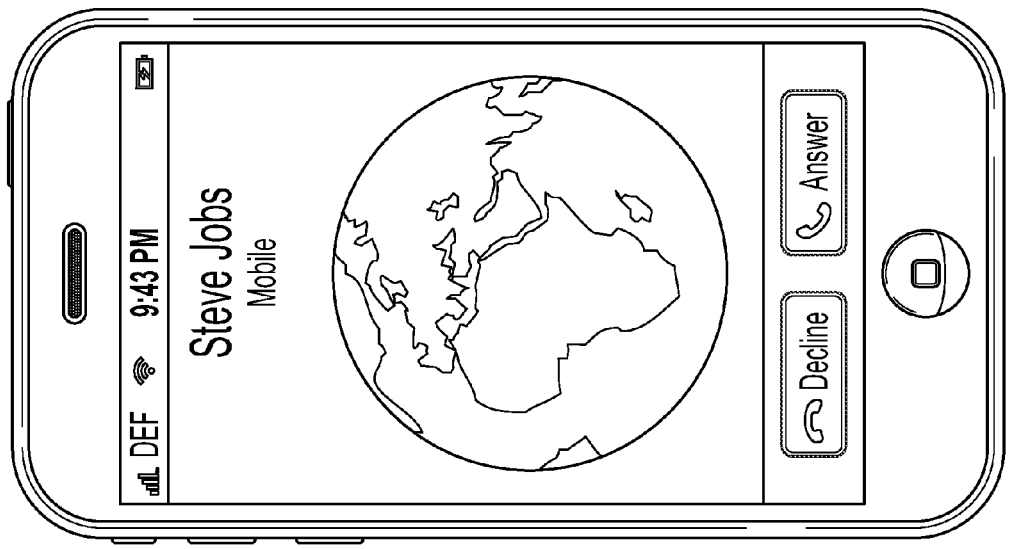
FIG. 27B
FIG. 27A

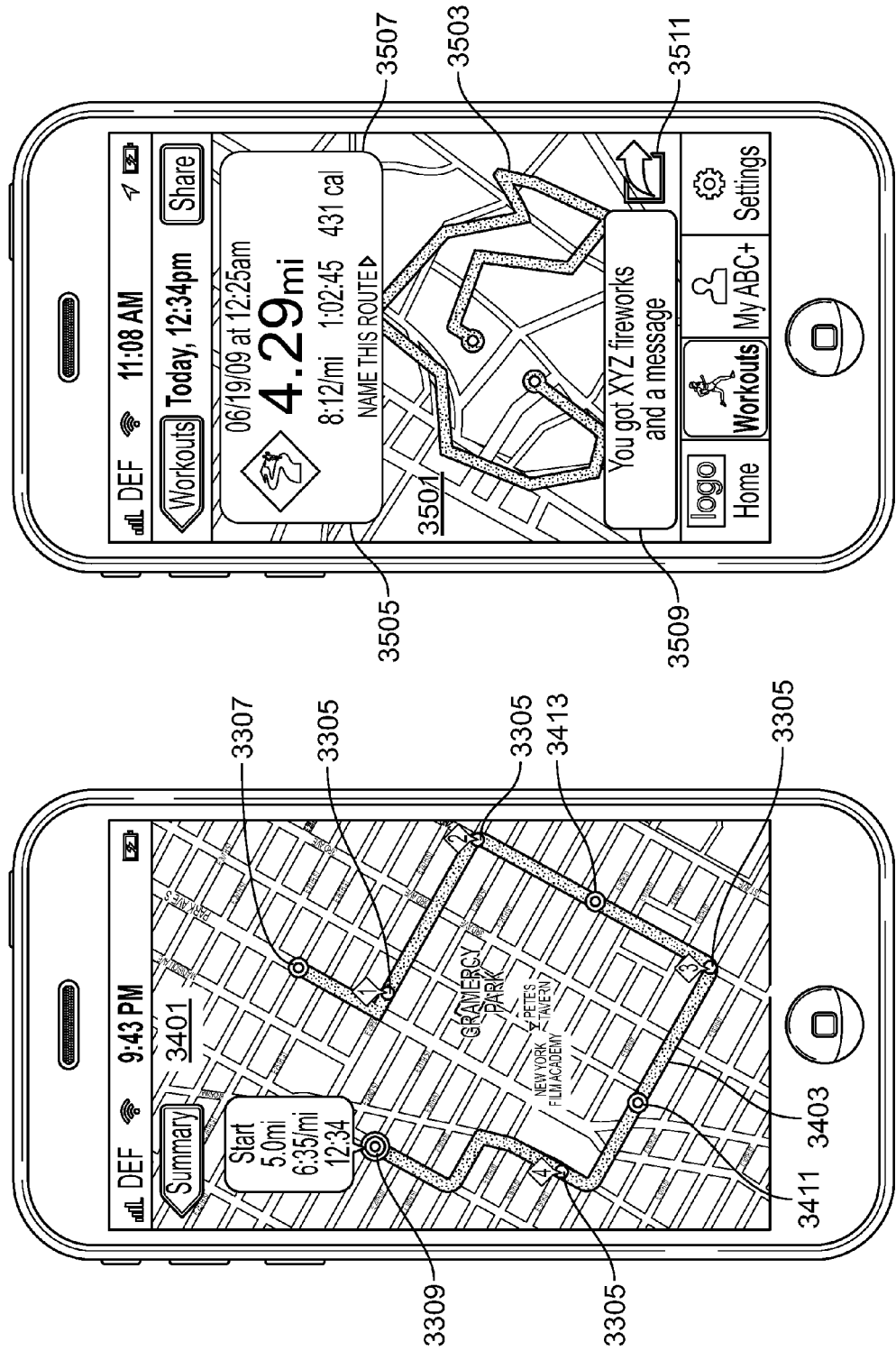

*...ter luck next time!*

YOUR TOTAL MILES

145.9 mi

🏃 31    ⏱ 8'42"    ⏲ 4:24:01    🔥 3442 cal
Runs    Avg Pace    Duration    Calories

- Start a New Run    >
- Challenge Me    >
- Play Tag    >

| logo Home | History | Settings |

DON'T GET TAGGED!

Userone has invited you to play a game of Tag using the app. To escape getting tagged IT, here's what you need to do:

DOWNLOAD THE APP

Available on the App Store ▶

JOIN THE GAME

If you're currently on your phone and have the app installed, you can just click this link to get started.

And if you're not on your phone, make sure you sign in or register with userone@gmail.com to verify the challenge.

RUN AS FAR AS YOU CAN

IT's simple: whoever has the shortest run before the game ends at 11:59 PM on Thursday, Nov 25th is tagged IT.

User One has also added this message:
The person who's tagged IT has to start a new game!

FIG. 76 ained. In other examples, the athletic activity performed may be automatically applied to a game through which the athletic activity was initiated.

METHODS AND SYSTEMS FOR ENCOURAGING ATHLETIC ACTIVITY

CROSS-REFERENCE TO RELATED APPLICATION

This application claims the benefit of priority from U.S. Provisional Application Ser. No. 61/423,723, entitled "METHODS AND SYSTEM FOR ENCOURAGING ATHLETIC ACTIVITY," and filed Dec. 16, 2010, the content of which is incorporated by reference in its entirety.

BACKGROUND

While most people appreciate the importance of physical fitness, many have difficulty finding the motivation required to maintain a regular exercise program. Some people find it particularly difficult to maintain an exercise regimen that involves continuously repetitive motions, such as running, walking and bicycling. Additionally, oftentimes, individuals might not be as motivated to exercise because of the extra effort that may be required in recording and tracking workout results. For example, an individual may be required to manually enter workout information such as a number of miles run, a route run, an average heartrate and the like into a database in order to track his or her progress. In another example, individuals may need to use special fitness-dedicated devices to automatically track workout results. In some instances, different types of fitness equipment may be required depending on if the individual is working out indoors or outdoors, on a treadmill or running an outdoor route and the like.

Motivation may also result from achieving progress in an individual's fitness level. However, progress often involves increasing or otherwise altering a workout regimen. For example, individuals may start running faster or for longer periods of time to increase endurance. In some cases, individuals might repeat the same workout, thus failing to challenge themselves to improve on previous performances. Without being prompted to perform a more strenuous workout, an individual might not see results as quickly or at all and thus become unmotivated.

BRIEF SUMMARY

According to one or more aspects, an athletic activity system, method and application may offer motivation to complete additional athletic activity. For example, athletic activity may be defined as an objective in a multi-user athletic activity game. A loser of the multi-user athletic activity game may be punished or suffer a predefined consequence. In one particular example, a losing individual may be required to initiate and complete a new game without losing in order to have his or her loser status/punishment cleared. In some arrangements, the loser status might also be removed from a user upon expiration of a predefined time period. In other arrangements, however, a loser status might not expire based on time.

According to another aspect, the multi-user game may include multiple game types. In one example, the game may require users to avoid registering the shortest run of all participants. In another example, the game may require users to exercise as much as possible. In yet another example, the game may require the users to avoid being the last to complete an activity. Other game types may also be defined. For example, users may customize their own game types including defining an objective, a game time period, a punishment/consequence and the like.

According to yet another aspect, a last-to-complete game type may include a random start time. For example, users might not know when the game will start so that a game creator does not have an unfair advantage (e.g., to be the first to complete the specified athletic activity).

According to still another aspect, punishments or consequences may include physical and/or visual effects. For example, a user interface may be altered to make accessing certain functions or information more difficult. In other examples, punishments may include real-time consequences such as payment of money or incurring a debt against other users.

According to another aspect, athletic activity performed during an athletic activity session may be applied to a user-selected game after the athletic activity has been completed. In other examples, the athletic activity performed may be automatically applied to a game through which the athletic activity was initiated.

According to still another aspect, methods and systems for automatically identifying and matching a user with other challenge participants may be provided. For example, the system may receive a request to initiate a run and to challenge one or more other users to the run from a first user. The system may allow the user to select and invite particular users to be challenged or, alternatively or additionally, automatically identify such other users. In one example, attributes of the first user may be determined and compared to the attributes of other users. The system might only identify challenges that are currently online. The identified users may then be invited to participate in the challenge. If a user accepts the challenge, the participants may compete in the challenge, at the conclusion of which, a winner may be declared. Rewards, accolades and other recognition may be provided to the winner. Additionally or alternatively, the system may automatically suggest a schedule for a further challenge between the two or more participants to encourage improvement and athletic activity.

These and other features of the present disclosure will become apparent from the following detailed description.

BRIEF DESCRIPTION OF THE DRAWINGS

FIGS. 27A-27H illustrate additional or alternative user interfaces that may be displayed while a user is conducting a run according to one or more aspects described herein.

FIG. 34 illustrates an example route information interface according to one or more aspects described herein.

FIGS. 35A-35C illustrate example route summary interfaces in which a map may be displayed according to one or more aspects described herein.

FIGS. 65A-65J illustrates example interfaces that may include workout reviews according to one or more aspects described herein.

FIG. 76 illustrates an example game invitation message according to one or more aspects described herein.

DETAILED DESCRIPTION

Athletic Activity Overview

Figure 1:
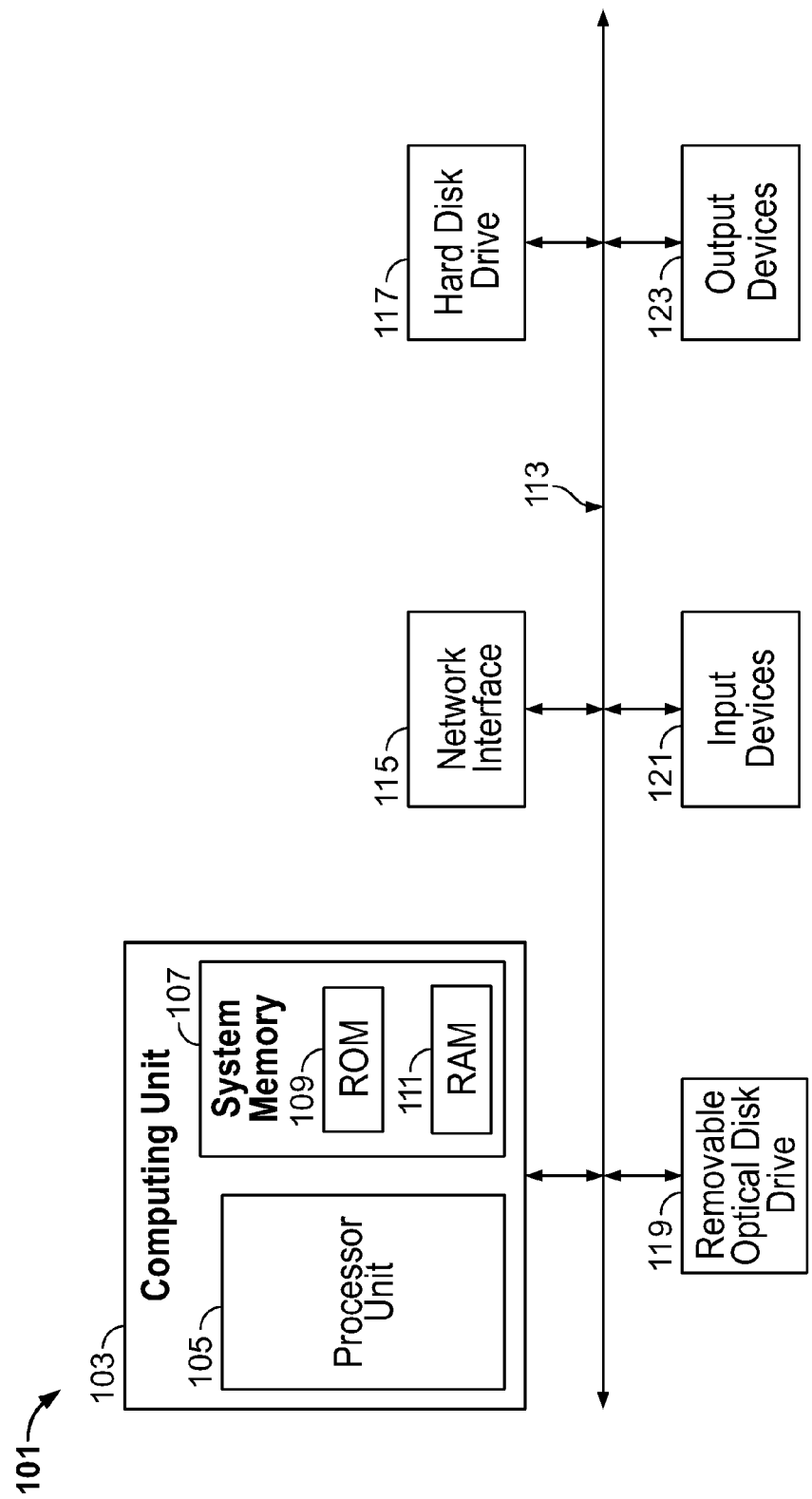
FIG. 1 illustrates a computing device that may be used to implement various examples of the invention.

Aspects of the invention relate to the measurement, collection, display and management of athletic and non-athletic information. As will be appreciated by those of ordinary skill in the art, athletic information must first be obtained from an individual person. With various implementations of the invention, one or more different athletic information monitoring devices may be used to measure and record athletic data corresponding to athletic activity performed by a person and convert that information into a form of currency. Typically, an athletic information monitoring device will incorporate a sensor for measuring parameters relating to the person being monitored, and a computing device for processing the parameters measured by the sensor.

Once an athletic information monitoring device has recorded athletic information for a person's athletic activity, the person may then transfer the recorded athletic information to one or more separate devices, in order to view the recorded athletic data. A user may, for example, download the recorded athletic information from an athletic information monitoring device to a separate collection device. The collection device may, in turn, transfer the athletic information collected from the athletic information monitoring device to a separate display configuration device, where the athletic information can be organized and configured for subsequent viewing with, e.g., still another device. As will be discussed in more detail below, various implementations of the invention will allow a person to record, collect and display athletic information using a group of computing devices communicating over a network, such as the Internet.

For example, some aspects described herein allow a person to measure and record athletic information using a special-purpose computing device. The user can then transfer the recorded athletic information to a local computing device, such as a personal desktop or laptop computer. More particularly, a user can download recorded athletic information from the athletic information monitoring device to a collection software tool on a local computer that acts as a "client" in a computer network. The collection software tool will then transfer the downloaded athletic information through the network to a remote "server" computer. A display configuration software tool on the remote server computer will then save the transferred athletic information. Later, a person can use the client computer or another local computer to retrieve the stored athletic information from the server computer. In response to a display request from a local computer, the display configuration software tool will configure the requested athletic information for display on the local computer, and then transmit the configured athletic information to the local computer for display.

Computing Device

Various examples of the invention may be implemented using electronic circuitry configured to perform one or more functions. For example, with some embodiments of the invention, the athletic information monitoring device, the collection device, the display device or any combination thereof may be implemented using one or more application-specific integrated circuits (ASICs). More typically, however, components of various examples of the invention will be implemented using a programmable computing device executing firmware or software instructions, or by some combination of purpose-specific electronic circuitry and firmware or software instructions executing on a programmable computing device.

Accordingly, FIG. 1 shows one illustrative example of a computer 101 that can be used to implement various embodiments of the invention. As seen in this figure, the computer 101 has a computing unit 103. The computing unit 103 typically includes a processing unit 105 and a system memory 107. The processing unit 105 may be any type of processing device for executing software instructions, but will conventionally be a microprocessor device. The system memory 107 may include both a read-only memory (ROM) 109 and a random access memory (RAM) 111. As will be appreciated by those of ordinary skill in the art, both the read-only memory (ROM) 109 and the random access memory (RAM) 111 may store software instructions for execution by the processing unit 105.

The processing unit 105 and the system memory 107 are connected, either directly or indirectly, through a bus 113 or alternate communication structure to one or more peripheral devices. For example, the processing unit 105 or the system memory 107 may be directly or indirectly connected to additional memory storage, such as the hard disk drive 115, the removable magnetic disk drive 117, the optical disk drive 119, and the flash memory card 121. The processing unit 105 and the system memory 107 also may be directly or indirectly connected to one or more input devices 123 and one or more output devices 125. The input devices 123 may include, for example, a keyboard, touch screen, a remote control pad, a pointing device (such as a mouse, touchpad, stylus, trackball, or joystick), a scanner, a camera or a microphone. The output devices 125 may include, for example, a monitor display, television, printer, stereo, or speakers.

Still further, the computing unit 103 will be directly or indirectly connected to one or more network interfaces 127 for communicating with a network. This type of network interface 127, also sometimes referred to as a network adapter or network interface card (NIC), translates data and control signals from the computing unit 103 into network messages according to one or more communication protocols, such as the Transmission Control Protocol (TCP), the Internet Protocol (IP), and the User Datagram Protocol (UDP). These protocols are well known in the art, and thus will not be discussed here in more detail. An interface 127 may employ any suitable connection agent for connecting to a network, including, for example, a wireless transceiver, a power line adapter, a modem, or an Ethernet connection.

It should be appreciated that, in addition to the input, output and storage peripheral devices specifically listed above, the computing device may be connected to a variety of other peripheral devices, including some that may perform input, output and storage functions, or some combination thereof. For example, the computer 101 may be connected to a digital music player, such as an IPOD® brand digital music player available from Apple, Inc. of Cupertino, Calif. As known in the art, this type of digital music player can server as both an output device for a computer (e.g., outputting music from a sound file or pictures from an image file) and a storage device. In addition, this type of digital music play also can serve as an input device for inputting recorded athletic information, as will be discussed in more detail below.

In addition to a digital music player, the computer 101 may be connected to or otherwise include one or more other peripheral devices, such as a telephone. The telephone may be, for example, a wireless "smart phone." As known in the art, this type of telephone communicates through a wireless network using radio frequency transmissions. In addition to simple communication functionality, a "smart phone" may also provide a user with one or more data management functions, such as sending, receiving and viewing electronic messages (e.g., electronic mail messages, SMS text messages, etc.), recording or playing back sound files, recording or playing back image files (e.g., still picture or moving video image files), viewing and editing files with text (e.g., Microsoft Word or Excel files, or Adobe Acrobat files), etc. Because of the data management capability of this type of telephone, a user may connect the telephone with the computer 101 so that their data maintained may be synchronized.

Of course, still other peripheral devices may be included with our otherwise connected to a computer 101 of the type illustrated in FIG. 1, as is well known in the art. In some cases, a peripheral device may be permanently or semi-permanently connected to the computing unit 103. For example, with many computers, the computing unit 103, the hard disk drive 117, the removable optical disk drive 119 and a display are semi-permanently encased in a single housing. Still other peripheral devices may be removably connected to the computer 101, however. The computer 101 may include, for example, one or more communication ports through which a peripheral device can be connected to the computing unit 103 (either directly or indirectly through the bus 113). These communication ports may thus include a parallel bus port or a serial bus port, such as a serial bus port using the Universal Serial Bus (USB) standard or the IEEE 1394 High Speed Serial Bus standard (e.g., a Firewire port). Alternately or additionally, the computer 101 may include a wireless data "port," such as a Bluetooth interface, a Wi-Fi interface, an infrared data port, or the like.

It should be appreciated that a computing device employed according various examples of the invention may include more components than the computer 101 illustrated in FIG. 1, fewer components than the computer 101, or a different combination of components than the computer 101. Some implementations of the invention, for example, may employ one or more computing devices that are intended to have a very specific functionality, such as a digital music player or server computer. These computing devices may thus omit unnecessary peripherals, such as the network interface 115, removable optical disk drive 119, printers, scanners, external hard drives, etc. Some implementations of the invention may alternately or additionally employ computing devices that are intended to be capable of a wide variety of functions, such as a desktop or laptop personal computer. These computing devices may have any combination of peripheral devices or additional components as desired.

Athletic Information Monitoring Device

Figure 2:
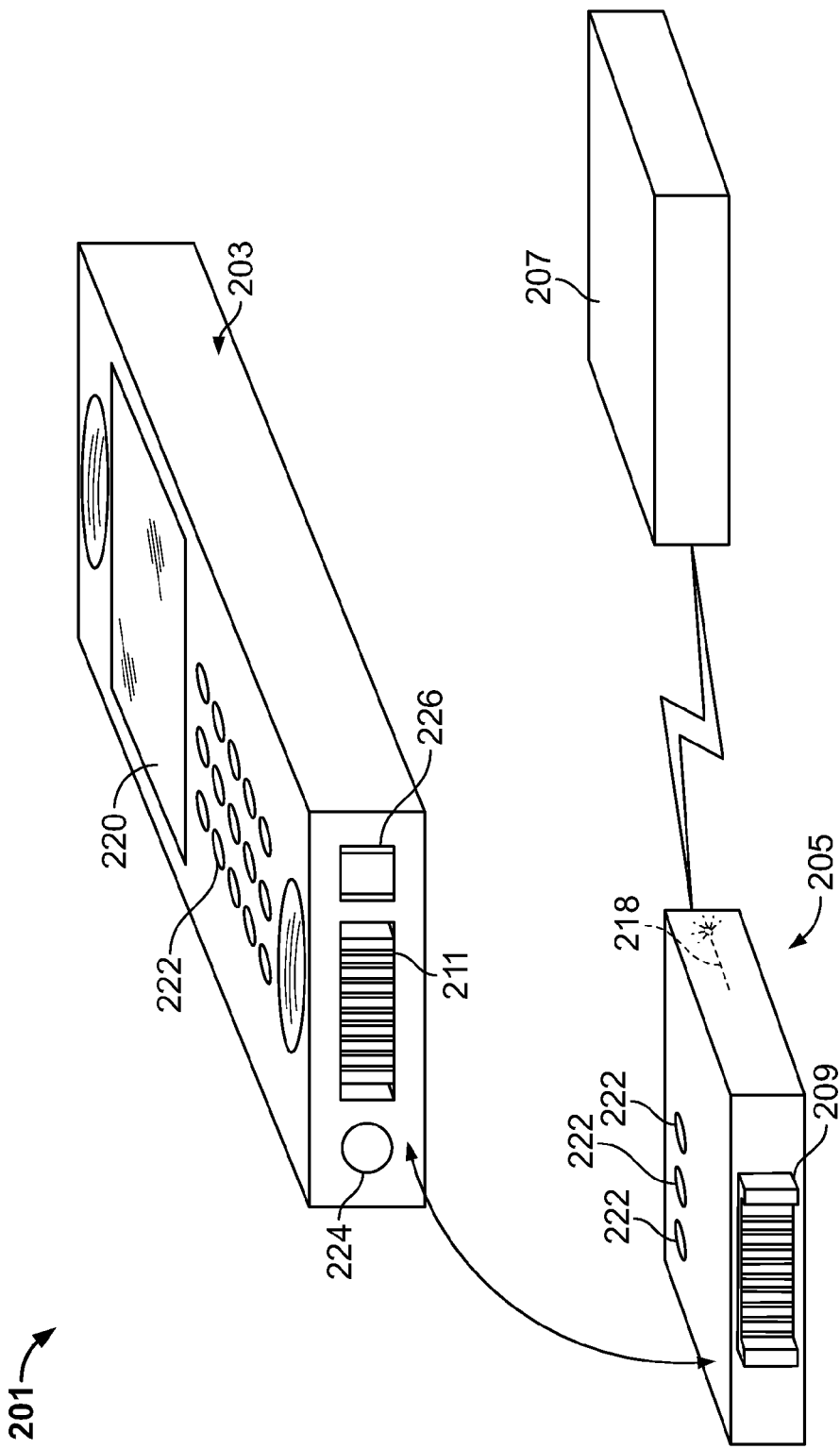
FIGS. 2 and 3 illustrate an example of an athletic information monitoring device that may be employed according to various examples of the invention.

FIG. 2 illustrates one example of an athletic information monitoring device 201 that may be employed according to various examples of the invention to measure athletic information corresponding a user's athletic activity. As shown in this figure, the athletic information monitoring device 201 includes a digital music player 203, an electronic interface device 205, and an athletic parameter measurement device 207. As will be described in more detail, the digital music player 203 is (releasably) connected to the electronic interface device 205, and the combination is worn or otherwise carried by the user while he or she is performing an athletic activity, such as running or walking. The athletic parameter measurement device 207 also is worn or carried by the user while he or she is performing an athletic activity, and measures one or more athletic parameters relating to the athletic performance being performed by the user. The athletic parameter measurement device 207 transmits signals to the electronic interface device 205 that correspond to the measured athletic parameter. The electronic interface device 205 receives the signals from the athletic parameter measurement device 207, and provides the received information to the digital music player 203.

Figure 3:
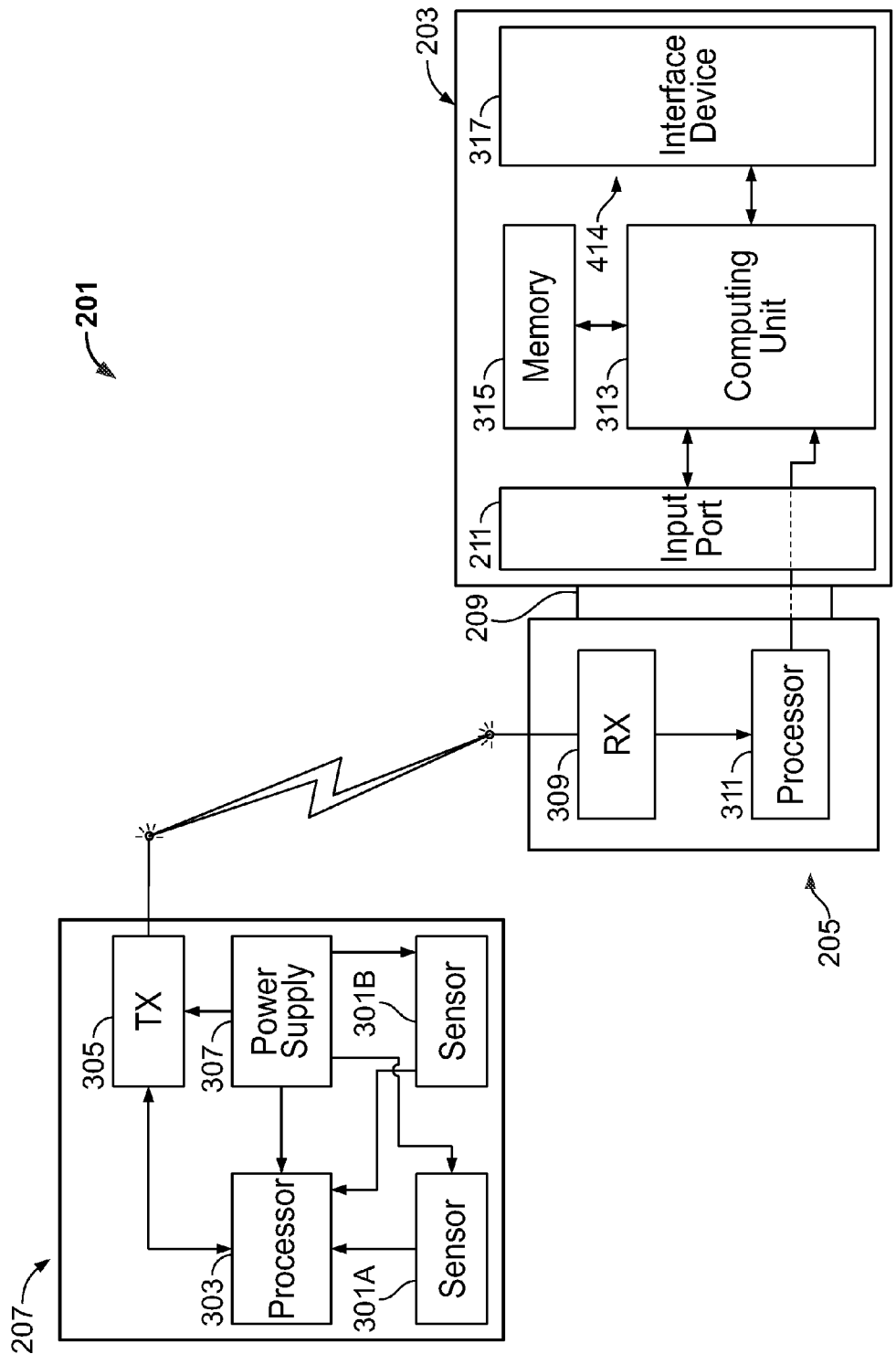
Figure 4:
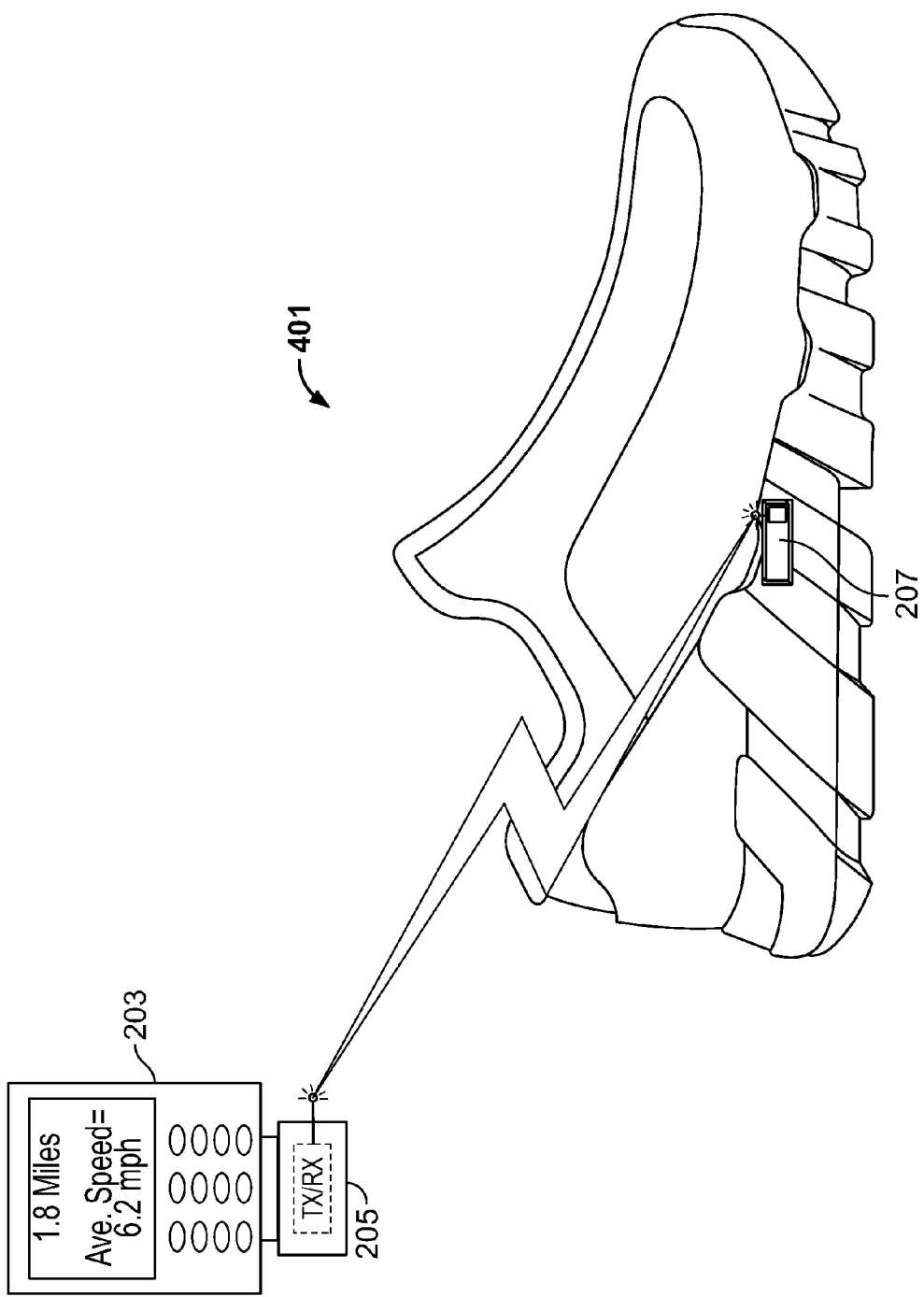
FIG. 4 illustrates one environment in which an athletic parameter measurement device according to various examples of the invention may be employed.

As shown in more detail in FIG. 3, the athletic parameter measurement device 207 includes one or more sensors 301 for measuring an athletic parameter associated with a person wearing or otherwise using the athletic parameter measurement device 207. With the illustrated implementations, for example, the sensors 301A and 301B may be accelerometers (such as piezoelectric accelerometers) for measuring the acceleration of the athletic parameter measurement device 207 in two orthogonal directions. The athletic parameter measurement device 207 is carried or otherwise worn by a user to measure the desired athletic parameter while the user exercises. For example, as shown in FIG. 4, the athletic parameter measurement device 207 may be located the sole of a user's shoe 401 while the user walks or runs. With this arrangement, the sensors 301 will produce electrical signals corresponding to the movement of the user's foot. As known in the art, these signals can then be used to generate athletic data representative of the athletic activity performed by the user.

The athletic parameter measurement device 207 also includes a processor 303 for processing the electrical signals output by the sensors 301. With some implementations of the invention, the processor 303 may be a programmable microprocessor. For still other implementations of the invention, however, the processor 303 may be a purpose-specific circuit device, such as an ASIC. The processor 303 may perform any desired operation on the signals output from the sensors 301, such as curve smoothing, noise filtering, outlier removal, amplification, summation, integration, or the like. The processor 303 provides the processed signals to a transmitter 307. The athletic parameter measurement device 207 also includes a power supply 307, for providing power to the sensors 301, the processor 303, and the transmitter 305 as needed. The power supply 307 may be, for example, a battery.

The athletic parameter measurement device 207 transmits the processed signals to the electronic interface device 205, as seen in FIG. 4. Returning now to FIG. 3, the electronic interface device 205 includes a receiver 309 which receives the processed signals transmitted by the transmitter 305 in the athletic parameter measurement device 207. The receiver 309 relays the processed signals to a second processor 311, which processes the signals further. Like the processor 303, the processor 311 may perform any desired operation on the processed signals, such as curve smoothing, noise filtering, outlier removal, amplification, summation, integration, or the like.

The processor 303 provides the processed signals to the digital music player 203. Referring back now to FIG. 2, the electronic interface device 205 includes a connector system 209 that physically plugs into and connects with a conventional input port 211 provided on digital music player 203. The input port 211 into which the connector system 209 of the electronic interface device 205 connects may be any desired type of input port for transferring data, such as a parallel data port, a serial data port, an earphone or microphone jack, etc.) The connector system 209 may include any suitable connecting devices, such as wires, pins, electrical connectors, and the like, so as to make an electrical connection or other suitable connection with corresponding elements provided in the input port 211 of the digital music player 203 (e.g., to allow electronic and/or data communications between the interface device 205 and the electronic interface device 205). If necessary or desired, additional securing elements may be provided to securely connect the interface device 205 to the digital music player 203, such as straps, hooks, buckles, clips, clamps, clasps, retaining elements, mechanical connectors, and the like.

Returning now to FIG. 3, the processor 311 provides the processed signals to the computing unit 313. The computing unit 313 may initially store the processed signals in the memory 315. Further, with some implementations of the invention, the computing unit 313 may operate on the processed signals provided by the athletic information monitoring device 201 to generate a set of athletic data corresponding to the athletic activity performed by the user. For example, if the athletic information monitoring device 201 includes accelerometers for measuring the movement of the user's foot, the computing unit 313 may analyze the processed signals from the athletic information monitoring device 201 to generate a set of athletic data describing the user's speed at specific instances during the user's athletic activity and the total distance traveled by the user at each of those specific instances. Various techniques for determining a user's speed from accelerometer signals are described in, for example, U.S. Pat. No. 6,898,550 to Blackadar et al., entitled "Monitoring Activity Of A User In Locomotion On Foot," and issued on May 24, 2005, U.S. Pat. No. 6,882,955 to Ohlenbusch et al., entitled "Monitoring Activity Of A User In Locomotion On Foot," and issued on Apr. 19, 2005, U.S. Pat. No. 6,876,947 to Darley et al., entitled "Monitoring Activity Of A User In Locomotion On Foot," and issued on Apr. 5, 2005, U.S. Pat. No. 6,493,652 to Ohlenbusch et al., entitled "Monitoring Activity Of A User In Locomotion On Foot," and issued on Dec. 10, 2002, U.S. Pat. No. 6,298,314 to Blackadar et al., entitled "Detecting The Starting And Stopping Of Movement Of A Person On Foot," and issued on Oct. 2, 2001, U.S. Pat. No. 6,052,654 to Gaudet et al., entitled "Measuring Foot Contact Time And Foot Loft Time Of A Person In Locomotion," and issued on Apr. 18, 2000, U.S. Pat. No. 6,018,705 to Gaudet et al., entitled "Measuring Foot Contact Time And Foot Loft Time Of A Person In Locomotion," and issued on Jan. 25, 2000, each of which are incorporated entirely herein by reference.

The athletic data set may also include a time value associated with each speed value and/or each distance value. If the athletic information monitoring device 201 can be employed to collect athletic information from different users, then the athletic data computing unit 313 may additionally prompt the user to identify himself or herself in some way. This identification information may then be included with the athletic data set generated from the information provided by the athletic information monitoring device 201. Once the computing unit 313 has generated a set of athletic data from the information provided by the athletic information monitoring device 201, the computing unit 313 may store the athletic data set in the memory 315. As will be discussed in more detail below, when the digital music player 203 subsequently is connected to a computing device implementing an athletic information collection tool, the computing unit 313 will download the athletic data to a display configuration tool hosted on a remote computing device.

While wireless communication between the between the athletic parameter measurement device 207 and the interface device 205 is described for the embodiments illustrated in FIGS. 2-4, any desired manner of communicating between the athletic parameter measurement device 207 and the interface device 205 may be used without departing from the invention, including wired connections. Also, any desired way of placing data derived from the physical or physiological data from the athletic parameter measurement device 207 in the proper form or format for display on or output from electronic device 210 may be provided without departing from the invention. For example, if desired, the athletic parameter measurement device 207 may be specially designed and/or programmed for use with one or more specific electronic devices, e.g., pre-programmed and/or wired to operate with a specific device or devices and to provide output data in a form and format suitable for those devices. In this situation, the interface devices 205 may be marketed and sold to specifically target certain electronic devices, such as specific models of digital music players and even other electronic devices, such as telephones, watches, personal digital assistants, etc. As another alternative, if desired, the interface devices 205 may be programmed at a later time to operate with a wide variety of different electronic devices, e.g., by downloading display or device driver and/or format data for specific electronic devices from the Internet, from disk, or from another source, etc.

If desired, in accordance with at least some examples of this invention, the electronic interface device 205 may further include a display 220 and/or a user input system 222, such as one or more rotary input devices, switches, buttons (as shown in the illustrated example in FIG. 2), mouse or trackball elements, touch screens, or the like, or some combination thereof. The display 220 may be employed to show, for example, information relating to music being played by the digital music player 203, information relating to the athletic information signals being received by the digital music player 203, athletic data being generated by the digital music player 203 from the received athletic information signals, etc. The user input system 222 may be employed, for example: to control one or more aspects of the processing of the input data received via interface device 205, to control input data receipt (e.g., timing, types of information received, on-demand data requests, etc.), to control data output to or by the electronic device 203, to control the athletic parameter measurement device 207, etc. Alternatively or additionally, if desired, the input system on the digital music player 203 (e.g., buttons 222, a touch screen, a digitizer/stylus based input, a rotary input device, a trackball or roller ball, a mouse, etc.), may be used to provide user input data to the interface device 205 and/or to the athletic parameter measurement device 207. As still another example, if desired, a voice input system may be provided with the interface device 205 and/or the digital music player 203, e.g., to enable user input via voice commands. Any other desired type of user input system, for control of any system elements and/or for any purpose, may be provided without departing from the invention.

The digital music player 203 may include additional input and/or output elements, e.g., such as ports 224 and 226 shown in FIG. 2, e.g., for headphones (or other audio output), power supplies, wireless communications, infrared input, microphone input, or other devices. If desired, and if these ports 224 and/or 226 would be covered when the interface device 205 is attached to the electronic device 203, the interface device 205 may be equipped with similar external ports to ports 224 and/or 226, and internal circuitry may be provided in the interface device 205 to enable the user to plug the same additional devices into the interface device 205 as they might plug into the digital music player 203 and still take advantage of the same functions (e.g., to thereby allow the necessary data, signals, power, and/or information to pass through the interface device 205 to the user, to another output, and/or to the digital music player 203).

It should be appreciated that, while some specific embodiments of the invention described above relate to a digital music player 203, alternate examples of the invention may be implemented using any portable electronic device. For example, with some implementations of the invention, the athletic parameter measurement device 207 may be used in conjunction with a mobile telephone, a watch, a personal digital assistant, another type of music player (such as a compact disc or satellite radio music player), a portable computer, or any other desired electronic device. Still further, some implementations of the invention may alternately or additionally omit the use of the interface device 205. For example, the athletic parameter measurement device 207 may be configured to communicate using the Bluetooth wireless communication protocol, so that it can be employed with Bluetooth-capable mobile telephones, personal digital assistants, watches or personal computers. Of course, still other wireless or wired communication techniques could be employed while omitting the interface device 205.

It also should be appreciated that, while a specific example of an athletic parameter measurement device 207 has been described above for ease of understanding, any type of desired athletic parameter measurement device 207 can be employed with various embodiments of the invention. For example, with some implementations of the invention, the athletic parameter measurement device 207 may be a heart rate monitor, a blood oxygen monitor, a satellite positioning device (e.g., a Global Positioning Satellite (GPS) navigation device) or other location determination system, a device for measuring the electrical activity of the user (e.g., an EKG monitor), or any other device that measures one or more physical parameters of the user. Still further, the athletic parameter measurement device 207 may measure one or more operational parameters of some device being manipulated by the user, such as the speed and/or distance of a bicycle, the speed and/or work performed by a treadmill, rowing machine, elliptical machine, stationary bicycle, the speed and/or distance traveled by skis (water or snow), skates (roller or ice), or snowshoes or the like worn by the user, etc.

Also, while the athletic parameter measurement device 207 has been described as being separate for the digital music player 203 or other portable electronic device that receives the signals from the athletic parameter measurement device 207, with some implementations of the invention the athletic parameter measurement device 207 may be incorporated into the digital music player 203 or other portable electronic device. For example, some implementations of the invention may employ a music player, mobile telephone, watch or personal digital assistant that incorporates accelerometers, a satellite positioning device, or any other desired device for measuring athletic activity. Still further, it should be appreciated that various implementations of the invention may employ a plurality of athletic parameter measurement devices 207, incorporated into the digital music player 203 or other portable electronic device, separate from the digital music player 203 or other portable electronic device, or some combination thereof.

Athletic Collection and Display Tools

Figure 5:
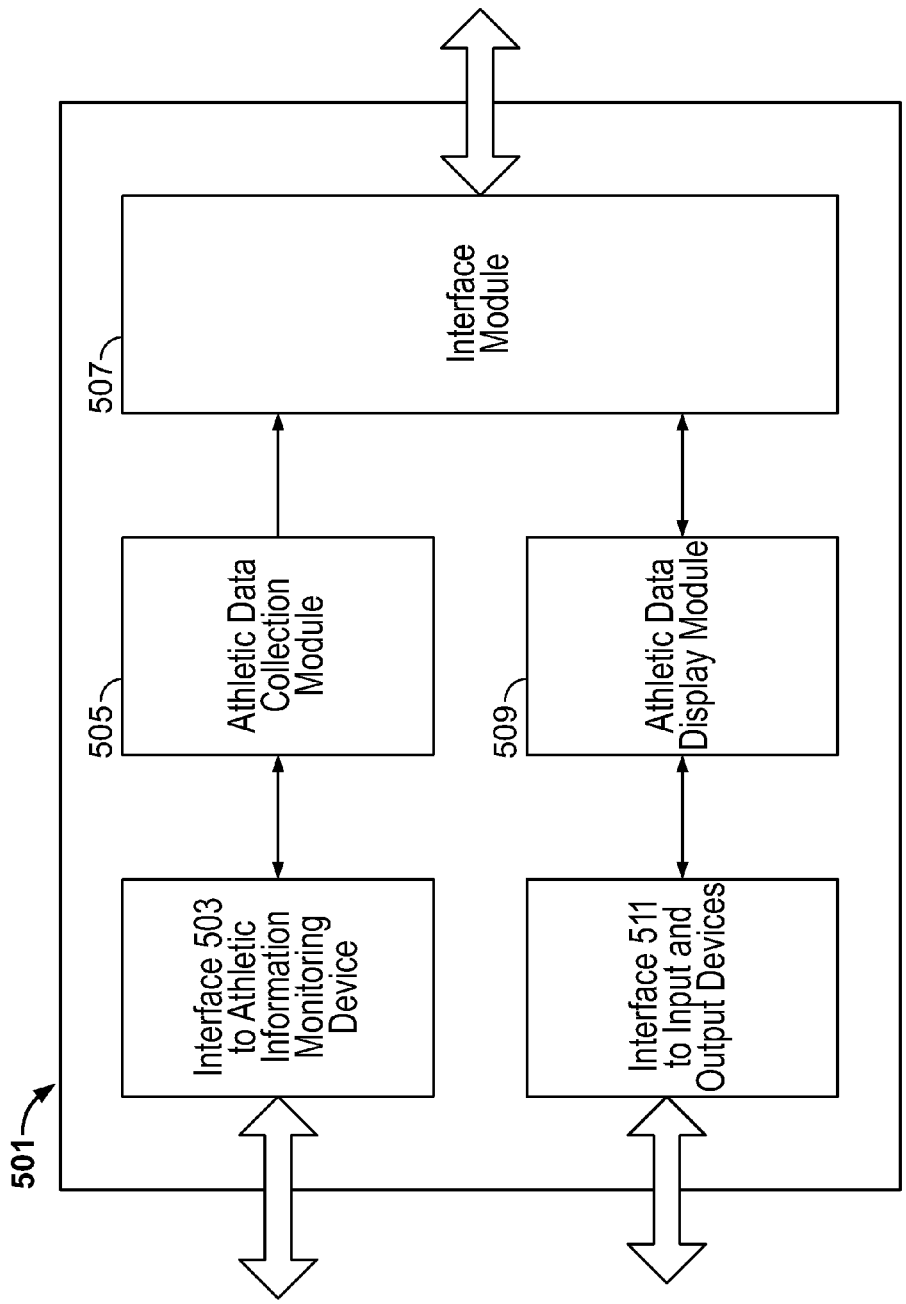
FIG. 5 illustrates an example of an athletic information collection and display device that may be employed to collect and/or display athletic data according to various implementations of the invention.

FIG. 5 illustrates an example of an athletic information collection and display device 501 that may be employed to collect and/or display athletic data according to various implementations of the invention. As will be discussed in more detail below, the athletic information collection and display device 501 may both collect and display athletic data. The athletic information collection and display device 501 may be implemented using any suitable variation of the computing device 101 previously described. In some situations, however, the information collection and display device 501 may be commercially implemented using a desktop or laptop personal computer using, e.g., a version of the Microsoft Windows operating system available from Microsoft Corporation of Redmond, Wash., a version of the Apple Macintosh operating system available for Apple Corporation of Cupertino, Calif., or a version of the Unix or Linux operating systems available from a plurality of vendors.

As shown FIG. 5, the athletic information collection and display device 501 includes an interface 503 for receiving data from the athletic information monitoring device 201. The interface 503 may be implemented using, e.g., electrical components, software components (such as application program interfaces (APIs)), or some combination thereof. The athletic information collection and display device 501 also has an athletic data collection module 505. With various examples of the invention, the athletic data collection module 505 may detect when the digital music player 203 or other portable electronic device storing one or more athletic data sets is connected to the athletic information collection and display device 501 through the interface 503, establish a communication session with the digital music player 203 or other portable electronic device to retrieve the athletic data set or sets. In some implementations of the invention, the athletic data collection module 505 may delete athletic data sets from the digital music player 203 or other portable electronic device after the athletic data sets have been retrieved.

With some examples of the invention, the athletic data collection module 505 may perform some further operations on the athletic data sets retrieved from the digital music player 203 or other portable electronic device. For example, if the athletic information monitoring device 201 can be employed to collect athletic information from different users, then the athletic data collection module 505 may additionally prompt the user to identify himself or herself (if this information was not previously obtained by the athletic information collection and display device 501). This identification information may then be included with the retrieved athletic data sets.

As previously noted, the athletic information collection and display device 501 typically will generate sets of athletic data from information measured by one or more athletic parameter measurement devices 207. With some embodiments of the invention, however, the athletic information collection and display device 501 may instead store the raw information provided by the athletic parameter measurement devices 207. With these embodiments, the athletic data collection module 505 may retrieve the raw information from the digital music player 203 or other portable electronic device, and then generate athletic data sets from the raw information itself. Of course, still other examples of the invention may divide functions relating to the generation of athletic data from the raw information measured by athletic parameter measurement devices 207 between the athletic data collection module 505 and the digital music player 203 or other portable electronic device as desired.

The athletic data collection module 505 may be implemented by, for example, software instructions executed by a computing unit 113 of a computing device 101. With some examples of the invention the athletic data collection module 505 may be implemented by a conventional software tool, such as a browser. Alternately, athletic data collection module 505 may be implemented by a purpose-specific software tool or by a conventional software tool enhanced to perform athletic data collection functions. For example, the athletic data collection module 505 may be implemented by a software tool that incorporates a conventional browser to perform a variety of functions. These functions may include, e.g., selecting, purchasing, and downloading music and video content in addition to collecting athletic data from a digital music player 203 or other portable electronic device.

Once the athletic data collection module 505 has collected the processed signals provided by the athletic information monitoring device 201, the athletic data collection module 505 transmits the athletic data set to an athletic data display configuration device 601 through an interface module 507. The athletic information collection and display device 501 may communicate with the athletic data display configuration device 601 through a conventional network, such as the Internet. With these configurations, the interface module 507 may be implemented using any conventional type of network interface, such as a network interface card. Of course, any type of desired hardware or software combination alternately may be used to allow the athletic data collection module 505 to send the collected athletic data to the athletic data display configuration device 601. With some implementations of the invention, the athletic data collection module 505 may automatically forward collected athletic data to the athletic data display configuration device 601. For example, the athletic data collection module 505 may attempt to forward collected athletic data to the athletic data display configuration device 601 immediately after collection, at a prescheduled interval, upon the detection of a network connection to the athletic data display configuration device 601, or some combination thereof. Alternately or additionally, the athletic data collection module 505 may prompt a user to specify when collected athletic data is sent to the athletic data display configuration device 601.

Figure 6:
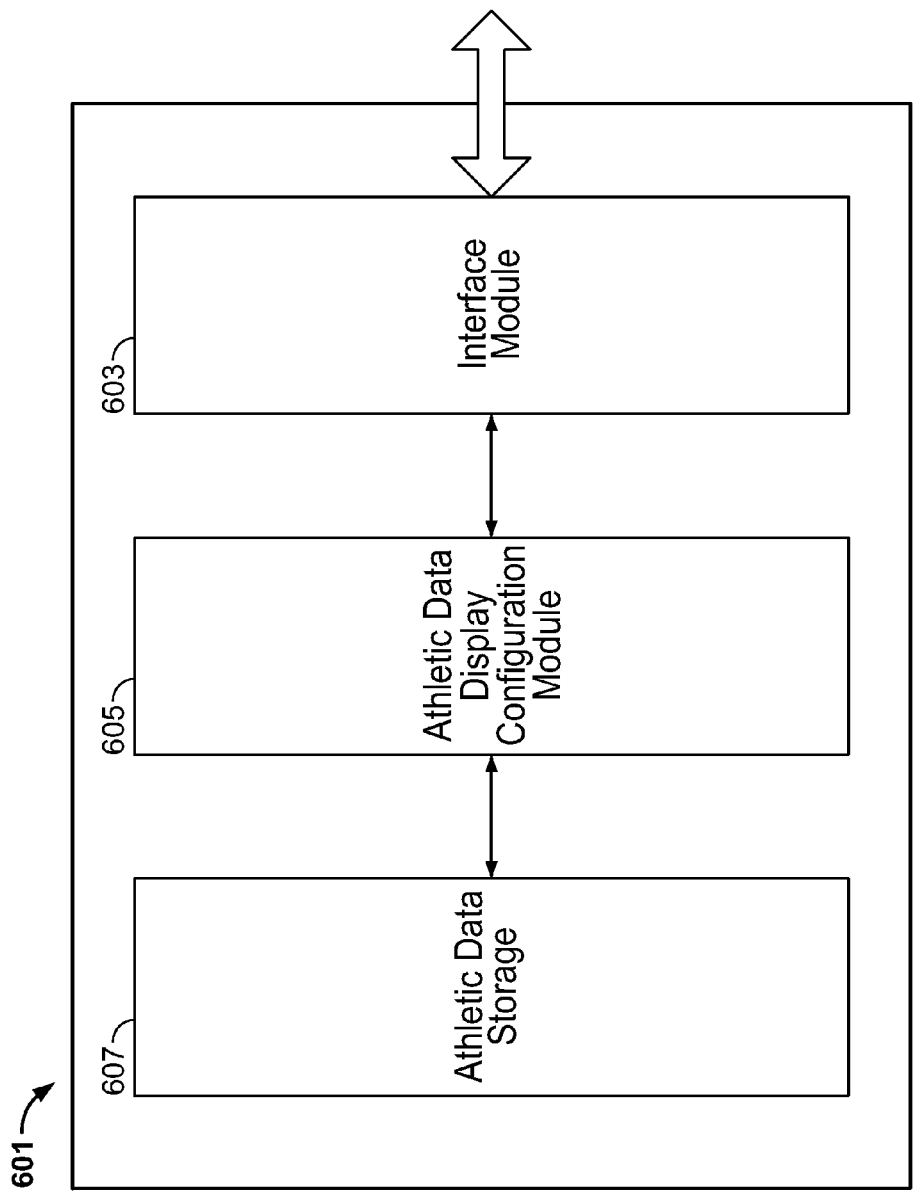
FIG. 6 illustrates an example of an athletic data display configuration device that may be employed according to various examples of the invention.

FIG. 6 illustrates an example of an athletic data display configuration device 601 that may be employed according to various examples of the invention. As seen in this figure, the athletic data display configuration device 601 includes an interface module 603 for communicating with the athletic information collection and display device 501. As previously noted, the athletic information collection and display device 501 may communicate with the athletic data display configuration device 601 through a conventional network, such as the Internet. With these configurations, the interface module 603 may be implemented using any conventional type of network interface, such as a network interface card. Of course, any type of desired hardware or software combination alternately may be used to allow the athletic data display configuration device 601 to communicate with the athletic information collection and display device 501.

The athletic data display configuration device 601 also includes an athletic data display module 605, and an athletic data storage 607. When the interface 603 of the athletic data display configuration device 601 receives athletic data from the athletic information collection and display device 501, it provides the received athletic data to the athletic data display configuration module 605. The athletic data display configuration module 603 may then store the athletic data in the athletic data storage 607 for future use. As will be discussed in more detail below, the athletic data display configuration module 605 also will retrieve athletic data from the athletic data storage 607, and configure the retrieved athletic data for display through one or more user interfaces in a manner that is meaningful to a user.

Returning now to FIG. 5, when a user wishes to view information relating to his or her athletic activities (or the athletic activities of another, as will be discussed in more detail below), the user submits this request to the athletic information collection and display device 501. More particularly, the user can employ conventional input and output devices, such as a keyboard, mouse, display and the like. The display request is then provided to an athletic data display module 509 through a conventional interface input/output interface 511. As well known in the art, the interface input/output interface 511 may be implemented using any desired combination of hardware and software components, such as conventional application programming interfaces (APIs) used to detect and process input from input devices, and to send data to and otherwise control output devices.

With some examples of the invention, the athletic data display module 509 may be implemented using any conventional tool for receiving input to request and control the display of data, and then subsequently displaying the data in the manner requested. For example, the athletic data display module 509 may be implemented using a conventional browser program, such as Microsoft Internet Explorer, Mozilla Firefox, or Opera executing on a computing unit 113. With still other embodiments of the invention, the athletic data display module 509 may be implemented using a conventional browser program that has been enhanced by one or more display tools, such as an ActiveX plug-in, a Java script or a version of the Macromedia Flash Player or Adobe Flash Player, available from Adobe Systems Incorporated of San Jose, Calif. In still other embodiments of the invention, the athletic data display module 509 may be implemented by, for example, a purpose-specific software tool for displaying athletic data.

As will be discussed in more detail below, when a user activates the athletic data display module 509, he or she is provided with a user interface prompting the use to select what collected athletic data he or she wishes to view, the format in which the user wishes to view the collected athletic data, etc. This user interface may be generated by the athletic data display module 509, the athletic data display configuration module 605, or some combination thereof. When a user employs the provided user interface to submit a request to view athletic data, the athletic data display module 509 relays the request to the athletic data display configuration module 605. In response, the athletic data display configuration module 605 configures the requested athletic data for display by the athletic data display module 509. For example, as will be discussed in more detail below, a user may request to view the total distance run by a user for each day in a one week period. In response, the athletic data display configuration module 605 will retrieve the relevant distance data from the athletic data storage 607. It will then configure the retrieved distance data to be displayed through a desired image (e.g., a bar graph), and provide the configured athletic data to the athletic data display module 509 for display to the user.

It should be noted that, with some embodiments of the invention, the data display configuration functions may be divided between the athletic data display module 509 and the athletic data display configuration module 605. For example, if the athletic data display module 509 is implemented by a simple browser, then the athletic data display module 509 may serve as a "thin client" for the athletic data display configuration module 605. That is, all of the data display configuration functions may be performed by the athletic data display configuration module 605. The athletic data display module 509 will then only display the information provided to it. Alternately, if the athletic data display module 509 is implemented by a purpose-specific software tool, then most or all of the data display configuration functions may be performed by the athletic data display module 509. With these examples, the athletic data display configuration module 605 may be used only to store and retrieve athletic data from the athletic data storage 607.

Athletic Activity Monitoring Using a Mobile Device

As noted above, various software (e.g., athletic display module 509 of FIG. 5) and hardware (e.g., athletic information collection and display device 501 of FIG. 5) may be used to track athletic activity and provide such information to an individual. In one arrangement, the software and/or hardware may be included in a mobile device such as a mobile communication device or mobile computing device. Such devices may include smartphones, mobile telephones, personal data assistants (PDAs), laptop computing devices, digital music players, tablet computers, wrist worn devices, and the like. Computer executable instructions in the form of a software application or applet may be stored in the mobile device, allowing the mobile device to perform various athletic activity tracking and monitoring functions. For example, the mobile device may offer feedback, challenges, suggestions, encouragement and other data in response to an individual's athletic performance. In one example, the computing device may challenge the individual to perform a more strenuous or more difficult workout than in a previous workout session in order to help the individual improve and achieve greater progress. By achieving more substantial progress, the individual may be more motivated to continue exercising on a regular basis.

Figure 7:
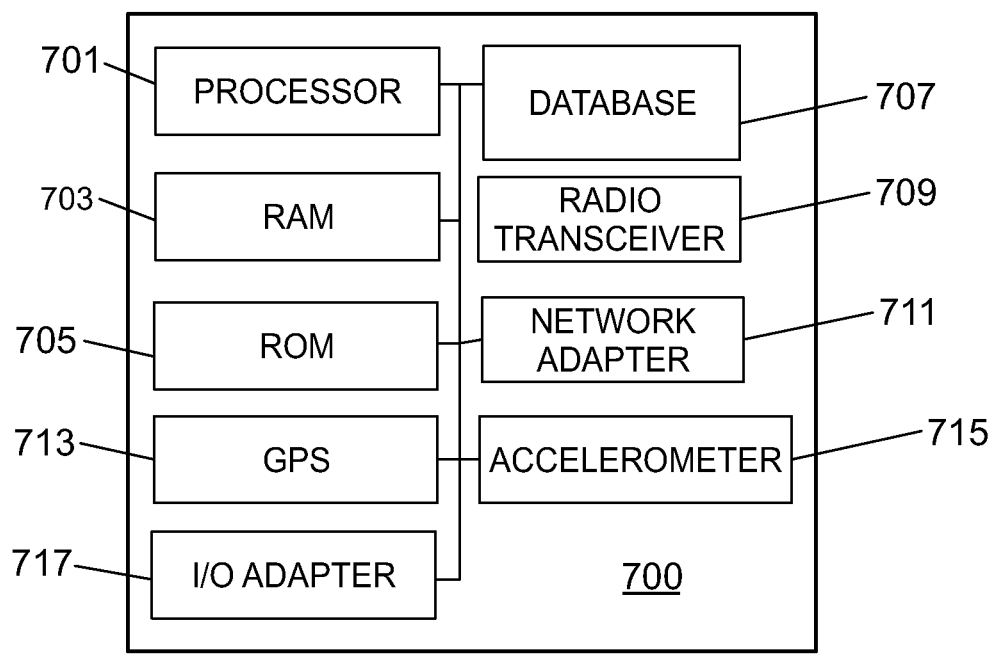
FIG. 7 illustrates an example mobile athletic activity monitoring device according to one or more aspects described herein.

FIG. 7 illustrates a block diagram of an example mobile device that may be used to track athletic activity information and provide various types of feedback to an individual. Mobile device 700 may include processor 701, RAM 703, ROM 705, database 707, radio transceiver 709, network adapter 711, global positioning system (GPS) device 713, accelerometer 715 and I/O adapter 717. Computer readable media such as RAM 703 and ROM 703 may be configured to store computer readable instructions that, when executed, cause an apparatus such as mobile device 700 to perform one or more functions described herein. Processor 701 may be configured to perform various calculations and execute instructions stored in RAM 703 and ROM 705. Database 707 may provide storage for data including user information, phone numbers, network addresses, e-mail addresses, software, images, documents and the like. I/O adapter 717 may be configured to facilitate the reception and output of data to one or more input or output devices including a touchscreen display, a speaker, audio jack, physical keyboard, microphone and the like.

The inclusion of GPS device 713 and accelerometer 715 in a single mobile device 700 allows device 700 to be used in multiple workout settings. For example, if an individual is running on a treadmill, the GPS device 713 would likely not be able to detect or provide significant exercise data since the individual is generally stationary. Instead, the mobile device may use the accelerometer to determine a number of steps the individual has taken, a speed/acceleration of the individual and the like. If, on the other hand, the individual is running outdoors such that the individual moves from one location to another, the GPS device 713 or recording of data therefrom (e.g., GPS device is always active, but recording is turned on and off) may be activated and used instead. In one or more arrangements, mobile device 700 may automatically detect whether GPS device 713 should be used or accelerometer 715 should be used (or whether data should be recorded from GPS device 713 or accelerometer 715). For example, if device 700 determines that the individual's location is not changing, accelerometer 715 or recording data therefrom may be activated and used (again, the device might always be active, but recording data from the device is turned on and off). In some arrangements, both GPS device 713 and accelerometer 715 may be used in conjunction with one another. Other sensors may also be included in mobile device 700 including a heart rate monitoring device to provide additional types of activity data. Additionally, in some instances, location may be determined using cellular triangulation if GPS is unavailable.

In one or more arrangements, mobile device 700 may automatically switch between a GPS without accelerometer setting, an accelerometer without GPS setting or a combination GPS and accelerometer setting (and in some cases, a cellular triangulation with accelerometer mode). The switching and determination of which mode to use may depend on a variety of factors including detected movement, GPS signal strength and availability, user preferences, location and the like. For example, if a GPS signal is low (e.g., below 50% strength, below 30% strength, below 10% strength, etc.), mobile device 700 may operate (e.g., record data from) both GPS device 713 and accelerometer 715 so that the accelerometer 715 data may supplement any potentially missing or inaccurate GPS information. Alternatively or additionally, GPS data and accelerometer data may be averaged or otherwise combined to determine an amount of athletic activity performed by the user. In another example, mobile device 700 may use and record data from the GPS device 613 without using or recording data from accelerometer 715 when the signal strength is above a predetermined level (e.g., 50%, 70%, 90%, etc.). In yet another example, if mobile device 700 detects movement via accelerometer 715 but does not detect change in position using GPS device 713, mobile device 700 may use accelerometer 715 without GPS device 713 for that workout. Further, if the device 700 begins detecting a GPS signal, device 700 may switch to GPS mode or a combination GPS/accelerometer mode. In other instances, an accelerometer 715 may be used without GPS device 713 if no GPS signal is available and/or a location of the user is indoors. The user location may automatically be determined using GPS (e.g., location, signal strength) or based on manual input.

In other examples, other sensors may be used in concert with a location determination system to provide alternative or additional activity information. For example, a heart rate sensor may be used to determine whether the user is performing athletic activity if a location determination system does not detect a change in a user's physical location (or a change above a predefined threshold distance or altitude).

Mobile device 700 or other computing systems may offer a variety of functions and options for defining a workout. For example, the system may offer the user options of starting a run from scratch or improving on a previously completed run. The run may then customized and encouragement and/or status information may be provided to the individual during and after the run.

Defining a Run—Overview

Figure 8:
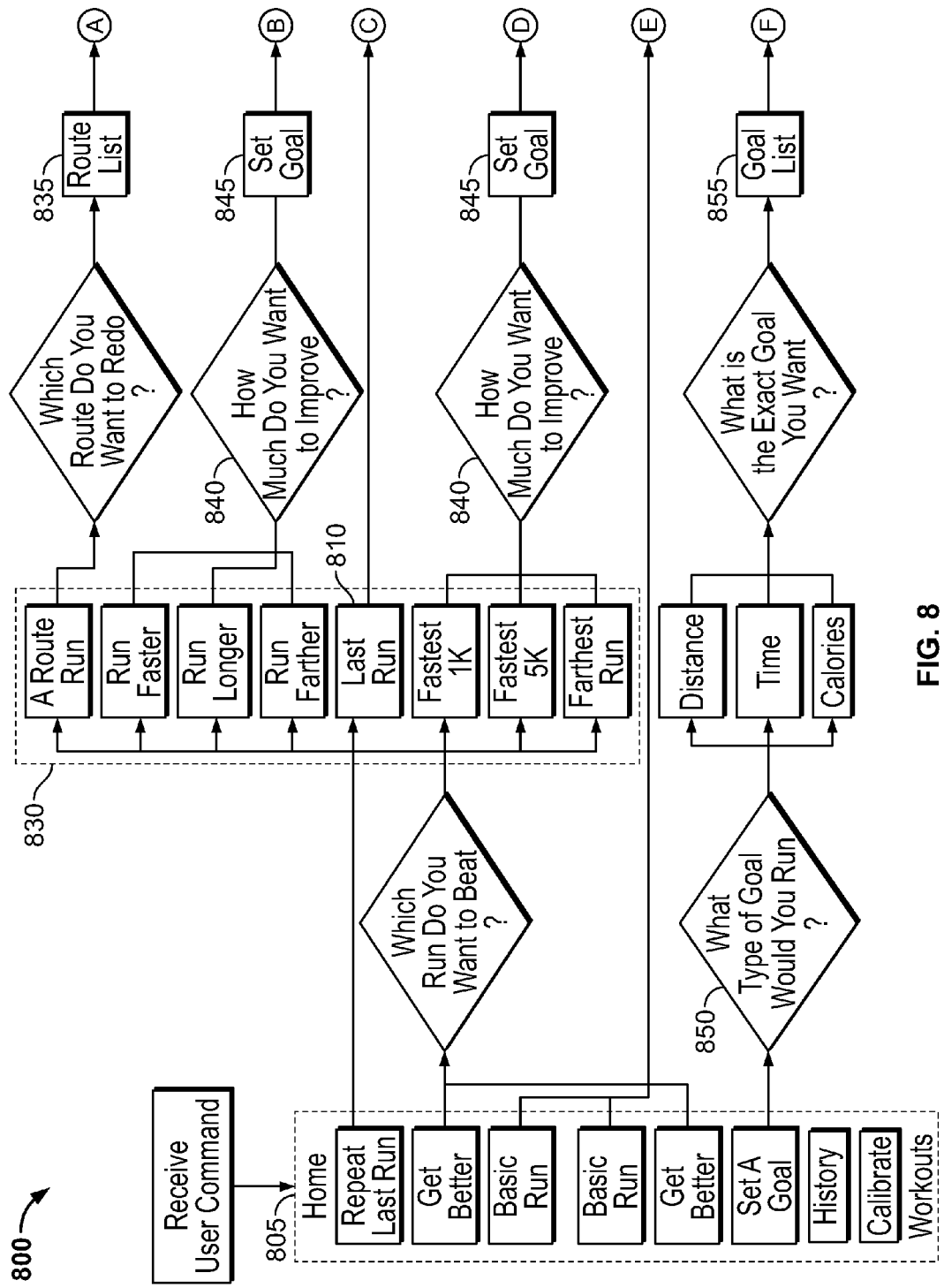
FIGS. 8 and 9 illustrate example methods for defining a workout according to one or more aspects described herein.
Figure 8:
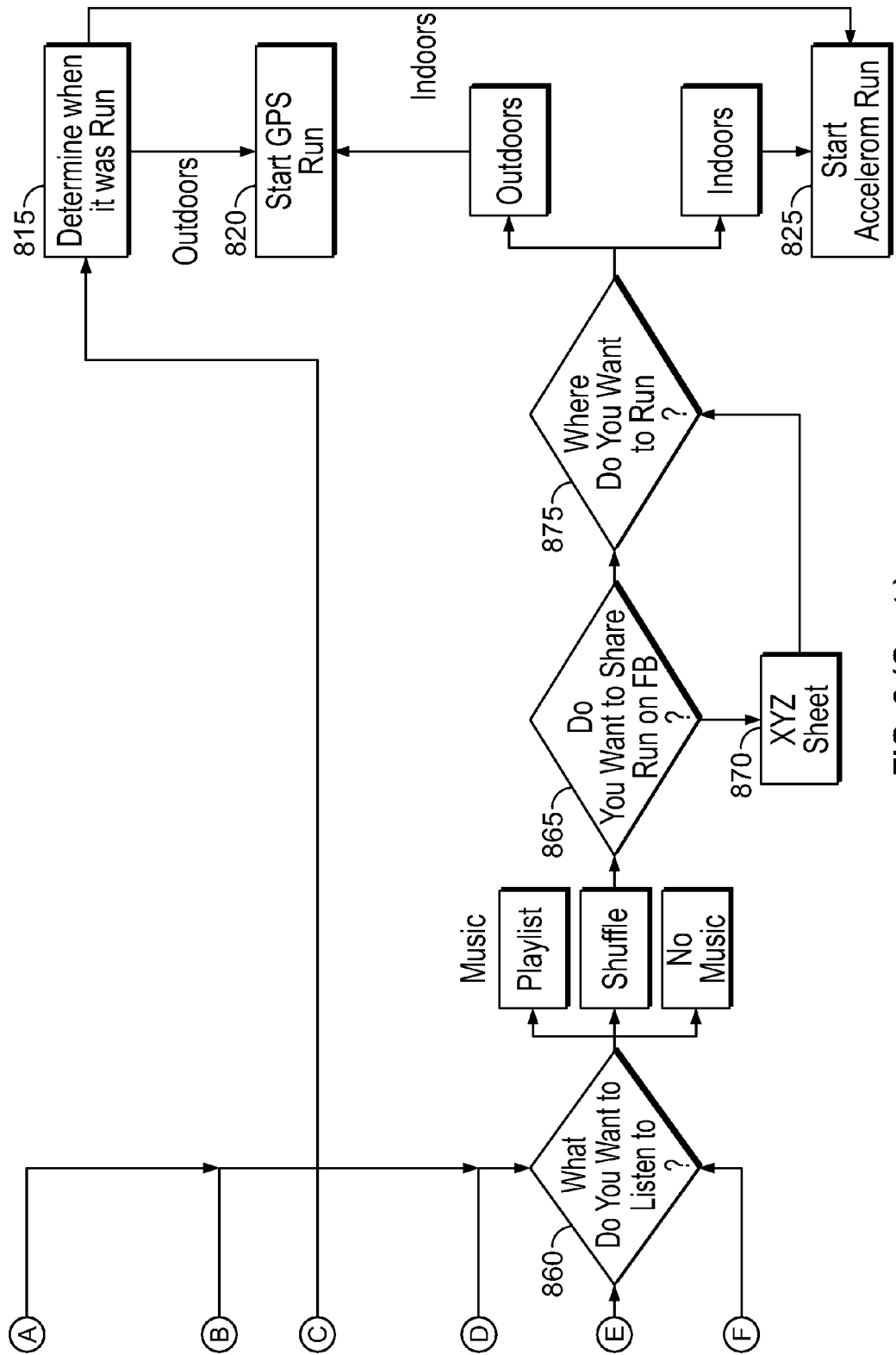

FIG. 8 is a flowchart illustrating an example process by which a user may define a run using a mobile device or other fitness monitoring device. Other options may also be provided in the process including posting the performance information to a social networking site or a news feed, synchronizing or sending data to an athletic activity performance monitoring service and the like. In step 800, a system such as mobile device 700 of FIG. 7 may receive user input corresponding to a command to initiate a workout. For example, the user input may comprise user selection of a workout option from a menu of applications or functions available on the system. In block 805, the system may subsequently offer the user multiple workout options in response to the command. For example, the system may provide options for repeating a last run, starting a basic run, improving on a past run, calibrating one or more sensing devices, viewing a workout history and/or setting a goal. The options may be categorized and displayed in separate sections or screens of a user interface. For example, a home screen may include a repeat last run option, a get better option and a basic run option while a workout screen may include the basic run option, the get better option, a goal setting option, a history option and a calibration option.

If the user chooses a repeat last run option, the user's most recent run may be retrieved from a database in step 810. This database may be local to the system or may be resident in a remote server. The system may then make a determination in step 815 as to where to the run took place, e.g., outdoors or indoors, since the location of the run may determine what sensors are used in tracking the activity. For example, if the previous run occurred outdoors, the system may initiate a run to be tracked and monitored using a GPS device in block 820. On the other hand, if the run occurred indoors, the system may initiate a run to be tracked and monitored using an accelerometer system as shown in block 825. Initiation of the run may include activation of the relevant firmware, hardware and/or software, defining workout parameters (e.g., setting a calorie burning goal for indoors versus a distance goal for outdoors), generating a workout interface (e.g., a gym image for indoor runs and outdoor scenery for outdoor runs) and the like. As noted herein, in some arrangements, both accelerometer and GPS systems may be used to track various workout statistics if the workout allows for the use of GPS while only non-GPS devices may be used for indoor workouts. Using a device may include recording data from that device. Repeating a last run may also include using the same music playlist or other audio content as the previous run. Alternatively or additionally, the user may be provided with an option and opportunity to customize the audio content for the current run.

If the user chooses to improve his or her workout performance, the user may be presented a second set of options in block 830. The options may offer various methods of improvement including running a specific route, running faster, running longer, running farther, setting a personal best (time-wise) in the 1K or 5K, or setting a personal best in a distance run. If the user selects an option to complete a particular route, the user may be presented with a route list in block 835. If, on the other hand, the user selects one of the other options, the user may be asked to input a corresponding improvement amount in block 840. The system may subsequently set the goal for the workout based on the user input in block 845. The amount by which the user wants to improve his or her performance may be defined in terms of percentages or absolute values. For example, if the user wishes to run farther, the user may define the number of additional miles he wishes to run or a percentage increase in the number of miles. The total number of miles may then calculated based on a most recent run or based on a personal best depending on the type of improvement selected. In one example, if a user selects the option to run farther, the improvement goal may be defined based on the user's last run. If, however, the user selects the option to set a personal best in distance run, the improvement goal may be automatically, semi-automatically and/or manually defined based on a previous or current personal best in distance. For example, the system may automatically set the goal as 5% above the user's personal best in distance. Alternatively or additionally, the user may be given the option of selecting the workout from which he would like to improve from all previously recorded workouts.

If the user chooses a goal setting option from a workout menu, the user may be asked to select a type of goal he would like to set in block 850. The various types of goals may include distance, time and calories. Other types of goals may also be set such a pace, heartrate, percentage incline run and the like. In one or more arrangements, the user may select more than on goal type so set multiple goal parameters for the run. Upon selecting the type of goal, the system may display a list of goals to the user in block 855. The list of goals may include one or more predefined and/or automatically defined goals such as run a marathon, run for 30 minutes and/or burn 300 calories. The list of goals may also provide an option for the user to customize the goal. For example, if no predefined selection is available for running 10 miles, the user may set a customized goal for running 10 miles. In another example, if the user wishes to burn 500 calories, but the predefined calorie goals are in 200 calorie increments, the user may set a customized 500 calorie goal instead of being forced to choose either 400 or 600 calories.

Once a user has selected a workout type and/or defined a goal for the workout type, the system may prompt the user to select the type of music he or she wishes to listen to during the workout in block 860. The various selections may include a predefined playlist (user or system created), shuffle (e.g., random selection of songs or random order of songs) or no music. In block 865, the system may determine whether the user wishes to publish workout information on a social networking site such as FACEBOOK. Alternatively or additionally, the system may determine whether the user wishes to synchronize workout data to an athletic activity monitoring service. If so, the user may be prompted to enter various identification or login information so that the system may automatically access the user's account and synchronize or post information thereto. The user may also be prompted to enter publishing or synchronization options including whether the information is to be made available to the general public, a select group of friends or users, whether all data is to be synchronized or just a particular type of data (e.g., calories, distance run, route, etc.) and the like.

If the user does not wish to publish or synchronize the data or once the user has completed filling in the synchronization/publication information in block 870, the system may allow the user to define an environment in which the workout will take place in block 875. For example, the user may select either an outdoor or indoor workout. In some arrangements, the user may also select a particular location or type of equipment. For example, the user may indicate that he or she wishes to run on a treadmill or to use an elliptical machine. In accordance with the defined environment, the system may initiate appropriate devices and sensors for detecting the results of the workout as described with respect to blocks 820 and 825. In some arrangements, the selection of a location or environment may also allow the device to more accurately calibrate its sensors and devices for that particular environment. Different sets of calibration data may be stored for different workouts, type of workouts and workout environments.

Figure 9:
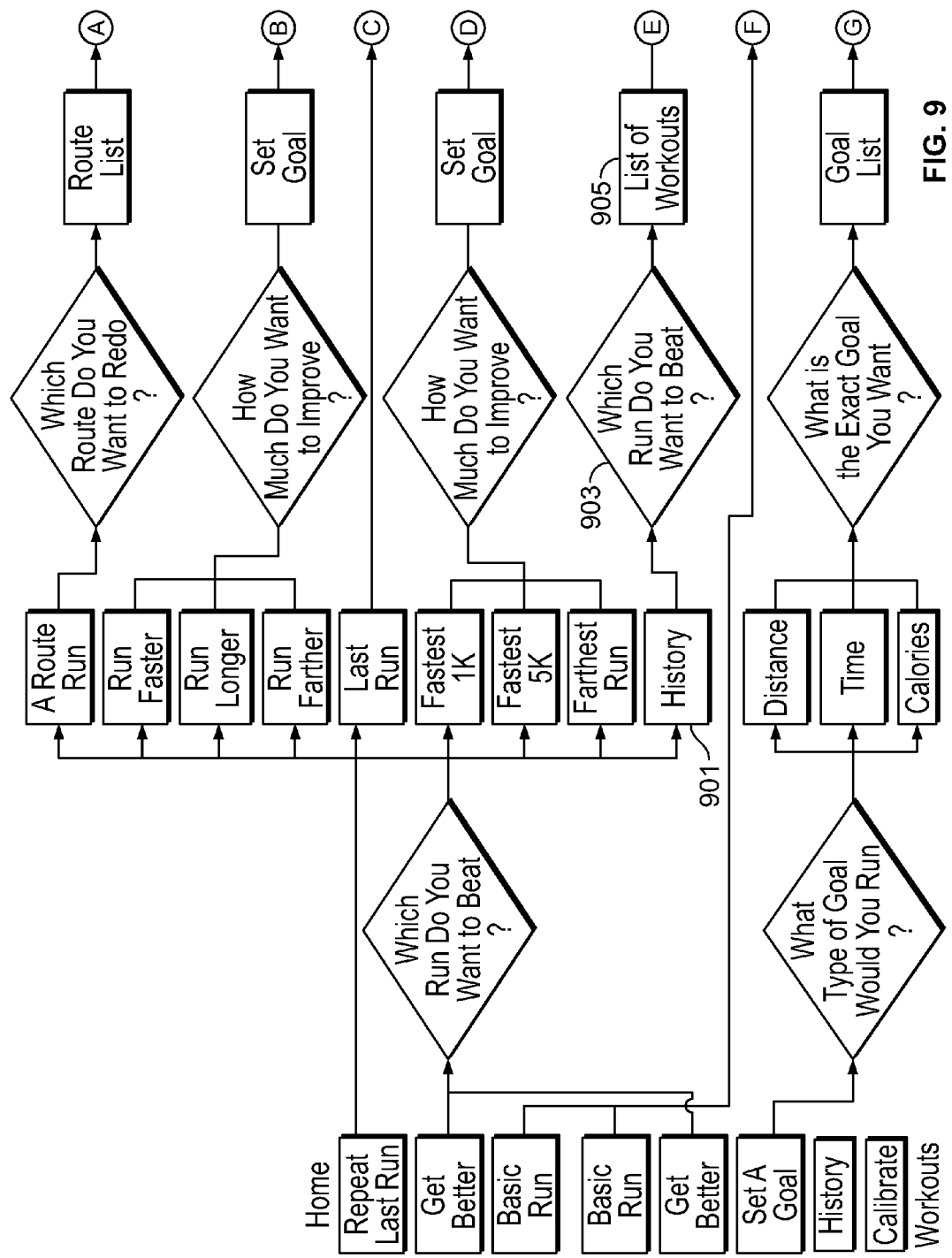

FIG. 9 illustrates example process flow by which a user may define and initiate a workout. The process flow of FIG. 9 may be similar to that described in FIG. 8, but with additional options and/or features. For example, the process flow of FIG. 9 may include an improvement option that allows a user to select a past run in blocks 901-905. The system may automatically select the workout parameter that the user is to improve or the user may select the parameter he or she would like to improve. Alternatively, the user may be expected to improve upon multiple or all parameters (e.g., calories and distance) during the workout. Furthermore, the process flow may include an audio option in block 907 that allows a user to overlay various ambient noises and sounds such as city noises (e.g., cars honking/driving by, police sirens, children playing, etc.), country sounds (e.g., crickets, wind blowing, farm animal noises) and the like. The ambient noises and sounds may be presented to the user for selection in a list of cities, locations and/or environments. For example, the list may include cities such as New York, D.C., Boston, Los Angeles and Chicago and locations such as a bar, a club, a park, a beach and the like.

The process flow may include another option for allowing a user to choose whether he or she would like to receive prompts during the workout to further improve the individual's workout in block 909. For example, halfway through the workout, the system may automatically generate and display a prompt asking whether the individual would like to increase the run time by an additional 5 minutes or if the individual would like to burn 50 more calories. The improvement or additional amount may correspond to a percentage of the unmodified goal/workout, an amount that would increase the workout to beat a personal best in an athletic activity metric and the like. If the user does not wish to receive such prompts or notifications, the prompts may be deactivated for the workout. Alternatively, if the user selects the option to receive prompts, the user may also be allowed to define when the prompts are given and under what conditions. For example, the user may specify that prompts are only to be given during the last 30 minutes of a 1 hour run and only when the user's heart rate is below a certain amount. In another example, a user may ask that prompts be provided when the individual is on pace to exceed a distance goal and is running faster than an expected pace. Various other types of parameters and conditions may also be used to define triggers for prompts that seek to further improve the individual's workout performance.

FIGS. 10A to 10G illustrates a sequence of user interfaces that may be generated and displayed when an individual begins a first run. A first run may be a new run for an individual who has no previously recorded workout history. When a user creates a first run, the user may initially be presented with a welcome interface 1000 of FIG. 10A. Interface 1000 may display user and workout information including a number of previous runs 1001 (e.g., 0 since the user does not have any previously recorded runs), average pace 1003, duration 1005 and calories burned 1007. Duration 1005 and calories burned 1007 measurements may be a total duration and total calories burned, respectively, across all runs performed or may be an average for each run. Interface 1000 may further display multiple options including an option to start a new run 1009 and an option to tour the features of the workout application 1011. Additionally or alternatively, interface 1000 may include options for accessing other aspects of the workout application including history option 1013 for display a list of previously recorded workouts and settings option 1015. Selection of settings option 1015 may cause a profile setup/edit interface to be displayed. In one arrangement, selecting new run option 1009 may also cause a profile setup/editing interface to be displayed if the user has no previous run history.

In one example, if no runs have been previously recorded, a history interface may be empty. FIG. 10G illustrates a history interface (e.g., display upon selecting history option 1013 of FIG. 10A) displaying a message 1051 that there are no saved runs. The interface may further include a run setup or initiation option 1053 to encourage the user to participate in a first run.

Figure 10B:
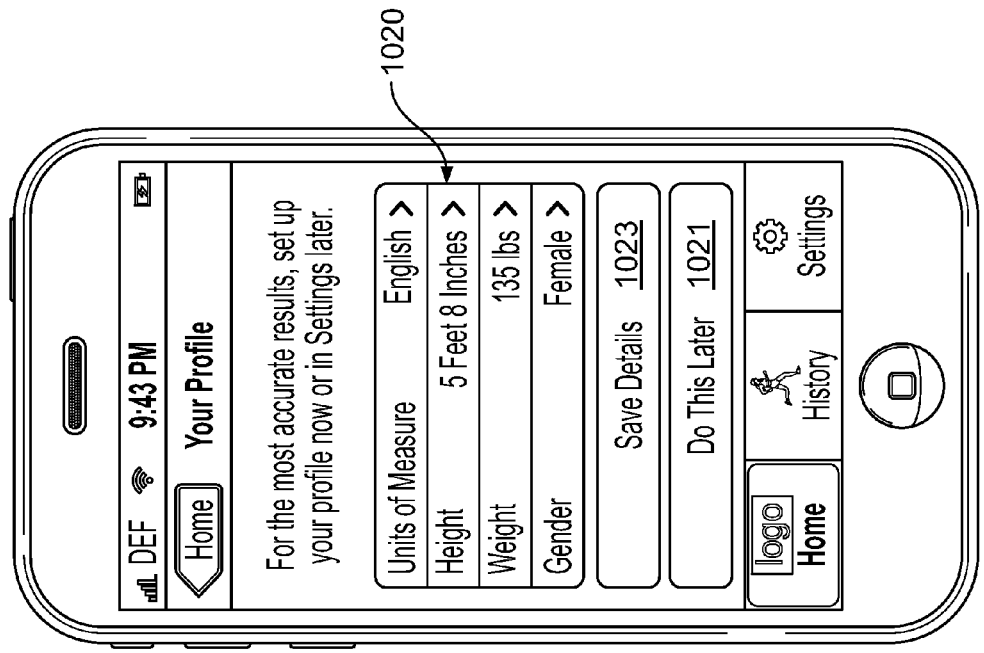
FIGS. 10A to 10G illustrate a sequence of user interfaces that may be generated and displayed when an individual begins a first run according to one or more aspects described herein.
Figure 10A:
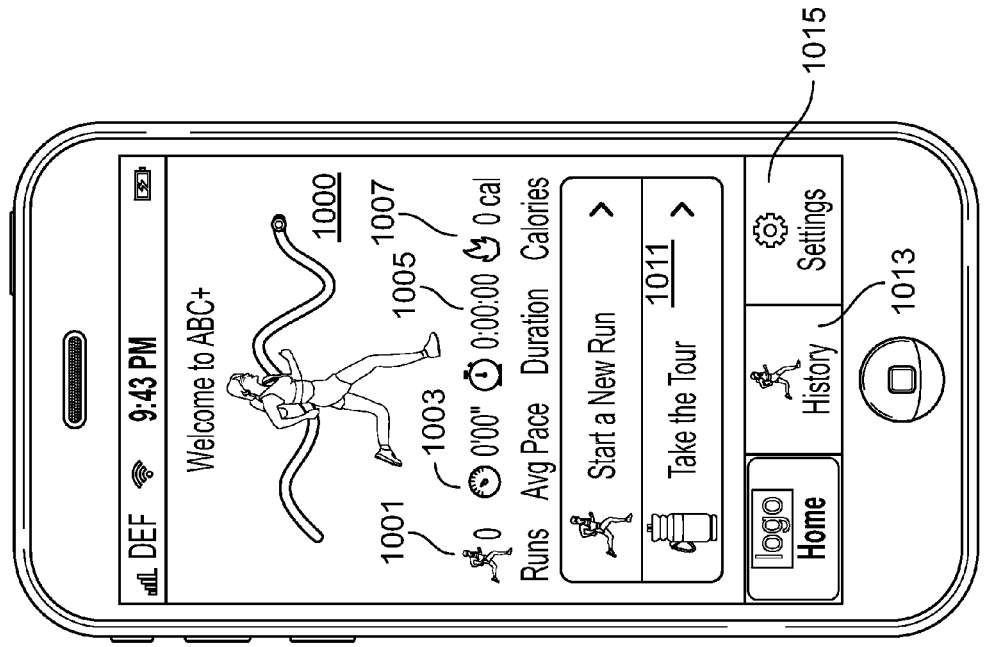
Figure 10D:
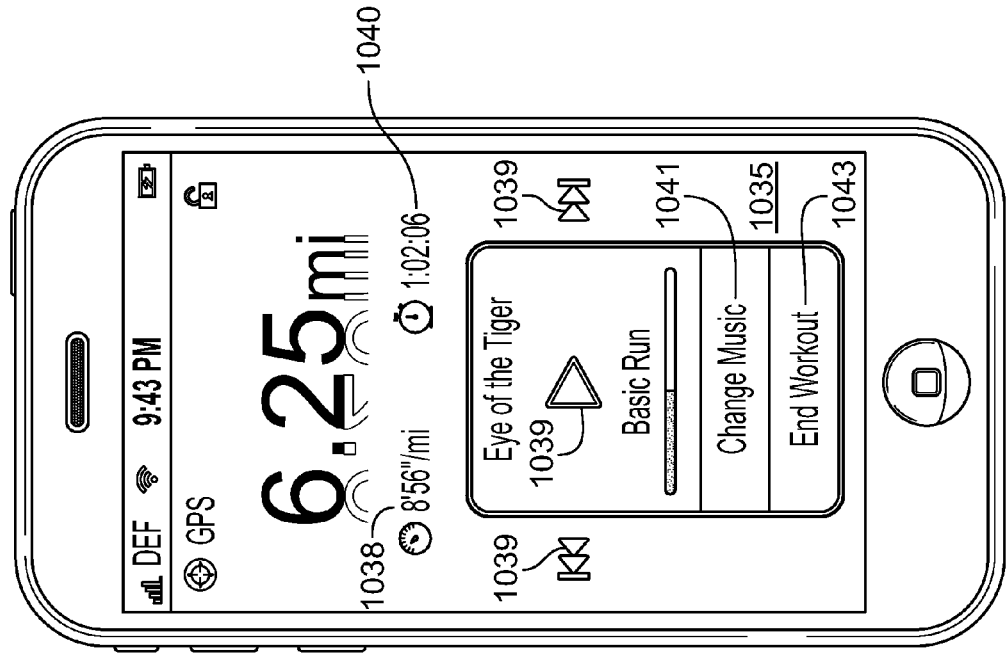

FIG. 10B illustrates a profile setup/editing interface 1020 that allows a user to configure various workout and workout recordation parameters. For example, interface 1020 may allow the user to define the units of measure to use and to set the user's height, weight and gender. Additional or alternative parameters may be changeable through interface 1020. The user may be provided with an option 1021 to skip a profile setup/editing function. If the user chooses to complete the profile setup, the user may save the profile information using option 1023. A user may navigate to other interfaces and screens such as home screen 1000 (FIG. 10A) by selecting home navigation option 1005.

Figure 10C:
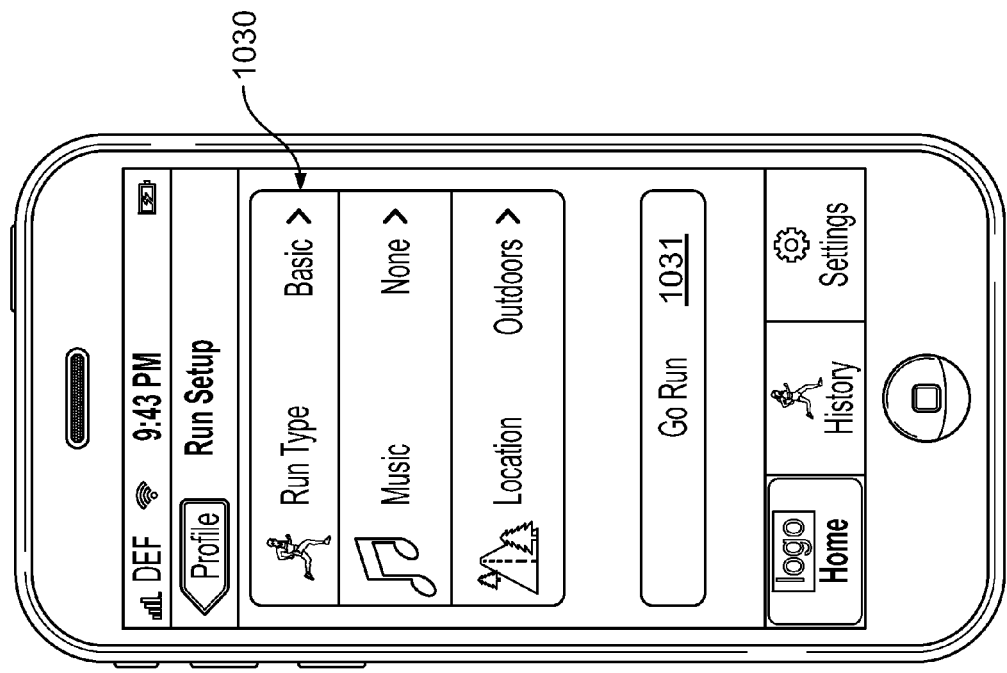
Figure 10F:
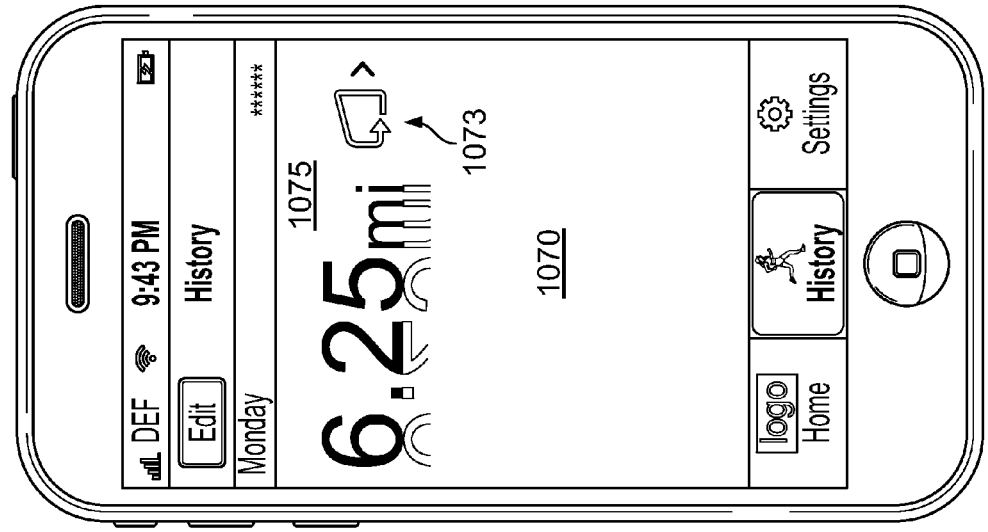

Once the user has completed setting up their profile or upon the user choosing to skip the profile definition menu, the user may be presented with a run setup interface 1030 as illustrated in FIG. 10C. Run setup interface 1030 may be configured to allow a user to define workout parameters for the new run. For example, the user may define the run type, the music that is to be played during the workout and the location, each of which are described in further detail herein. Once these parameters have been defined, the user may begin the run using option 1031.

FIG. 10D illustrates an in-run interface 1035 wherein a current distance run 1037 is displayed along with a pace 1038 and an amount of time spent in the workout 1040. The user may also be provided with options 1039 for controlling the playing of audio content, changing the audio content being played 1041 and ending the workout 1043.

Figure 10E:
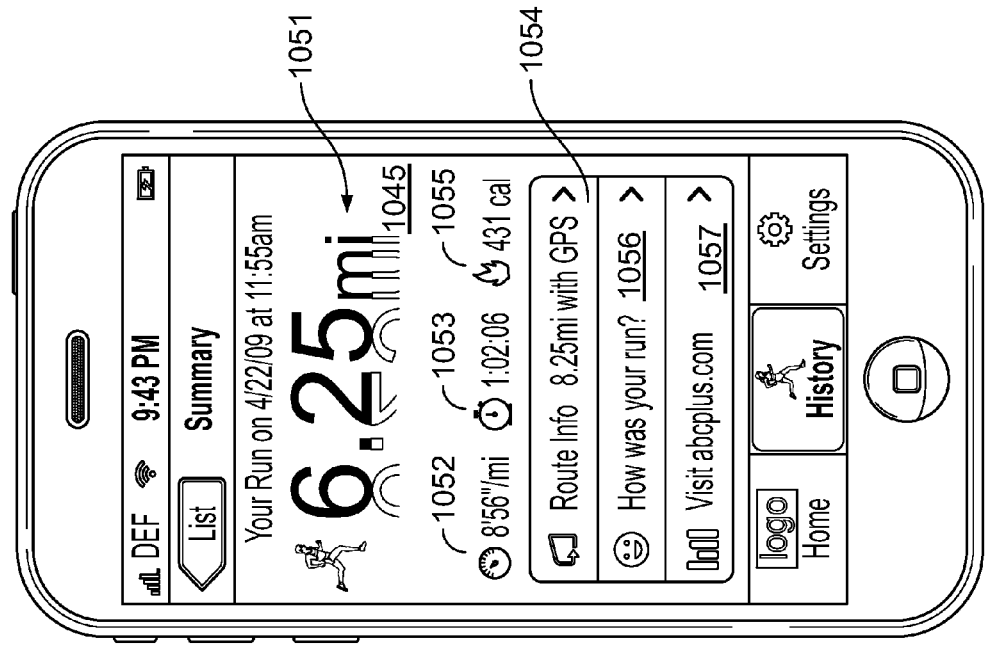
Figure 10G:
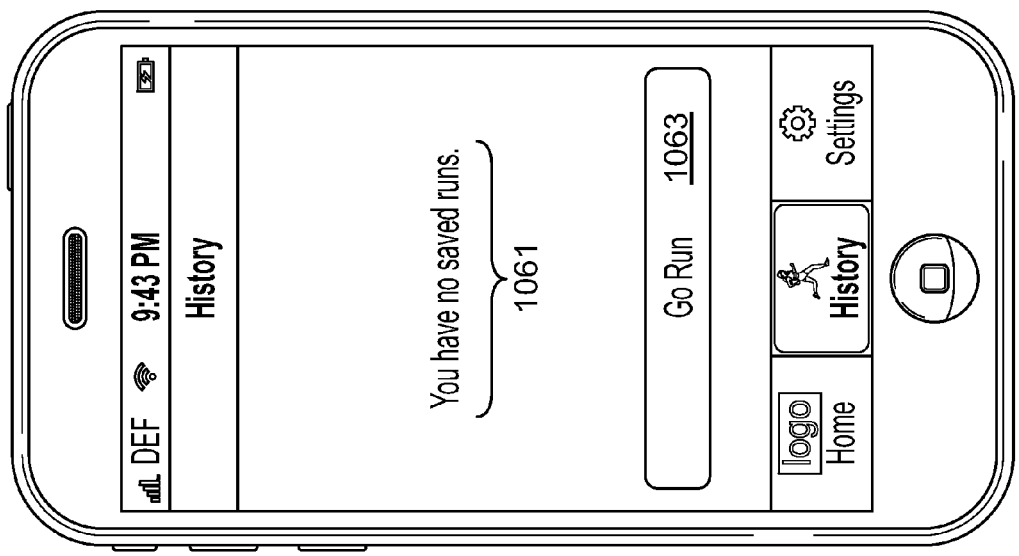

In FIG. 10E, interface 1045 displayed a workout summary upon completion or ending of the run. For example, summary interface 1045 displayed a total distance run 1051, pace 1052, time spent running 1053 and calories burned 1055. Interface 1045 may further display option 1054 for displaying a route that the user run if the run was recorded using a GPS device. Other options may include an option 1056 to tag the run with the user's emotional or mental state (e.g., a mood) and an option 1057 to visit an athletic activity service provider site. Visiting the athletic activity service provider site may allow the user to view additional workout information that has been collected by the service provider for the user. This may allow the mobile device to minimize the amount of storage necessary in the mobile device, instead storing workout data in the service provider site.

Once the user has completed his or her first run, a history interface such as interface 1070 of FIG. 10F may include an entry 1075 corresponding to the first run. The workout entry 1075 may be identified in interface 1070 by one or more workout statistics such as a distance run. Additionally or alternatively, various icons or tags such as icon 1073 may be displayed in association with the entry 1075 to indicate that certain types of information are available for that entry 1075. For example, icon 1073 may indicate that a GPS route was recorded for the workout. Selection of entry 1075 may allow the user to view the recorded GPS route along with other details of the workout (e.g., calories burned, duration of the workout, user's mood after the workout).

Figure 11A:
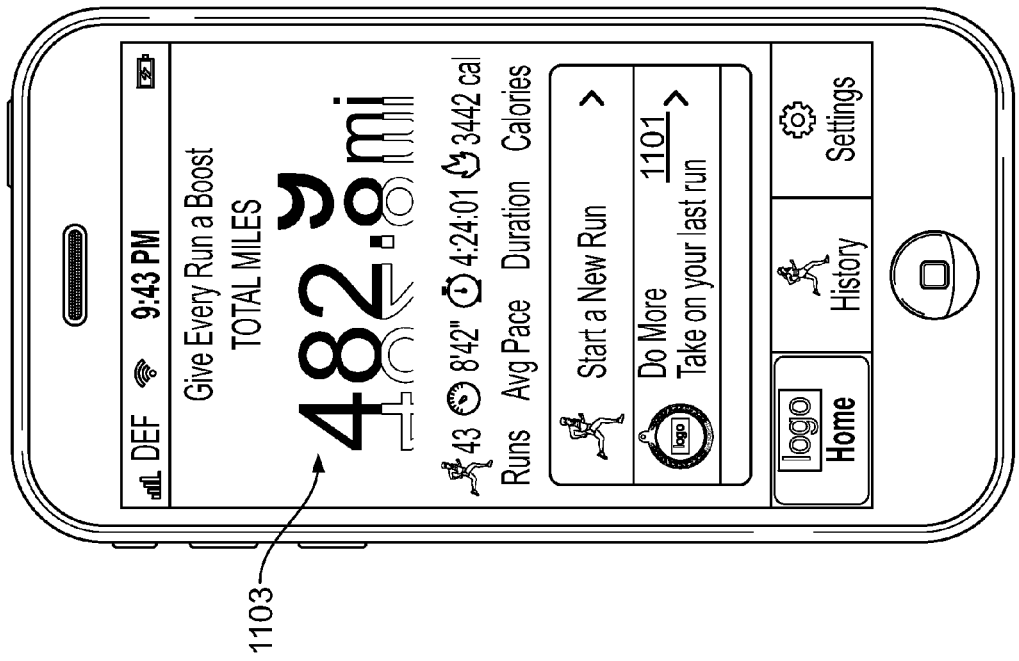
FIGS. 11A-11E illustrates a series of interfaces that may be generated and displayed after the user has completed and recorded a first run according to one or more aspects described herein.

FIGS. 11A-11E illustrates a series of interfaces that may be generated and displayed after the user has completed and recorded a first run. For example, FIG. 11A illustrates home interface 1100 that may be displayed for subsequent runs or workouts. Instead of displaying a tour option (e.g., 1011 of FIG. 10A), home interface 1100 may display option 1101 that allows a user to perform a workout that improves upon a previous workout. The previous workout may be chosen by a user or may be automatically selected. In one example, the selected previous workout may be the most recently recorded workout. Additionally, in contrast to a general image as displayed in interface 1000 of FIG. 10A, a total distance 1103 or other metric for all workouts recorded may be displayed in interface 1100.

Figure 11C:
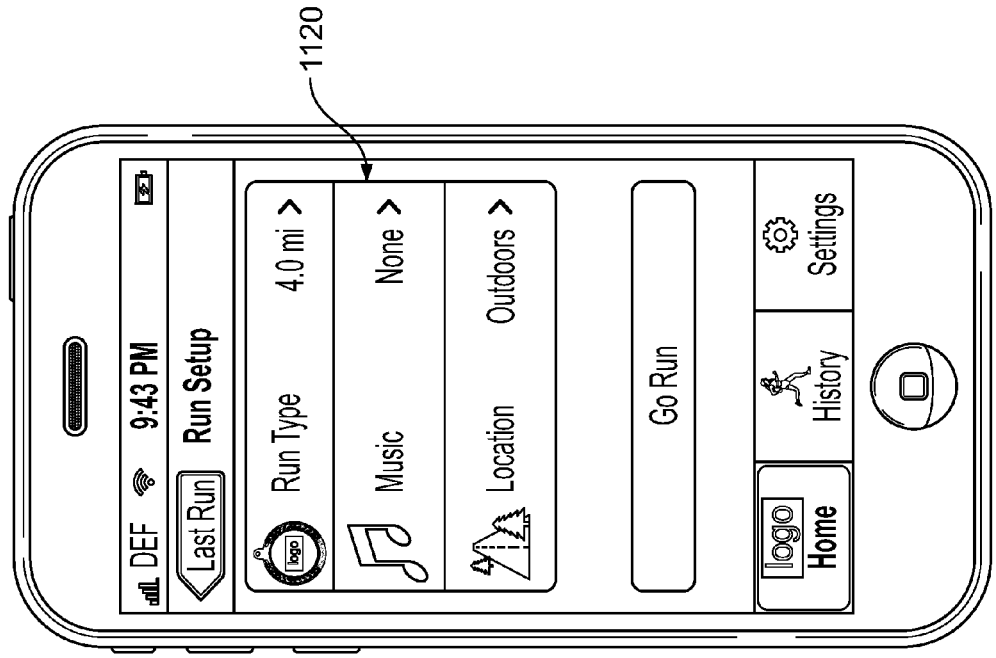
Figure 11B:
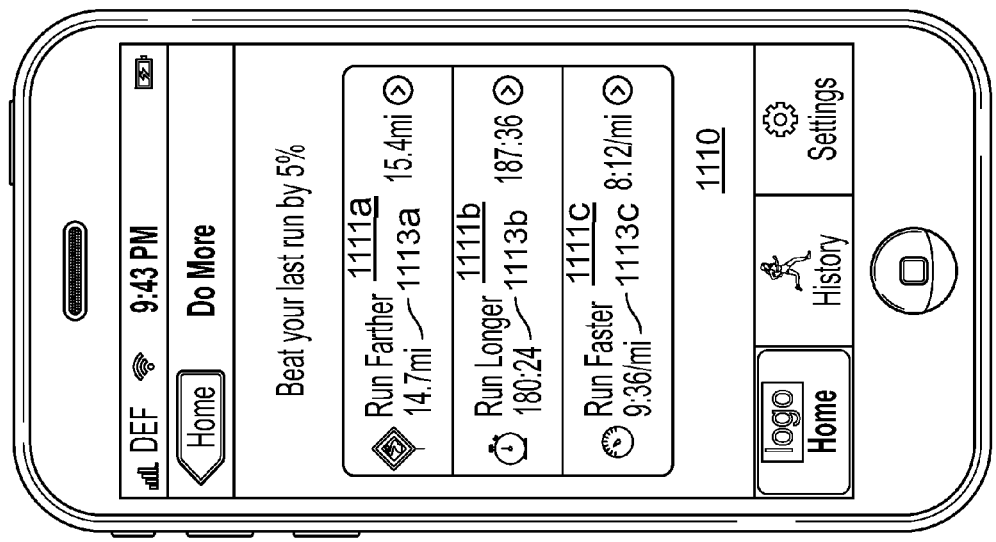

FIG. 11B illustrates interface 1110 that displays a variety of different workouts 1111 that may be selected by a user. Each of workouts 1111 may be generated by setting a goal that improves upon a previous workout by a predefined amount. For example, in interface 1110 workouts 1111 may be automatically generated by increasing one or more parameters of a previous workout by 5% or some other percentage or predefined amount. Accordingly, the user is able to challenge himself or herself to run farther, longer or faster. In one or more arrangements, the user may select the amount by which a previous workout's results are increased to define suggested workouts 1111. Each of suggested workouts 1111 may display the recorded metric for the previous workout 1113 along with the suggested or goal metric 1115 for the current workout. This allows the user to determine the amount of improvement that he or she would be achieving in choosing each of suggested workouts 1111.

As an alternative to selecting an improvement workout through interface 1120 of FIG. 11C, a user may choose to define a run that is not based on a previous workout. Similar to interface 1030 of FIG. 10C, interface 1120 may allow the user to define various parameters of the run including a run type, audio content to be played during the workout and a location.

In one or more arrangements, if a user completes an improvement run, a workout summary may include additional information. For example, summary interface 1130 of FIG. 11D includes a medal or other indicator/message 1131 congratulating the user for completing the improvement run. Audio icon 1133 may provide an indication that an audio message is available to the user. For example, the audio message may include words of encouragement (e.g., from a celebrity, a friend, or generic voice). Upon selection of icon 1133, the message may be played. Indicator/message 1131 may also be displayed upon achieving other predefined goals such as performing 50 workouts, running 100 miles total (e.g., across all previous workouts), running 10 miles in 1 session, running 26.2 miles in one session, running for 30 minutes in a single session, running for 100 hours across all sessions and the like.

Figure 11E:
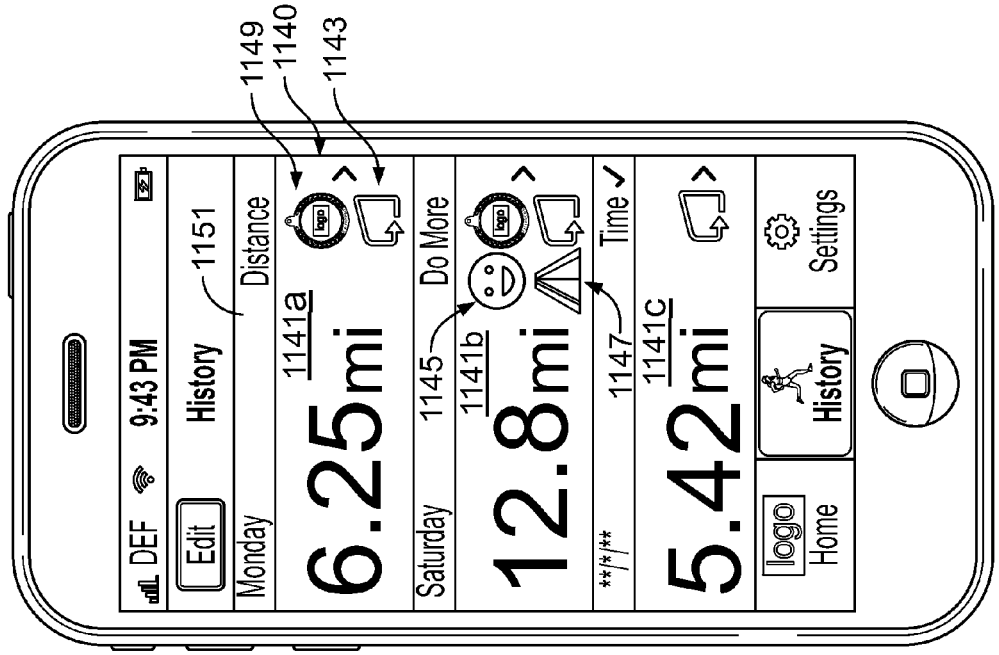
Figure 11D:
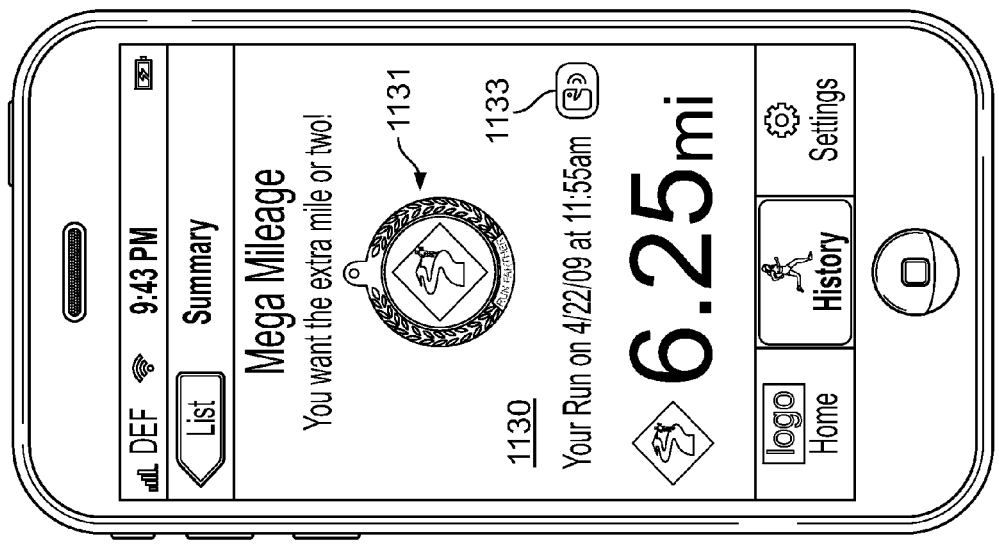

FIG. 11E illustrates another example history interface 1140 that includes a listing of multiple workouts. Each entry 1141 in listing may be identified by a run type label 1151. For example, run type label 1151 may indicate that the run is a time run, an improvement run, a distance run and/or a basic run. In addition to a route indicator 1143, listing 1141 may include additional indicators for each entry that may indicate various attributes of the corresponding workout. For example, a face icon such as icon 1145 may indicate that mood information was tagged for the workout. Additionally, a road icon 1147 may indicate that the workout was performed outdoors while a medal icon 1149 may indicate that an achievement was completed during the workout. History interface 1140 may display a list of all workouts stored on the device or, in some instances, only a predefined number of most recently recorded workouts.

Figure 12B:
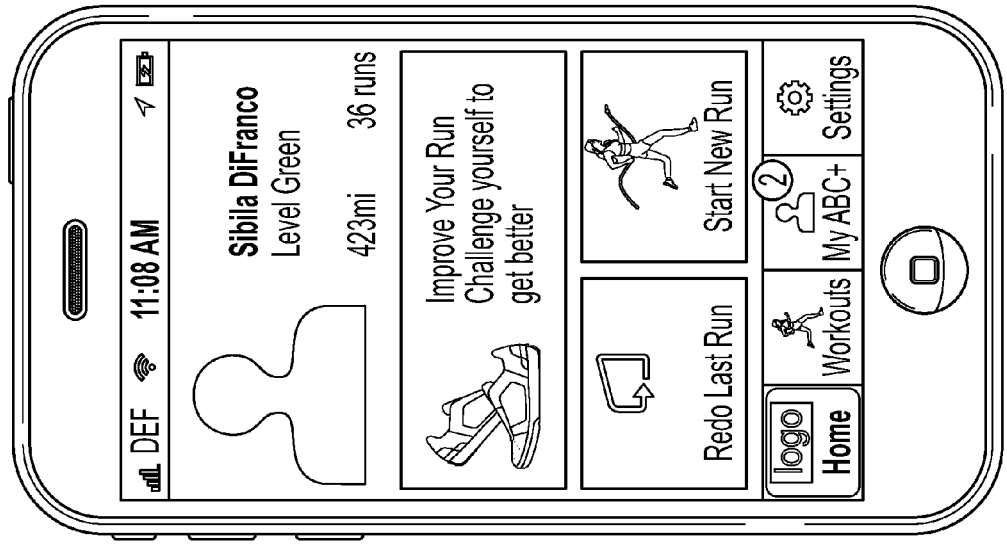
FIGS. 12A and 12B illustrate another example home screen interface that may be generated and displayed according to one or more aspects described herein.
Figure 12A:
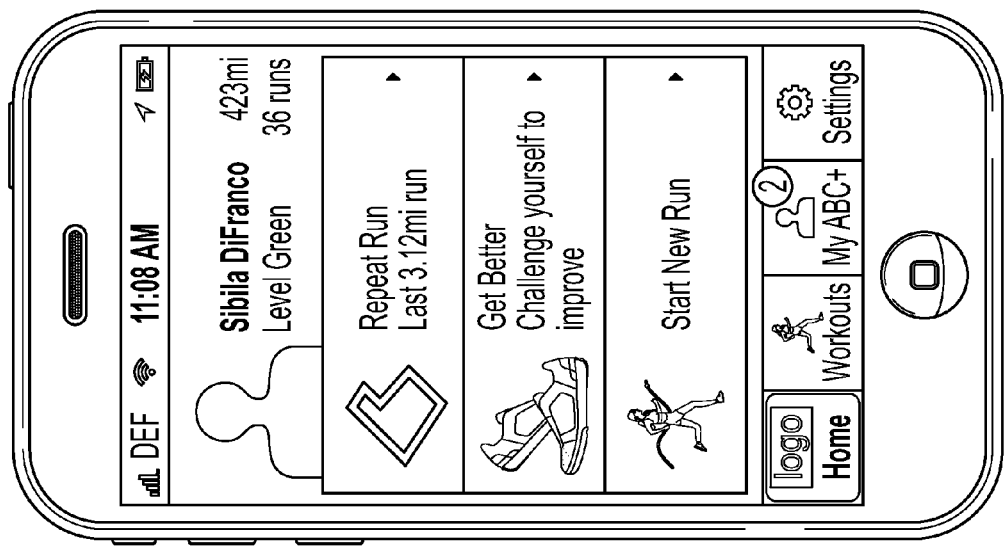

FIGS. 12A and 12B illustrates another example home screen interface that may be generated and displayed.

Run Type Selection

As illustrated in FIG. 10C, a run setup interface may allow the user to define the run type. For example, the user may wish to perform a distance run where the objective is reaching a certain distance, a time run where the goal is to run for a certain amount of time and/or a basic run where no objectives are set. If the user has completed and recorded at least a first run, the user may also be able to select an improvement run type in which the objective is to improve at least one metric from a previous workout. This latter option might only be available and displayed if a previous run has been completed and recorded.

Figure 13B:
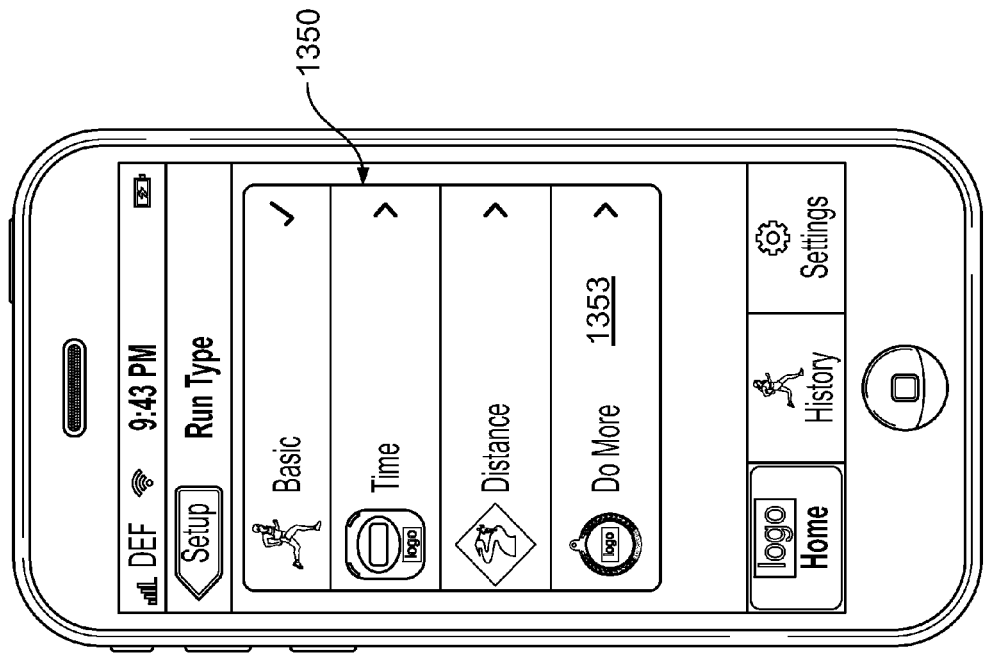
FIG. 13B illustrates an example run type selection interface that may be displayed when a user has a recorded run history according to one or more aspects described herein.
Figure 13A:
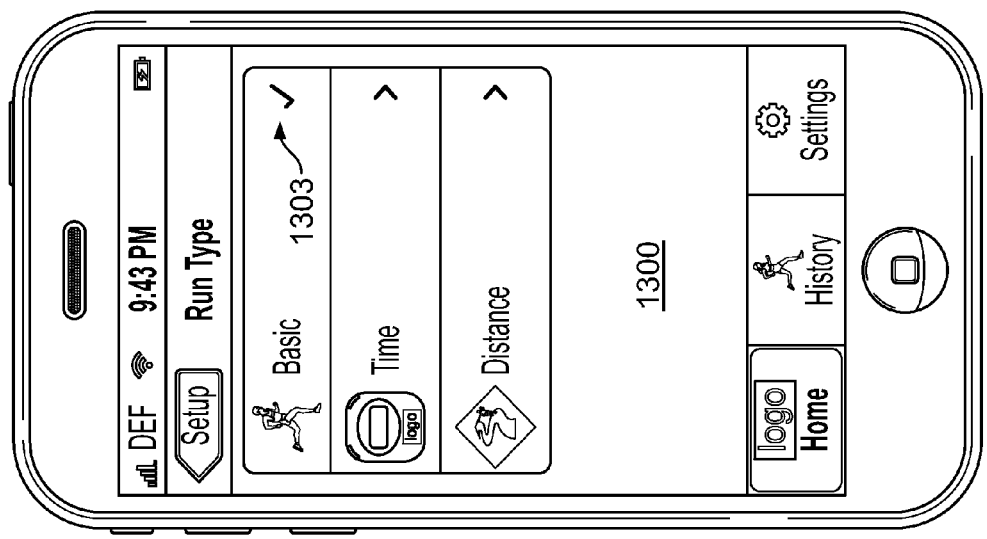
FIG. 13A illustrates an example run type selection interface for display when a user has no previous run history according to one or more aspects described herein.

FIGS. 13A and 13B illustrates a run type selection interface 1300 for display when a user has no previous run history and run type selection interface 1350 that may be displayed when the user has a recorded run history, respectively. Interfaces 1300 and 1350 may be similar except for the inclusion of a "Do More" or improvement run option 1353 in interface 1350 of FIG. 13B. A currently selected run type may be identified by an indicator such as check mark 1303.

Figure 14B:
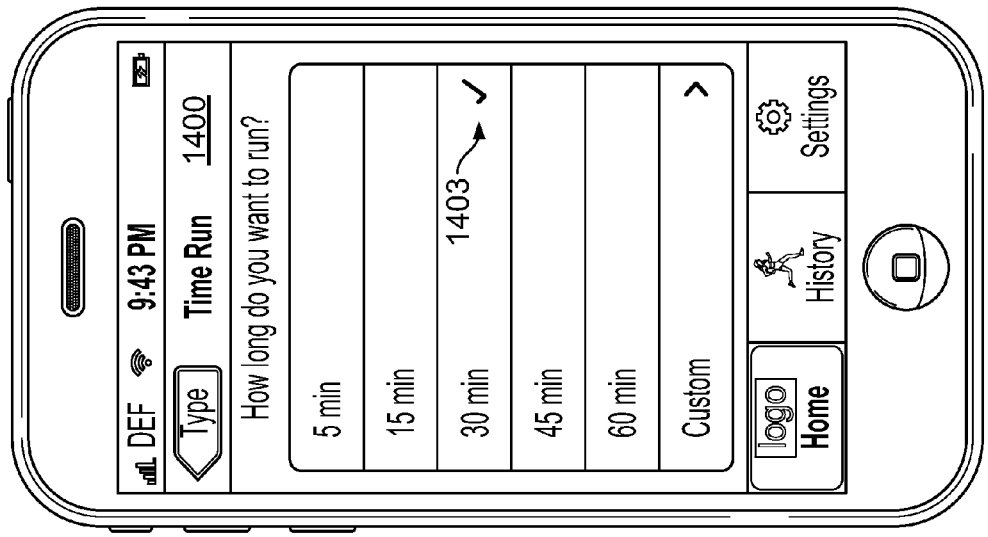
FIGS. 14A-14G illustrates a series of example user interfaces for defining a time run according to one or more aspects described herein.
Figure 14A:
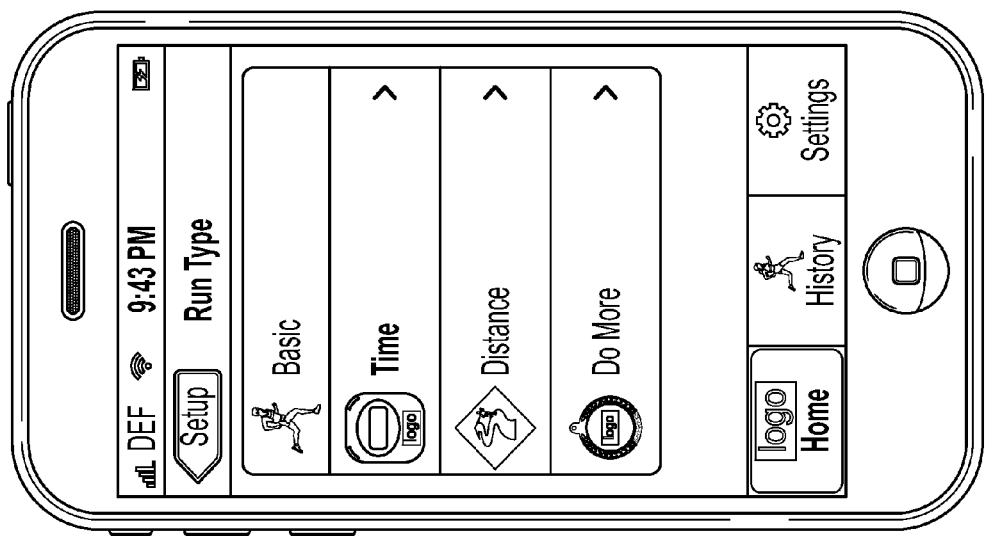
Figure 14D:
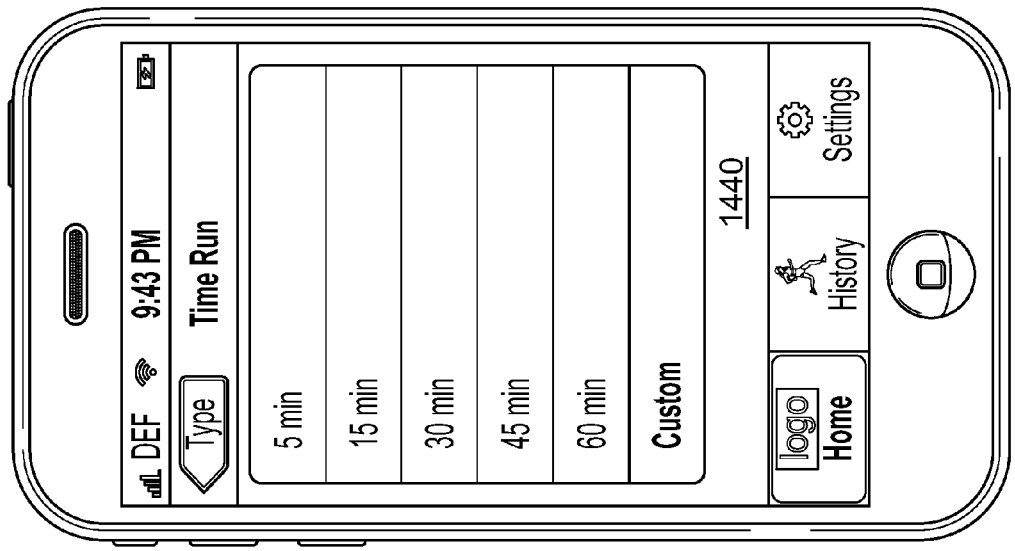
Figure 14C:
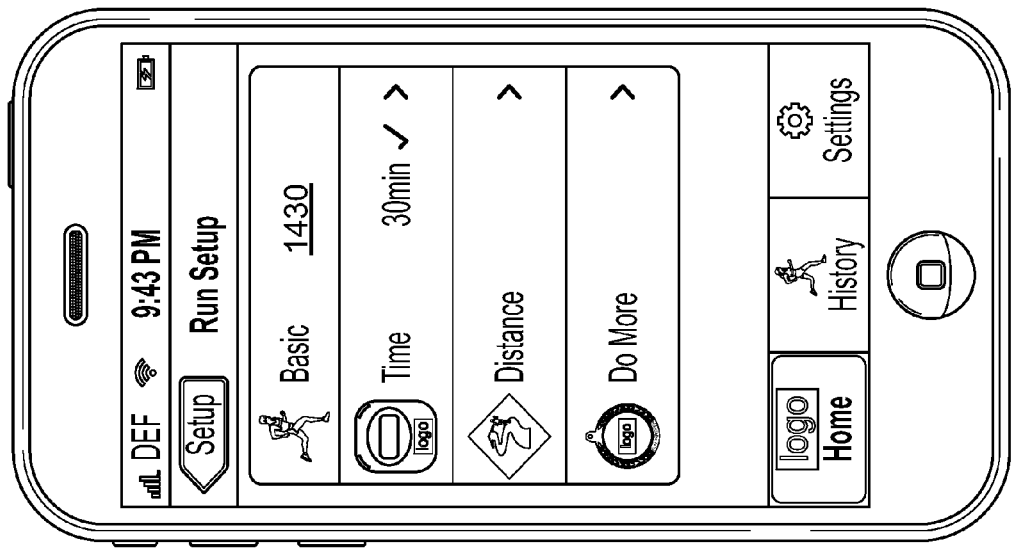
Figure 14F:
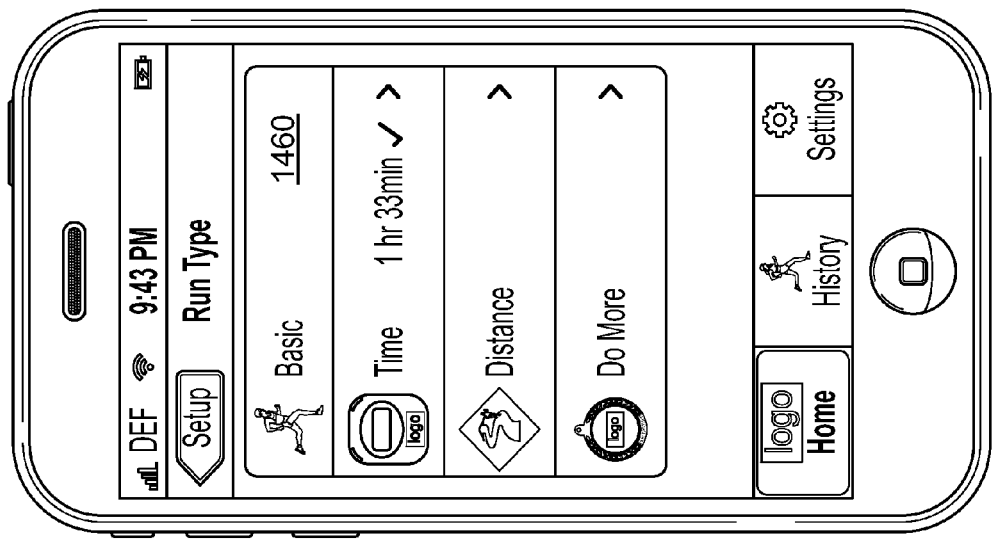

FIGS. 14A-14F illustrates a series of user interfaces for defining a time run. In FIG. 14A, a user has selected the time option. Accordingly, the time run type may be displayed differently than the other available run types. Subsequently, a user may be presented with time selection interface 1400 of FIG. 14B. Time selection interface 1400 may include multiple predefined times (e.g., 5 minutes, 15 minutes, 30 minutes, 45 minutes and 60 minutes) and a custom time option. A currently selected time (e.g., 30 minutes) may be identified by a selection mark 1403. Once the user has selected a time, the user may be returned to the run type selection interface where the selected run time is displayed in association with the time run type option. FIG. 14C illustrates run type interface 1430 that is displayed upon a user selecting a time run type and selecting a corresponding amount of time (e.g., through interface 1400 of FIG. 14B).

Figure 14E:
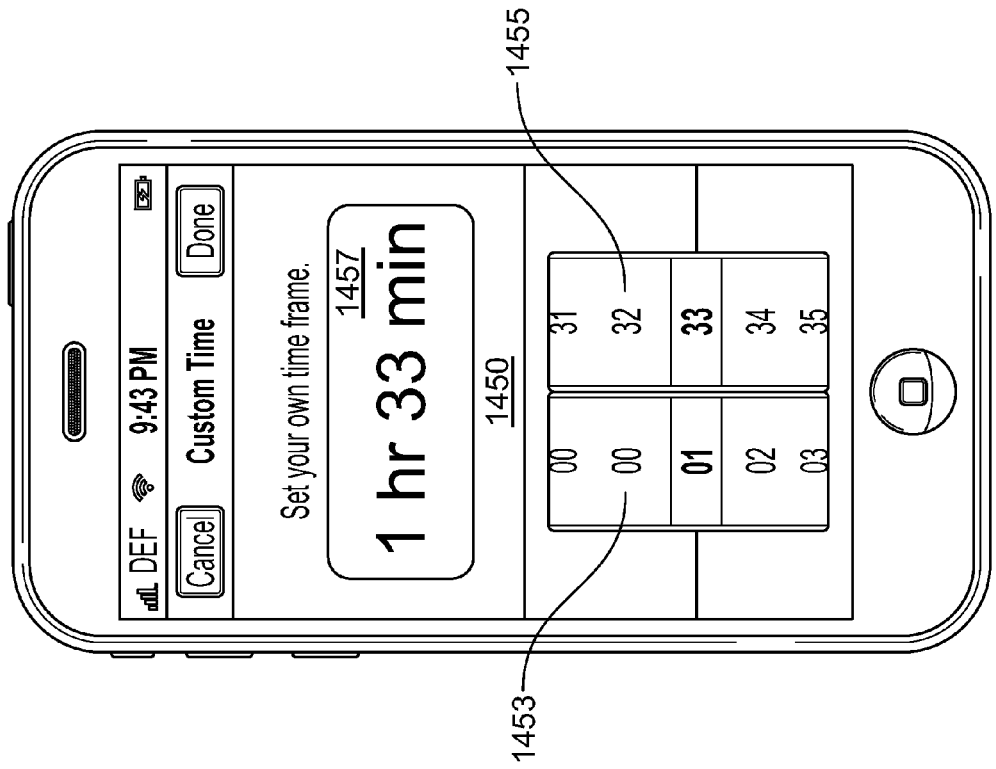
Figure 15A:
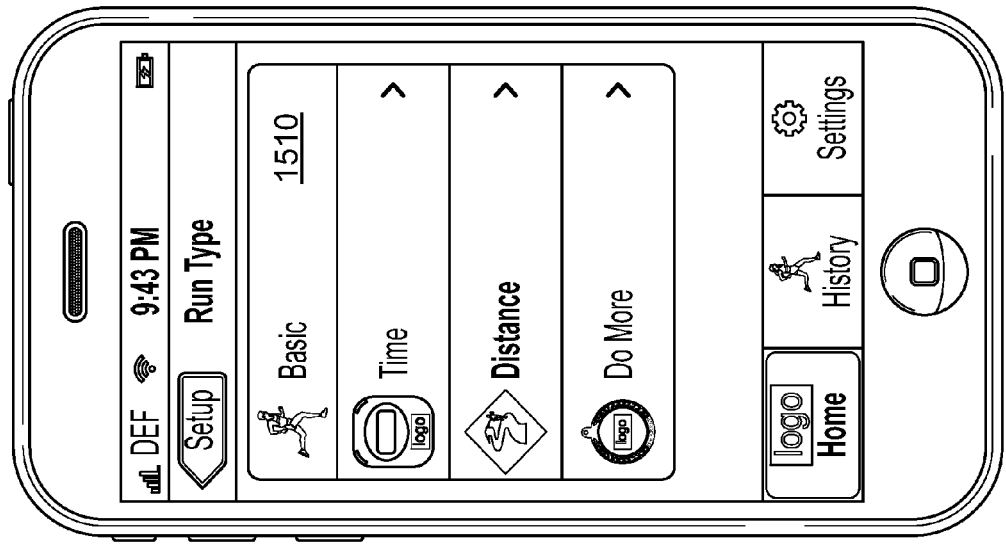
FIGS. 15A-15G illustrates a series of example user interfaces that may be displayed upon a user selecting a distance run type according to one or more aspects described herein.
Figure 14G:
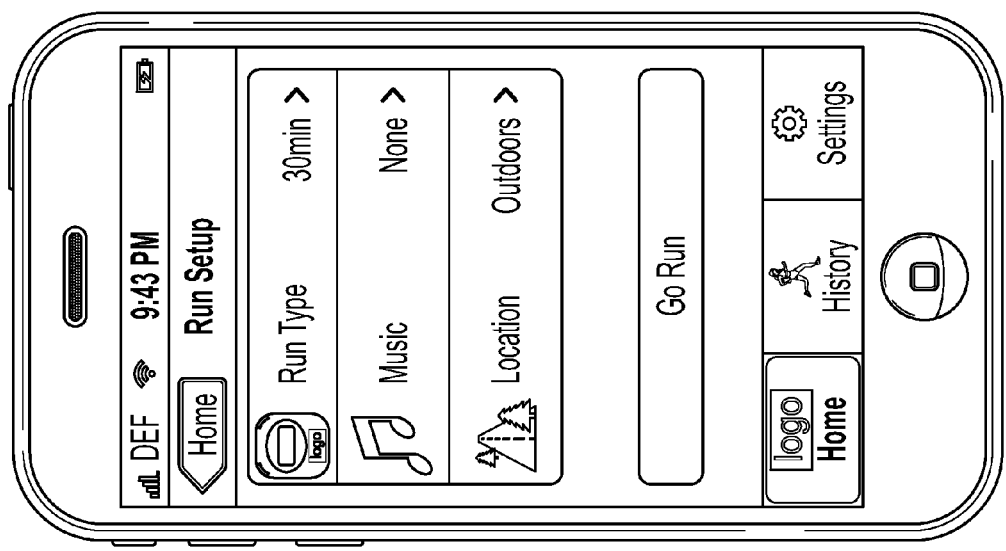

FIG. 14D illustrates interface 1440 in which a user selects a custom time option. In FIG. 14E, a user may be presented with an interface 1450 through which the user may manually define an amount of run time. For example, scroll wheels 1453 and 1455, may be provided to allow a user to define a number of hours and a number of minutes, respectively. The currently selected time may be displayed in portion 1457. As with FIG. 14C, FIG. 14F may display an interface such as interface 1460 in which the selected time may be displayed in association with the selected run type. In another example, FIG. 14G illustrates a run setup main menu indicating the run type as a 30 minute run. By identifying the run with the "30 min" tag, the application and device may indicate to the user that the currently defined run type is a time run and that the current time set is 30 minutes.

Figure 15C:
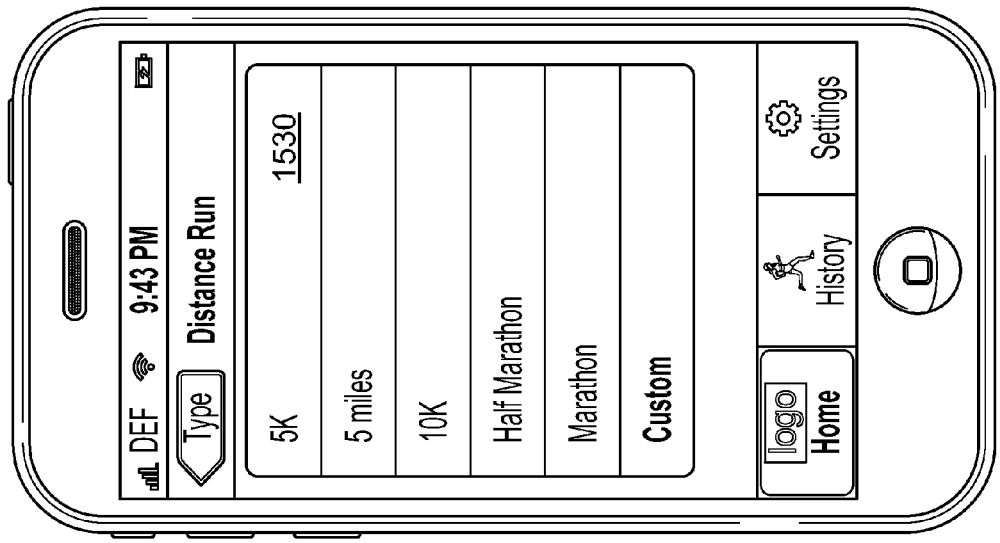
Figure 15B:
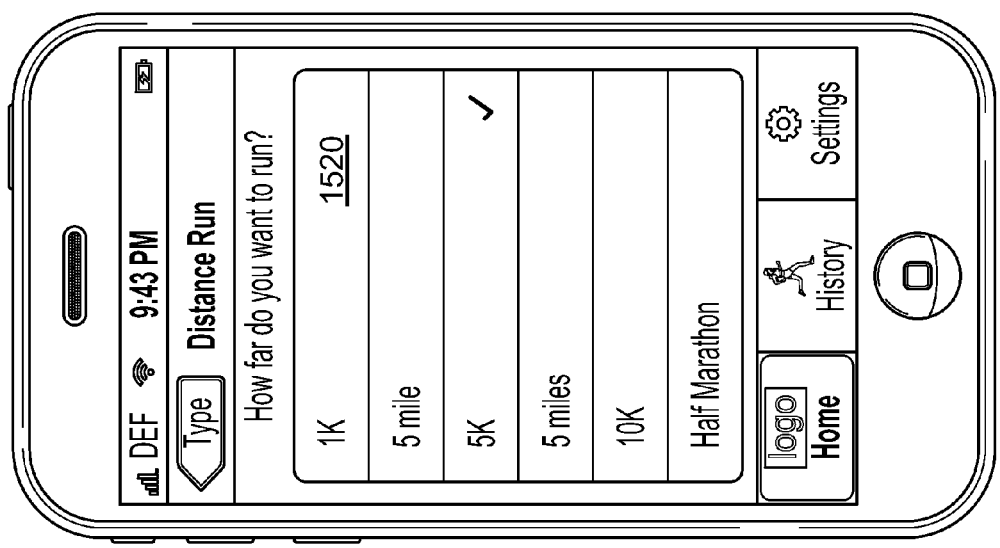
Figure 15E:
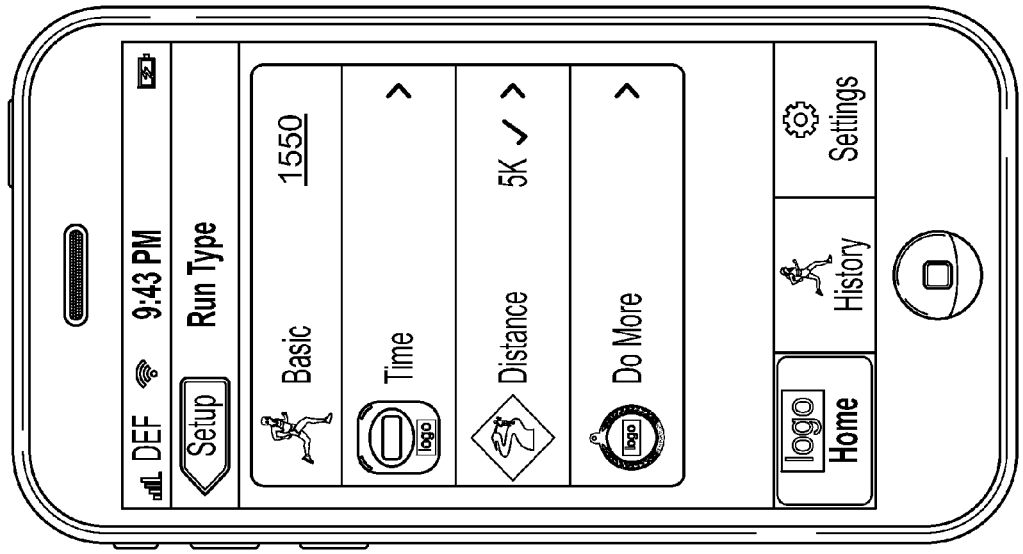
Figure 15D:
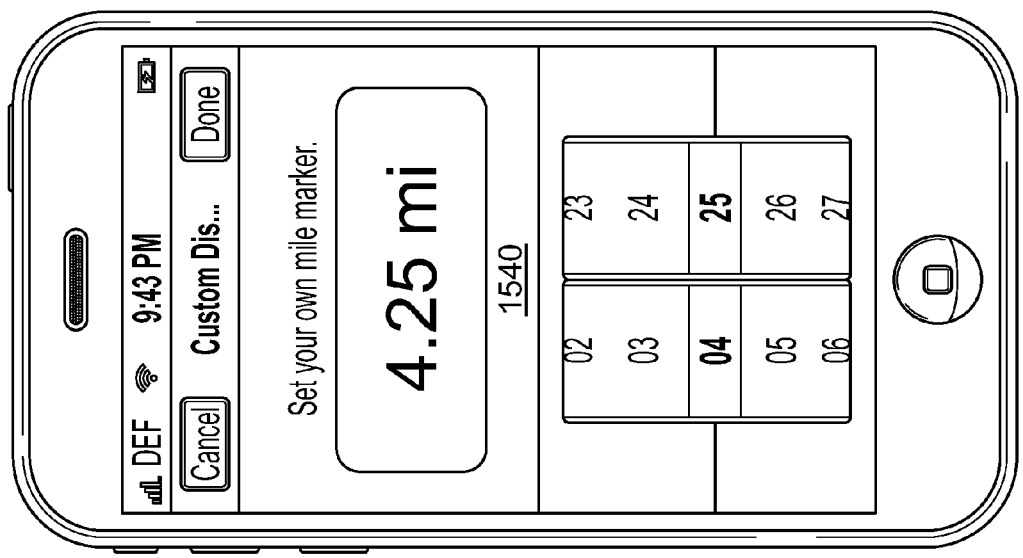
Figure 15G:
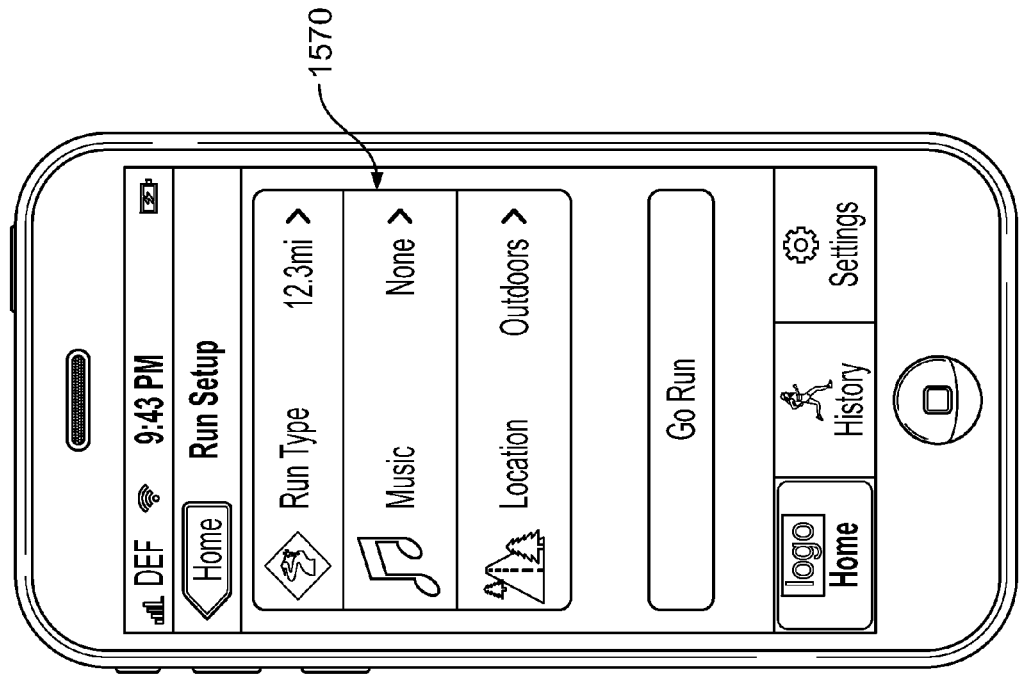
Figure 15F:
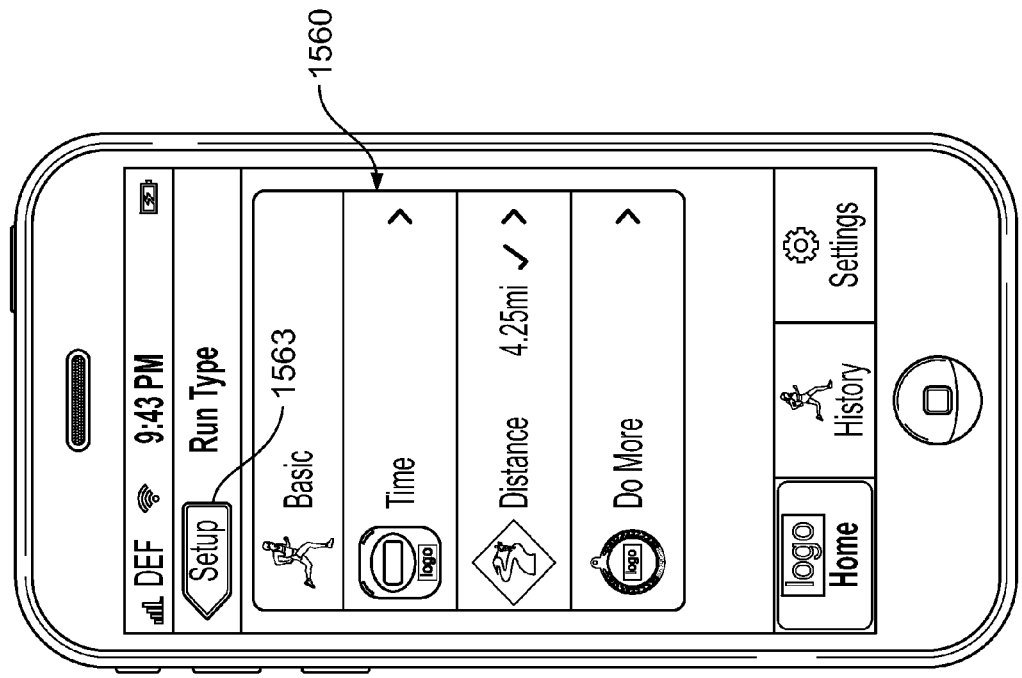

FIGS. 15A-15F illustrates a series of user interfaces that may be displayed upon a user selecting a distance run type. Similar to time selection, a user may select a distance option in interface 1510 of FIG. 15A and subsequently be presented with a list of run distance options in interface 1520 of FIG. 15B. For example, the list may include a 1K run, a 5 mile run, 5K run, a 10K run, a half marathon, a marathon and a custom distance. Selection of one of the predefined distances such as a 5K run may cause the 5K predefined distance to include a selection indicator. Alternatively, and as illustrated in FIGS. 15C and 15D, a user may select a custom distance in interface 1530 of FIG. 15C and subsequently manually define a custom distance in interface 1540 of FIG. 15D. Once the distance has been defined, the user may be returned to the run type selection interface in which the distance option is displayed with a selection indicator as illustrated in FIGS. 15E and 15F. The selected distance may also be displayed in association with the distance run type option. For example, in interface 1550 of FIG. 15E, "5K" may be displayed in the distance run type option to indicate that a 5K distance has been defined as the objective for the run. In another example, FIG. 15F illustrates an interface 1560 that displays a custom run distance such as 4.25 miles.

The user may confirm that the run type and run type settings are correct and return to a main setup interface using option 1563. Upon returning to the main run setup menu, the user may view the currently defined run parameters. For example, FIG. 15G illustrates interface 1570 that displays a distance of 12.3 miles with the run type parameter. The indication of mileage as opposed to time may signify that the run is a distance run rather than a time run.

Figure 16B:
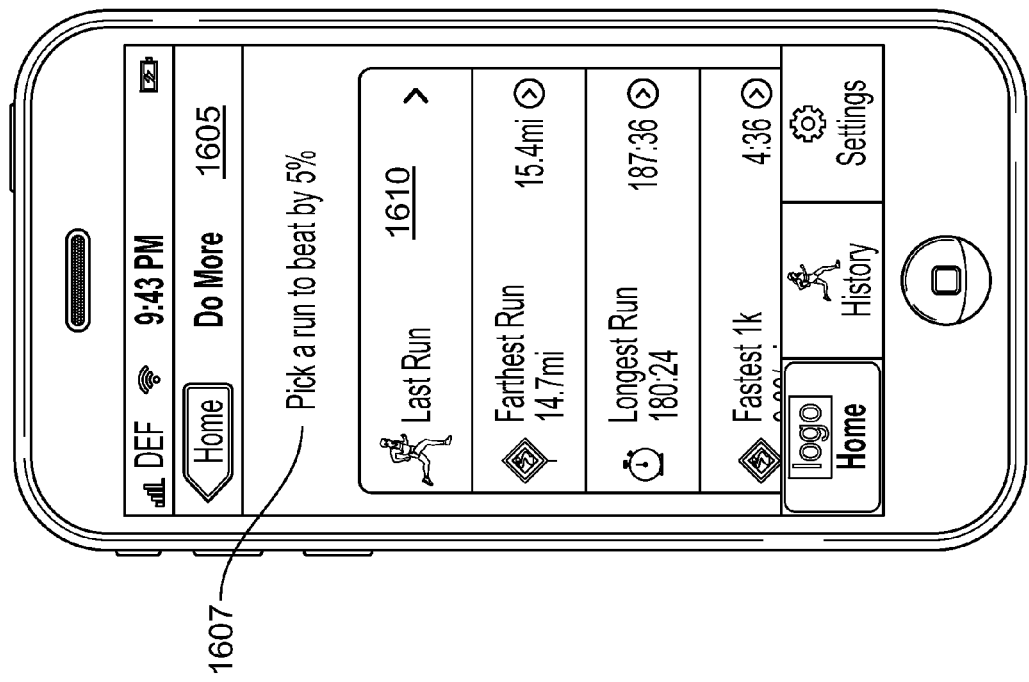
FIGS. 16A-16F illustrate a series of example user interfaces that may be generated and displayed upon a user selecting an improvement run type according to one or more aspects described herein.
Figure 16A:
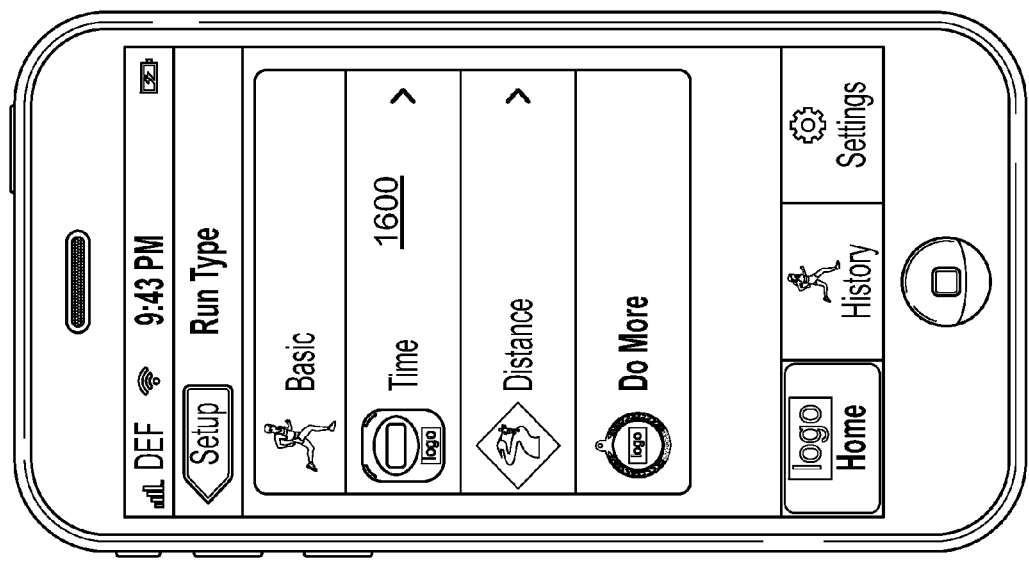
Figure 16D:
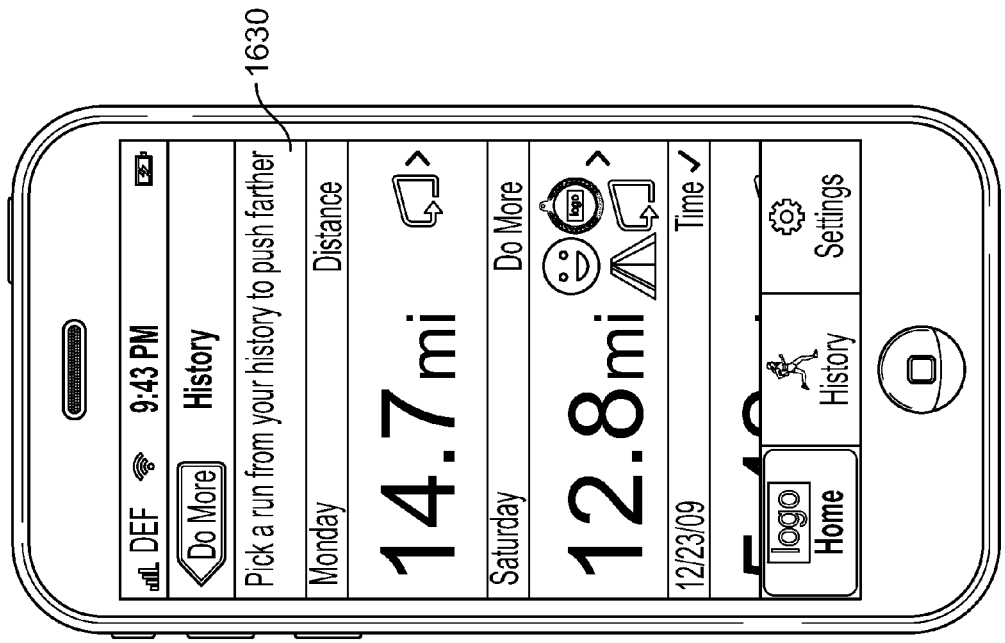
Figure 16C:
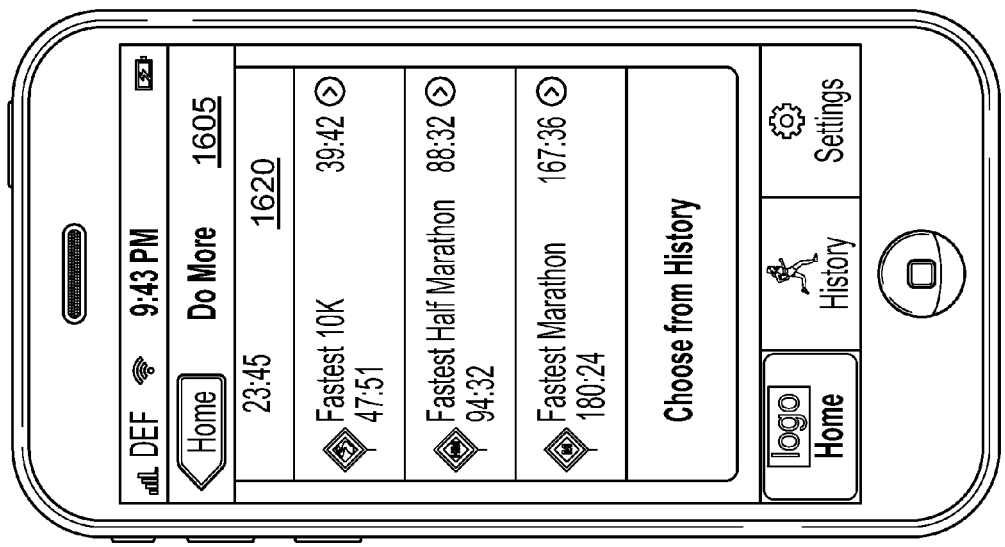

FIGS. 16A to 16F illustrates a series of user interfaces that may be generated and displayed upon a user selecting an improvement run type. As illustrated in FIG. 1600 of FIG. 16A, the "Do More" or improvement run type may be displayed in an alternate state (as compared to time, basic and distance run types) upon the user selecting the improvement run type. FIGS. 16B and 16C illustrate portions 1610 and 1620 of an improvement option listing and selection interface 1605. For example, in portion 1610, the user may select from a last run option (e.g., to beat one or more statistics of a previous run), a farthest run, a longest duration run and a fastest 1K run. Portion 1620 may include a fastest 10K run, a fastest half marathon, a fastest marathon and a history selection option. The objective of improvement run may be automatically defined to exceed a previous run (e.g., the longest run, the furthest run or the fastest 1K run) by a predefined amount. In one example, the objective may be to exceed the previous workout by 5%. The improvement amount may be indicated in portion 1607 of FIG. 16B. The improvement amount may be user defined, automatically set by the device or application, defined by an athletic activity monitoring service provider and the like.

If a history option is selected, e.g., from portion 1620 of FIG. 16C, the user may be presented with a listing of recorded runs. FIG. 16D illustrates a history interface 1630 displaying a list of recorded previous runs. The user may then select from one of the previously recorded run to improve. For example, the user may elect to improve upon a previous 14.7 ml run by 5%. Upon selecting the previously recorded 14.7 mile run, the user may be presented with interface 1640 of FIG. 16E in which the user may select a statistic recorded in the 14.7 mile on which to improve. The system and application may automatically calculate the objectives with the improvement amounts added. For example, a user may select options to run farther, run for longer amounts of time and run at a faster pace.

Figure 16F:
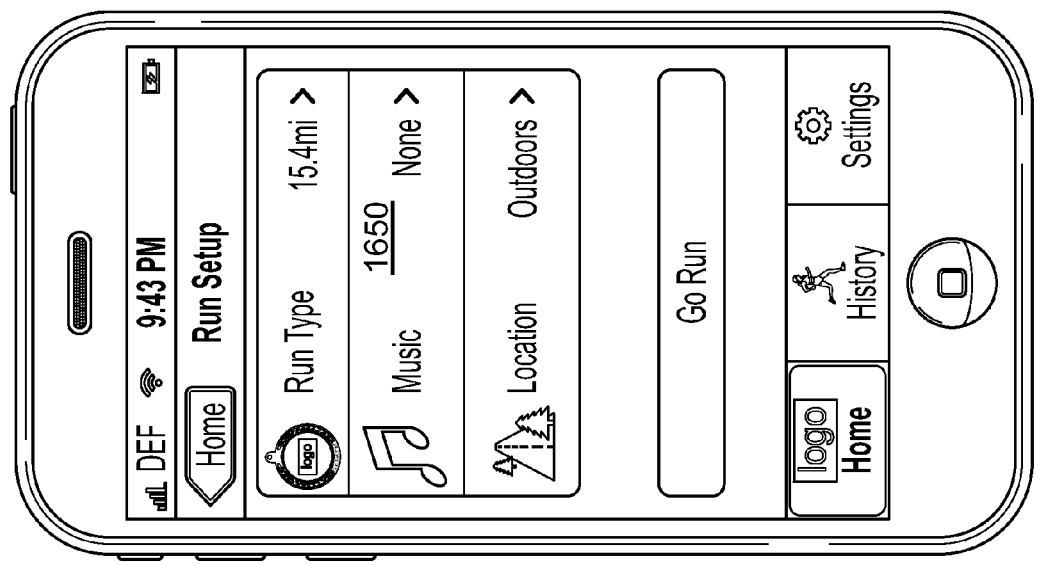
Figure 16E:
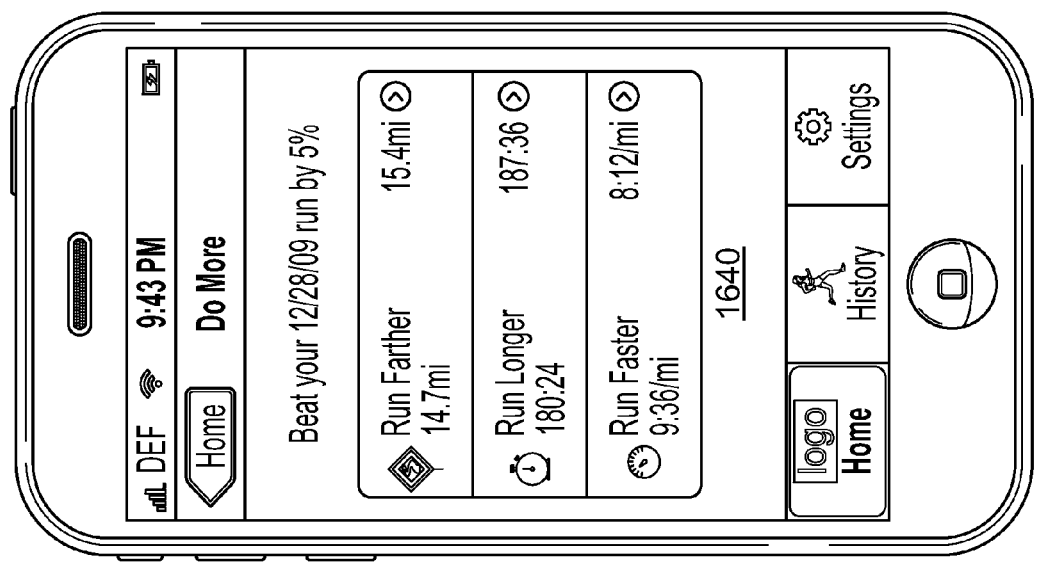
Figure 18A:
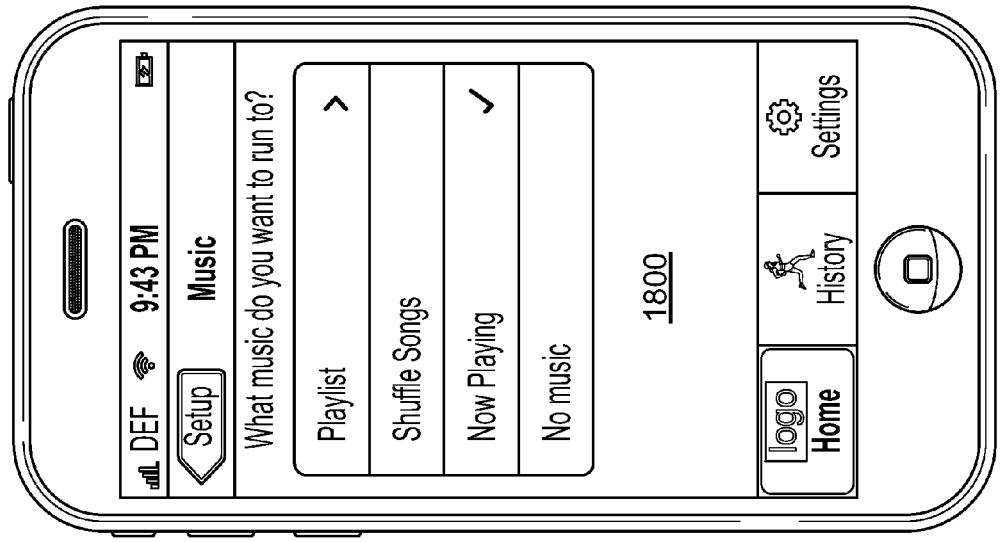
FIGS. 18A-18E illustrate a series of example audio content selection interfaces that may be generated and displayed upon selection of the audio content definition option according to one or more aspects described herein.

Once the desired improvement has been selected and defined, the user may be returned to a run setup menu such as interface 1650 of FIG. 16F in which the selected objective is displayed in association with the run type.

Training Audio Selection

Figure 17:
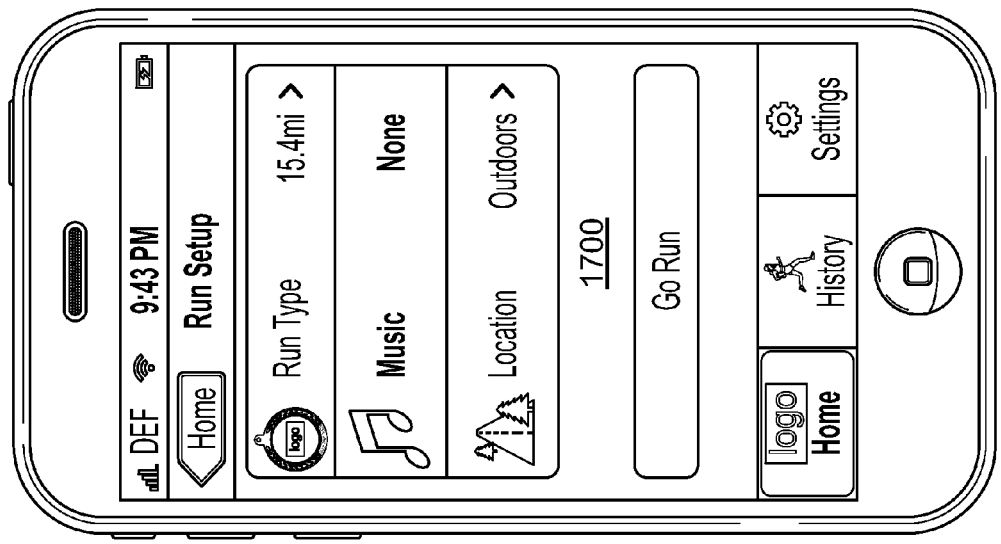
FIG. 17 illustrates an example through which a user may select a music definition option according to one or more aspects described herein.

In conjunction with selecting the run type, the user may also select audio content to be played during the workout. The user may also elect not to have any audio content playing during the workout. FIG. 17 illustrates a user selecting a music option from interface 1700. The music option may include a display of the current selected audio option. For example, if no audio content has been selected, the word "None" may be displayed within the selection button. Alternatively, a selected playlist name or selection algorithm/parameter (e.g., random, category of music) may be displayed.

Figure 18C:
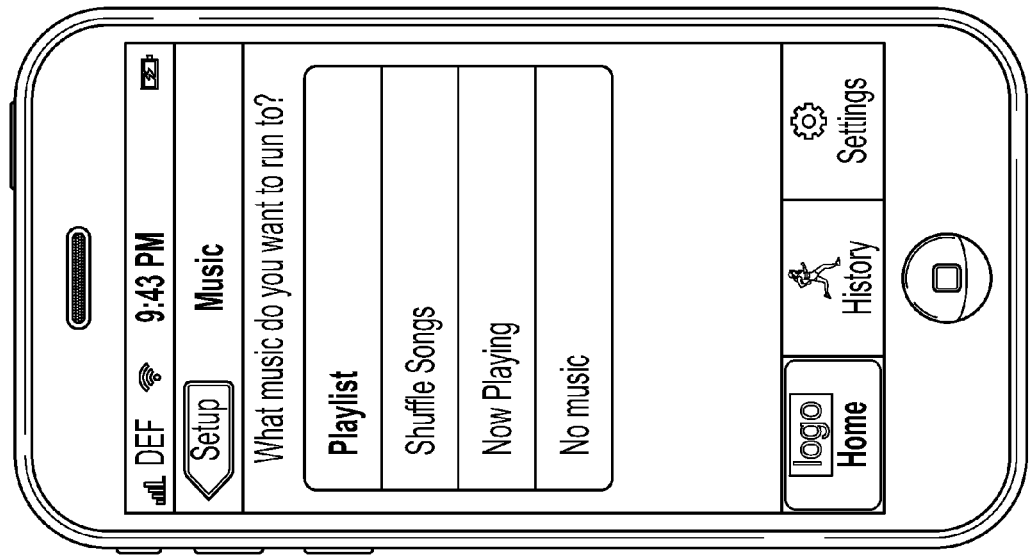
Figure 18B:
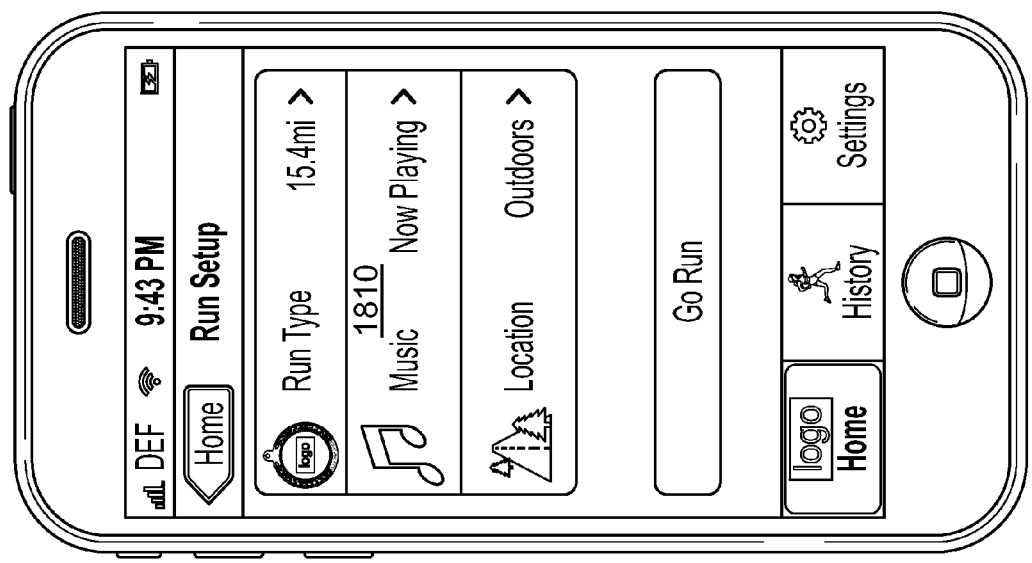

FIGS. 18A-18E illustrate a series of audio content selection interfaces that may be generated and displayed upon selection of the audio content definition option. For example, in FIG. 18A, interface 1800 may include a plurality of predefined audio content options including a playlist selection option, a shuffle option, a now playing option and a no music option. Shuffle option may allow a user to randomly select songs from all available songs. In some arrangements, the shuffle option may play the audio content in a random order as well (e.g., not necessarily in accordance with an order in which the audio content is stored or listed in a database of all available songs). Selection of now playing option may cause a current playlist or audio content category, artist, album or the like to be selected. If no audio is currently being played, the now playing option may select the most recently played or selected audio content. FIG. 18B illustrates run setup interface 1810 in which the user's selection of the now playing option is reflected in the music selection option.

Figure 18D:
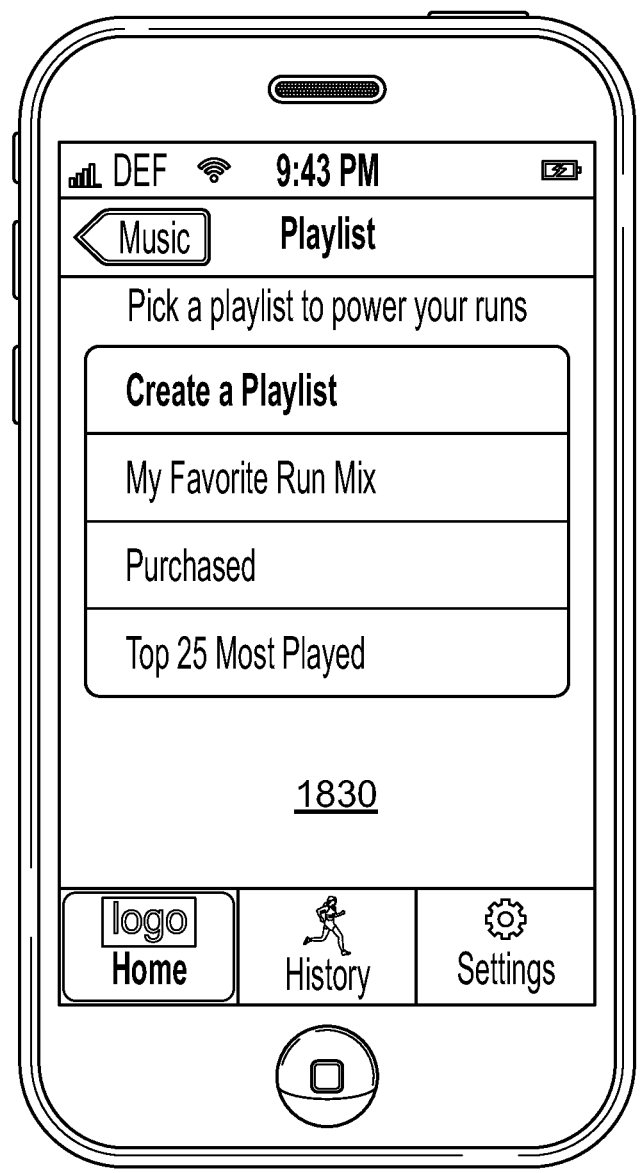

If, on the other hand, the user selects the playlist option (as illustrated in FIG. 18C), the user may be presented with a playlist selection interface. FIG. 18D illustrates an example playlist selection interface, i.e., interface 1830, in which the user may create a new playlist, select a favorite run mix playlist, a playlist comprising all purchased music and a playlist including the top 25 most played audio items. The favorite run mix playlist may be automatically generated by the device based the frequency that audio content or audio content playlist is played during workouts. Accordingly, the favorite run mix playlist may differ from the top 25 most played audio items as the top 25 most played may be determined based on a total frequency during workout and non-workout times while the favorite run mix playlist may be generated based only on audio content played during workouts.

Figure 18E:
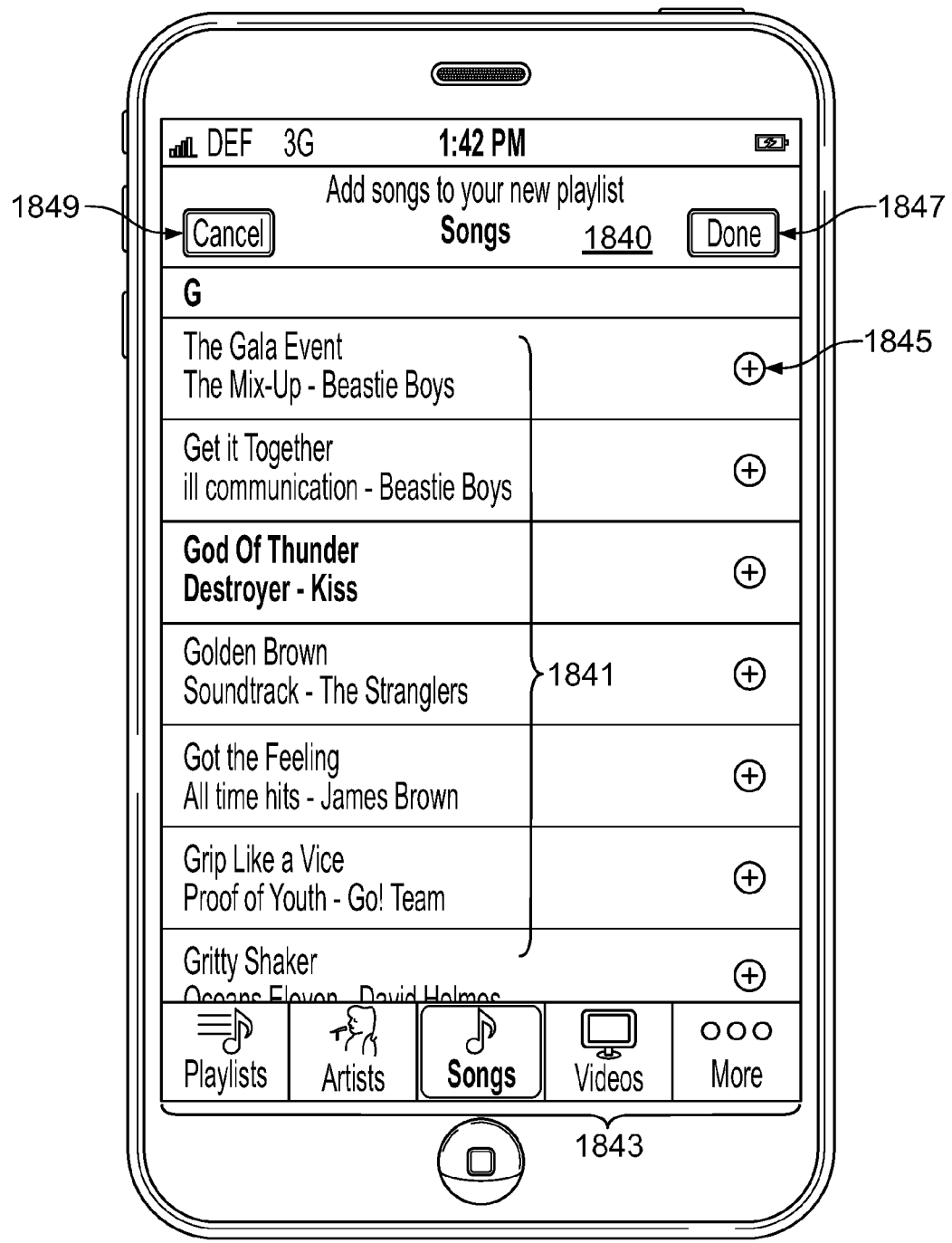

By selecting the playlist creation option, the user may be presented with an audio content list 1841 in a song selection interface 1840 of FIG. 18E. The user may be able to sort the list of audio content items using options 1843. For example, the user may sort or view the list by playlist membership, artist, songs and videos. The user may add audio content items to the list by select each desired item from the list. An add/remove indicator 1845 may change in appearance depending on if the corresponding audio content item is currently in the playlist being created. For example, if the audio content item is not in the playlist, indicator 1845 may be displayed as a plus symbol while if the audio content is in the playlist, indicator 1845 may be displayed as a minus symbol. Once the user has finished adding audio content to he playlist, the user may select option 1847 to continue the run setup. Alternatively, the user may cancel playlist creation by selection cancel option 1849. In one or more arrangements, audio content may be suggested or recommended to the user based on the user's previous workout performance during those audio content items. For example, if a user ran at an above average pace or ran an above average distance during a particular audio content item, the device may suggest that the audio content item be added to the playlist. The same process may be used to automatically generate a suggested playlist. For example, a playlist may be generated by selecting the 25, 30, 40, 50 or other number of songs during which the user exhibited the best workout performance (e.g., as defined by a particular statistic or metric such as calories burned, distance, pace and/or combination thereof).

Figure 19B:
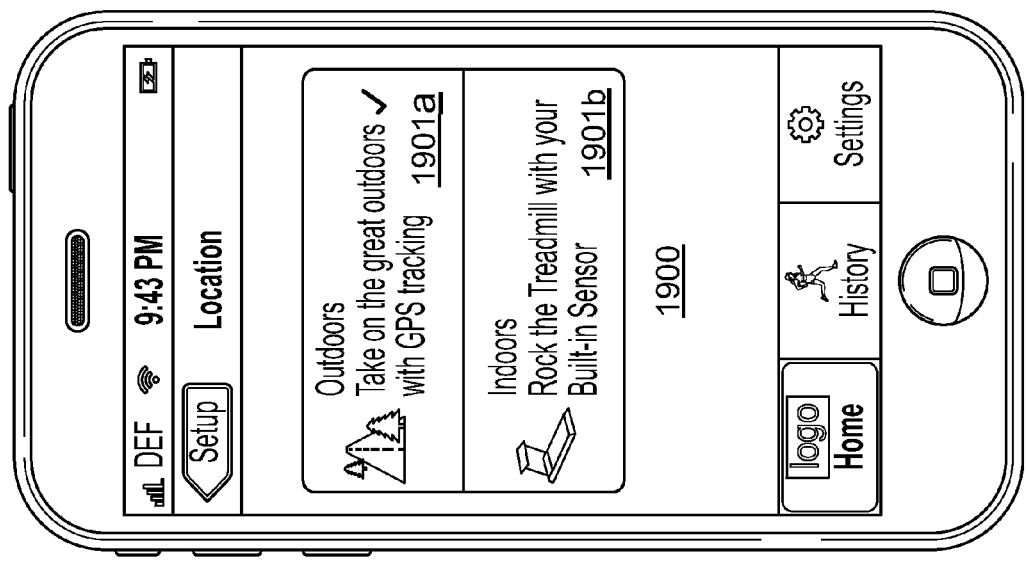
FIGS. 19A-19C illustrate a series of example location definition interfaces according to one or more aspects described herein.
Figure 19A:
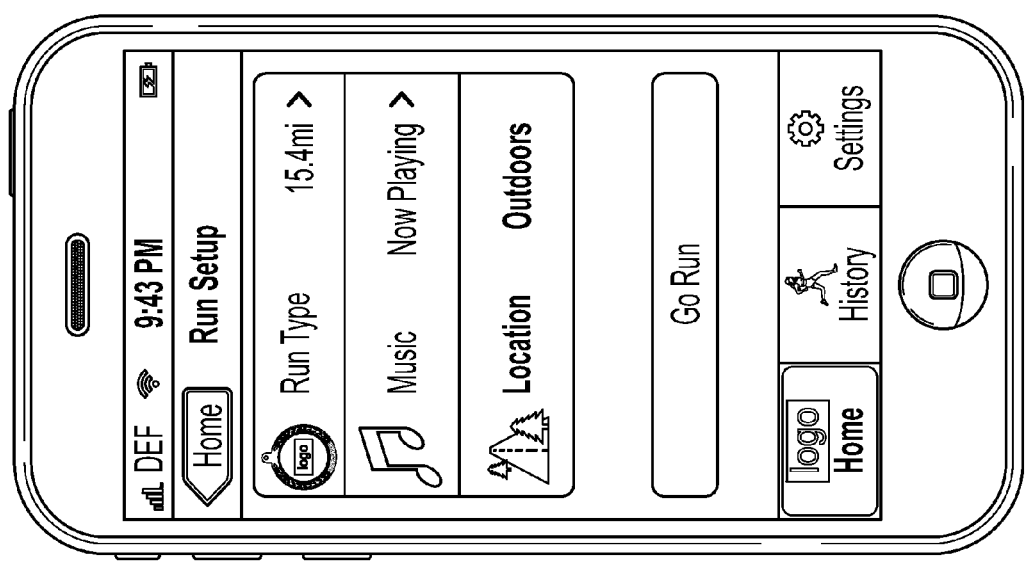
Figure 20A:
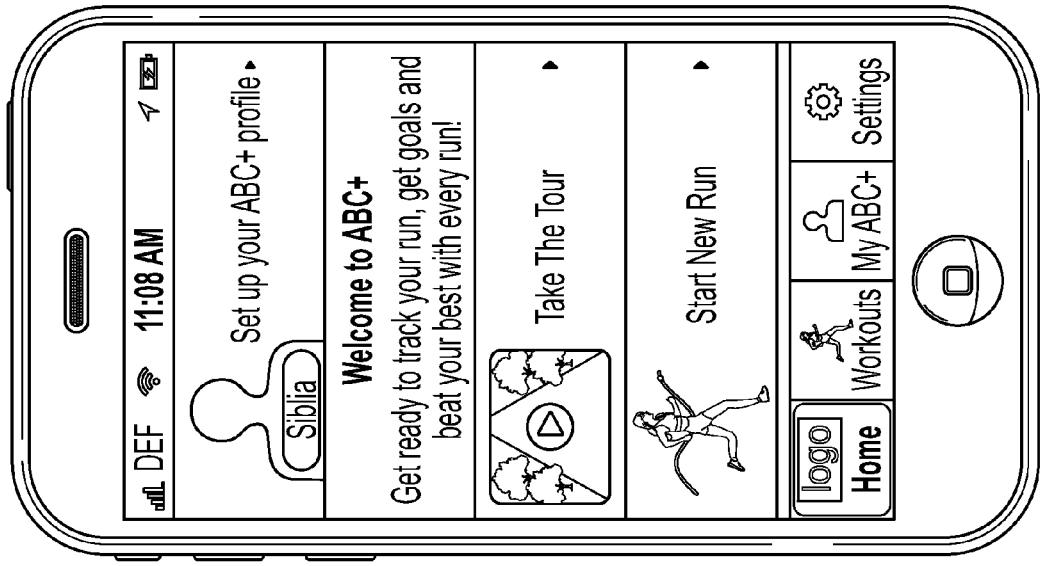
FIGS. 20A-20Z illustrate additional example interfaces that may be displayed for setting up a run according to one or more aspects described herein.
Figure 19C:
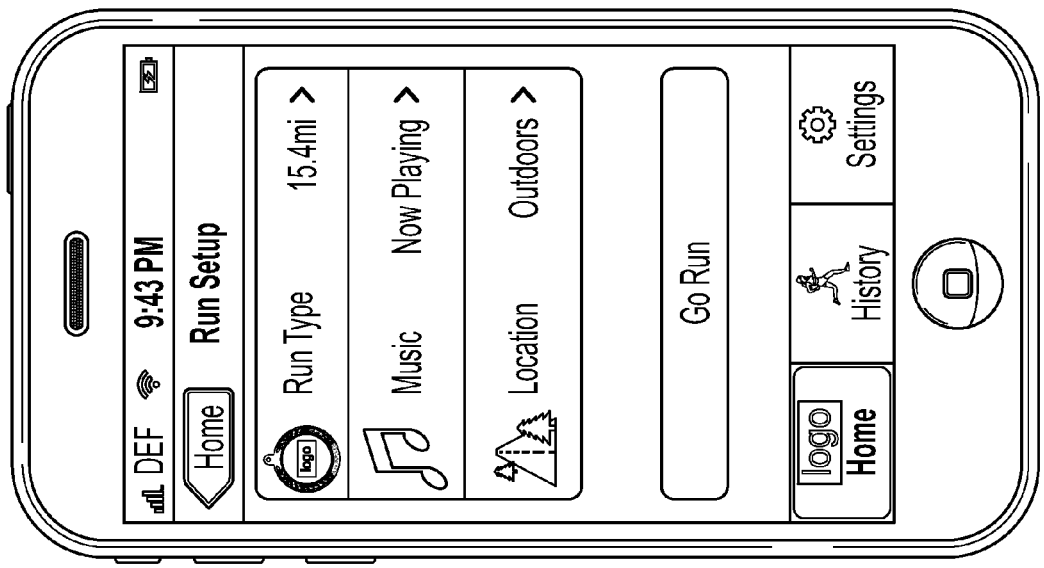

In addition to music selection and run type definition, the user may further define the location of the workout. FIGS. 19A-19C illustrate a series of location definition interfaces. Upon the user selecting a location setup option, the user may be presented with multiple available predefined locations 1901 in interface 1900 of FIG. 19B. Locations 1901 may include an outdoors environment and an indoor workout environment. Other locations and types of locations may be defined such as cities, landmarks and other categories of locations (e.g., parks). As noted herein, the selection of a particular location or location type may affect the types of sensors or devices that may be used for athletic activity monitoring. Additionally or alternatively, the algorithm used to measure athletic activity might also be affected by the selected location.

Figure 20C:
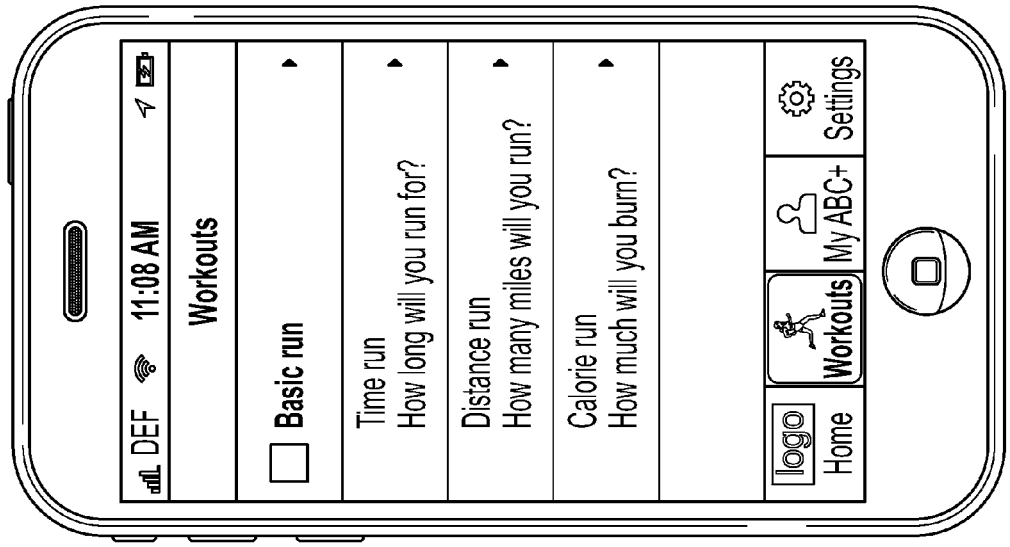
Figure 20B:
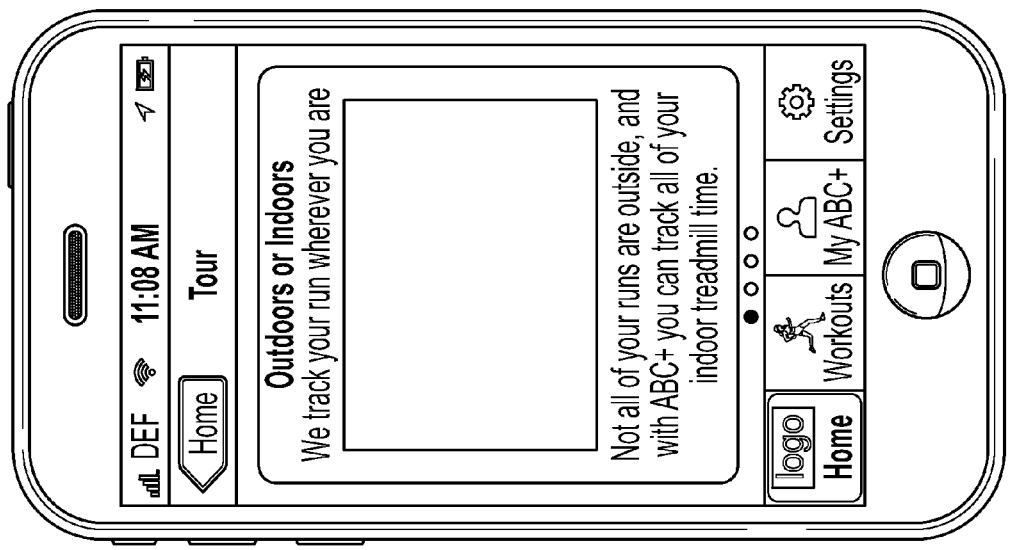
Figure 20E:
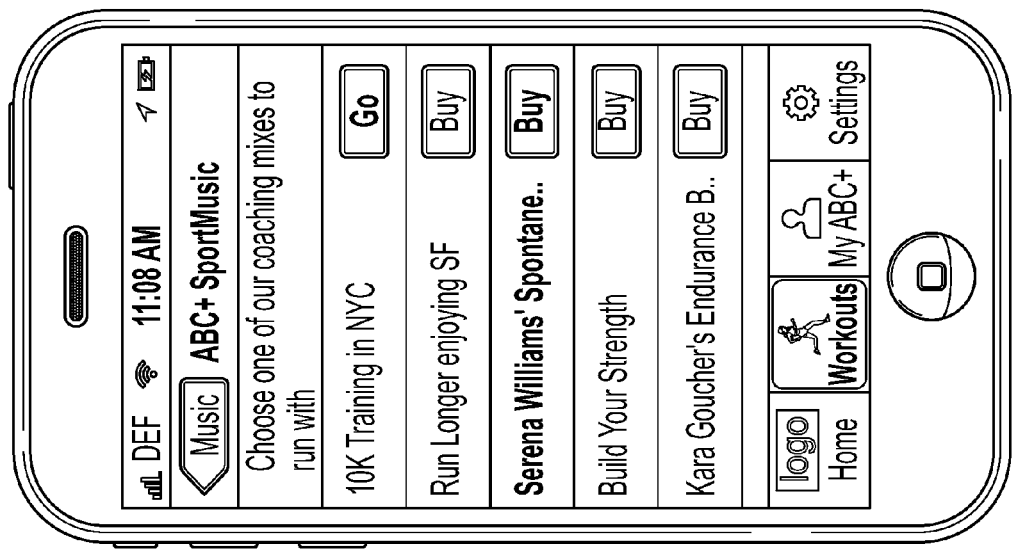
Figure 20D:
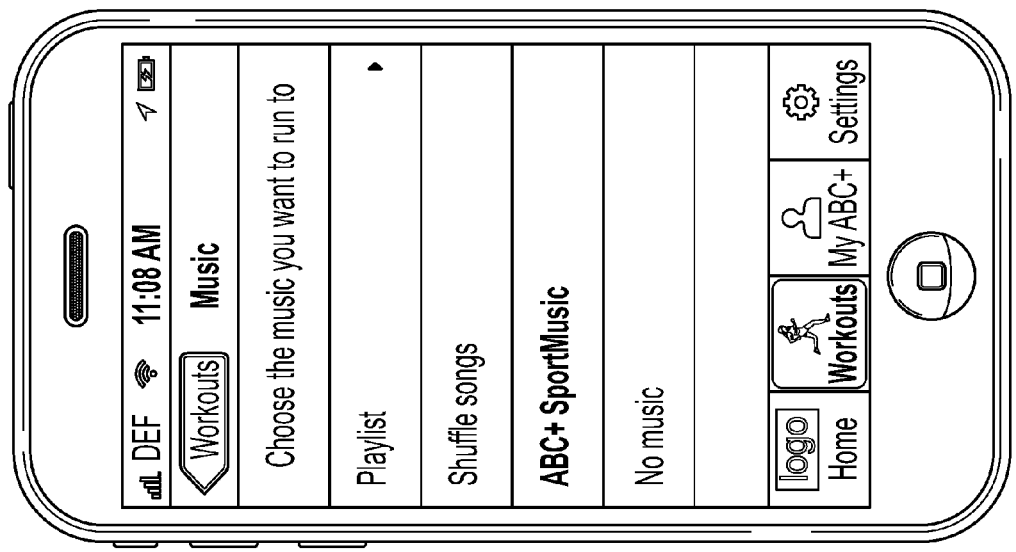
Figure 20F:
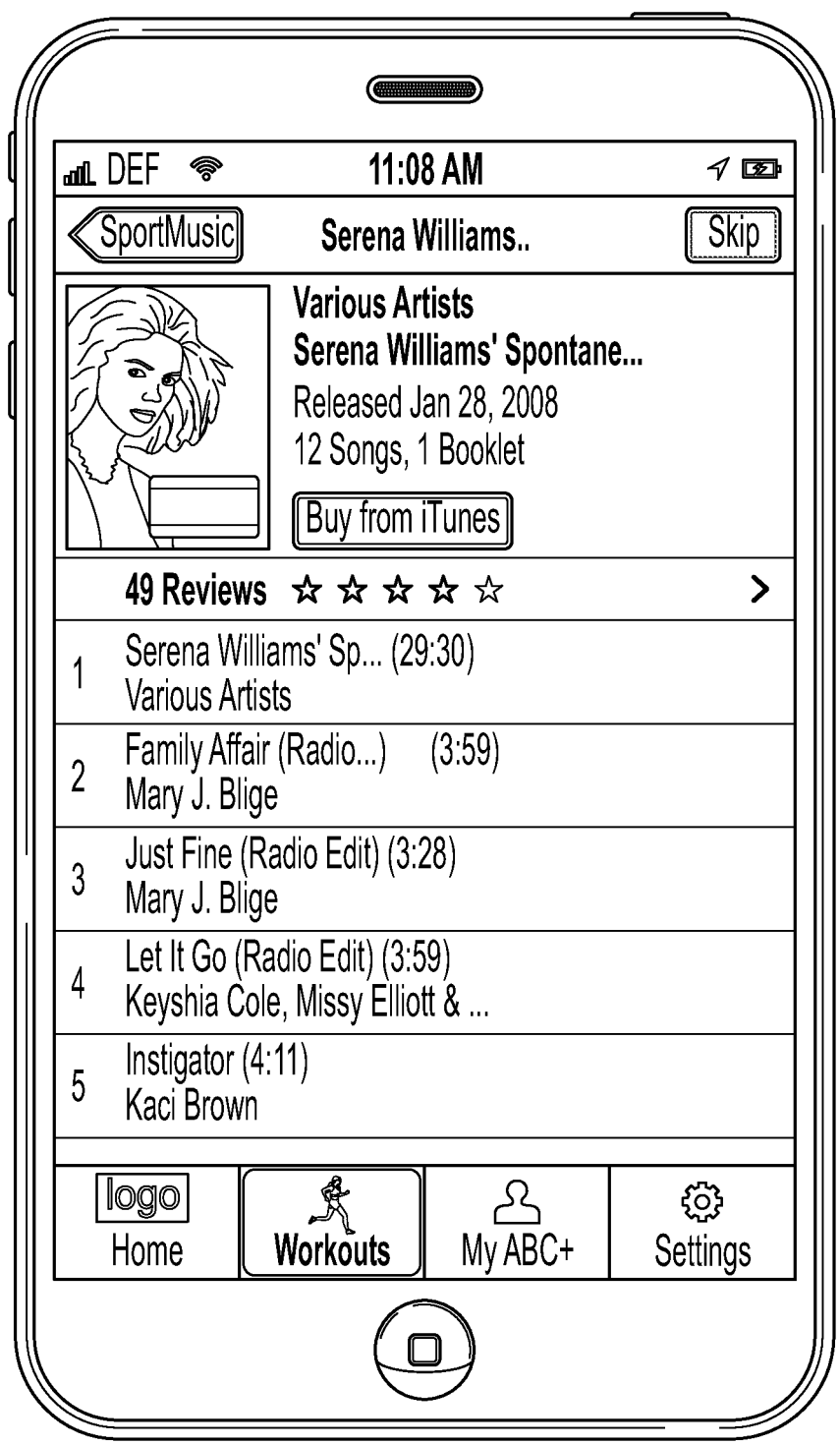
Figure 20H:
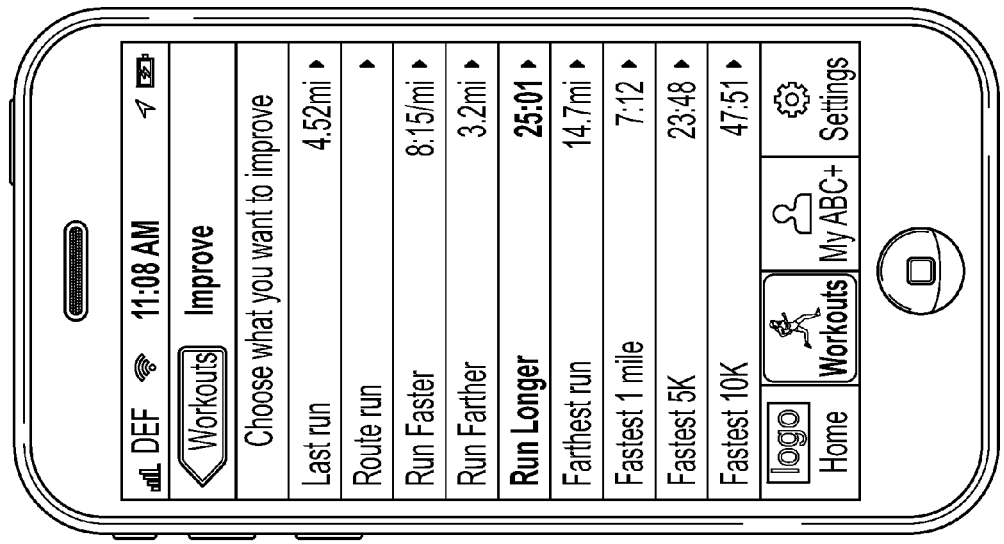
Figure 20G:
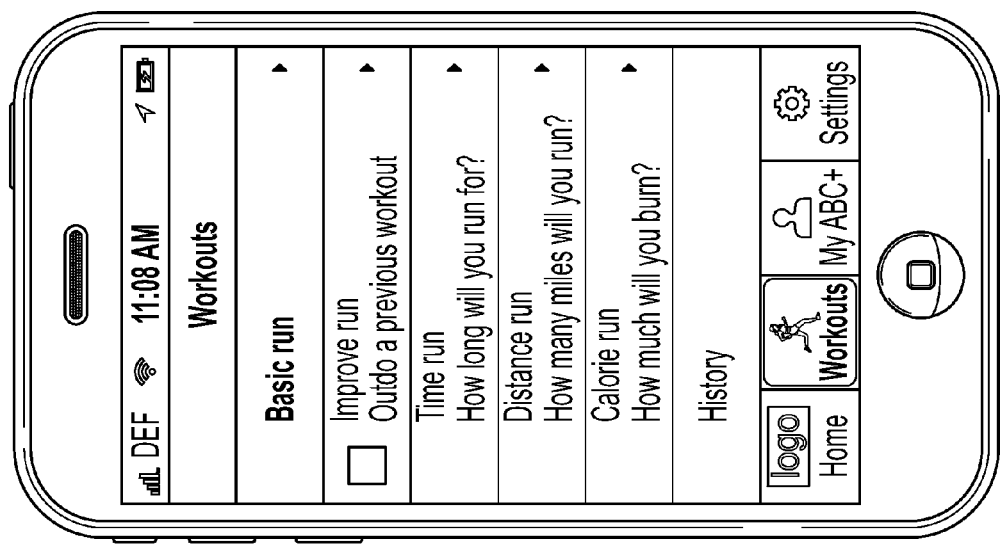
Figure 20J:
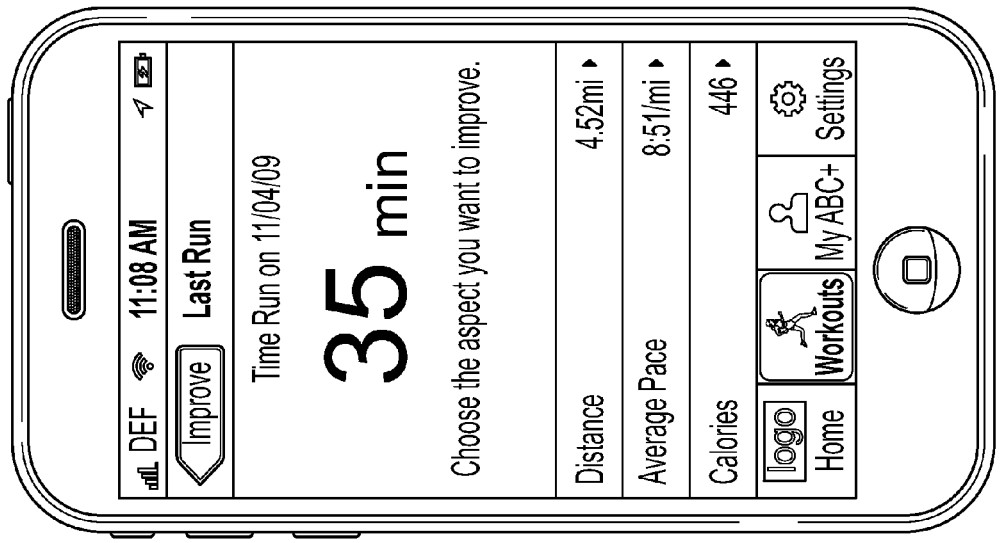
Figure 20I:
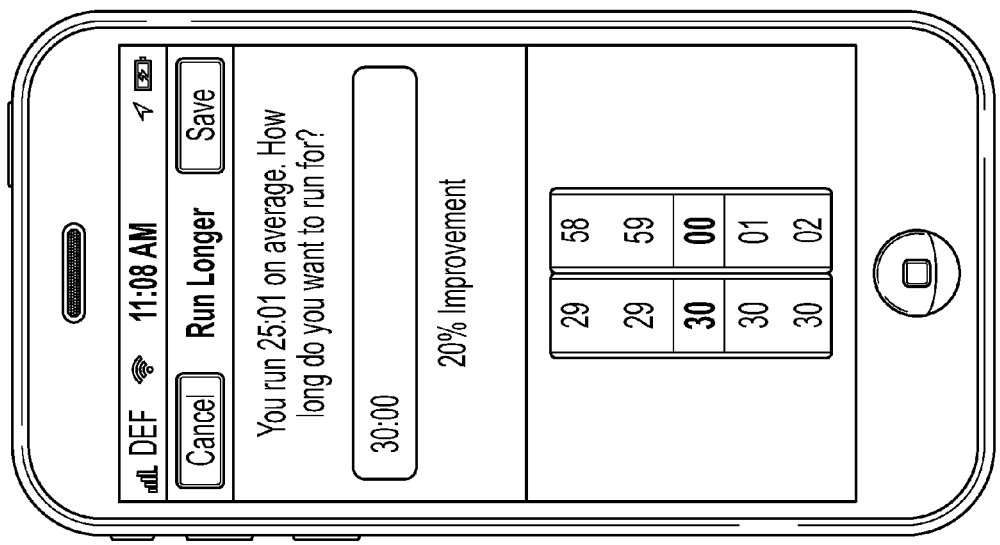
Figure 20L:
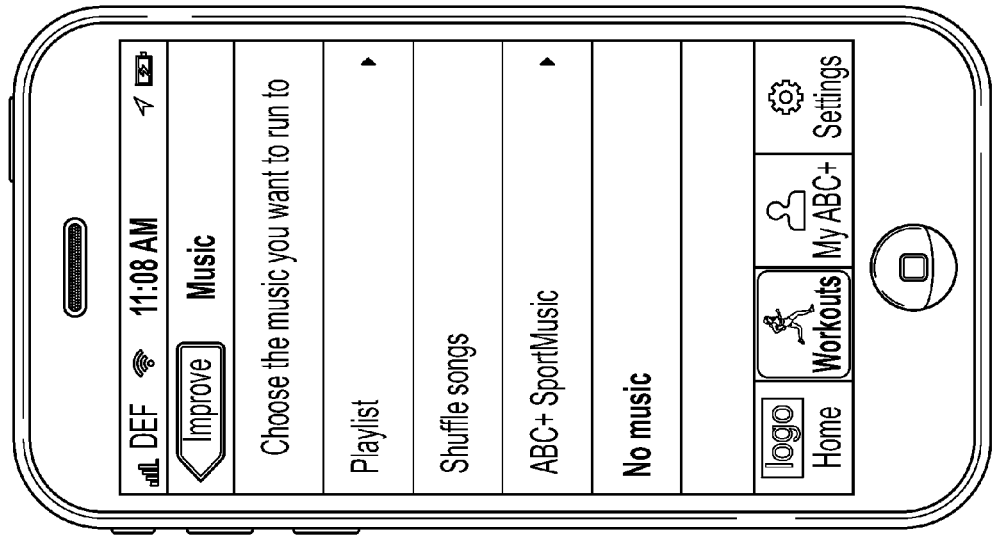
Figure 20K:
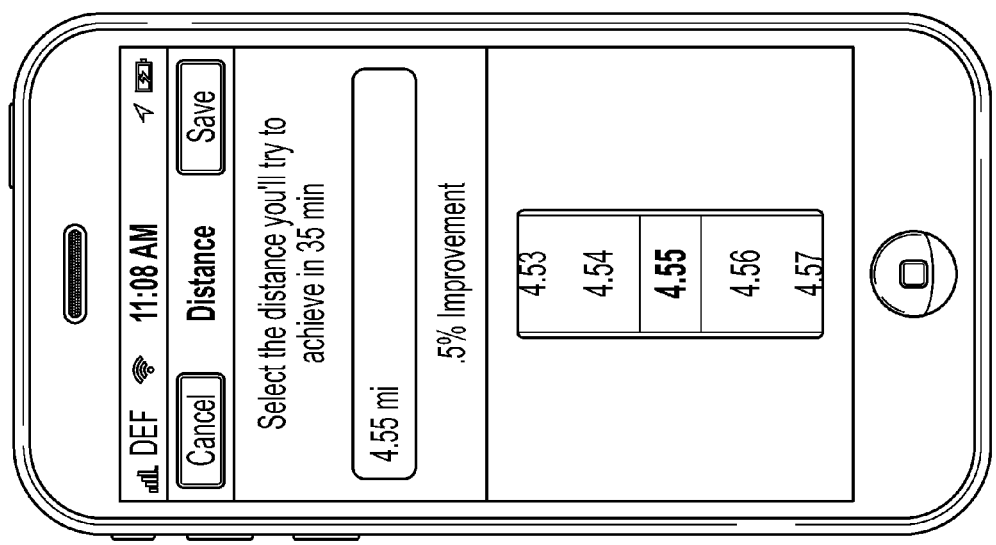
Figure 20N:
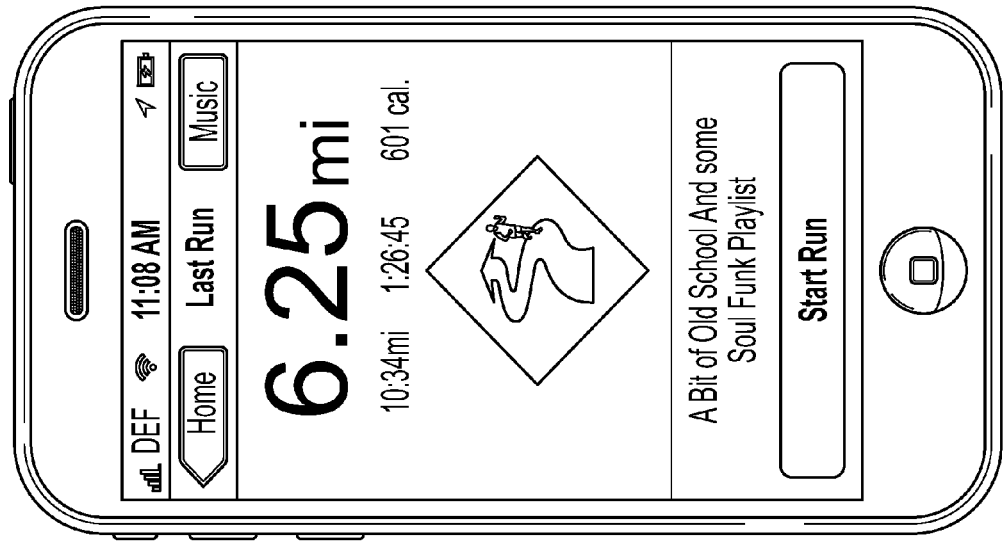
Figure 20M:
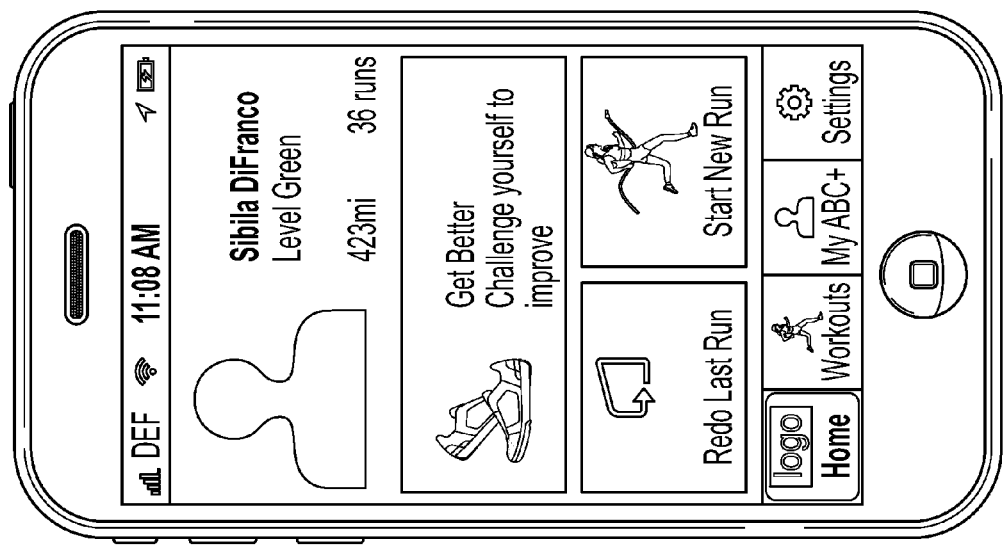
Figure 20P:
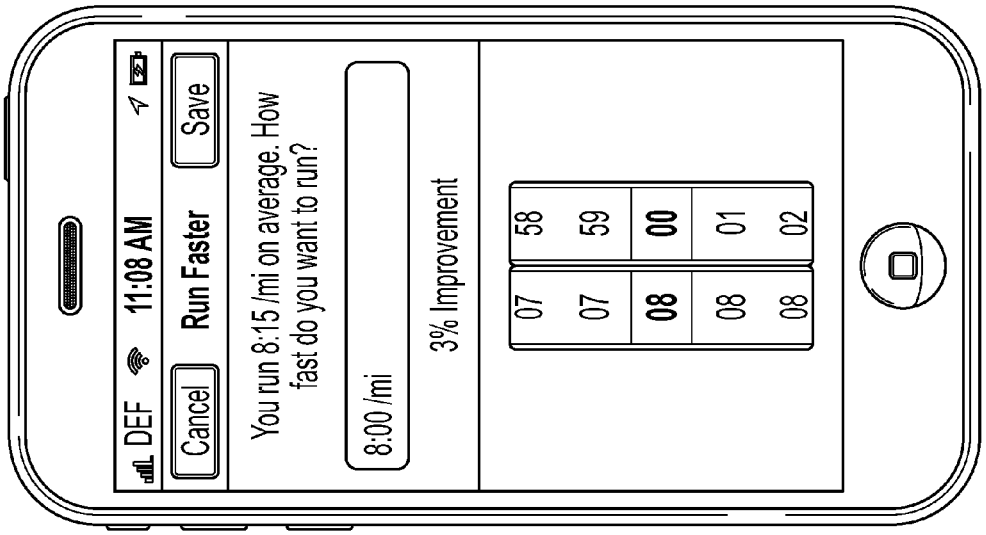
Figure 20O:
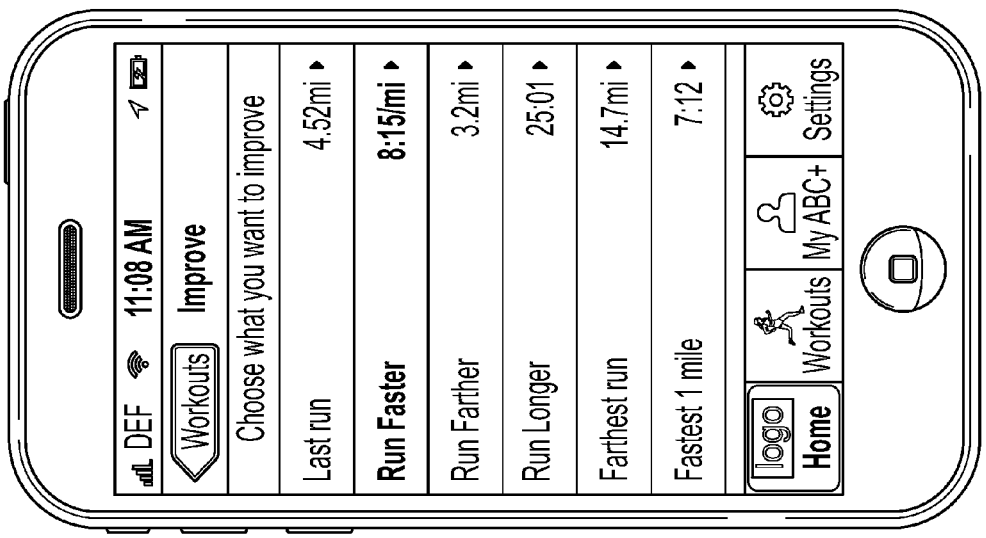
Figure 20R:
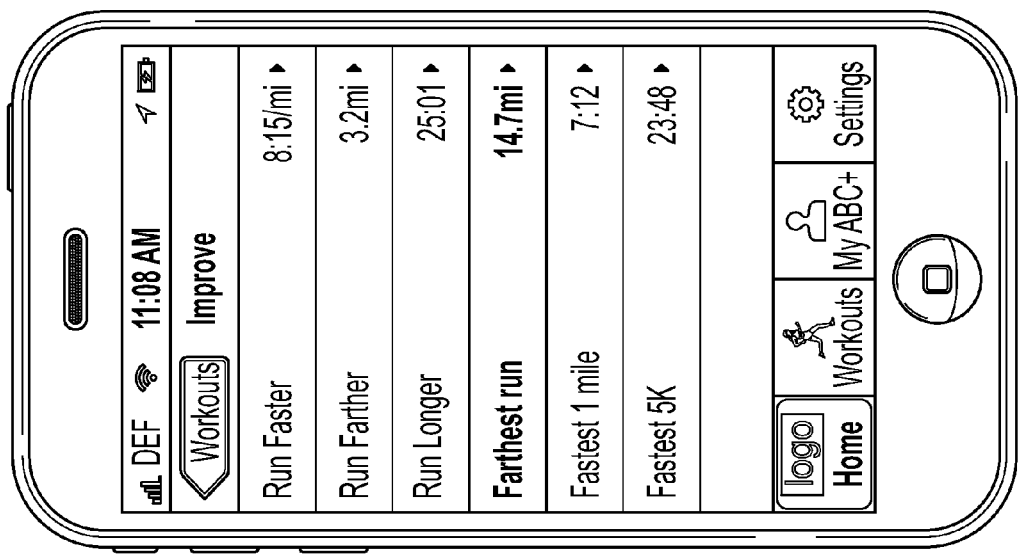
Figure 20Q:
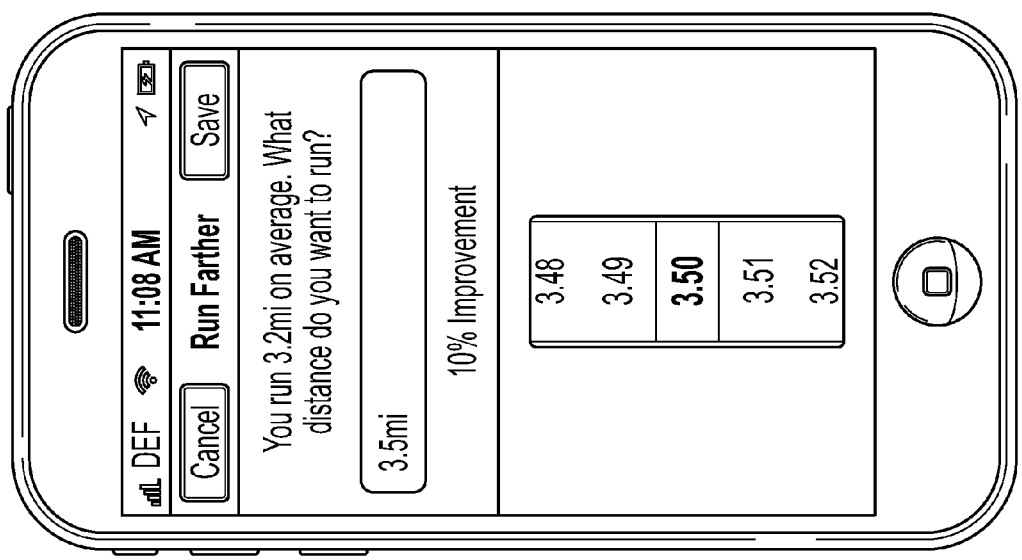
Figure 20T:
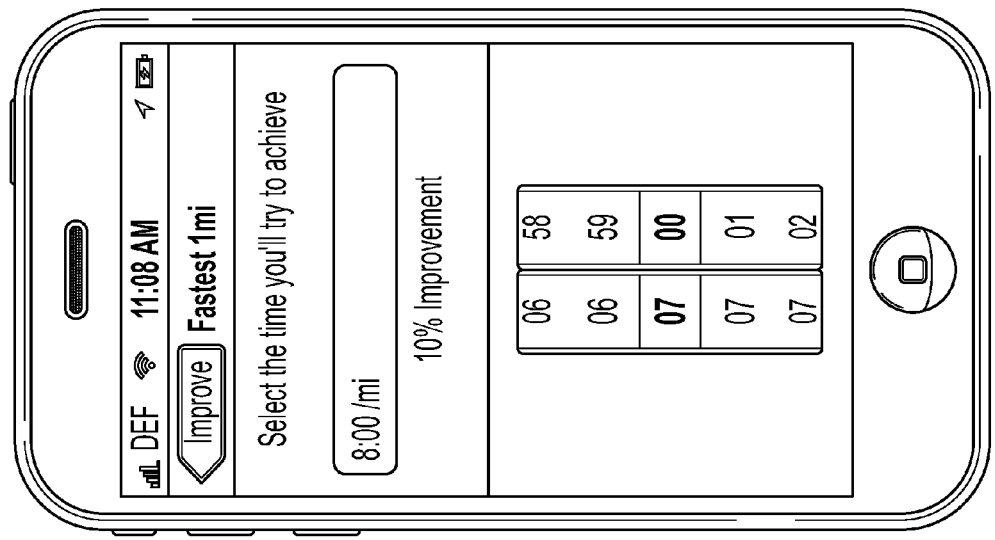
Figure 20S:
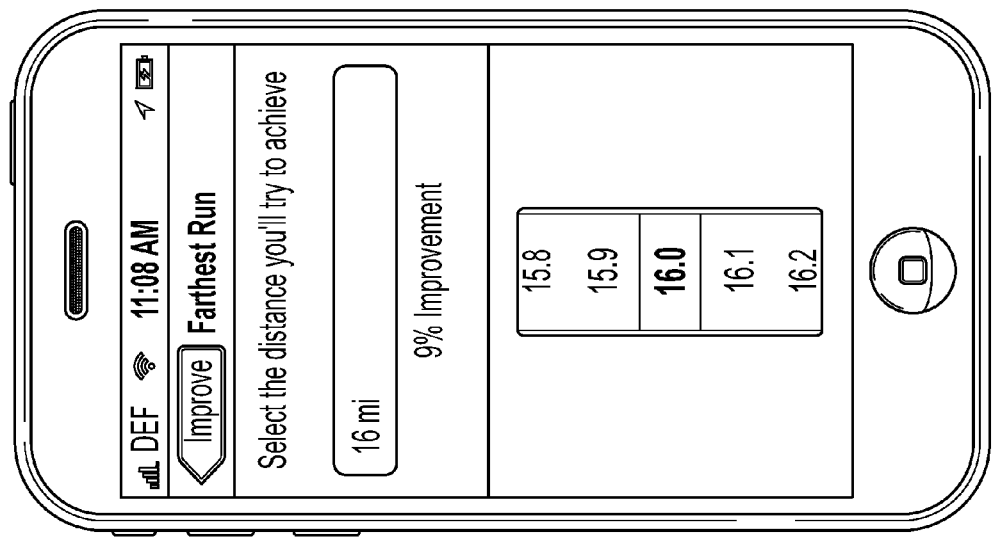
Figure 20V:
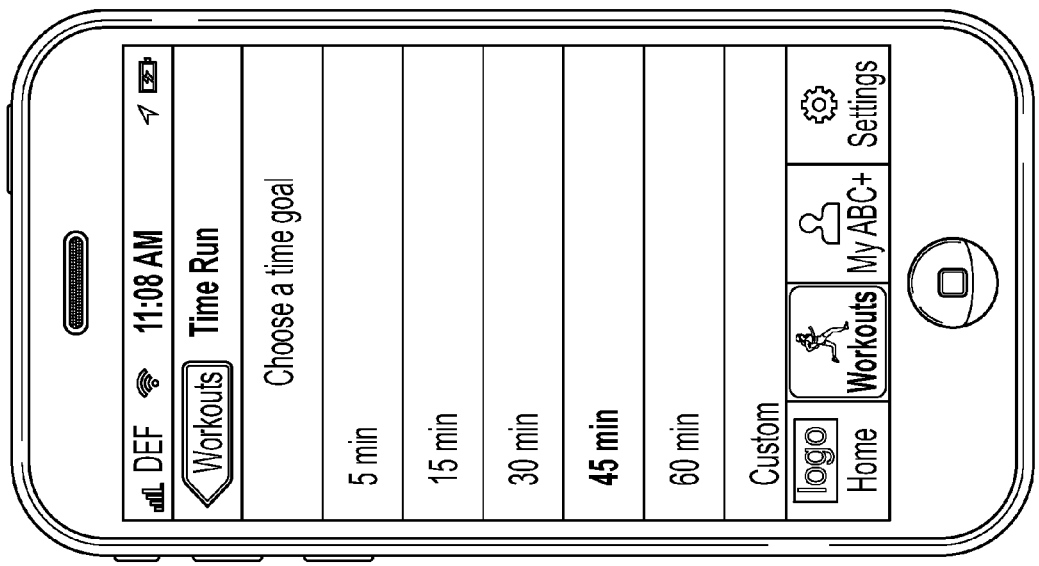
Figure 20U:
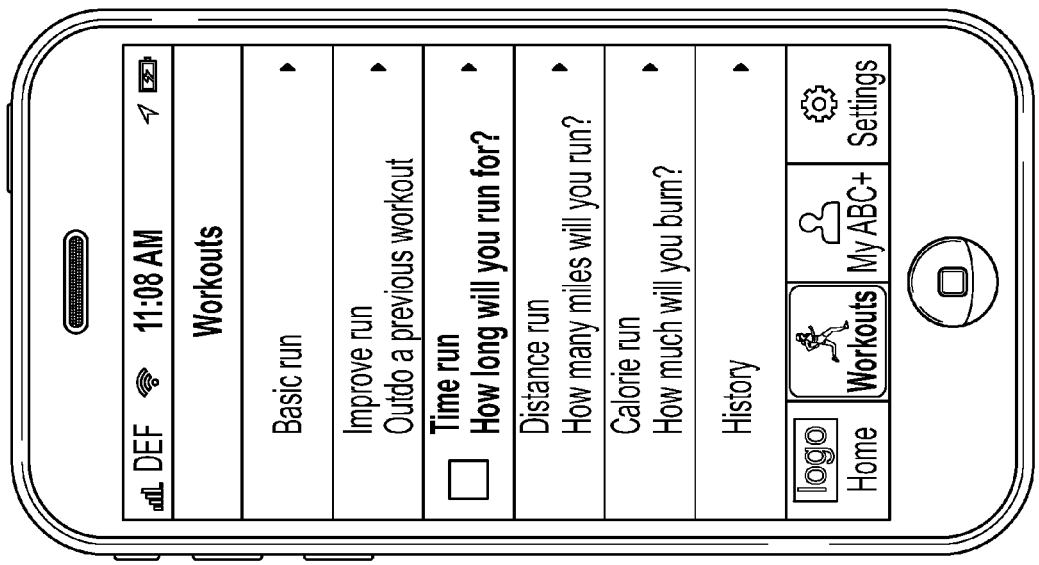

FIGS. 20A-20Z and FIGS. 21A-21D illustrate additional example interfaces that may be displayed for setting up a run. For example, FIG. 20N illustrates an interface that allows a user to repeat a previous run (e.g., with the same objectives, route, equipment, music). FIGS. 20P, 20Q, 20S and 20T illustrate example user interfaces through which a user may manually define an objective for an improvement run. The user may modify the pace the user wishes to achieve for the run. The interfaces may provide an indication of the amount of improvement reflected by the selected pace. For example, 8:00/ml may represent a 3% improvement over a fastest pace of 8:15/ml. In another example, 3.5 ml may represent a 10% improvement of a previous farthest run of 3.2 ml. In yet another example, the setting of a 16 ml goal may represent a 9% improvement over a previously farthest run of 14.7 ml.

Figure 20X:
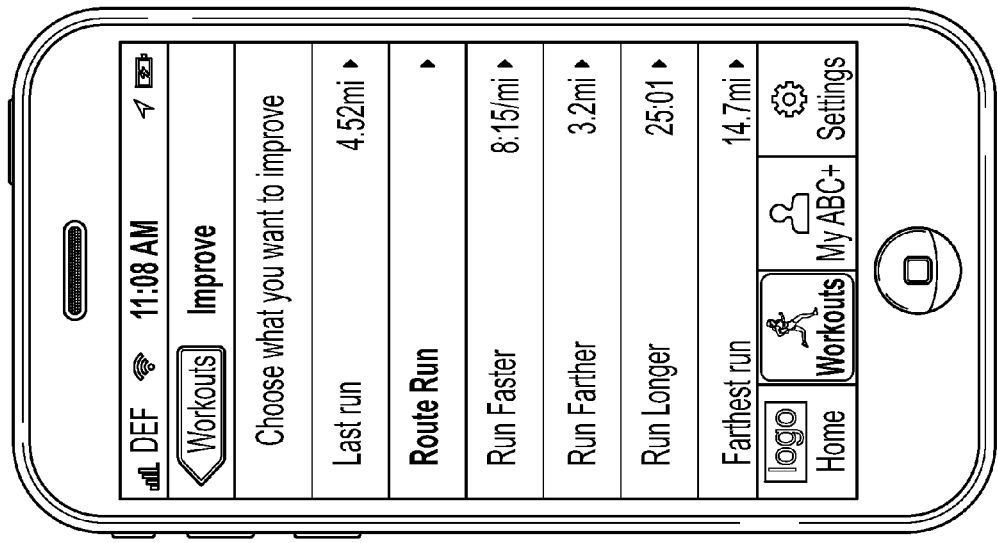
Figure 20W:
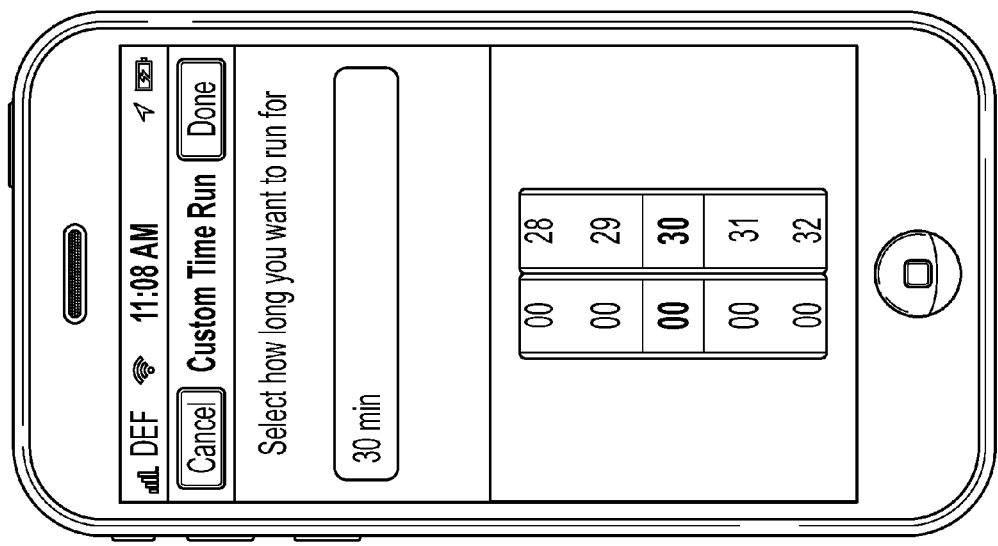
Figure 20Z:
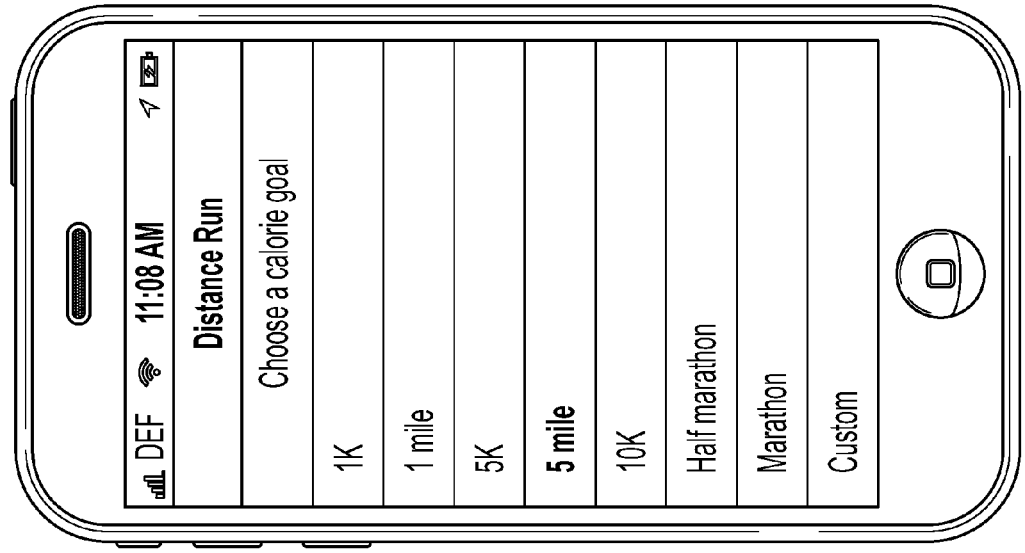
Figure 20Y:
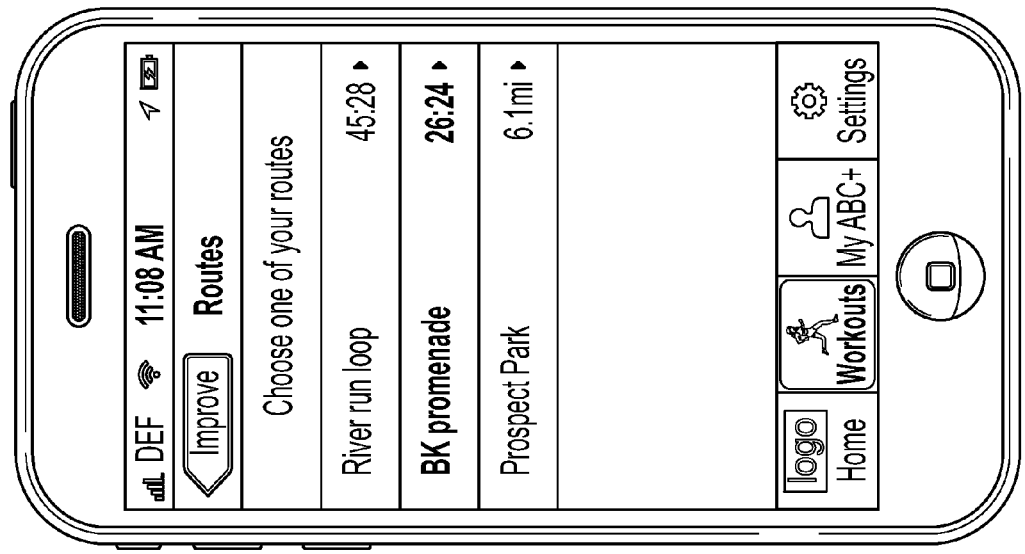
Figure 21B:
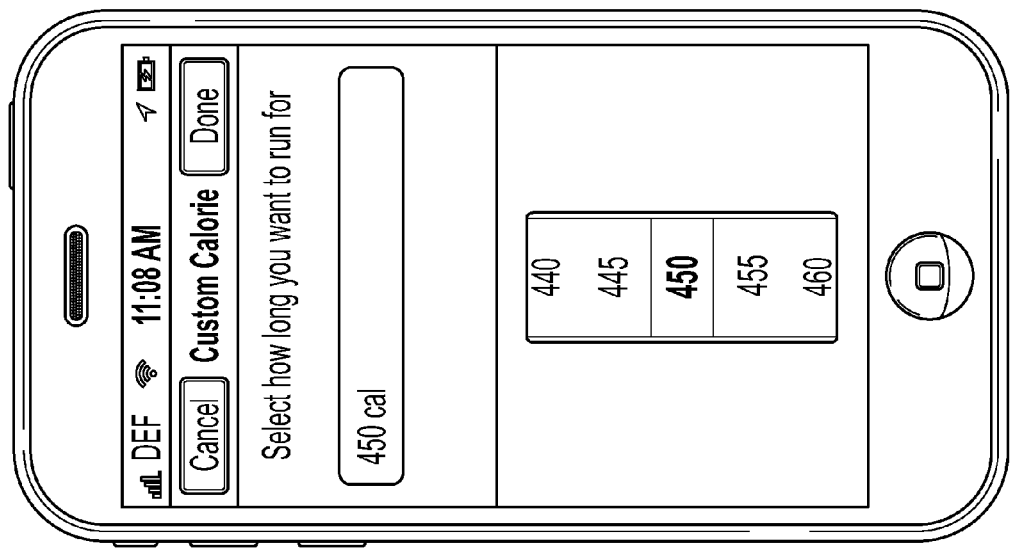
FIGS. 21A-21D illustrate additional example interfaces that may be displayed for setting up a run according to one or more aspects described herein.
Figure 21A:
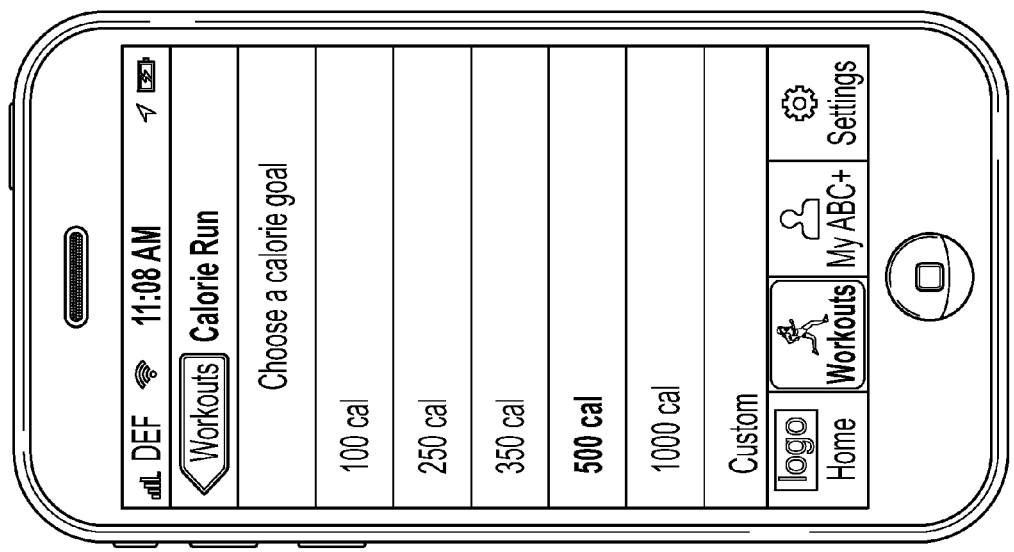
Figure 21D:
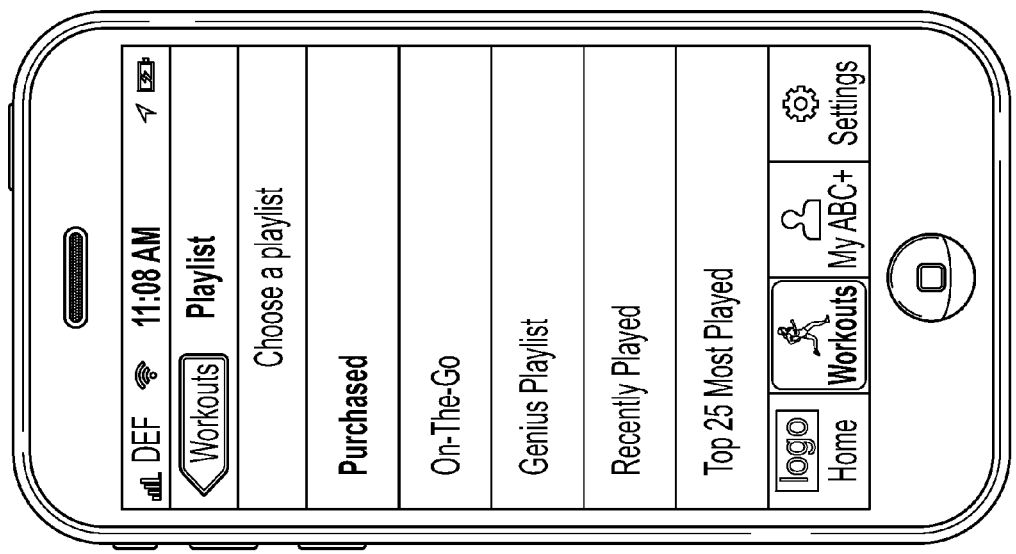
Figure 21C:
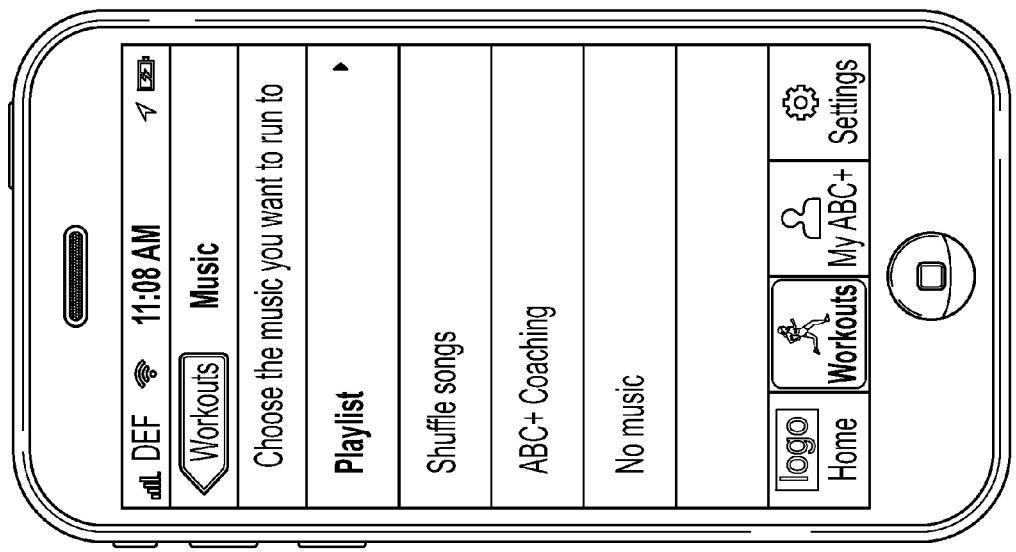

FIGS. 20X and 20Y illustrate interfaces that may be displayed upon a user selecting a route run. A route run may include runs for which a user wishes to select a specific route. The routes may be listed, as shown in FIG. 20Y, with corresponding route information such as a previous run time for the route or the distance of the route. The run time may correspond to fastest time achieved for the route or may be correspond to a most recent time achieved.

Mid-Run

Figure 22A:
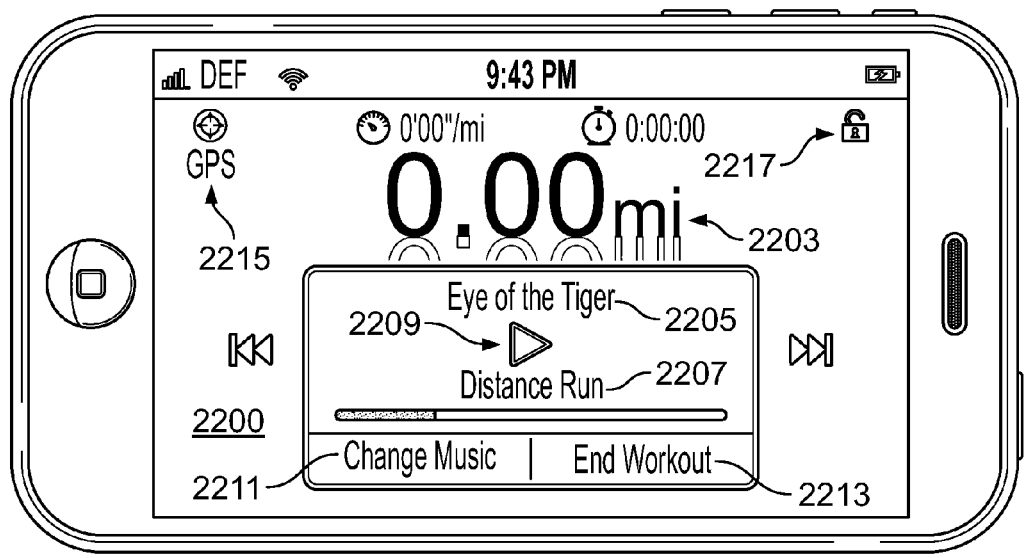
FIGS. 22A-22D illustrate various example interfaces that may be displayed to a user during a user's workout.
Figure 22B:
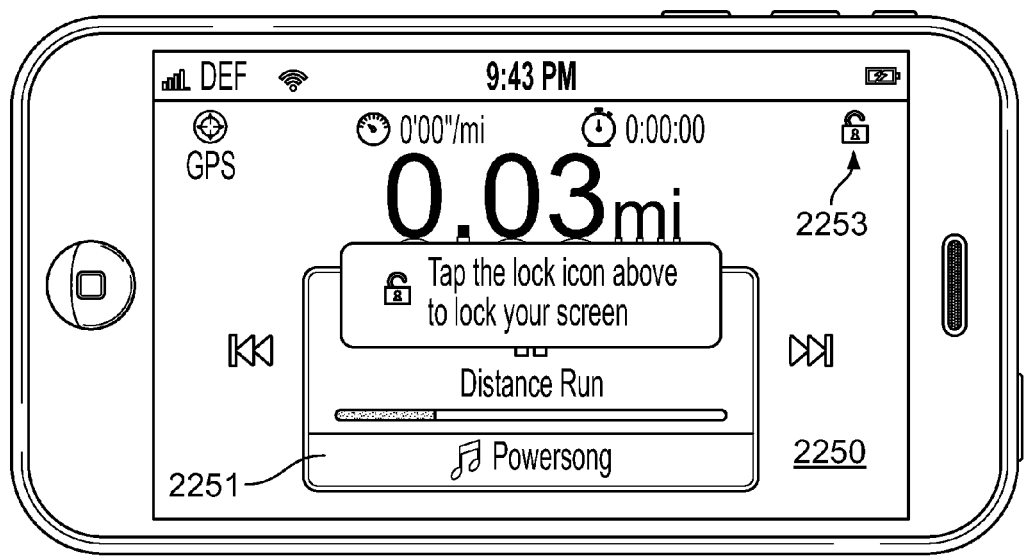
Figure 22D:
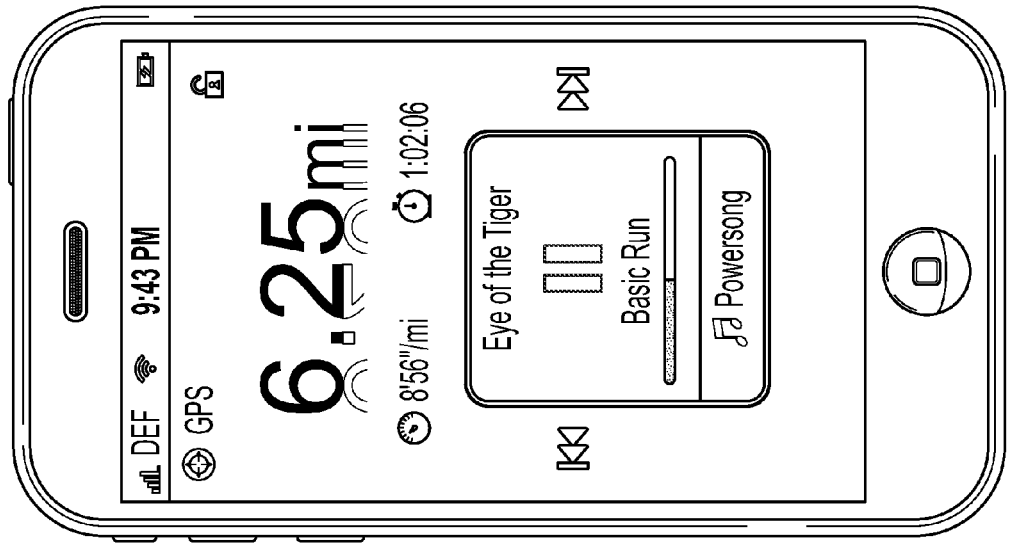
Figure 22C:
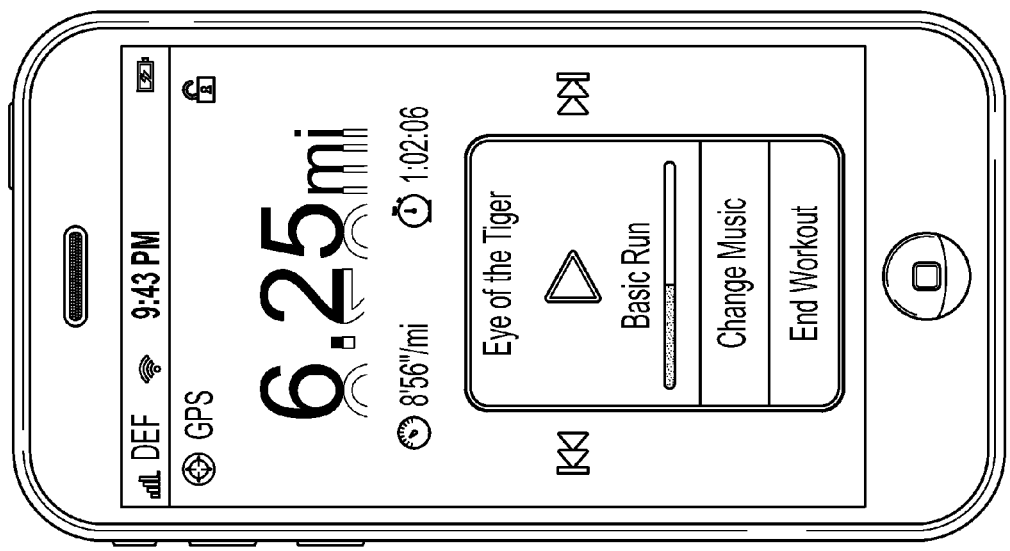

FIGS. 22A-22D illustrate various example interfaces that may be displayed to a user during a user's workout. FIGS. 22A and 22B illustrate an in-run interface in a landscape mode while FIGS. 22C and 22D illustrate an in-run interface in a profile mode. In FIGS. 22A and 22C, interface 2200 displays a current workout progress 2203 (e.g., distance, time and pace), the current audio content being played 2205 and the run type 2207 while audio content is paused. Interface 2200 may further include a play option 2209 (e.g., to resume or start playing of audio content). While audio is paused, interface 2200 may provide options 2211 and 2213 to change the music or to end the workout, respectively. 2200 may further provide additional indicators such as a GPS indicator 2215 to identify when GPS information/data is available and a lock indicator 2217 to indicate if the device is locked to input (e.g., to prevent accidental input).

Interface 2250 in FIGS. 22B and 22D displays progress information while audio content is still playing. Interface 2250 may include information similar to that displayed in interface 2200 of FIGS. 22A and 22C, but, instead of displaying a change music option and an end workout option, interface 2250 may include a powersong option 2251. Powersong option 2251 allows the user to activate a song that he or she may find particularly motivating. Thus, if the user feels that he or she is slowing down or, alternatively, that they have a lot of energy, the user may activate the power song to maximize performance during that segment of the workout. In one or more arrangements, interface 2250 may include an instructional message advising the user on how to lock the interface to prevent accidental input. The message may include, for example, tapping or otherwise interacting with lock indicator 2253.

Figures 23A, 23B:
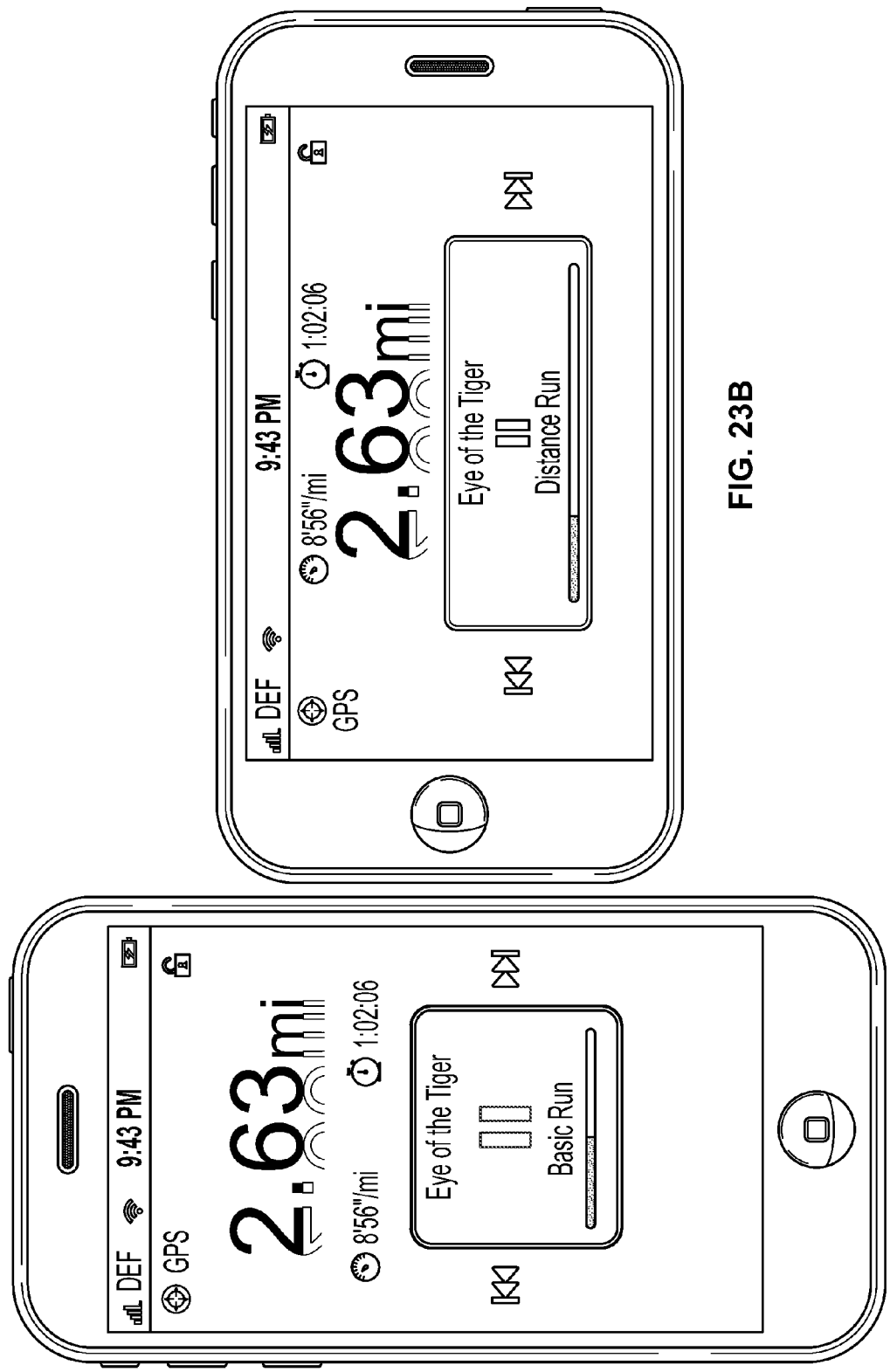
FIGS. 23A and 23B illustrate example in-run interfaces displaying workout information without a power song option.

In some arrangements, no power song may have been selected or be available. Accordingly, the interface might not provide a power song option. FIGS. 23A and 23B illustrate example in-run interfaces displaying workout information without a power song option.

Figure 24B:
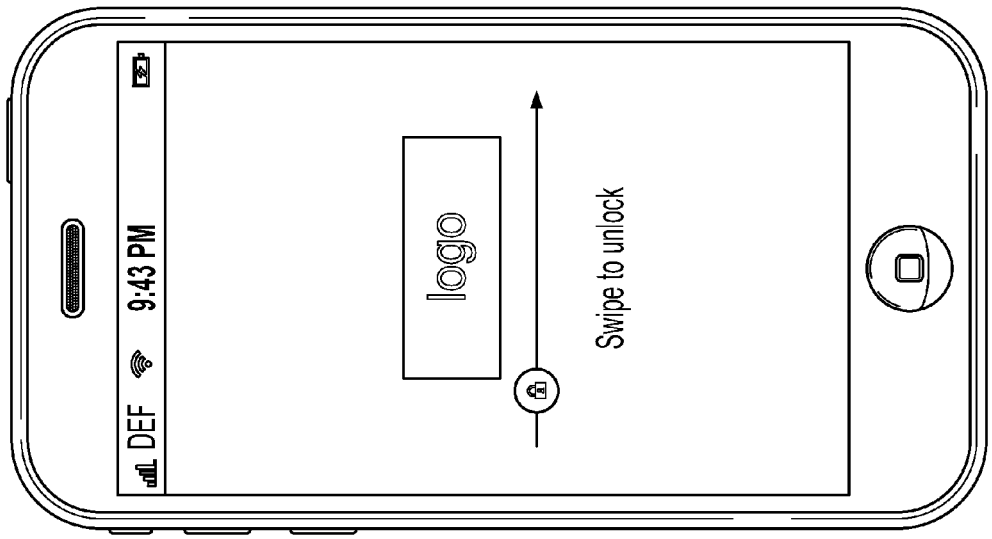
FIGS. 24A-24F illustrate example lock interfaces that may be displayed upon the user locking the interface (e.g., to prevent input) or upon the expiration of a time period during which no user input is detected according to one or more aspects described herein.
Figure 24A:
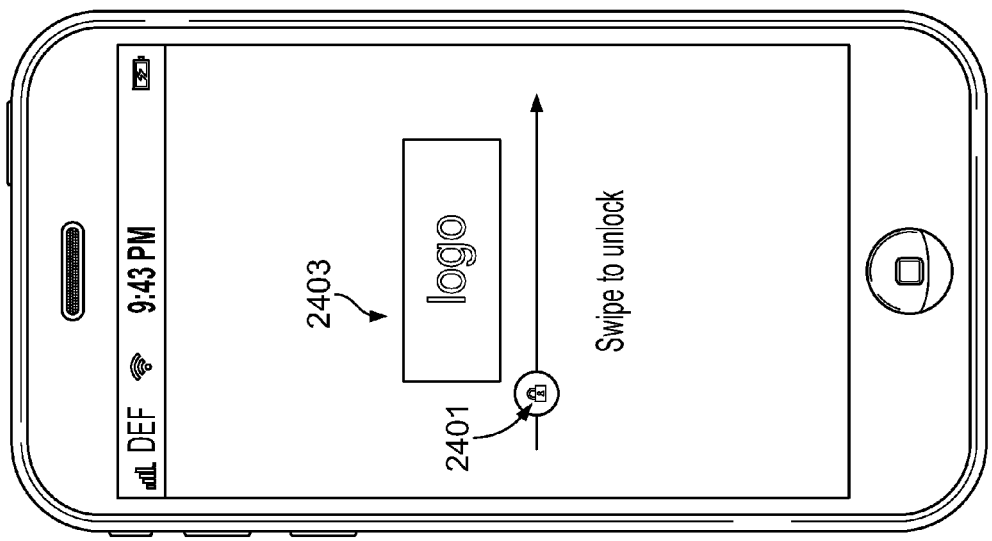
Figure 24D:
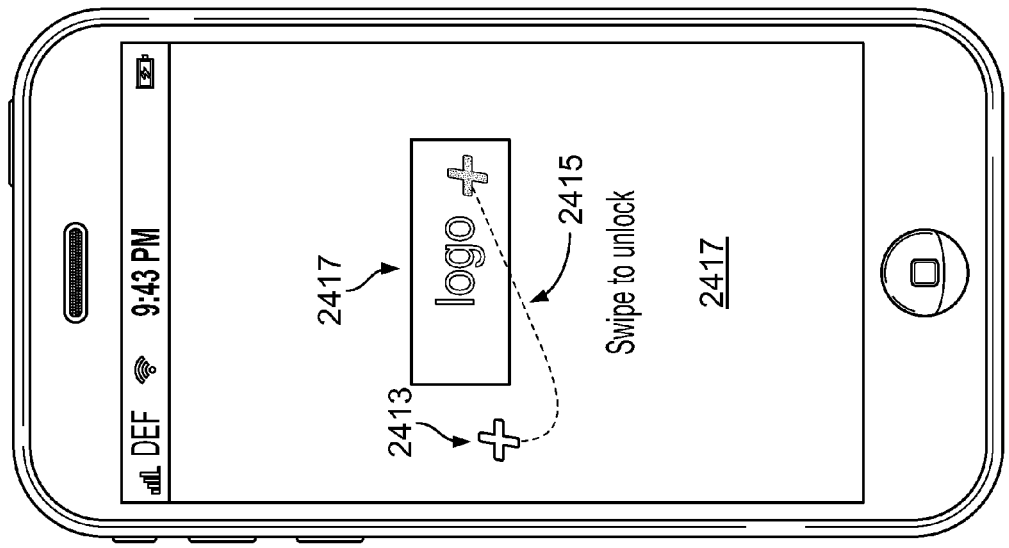
Figure 24C:
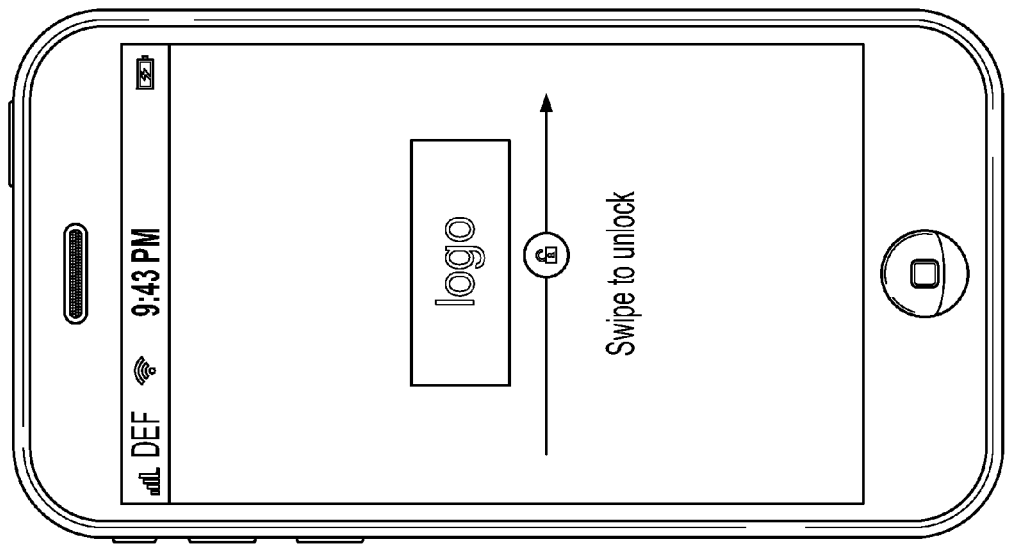
Figure 24F:
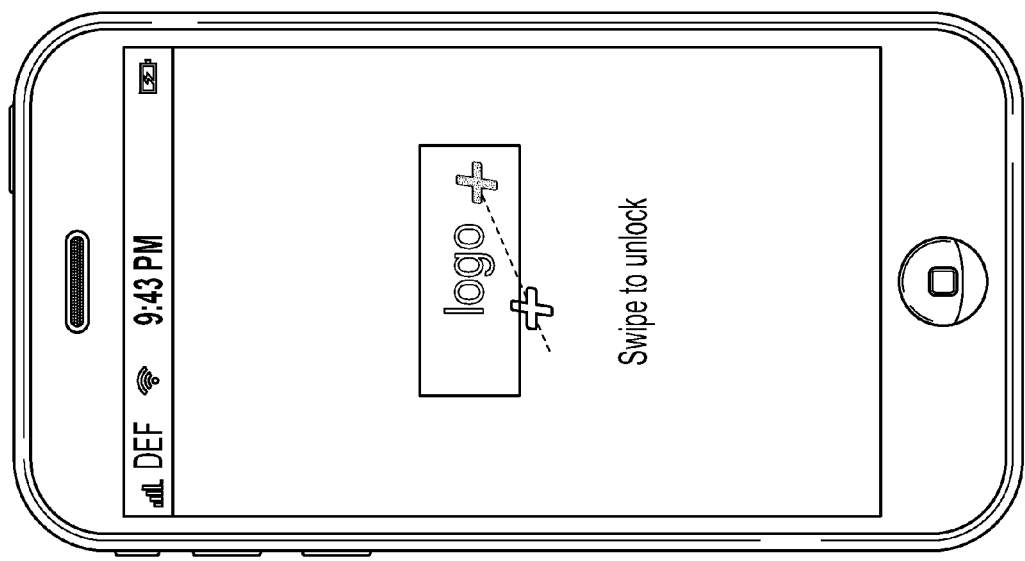
Figure 24E:
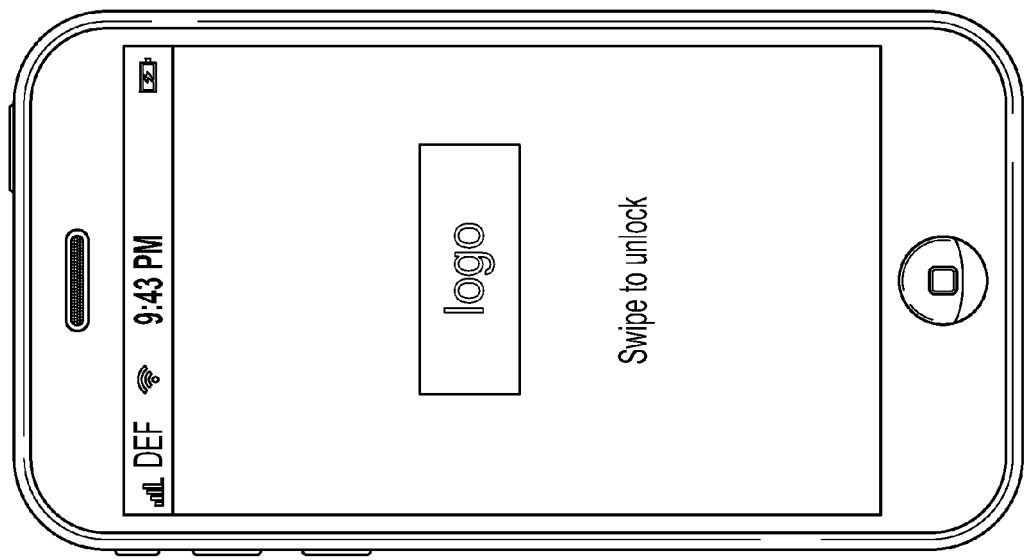

FIG. 24A-24F illustrate example lock interfaces that may be displayed upon the user locking the interface (e.g., to prevent input) or upon the expiration of a time period during which no user input is detected. For example, FIGS. 24A-24C illustrate that a user may unlock the interface by moving a lock symbol 2401 from a left position to a right position. The unlock progress may be indicated by not only the position of symbol 2401 but also by the filling of an outlined image such as image 2403. That is, the device may be unlocked for receiving input upon image 2403 being completely filled. Filling image 2403 may be accomplished by moving symbol 2401 from the left position to a right position. Various different motions, patterns and images may be used for unlocking the device. For example, FIGS. 24D-24F illustrate interface 2410 where the unlock symbol is represented by a plus sign 2413 and where the user must move symbol 2413 along a curved check mark path from 2415. The movement path may correspond to a shape or appearance of the image (e.g., image 2417) or portion thereof.

Figure 25B:
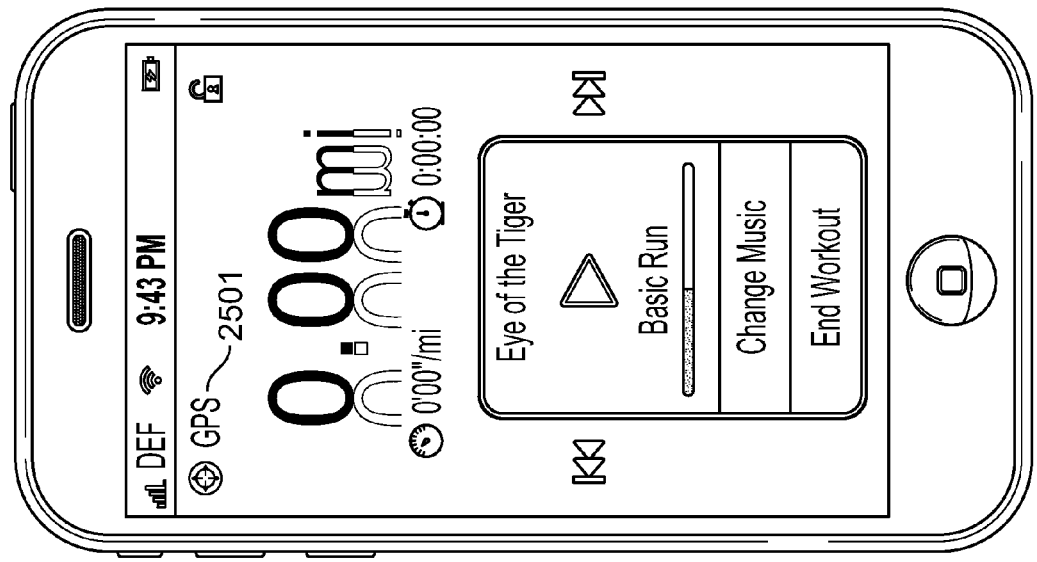
FIGS. 25A-25F illustrate various example user interfaces that may be used to convey a GPS availability and status according to one or more aspects described herein.
Figure 25A:
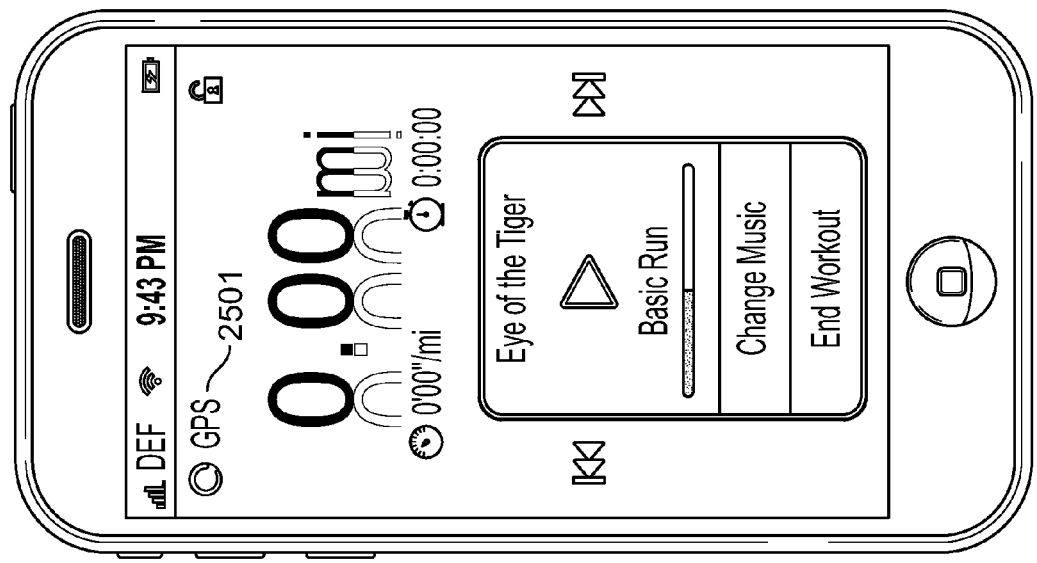
Figure 25C:
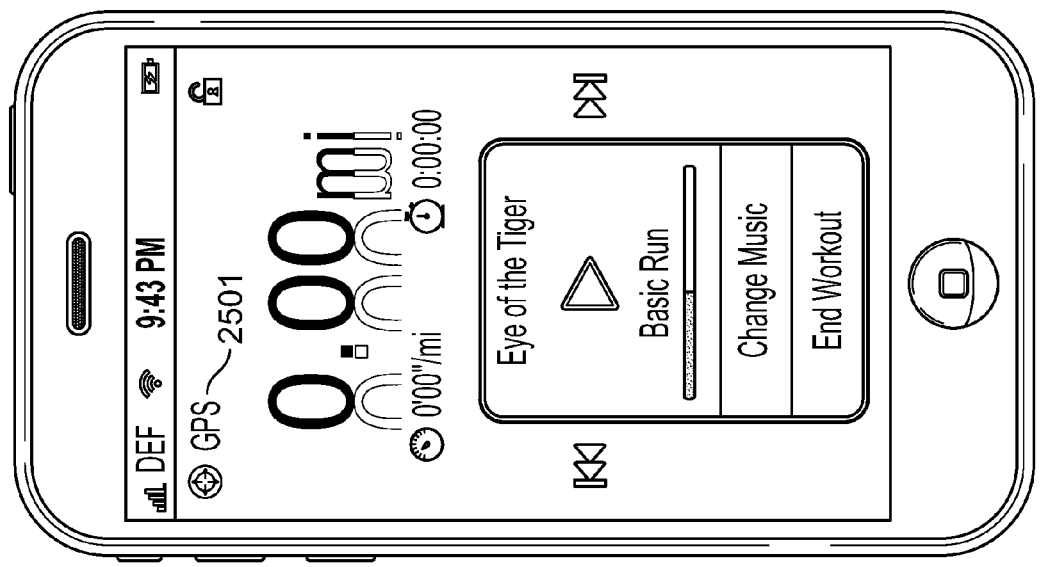
Figure 25D:
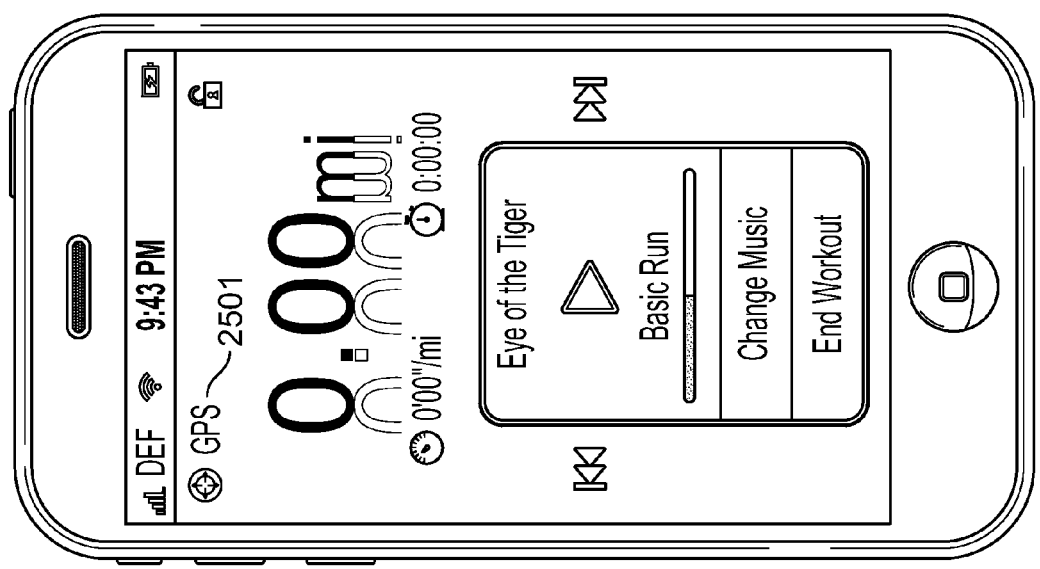

FIGS. 25A-25E illustrate various example user interfaces that may be used to convey a GPS availability and status. For example, FIG. 25A illustrates GPS indicator 2501 in a signal searching mode. FIG. 25B illustrates GPS indicator 2501 if no signal is available or detected. In particular, an outer ring of the GPS indicator 2501 may be displayed in a first state (e.g., as an outline or substantially transparent). FIGS. 25C and 25D illustrates GPS indicator 2501 in second and third states indicating a weak and a strong signal, respectively. The signal strength may be represented by various aspects of indicator 2501 including a transparency level (e.g., more transparent when signal is weaker), a color, a pattern, an animation (e.g., rotating, flashing, fading in and out, etc.) and/or combinations thereof.

In one or more arrangements, if the GPS signal is weak, a message may be displayed notifying the user of the same. For example, interface 2520 of FIG. 25E displays message 2521 that indicates the GPS signal is weak and that the time and distance of the run may still be tracked. For example, instead of using GPS data when it is unavailable, the device may activate and/or begin recording accelerometer data. In one or more arrangements, use of an accelerometer or other sensor (e.g., cellular triangulation) may also be indicated visually in an interface (e.g., using an icon, word, or the like).

Figure 25F:
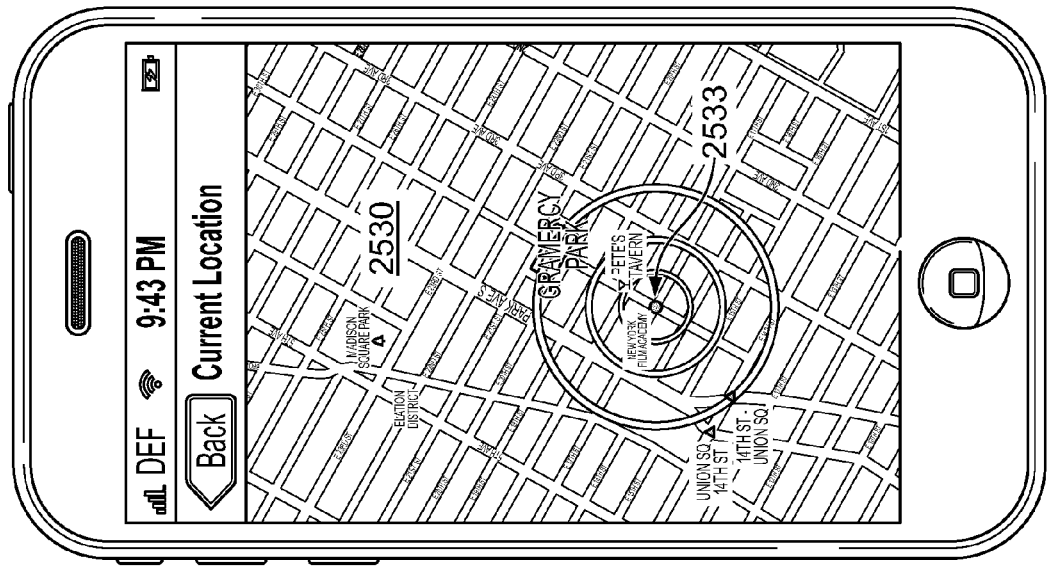
Figure 25E:
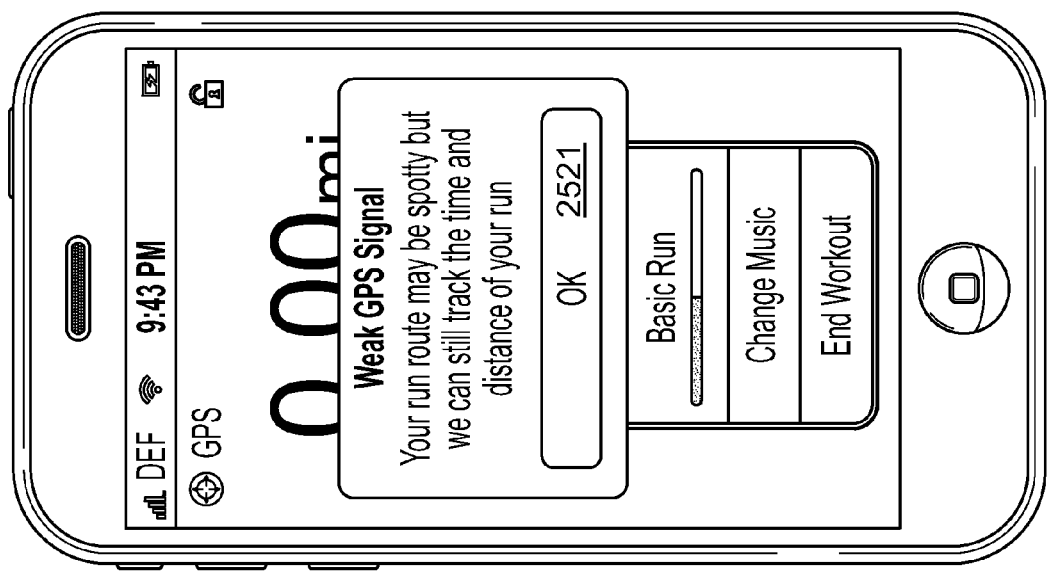

Additionally, a user may select GPS indicator 2501 of FIGS. 25A-25D to view a map identifying the user's current location. Other options or indicators may also be displayed for allowing the user to access the map mode. FIG. 25F illustrates map 2530 with the user's location identified by indicator 2533.

Figure 26B:
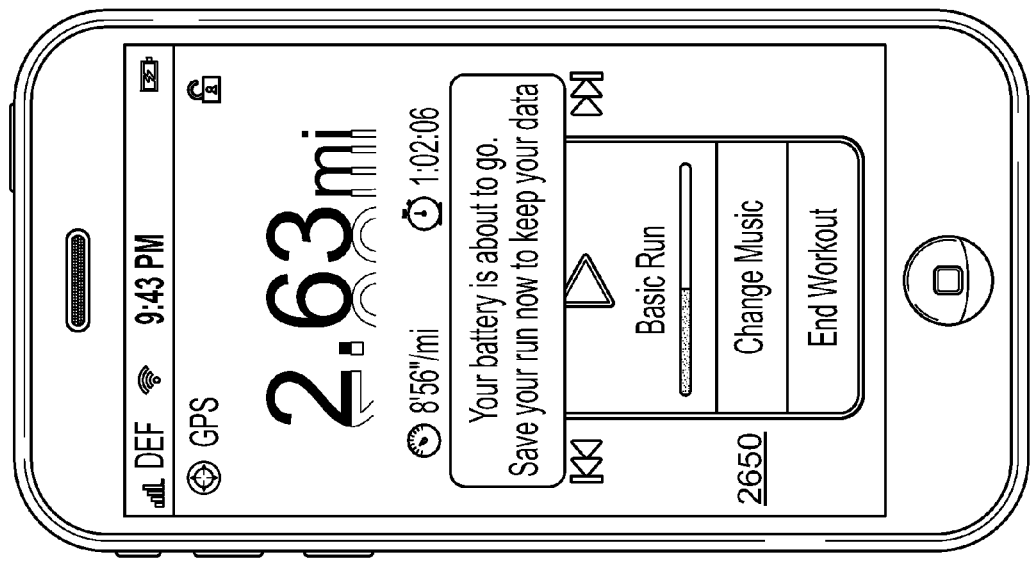
FIGS. 26A and 26B illustrate example alerts that may be provided to the user according to one or more aspects described herein.
Figure 26A:
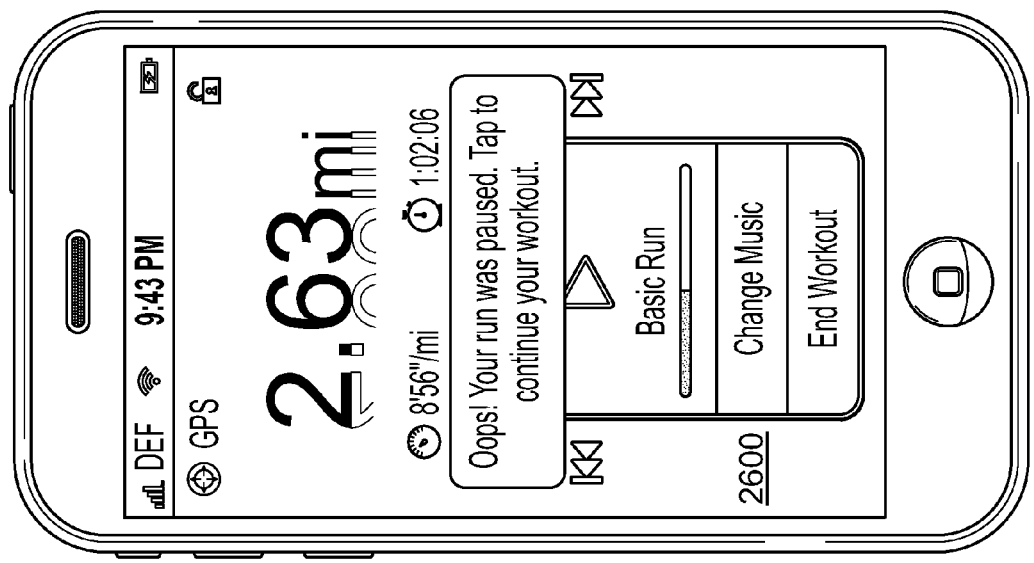

A user may be provided with various alerts during the run upon detection of various events. For example, in interface 2600 of FIG. 26A, the user may be provided with a message indicating that the run was pause and instruction on how to resume the workout (e.g., tap to resume). In another example, interface 2650 of FIG. 26B may display a message upon detecting that the battery is about to run out. The message may advise the user to save the workout prior to the battery being depleted. The message may be displayed when the battery is projected to become depleted in a specified amount of time, e.g., 5 minutes, 10 minutes, 15 minutes, 30 seconds, etc.

Figure 27C:
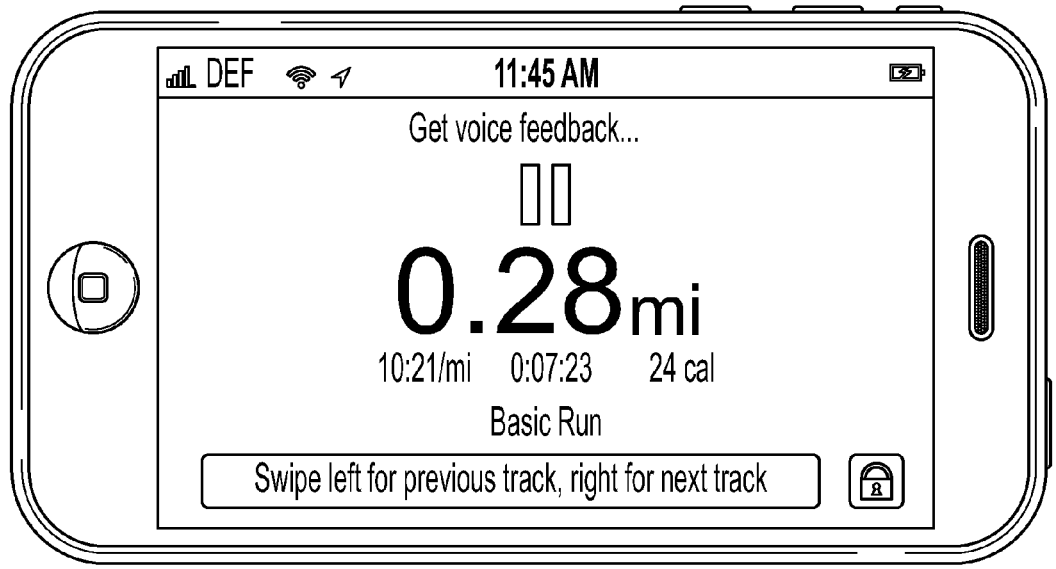
Figure 27D:
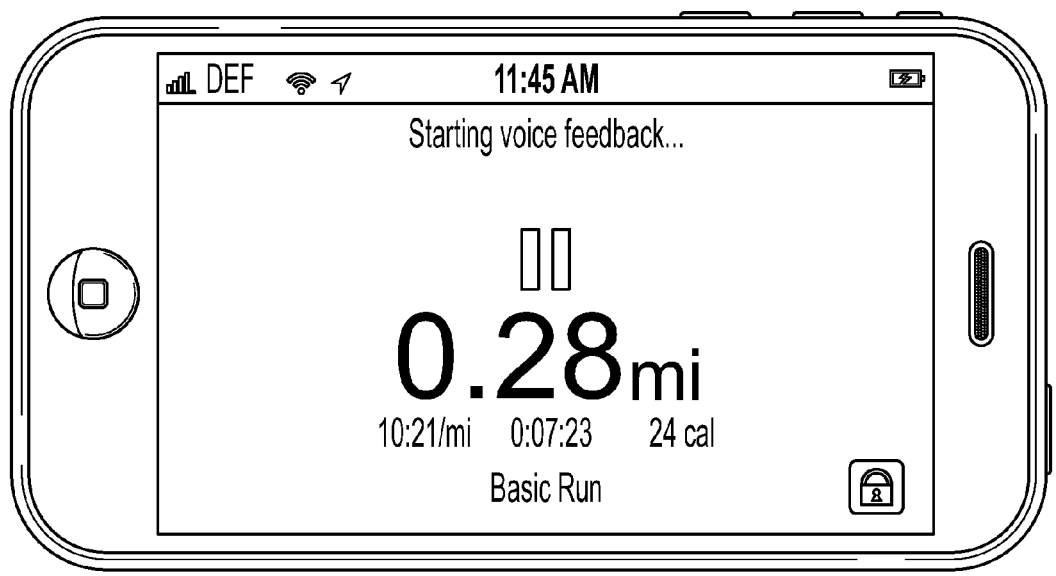
Figure 27F:
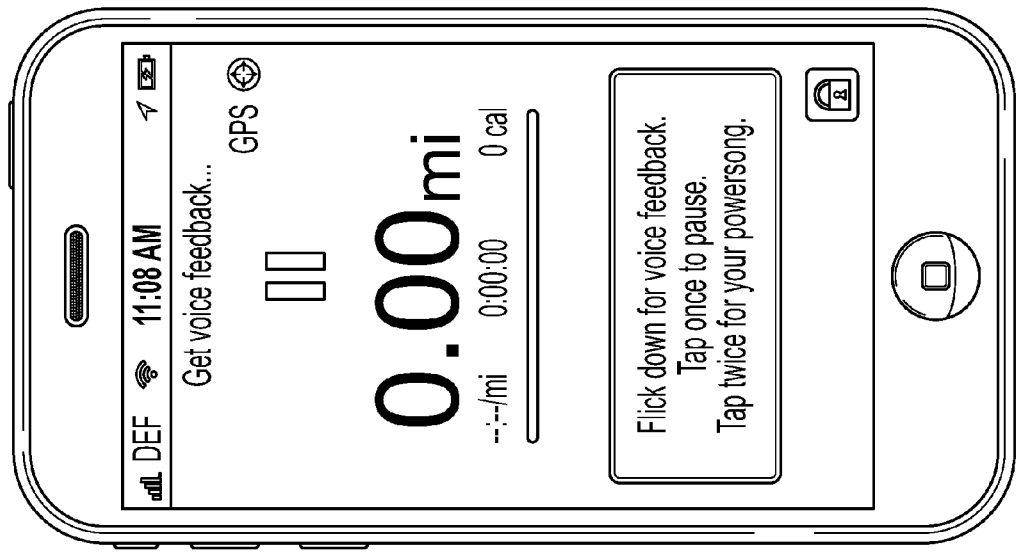
Figure 27E:
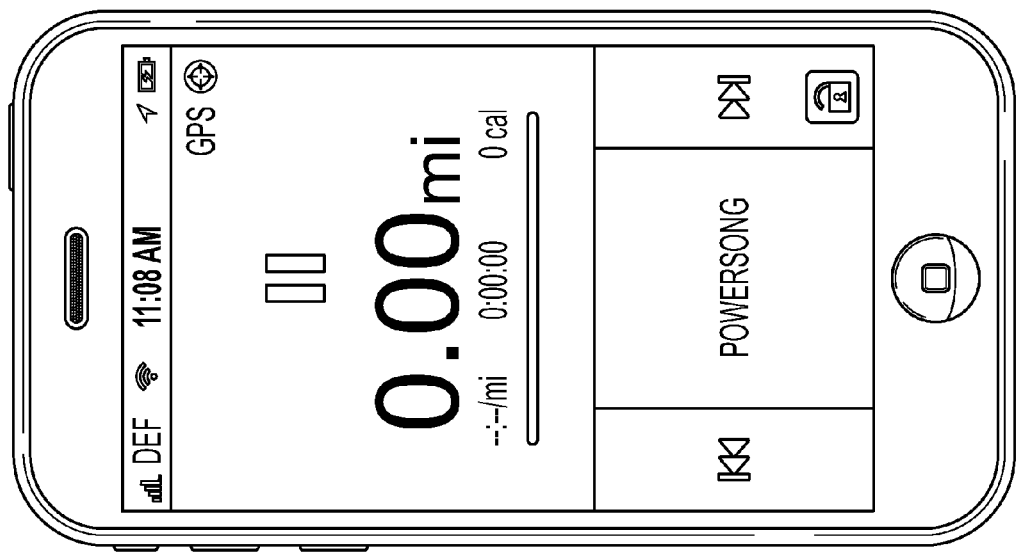
Figure 27H:
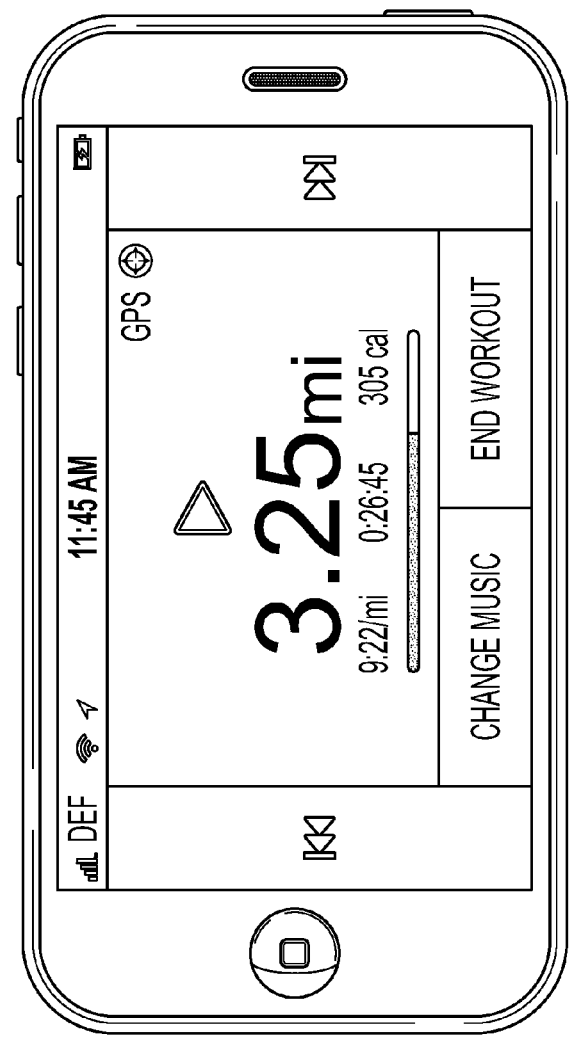

FIGS. 27A-27H illustrate additional or alternative user interfaces that may be displayed while a user is conducting a run. For example, FIG. 27B illustrates an interface displaying a notification message providing instructions for deactivating buttons and activating gesture commands. Gestures may include touch-sensitive motions that correspond to various commands. For example, swiping a user's finger to the right may be used to progress to a previous audio content item and to the left to progress to a next audio content item. In another example, a user may flick or swipe downwards (e.g., in relation to the orientation of the device) to receive voice feedback. Voice feedback may include a vocalization of a current amount of progress (e.g., a distance currently run, an amount of time, a pace, calories burned). Further, tapping once may correspond to pausing the run and/or audio content while tapping twice may automatically activate a power song. Accordingly, the user might not need to view the display to control the device. Additionally, no information including visible options and buttons might need to be displayed for the user to appropriate adjust the functionality and features of the application and device.

Figure 27G:
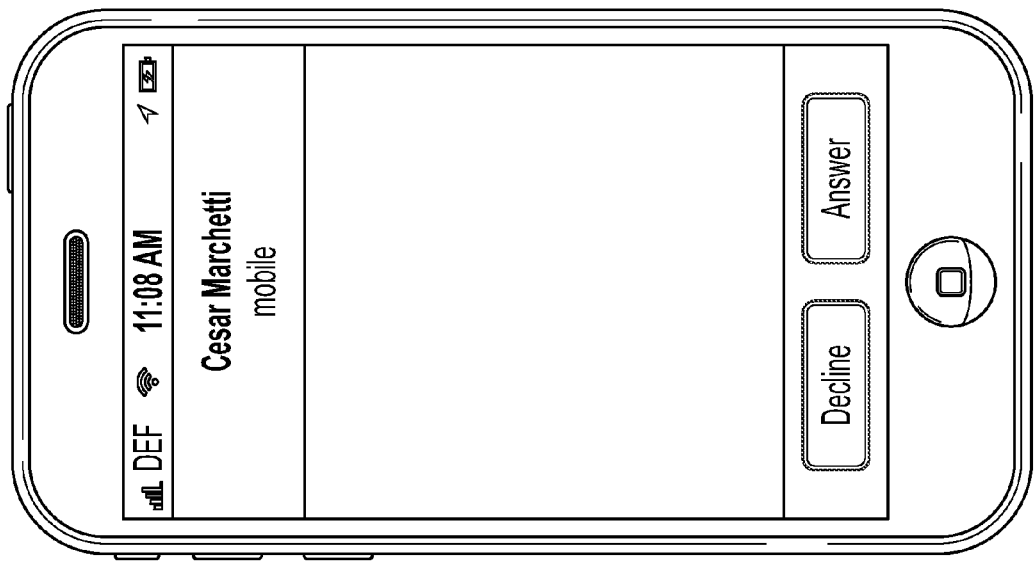

In FIG. 27G, an interface is displayed for when a user receives a voice call during the workout. The interface may be automatically displayed, replacing the in-run workout interface as displayed in FIGS. 27C and 27D. If the user answers the call, the workout and playing of audio content may be automatically paused. Alternatively, if the user declines the call the workout may automatically be continued without interruption (e.g., the interface of FIGS. 27C and 27D may be displayed once more).

In addition to the selected audio content, the fitness monitoring device and application may play other audio content configured to encourage or notify the users of certain events or situations. For example, various sounds such as trumpets, applause, fireworks or other generally encouraging audio may be played when the user reaches certain milestones or goals such as completing each mile, running 1K, setting a new fastest pace for a specified distance and the like. In other examples, the user may be provided with encouraging or instructional messages such as "You are 5 seconds behind target pace. Speed it up" or "You are 20 seconds ahead of target pace. Keep it up." Other messages may include "You're halfway to your goal and you're running [ahead of/behind] target pace" and "You're almost there. I'm wondering if you can run the length of one extra song? Double tap to accept!" In this latter example, the user may be challenged to further improve on the run during the run. The user may accept the challenge, at which time the workout may be automatically extended in accordance with the challenge (e.g., extending the run for 1 more song).

Figure 28B:
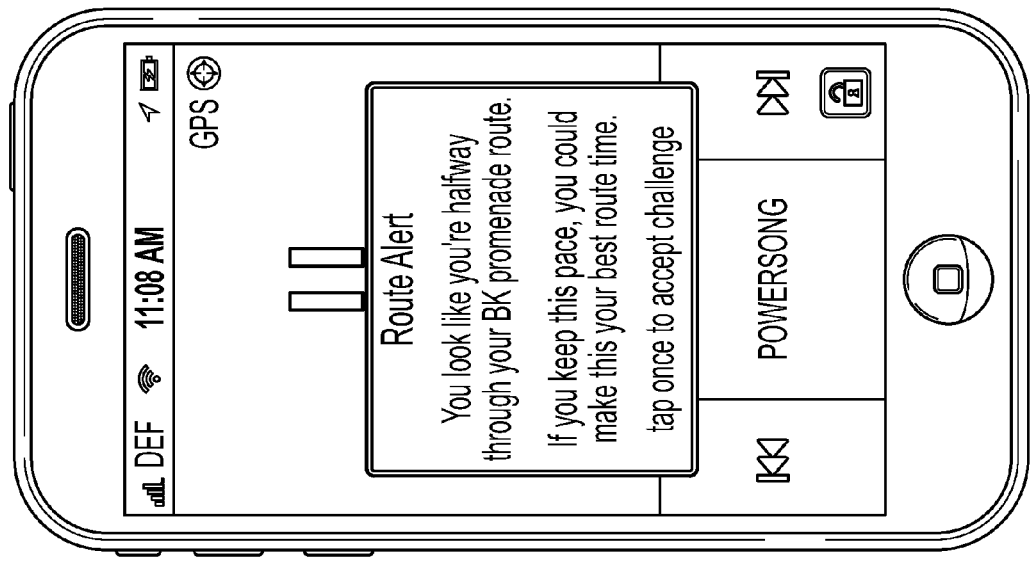
FIGS. 28A and 28B illustrate additional example alerts that may be textual in nature and may be accompanied by corresponding audio messages according to one or more aspects described herein.
Figure 28A:
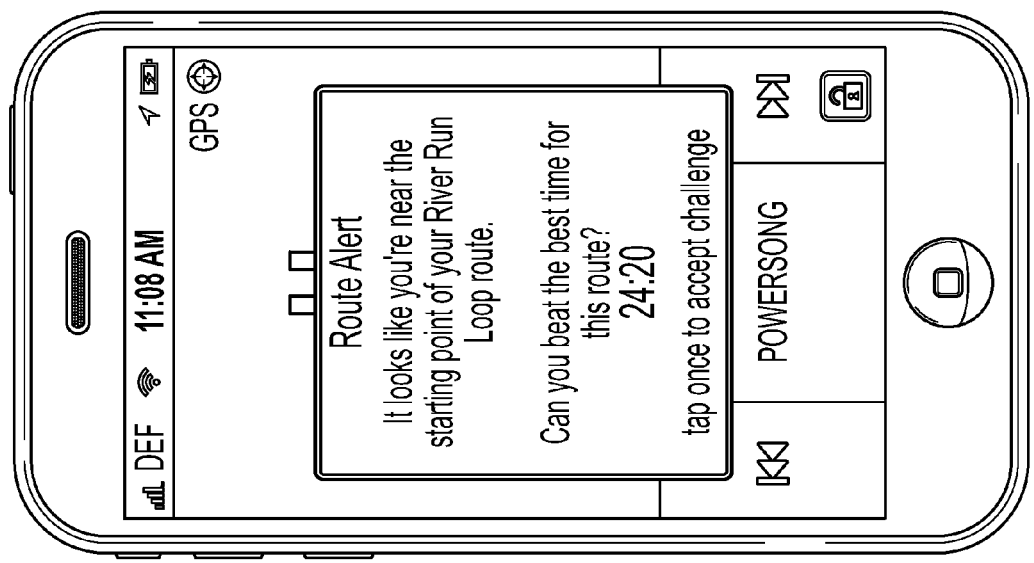

FIGS. 28A and 28B illustrate further alerts that may be textual in nature and may be accompanied by corresponding audio messages. For example, in the interface of FIG. 28A, the user is presented with an alert challenging him or her to beat the best time for a particular route (e.g., if the route was run before). In the interface of FIG. 28B, the user may be provided with a challenge alert to keep up a current pace to achieve a best route time. In each case, various types of gestures or other interactions may be used to accept the challenge. These interactions may include tapping the screen of the device, making a gesture, speaking a voice command, pressing a physical button on the device and the like.

Audio messages may also provide advice or warnings. For example, a message may indicate that there is a hill coming up on the route (e.g., within 0.25 miles, within 0.5 miles, etc.).
Post-Run After a user completes his or her run, the user may be presented with a workout summary. Additionally, the device may select, generate and/or display words of encouragement or indications that the user has reached a goal or milestone. For example, a user may receive accolades or motivational messages when the user has recorded his or her longest run (duration or distance) or fastest run (e.g., for a 1K, 10K or other predefined distance). The message may be textual in nature, include audio output, provide haptic feedback and/or combinations thereof. Workout summaries may include different information or options depending on the location of the workout (e.g., indoors or outdoors). For example, a workout summary for an indoor workout may include a calibration function to insure accuracy of the data recorded while an outdoor workout summary might not include the calibration function. The difference in workout summary functionality may be attributable to the accuracy with which a GPS device is able to track distance and/or pace.

Figure 29:
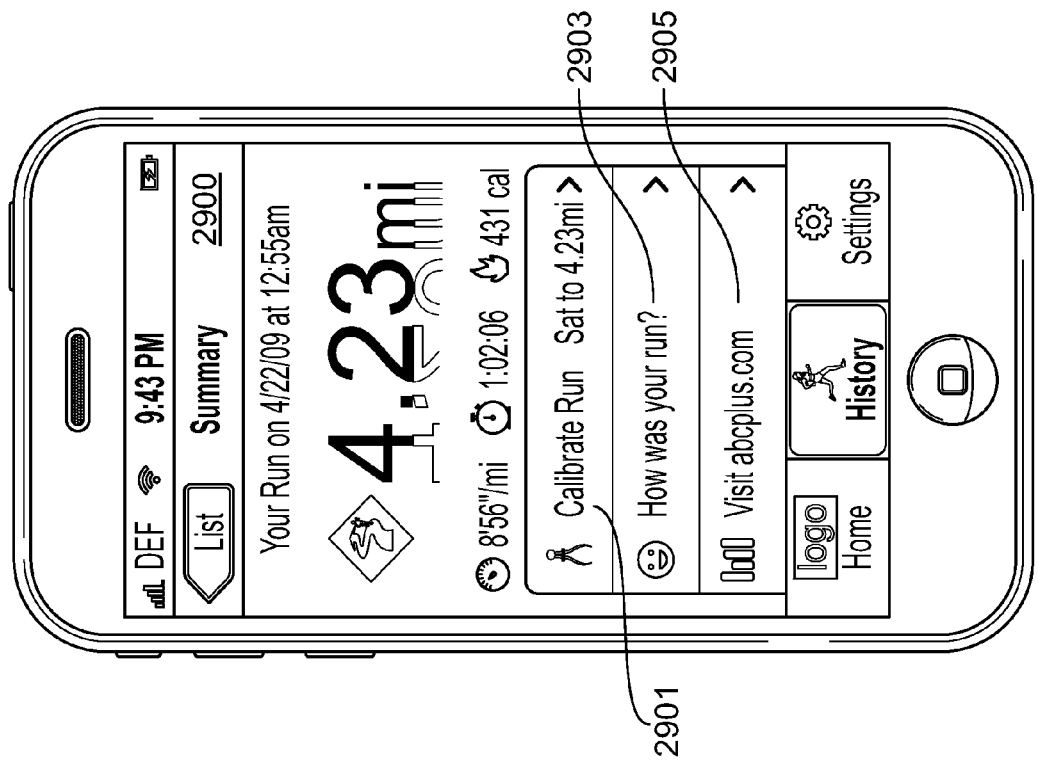
FIG. 29 illustrates an example workout summary for an indoor run according to one or more aspects described herein.

FIG. 29 illustrates a workout summary for an indoor run. In addition to run statistics such as a distance run, pace, time and calories burned, interface 2900 includes a calibrate run option 2901, a mood tagging option 2903 and a service provider site option 2905. Selection of calibrate run option 2901 may allow the user to insure that the recorded statistics of the run is accurate. For example, if the device determines that the user has run 4 miles, but the user actually ran 4.25 miles, the user may adjust the amount through the calibration option 2901.

Figure 30A:
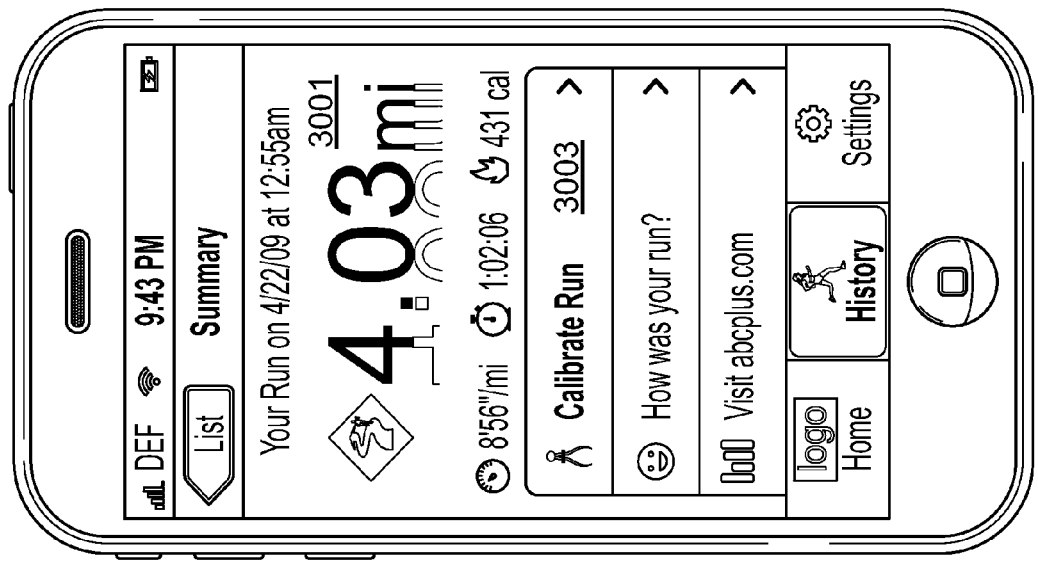
FIGS. 30A-30C illustrate a sequence of example user interfaces in which a user may calibrate the distance run according to one or more aspects described herein.
Figure 30C:
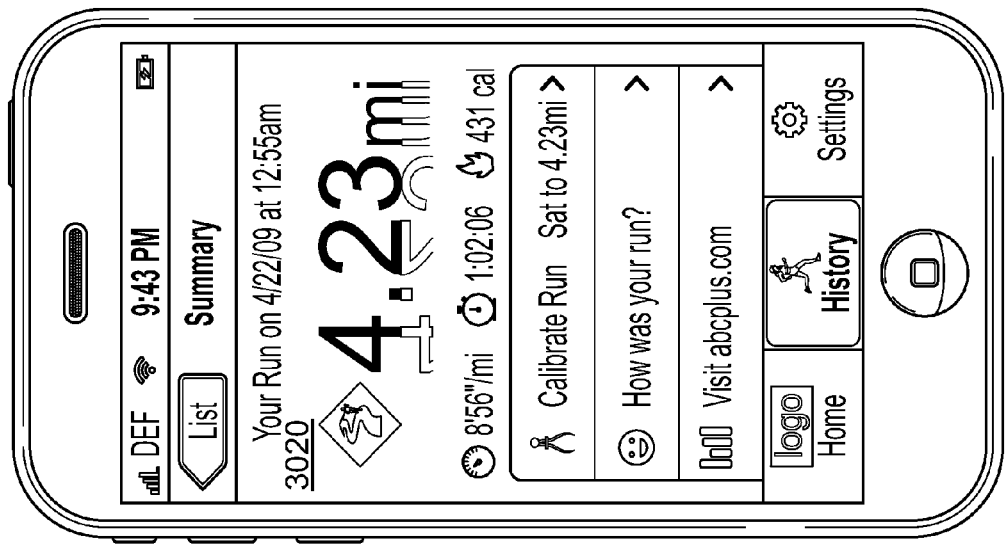
Figure 30B:
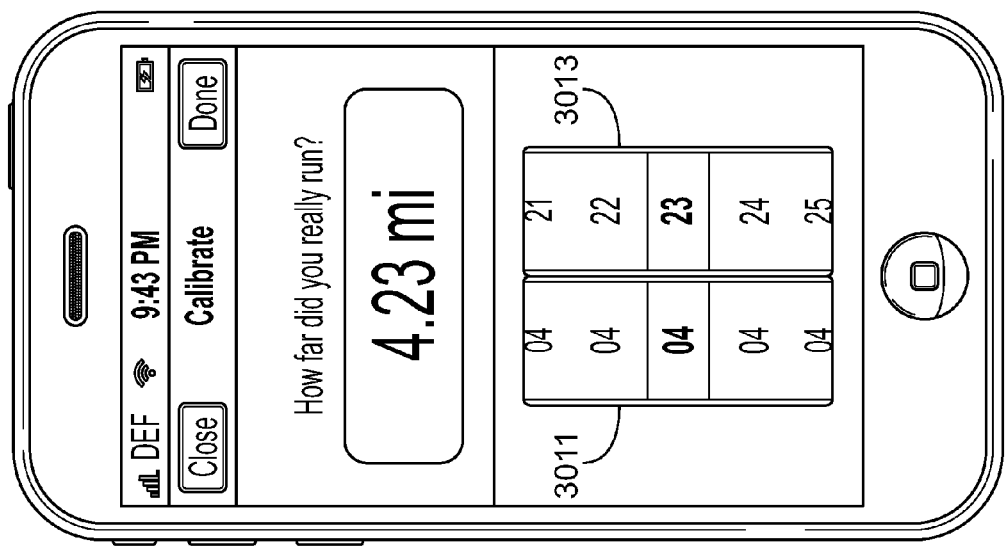

FIGS. 30A-30C illustrate a sequence of user interfaces in which a user may calibrate the distance run. In interface 3001 of FIG. 30A, for example, the workout summary indicates the device detected a total of 4.03 miles run by the user. If the value is not accurate, the user may select calibrate option 3003. FIG. 30B illustrates calibration interface 3010 in which a user may select the number of miles actually run using scroll wheels 3011 and 3013. Once the user has finalized the calibration, the user may return to a workout summary interface such as interface 3020 of FIG. 30C. Interface 3020 may now include the calibrated distance instead of the original distance detected by the device.

Figure 31B:
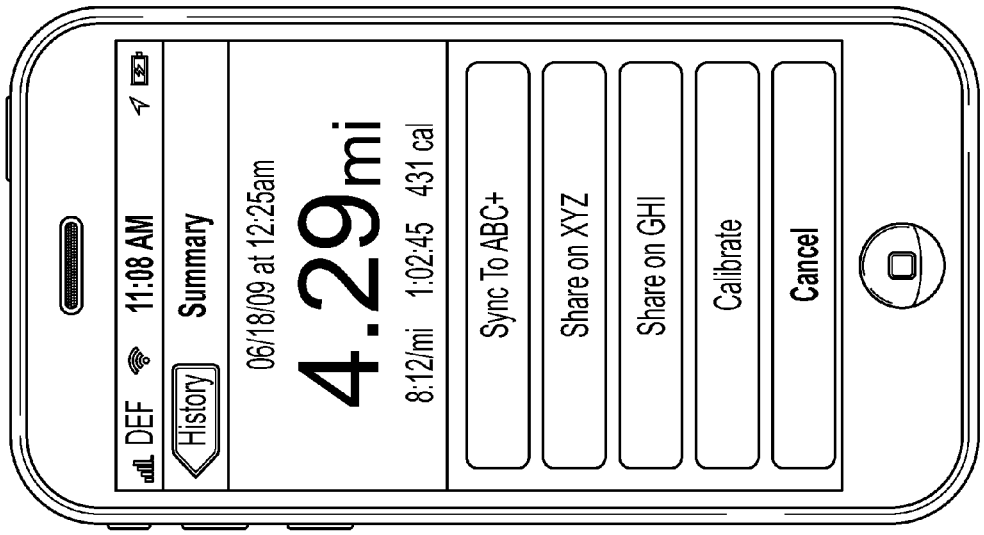
FIGS. 31A-31C illustrate further example interfaces through which the user may calibrate an accelerometer or non-GPS runs according to one or more aspects described herein.
Figure 31A:
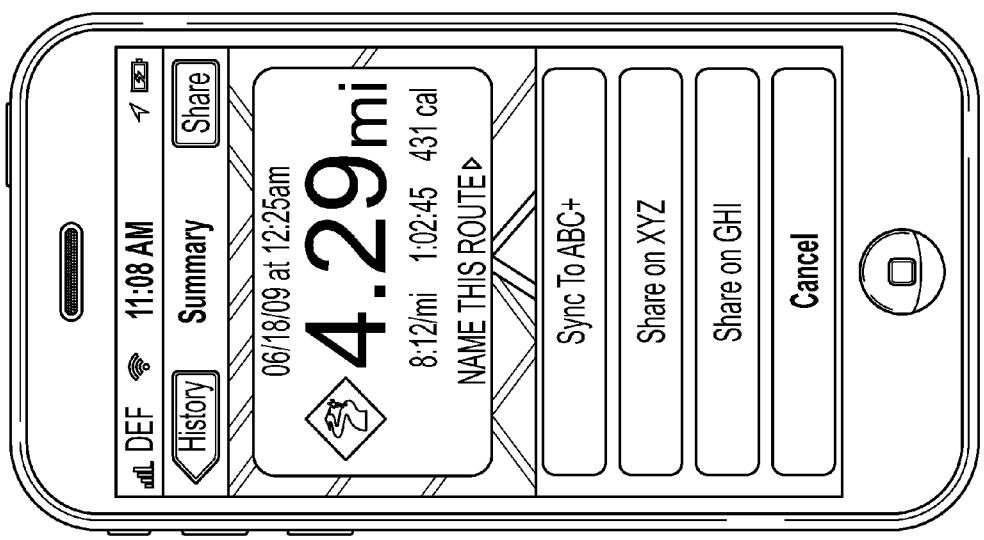
Figure 31C:
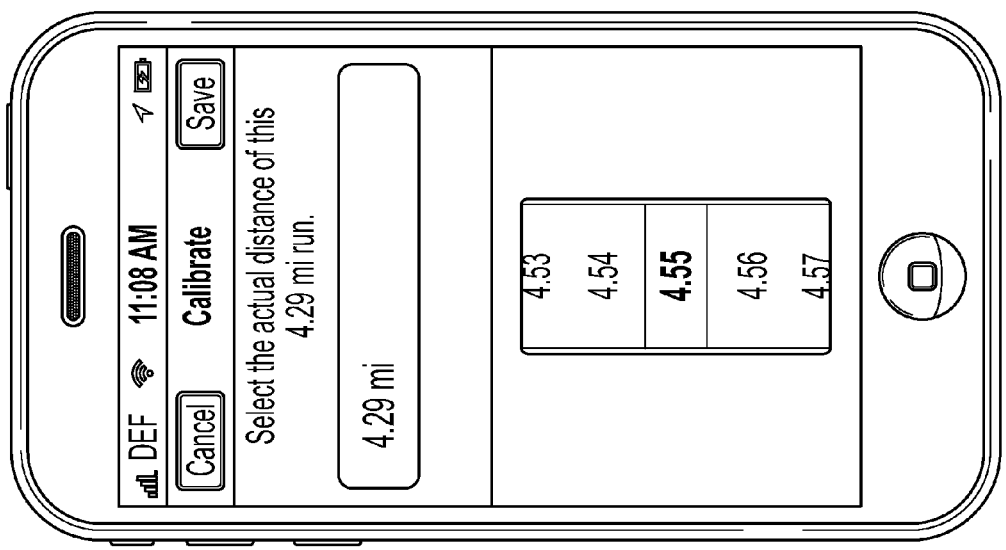

FIGS. 31A-31C illustrate additional example interfaces through which the user may calibrate an accelerometer or non-GPS runs.

Figure 32A:
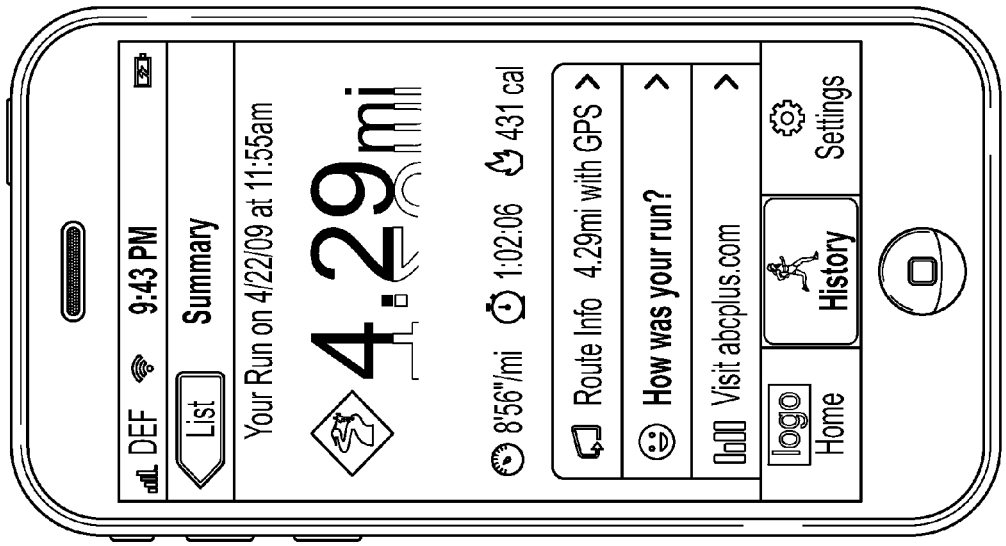
FIGS. 32A-32C illustrate a sequence of user interface through which a user may tag the run based with various types of information.
Figure 32B:
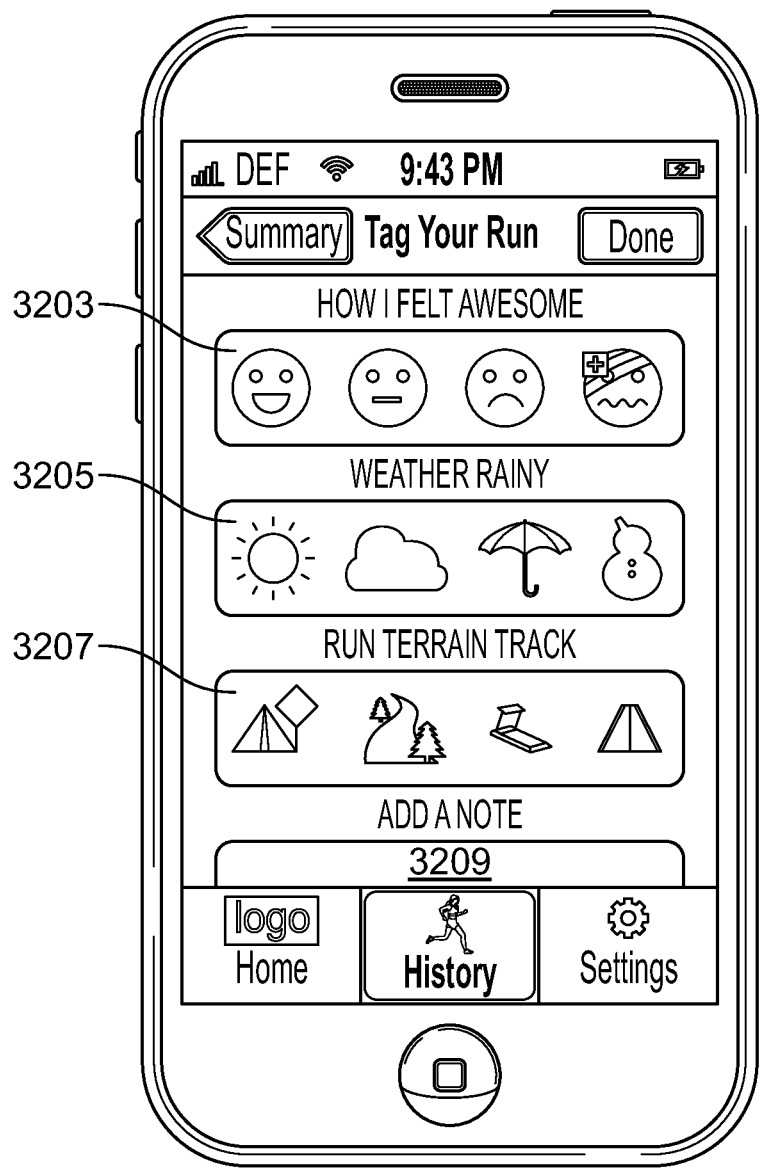
Figure 32C:
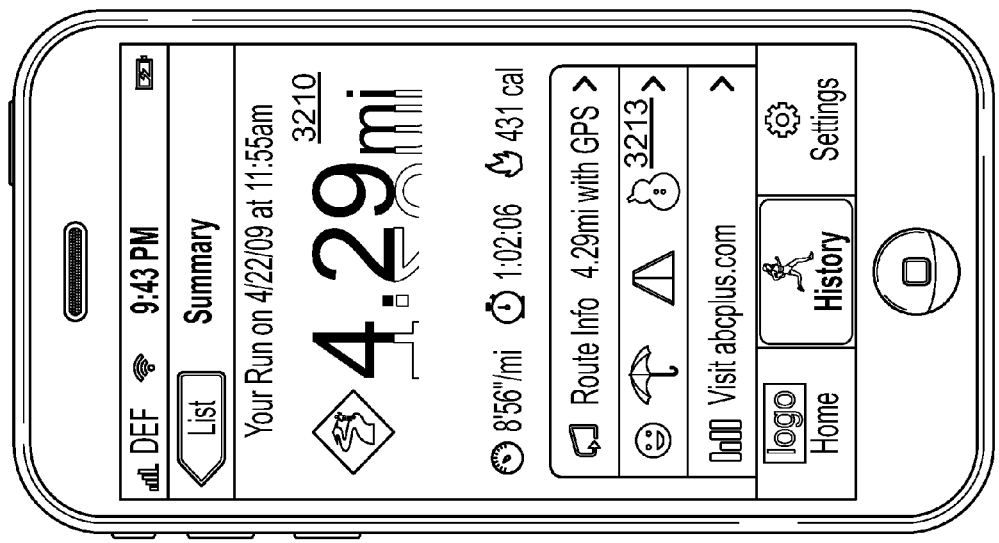

FIGS. 32A-32C illustrate a sequence of user interface through which a user may tag the run based with various types of information. For example, in interface 3201 of FIG. 32B, a user may specify how he or she felt after the run by choosing a mood indicator 3203, weather conditions during run by choosing weather options 3205, a terrain type by selecting a terrain option 3207 and enter notes in notes section 3209. Terrain option 3207 may include exercise equipment such as a treadmill, outdoor terrains such as straight road, a dirt path, a winding road and the like. The user might not be required to enter any of the tags. Thus, the user may tag one, two, or all of the tagging options 3203-3209.

Once the user has completed entering desired tags, the device may return the user to the workout summary interface. FIG. 32C illustrates a summary interface 3210 that displays the tags defined by the user in the workout summary. In particular, the tag icons (e.g., a happy face for a good mood or an umbrella for rainy conditions) may be displayed in the tag option section 3213. The tag icons may replace the text that was previously displayed prior to tagging being completed (e.g., as shown in the interface of FIG. 32A). In one or more arrangements, selecting, hovering over or otherwise interacting with the tagged icons may cause detailed information to be displayed (e.g., in information bubbles).

Figure 33A:
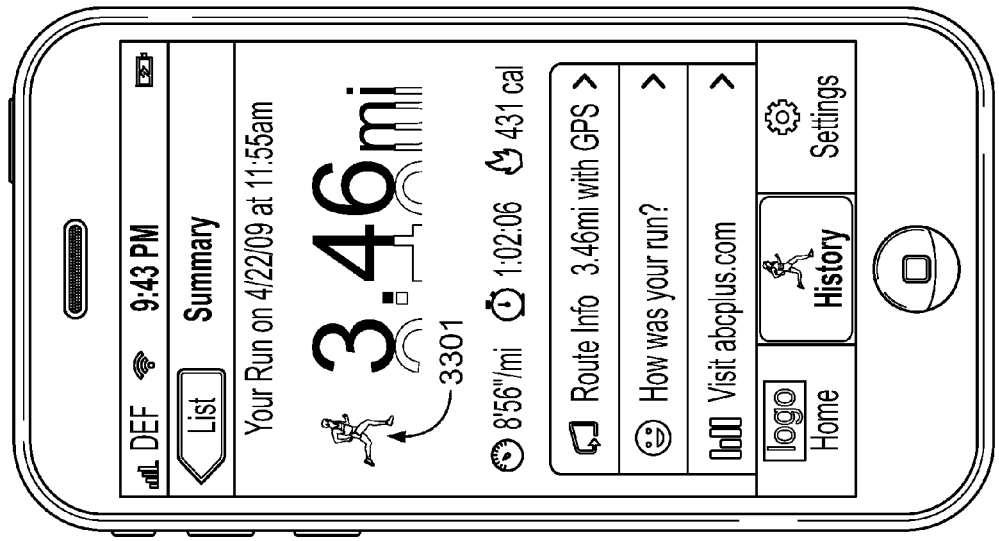
FIGS. 33A-33C illustrate example workout summaries for outdoor runs according to one or more aspects described herein.
Figure 33C:
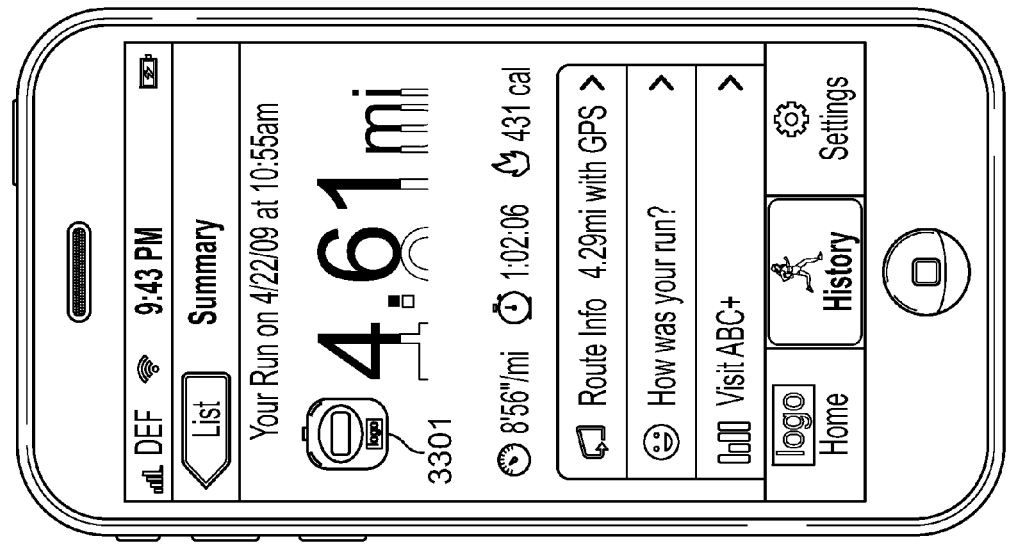
Figure 33B:
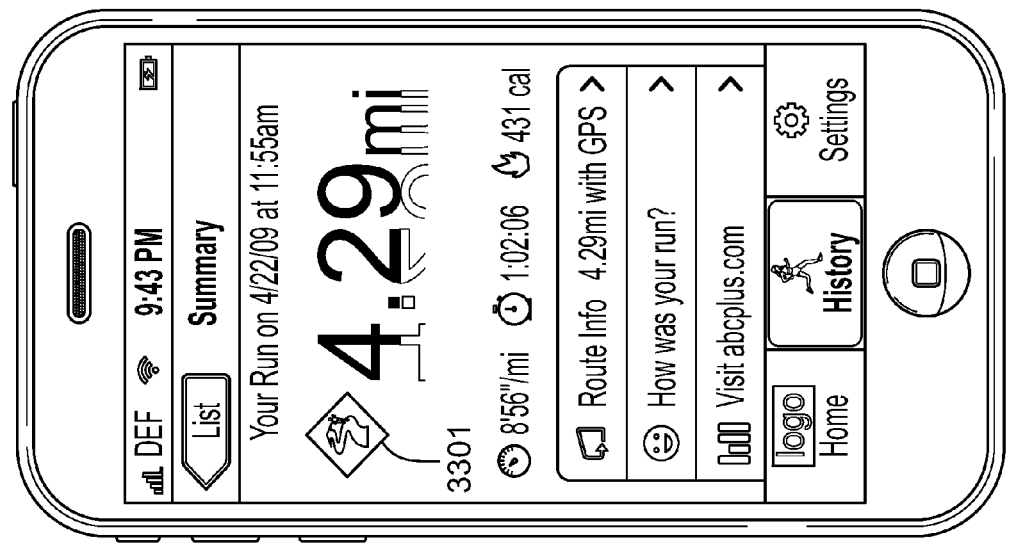

FIGS. 33A-33C illustrate workout summaries for outdoor runs. FIG. 33A illustrates a workout summary for a basic run (e.g., a run without any objectives or goals) while FIG. 33B illustrates a workout summary for a distance run and FIG. 33B illustrates a workout summary for a time run. The run type may be identified by an icon 3301. As noted, an outdoor workout summary might not include a calibrate functionality since the GPS may be considered more reliable and accurate than sensors used to determine an indoor workout (e.g., an accelerometer). Accordingly, each of the interfaces of FIGS. 33A-33C may include a route information option that displays the route taken by the user during the run. For example, upon selection the route information option, the user may be presented with a map with a line identifying the path taken.

FIG. 34 illustrates a route information interface displaying map 3401 along with a line 3403 representing a user's running path. Mile markers 3405 may also be displayed on line 3403 to identify the various mileage points of the run. Additionally, start and end indicators 3407 and 3409, respectively, may be provided in the interface. Still further, the user's fastest and slowest pace points may be identified by markers 3411 and 3413, respectively. Other information may also be displayed to the user depending on the user's preferences. For example, the user may request that time markers be displayed (e.g., every 5 minutes, every minute, every 10 minutes, every hour). Selecting, hovering over or otherwise interacting with the markers 3405-3413 may provide additional detail information including a song played at the point identified by the marker, a pace, a distance, a time, a user's heart rate and/or other information.

Figure 35C:
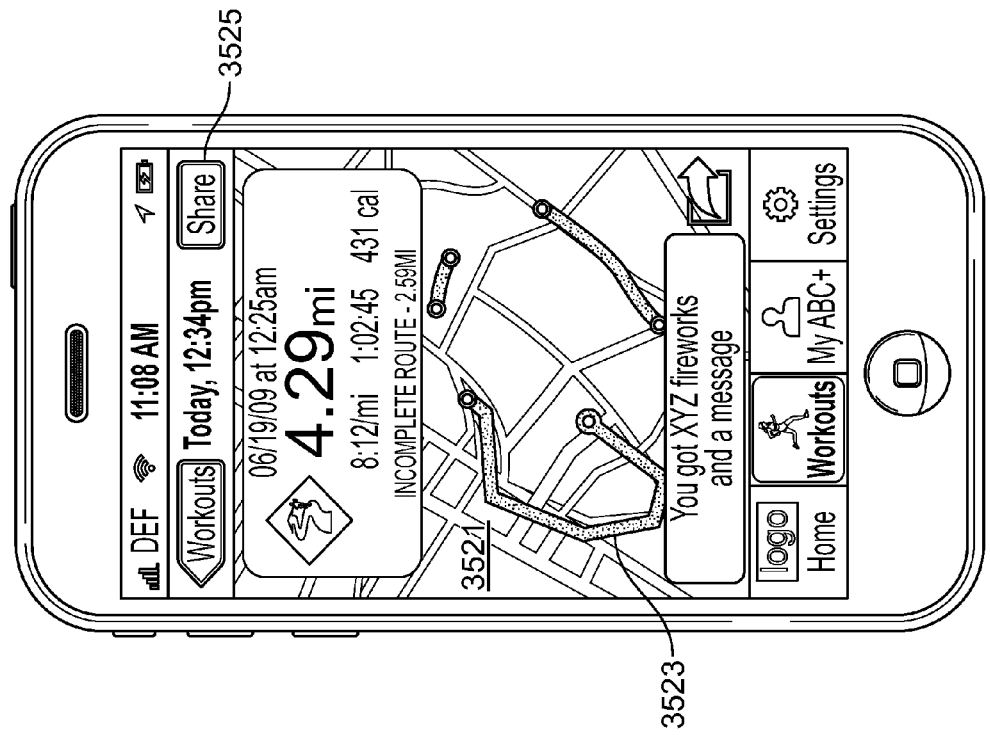
Figure 35B:
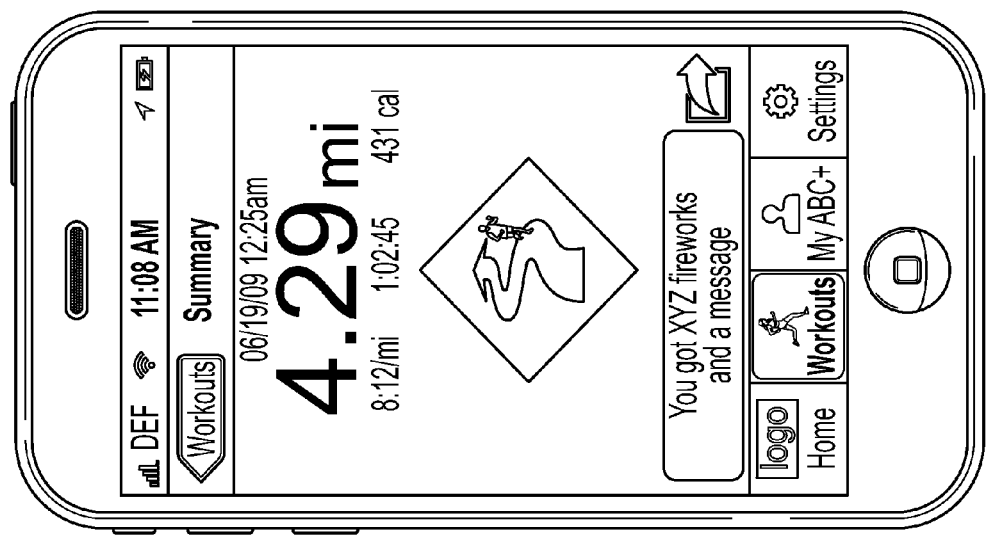

FIGS. 35A-35C illustrate example route summary interfaces in which a map may be displayed if the run was recorded using a GPS or other location determination system while non-GPS recorded runs might not include a map. For example, in FIG. 35A, a map 3501 may be displayed along with a line 3503 representing the route the user took during the run. A summary display 3505 may also be displayed with an option 3507 to name the route. By naming the route the user may be able to more readily identify and select the route for future workouts. According to one or more arrangements, the interface may further include notification 3509 that indicates the user has received messages, accolades or motivational items and an option 3511 to access those messages, accolades and motivational items. In one example, the messages or motivational items may be provided through a social networking site that may be linked to the user's athletic activity monitoring device and/or account.

Figure 36:
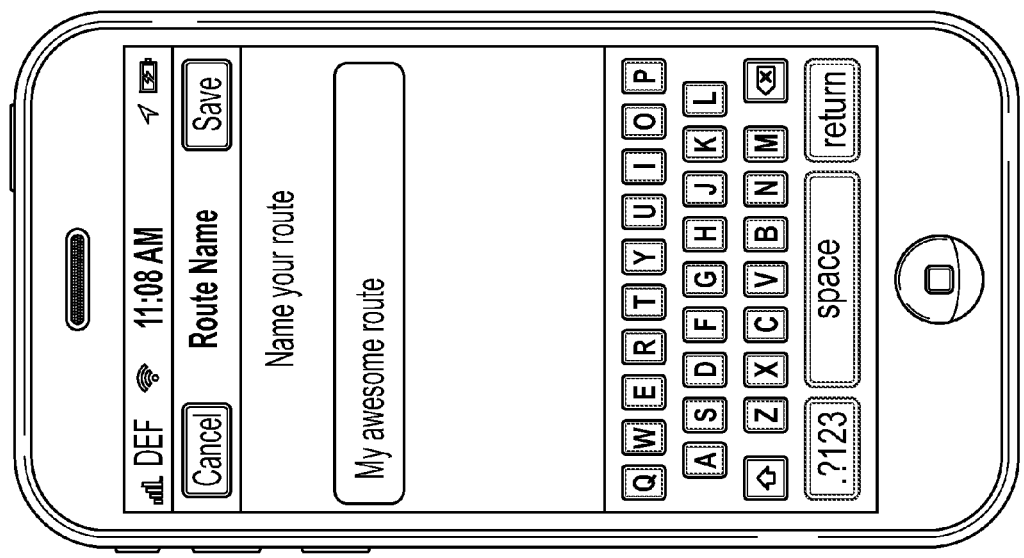
FIG. 36 illustrate an example route naming interface according to one or more aspects described herein.

FIG. 36 illustrates an example route naming interface.

FIG. 35C illustrates a map 3521 including a route summary for a run that was only partially recorded using a GPS device. Accordingly, portions of the route 3523 may be missing due to a lack of GPS data for those portions of the run. Additionally or alternatively, route and workout information may be shared with one or more other users, friends, social network sites and the like. For example, a share option 3525 may be displayed and selected by the user to share the information. Sharing of workout and route information, achievements and the like is discussed in further detail below. In one or more configurations, if GPS data is unavailable, a mobile device may switch to cellular signal triangulation to determine a current position. This information, along with accelerometer data, may provide substitute workout information to fill in any missing GPS information. For example, cellular triangulation may provide location of the runner based on a predefined schedule (e.g., continuous, every 30 seconds, every 5 seconds, every 15 seconds, every minute, aperiodic schedules) while the accelerometer may provide pace and distance information to corroborate the user's location determined using the triangulation data. Portions of a route (e.g., route 3523) that are measured using cellular triangulation and accelerometer systems may be displayed differently (e.g., different color, different pattern) than portions of the route recorded using GPS data.

Figure 37A:
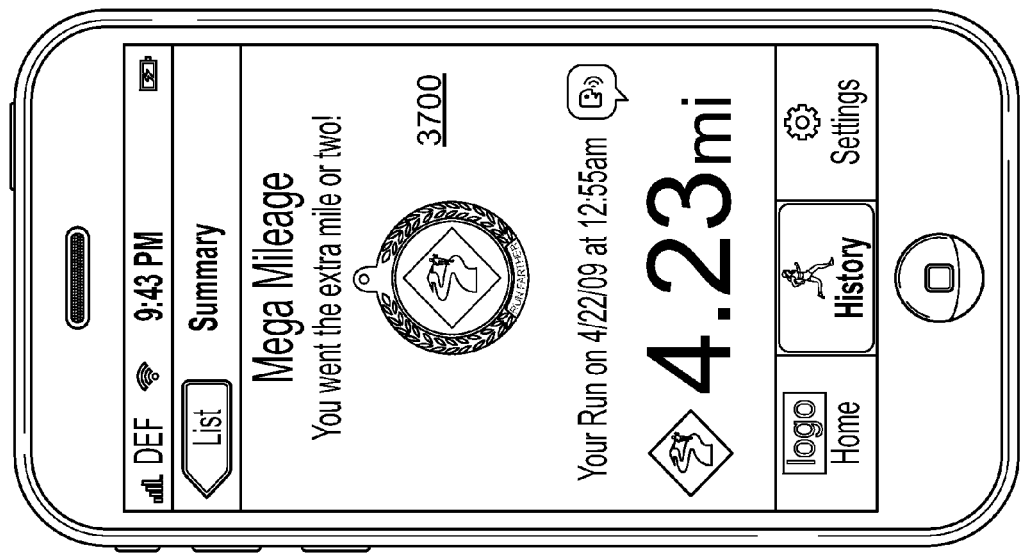
FIG. 37A illustrates an example summary interface displaying a mileage medal for setting a new distance record according to one or more aspects described herein.

When the user completes an improvement run, the user may be presented with additional information in the workout summary. For example, if the user completed the objective set in the improvement run, the user may be provided with a medal or other indicator for the achievement. In FIG. 37A, summary interface 3700 displays a mileage medal for setting a new distance record. The medal may be added as an indicator or tag for the workout entry in a workout history.

Figure 37C:
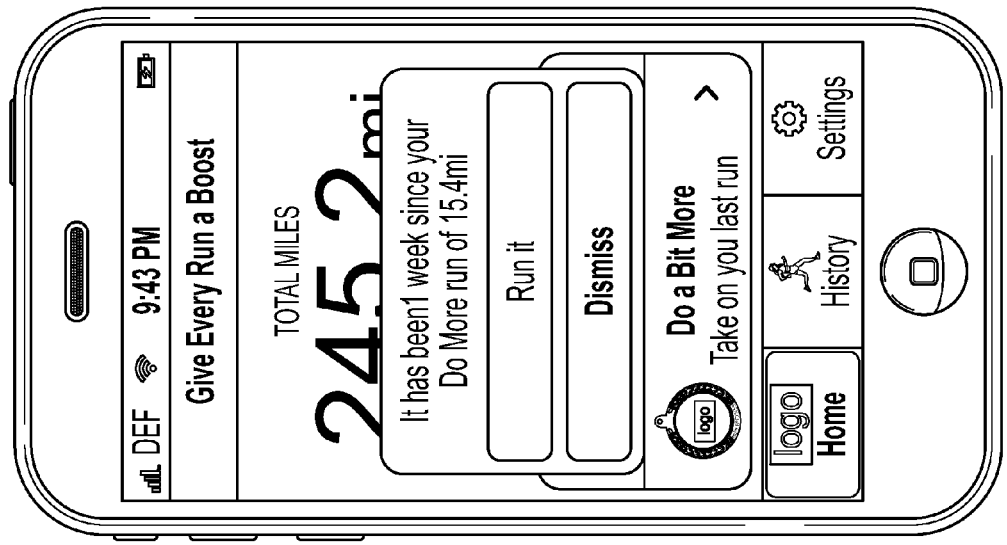
FIG. 37C illustrates an example reminder interface.
Figure 37B:
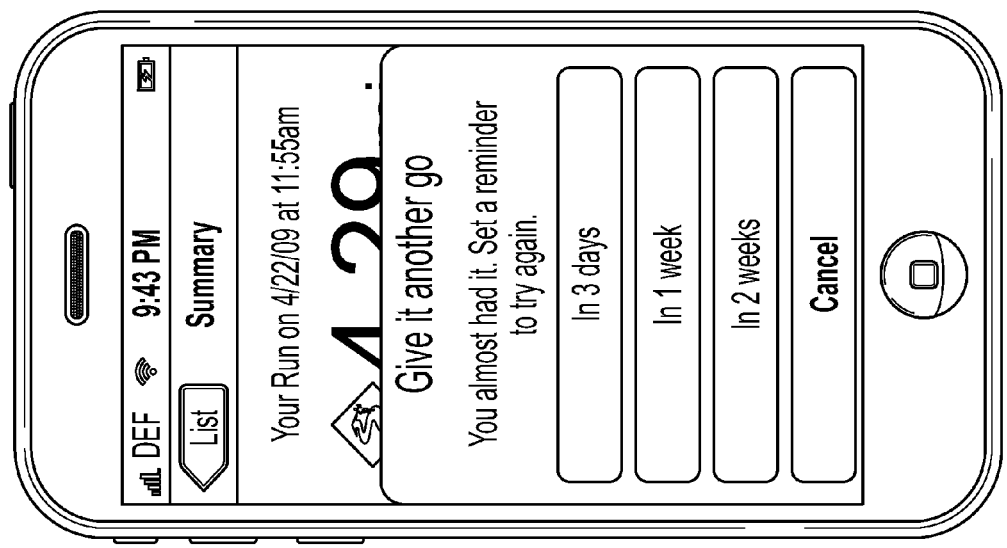
FIG. 37B illustrates an example interface that may be displayed if a user fails to complete an objective or goal.

If, however, the user does not reach the goal or objective of the improvement run, the device may display an interface 3710 of FIG. 37B that encourages the user to try the improvement run again (e.g., with the same objective or goal). For example, interface 3710 may provide a selection menu that asks the user to set a time (e.g., in 3 days, in a week in 2 weeks, etc.) to re-try the improvement run.

Reminders may be provided to the user regardless of whether the user completed the improvement run. The reminder may be used to motivate the user to achieve additional improvements or to remind the user to re-try an improvement run that he or she previously attempted but did not complete. FIG. 37C illustrates an example reminder interface. In interface 3720, the user may choose to initiate or schedule a run or to dismiss the reminder.

Figure 38B:
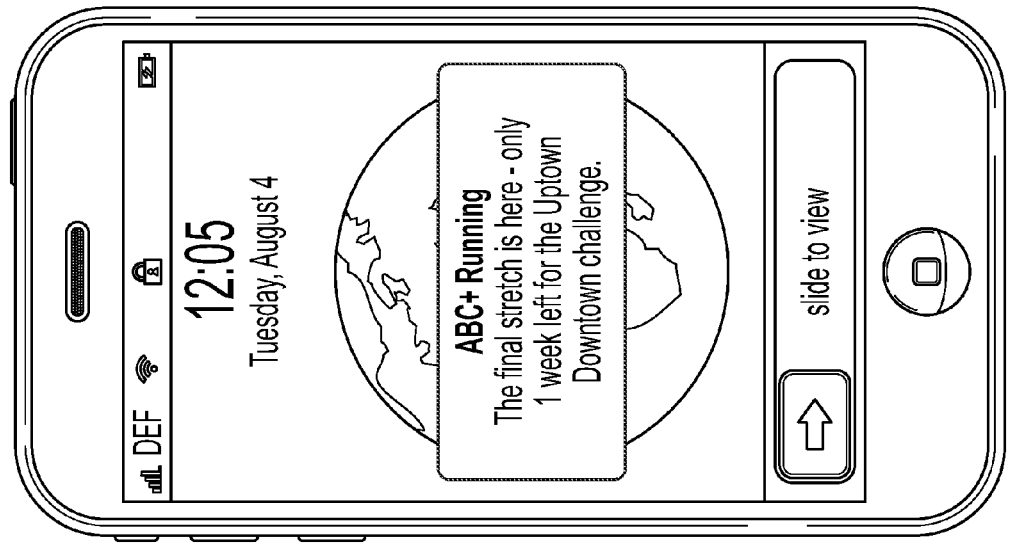
FIGS. 38A and 38B illustrate further example alert and reminder messages that may be displayed to a user according to one or more aspects described herein.
Figure 38A:
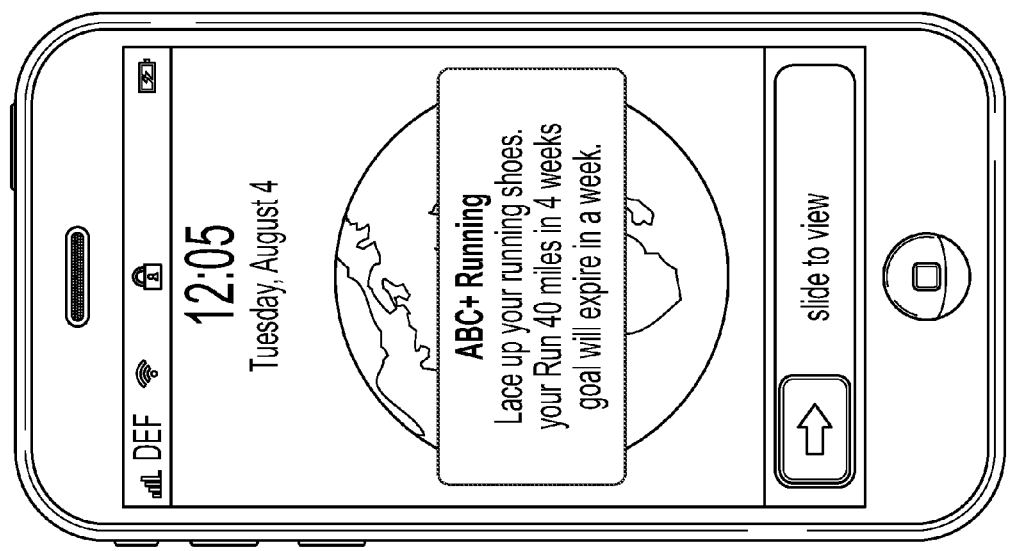

FIGS. 38A-38B illustrate further example alert and reminder messages that may be displayed to a user. The alerts or messages may be triggered and generated by the mobile device or may be received from a remote network server. For example, the mobile device may receive push notifications from a remote fitness monitoring service provider. Notifications may also include messages from other users, friends, system administrators, coaches and the like.

Figure 39B:
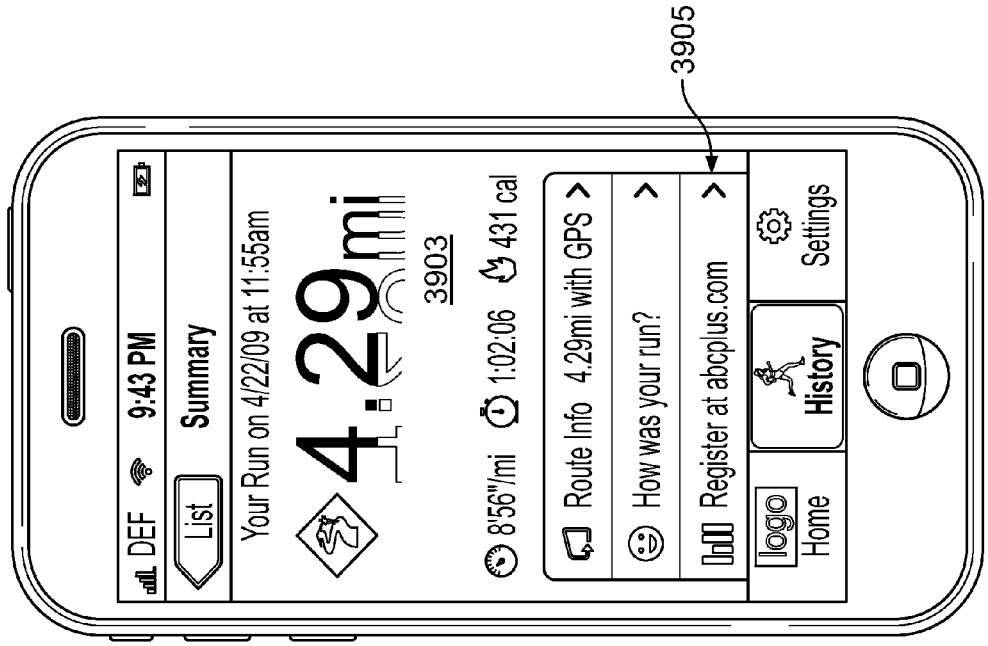
FIG. 39B illustrates an example workout summary interface that includes a registration option according to one or more aspects described herein.
Figure 39A:
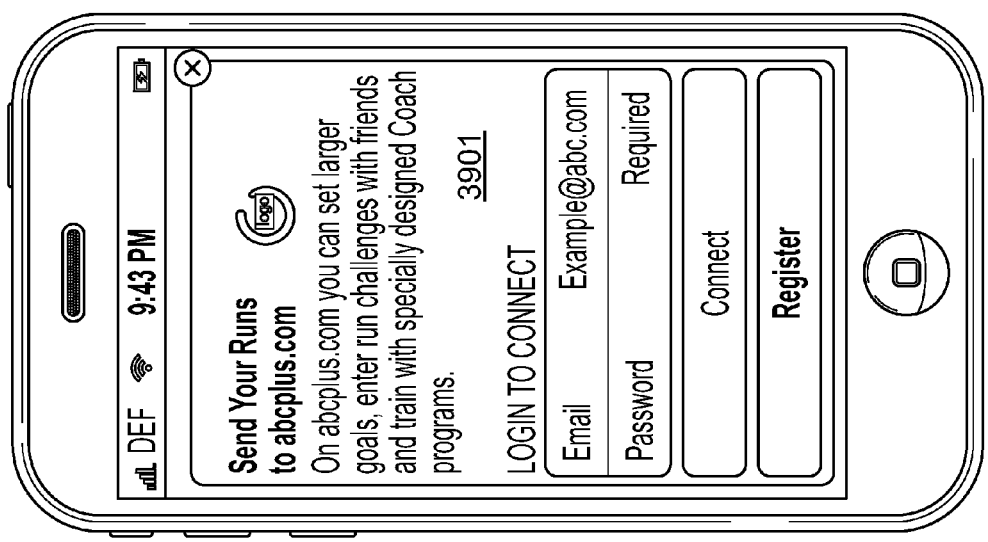
FIG. 39A illustrates an example interface that may be displayed if the user is a member of the service provided by an athletic activity monitoring service provider according to one or more aspects described herein.

As described herein, a user may synchronize workout data with an athletic activity monitoring service provider. If a user has completed his or her first run, the device may display various interfaces in conjunction with the workout summary that allow the user to synchronize his or her data with the service provider. FIG. 39A illustrates an interface 3901 that may be displayed if the user is a member of the service provided by the fitness monitoring service provider. FIG. 39B, on the other hand, illustrates workout summary interface 3903 that includes an option 3905 to register with the service provider.

Figure 40B:
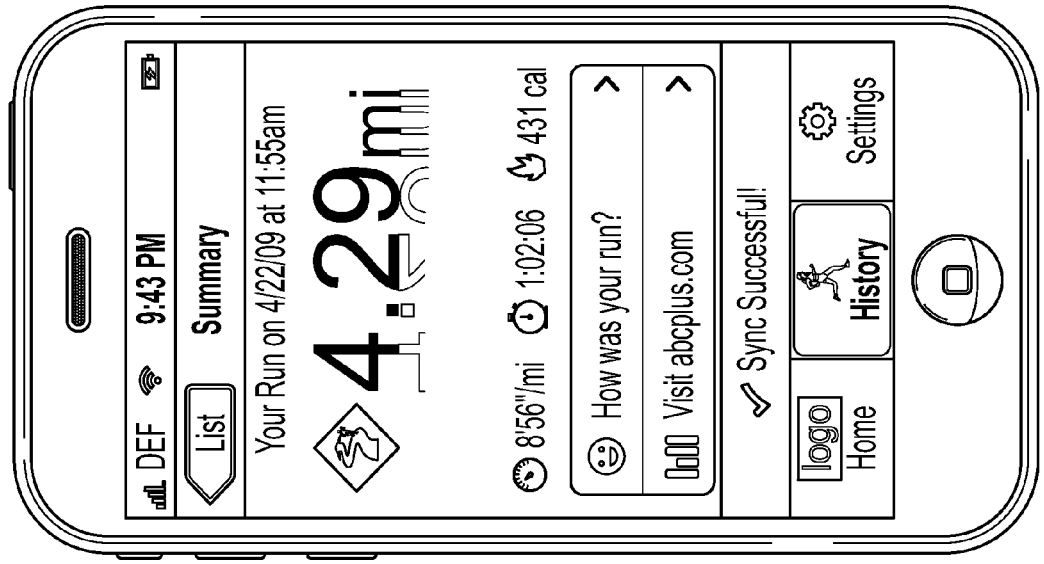
FIGS. 40A-40C illustrate a sequence of example interfaces through which data may be synchronized with a service provider according to one or more aspects described herein.
Figure 40A:
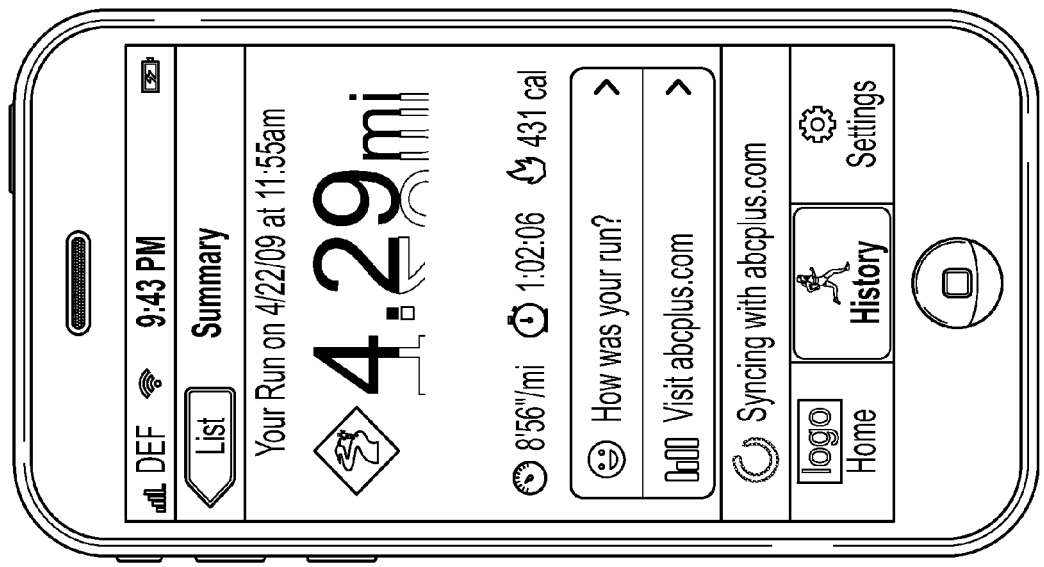
Figure 40C:
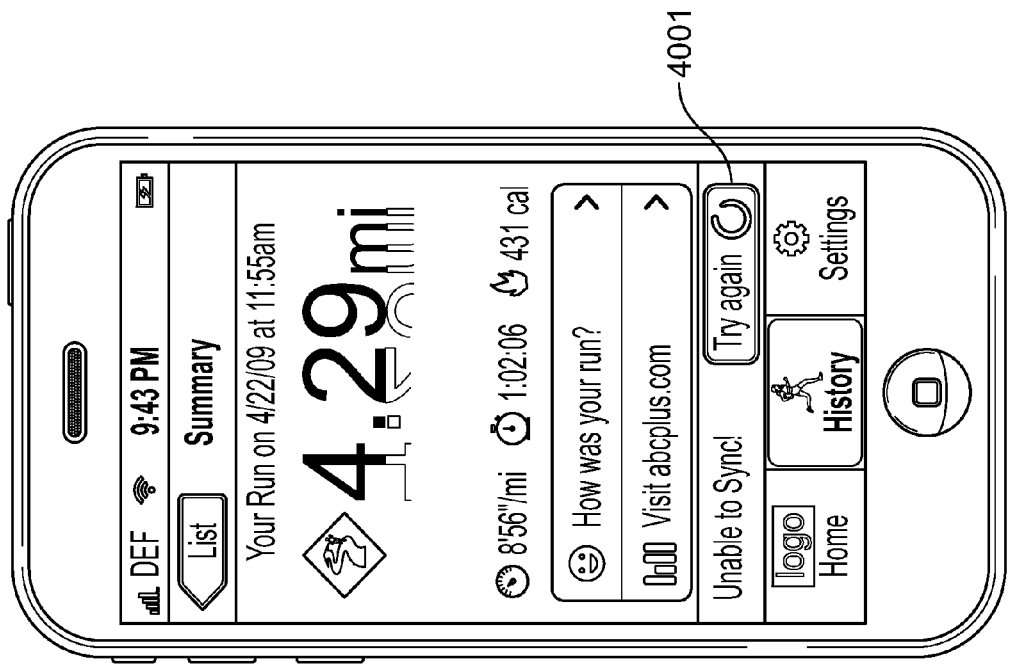

Workout data may be synchronized during a workout summary phase or while viewing a workout history. FIGS. 40A-40C illustrate a sequence of interfaces through which data may be synchronized with the service provider. For example, in the interface of FIG. 40A, the interface may indicate a synchronization in progress message while the interface of FIG. 40B indicates a successful synchronization message. In another example, the interface of FIG. 40C indicates an unsuccessful synchronization message with an option 4001 to reattempt the synchronization.

Figure 41A:
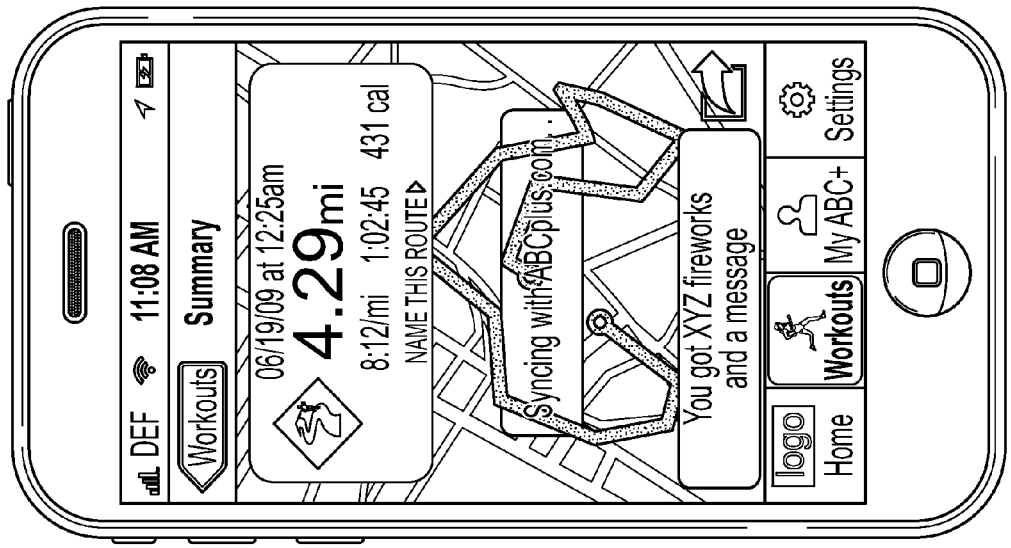
FIGS. 41A-41C illustrate example workout summary interface through which synchronization may be conducted.
Figure 41C:
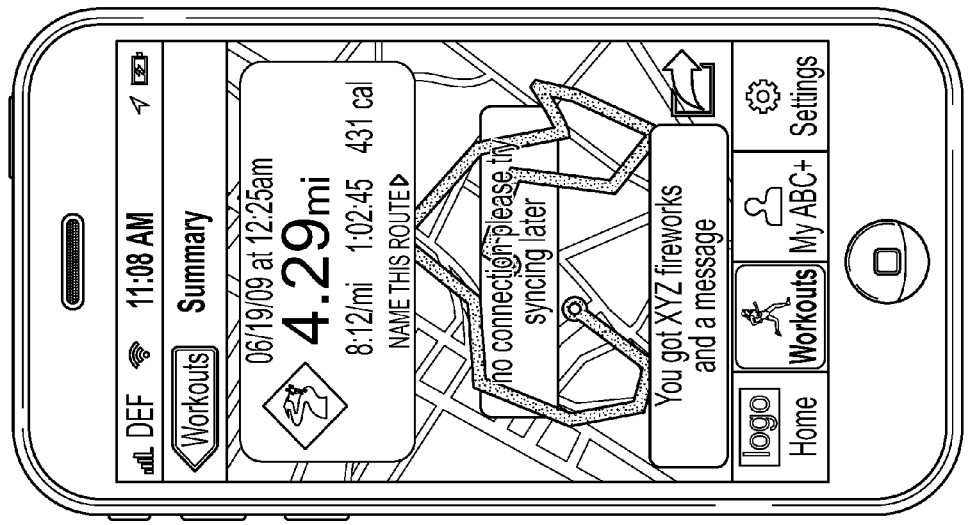
Figure 41B:
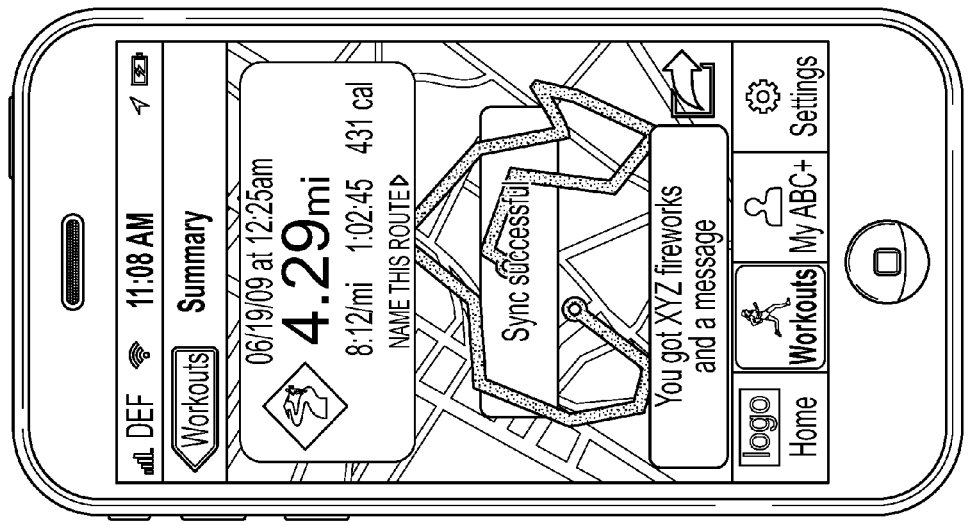

Synchronization may also be performed in a route summary screen such as those illustrated in FIGS. 41A-41C. For example, each of the route summary interfaces may be overlaid with a semi-transparent message that indicates the data is being synched, has been synched or that a connection is not available.

Figure 42B:
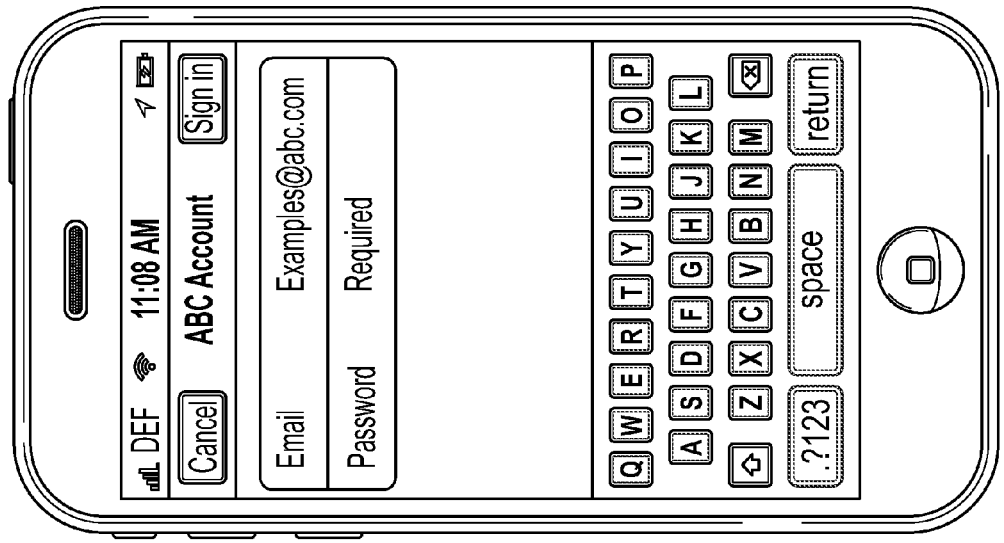
FIGS. 42A-42C illustrate example interfaces through which a user may synchronize athletic activity data by login into or creating a service provider account according to one or more aspects described herein.
Figure 42A:
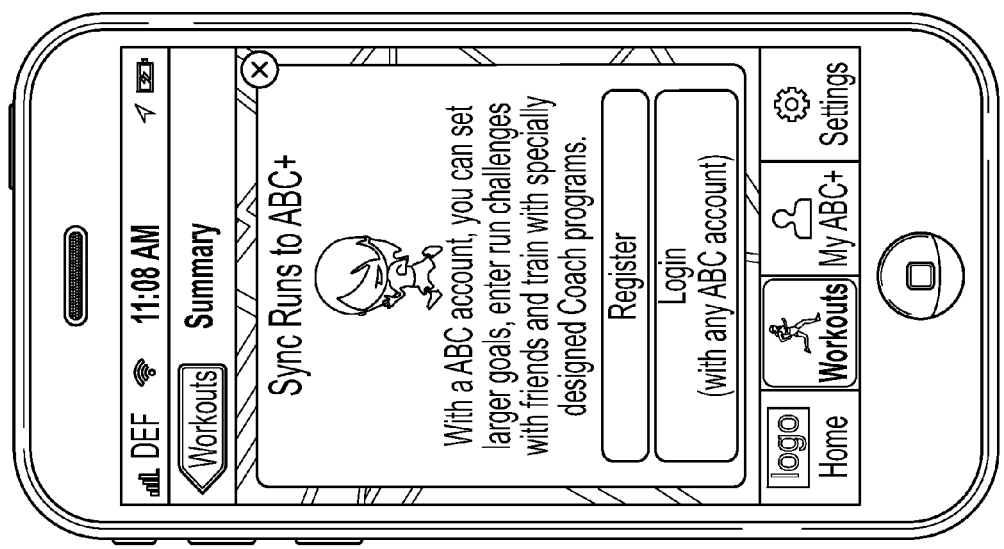
Figure 42C:
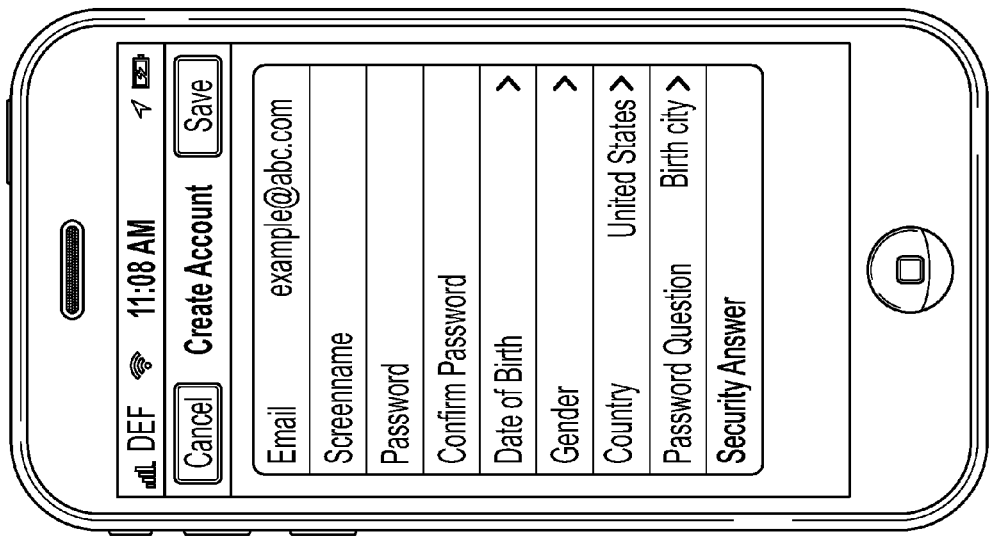

Additionally or alternatively, a synchronization message may include asking the user to register or login as illustrates in FIG. 42A. The user may subsequently login or create an account through interfaces of FIGS. 42B and 42C, respectively.

Figure 43:
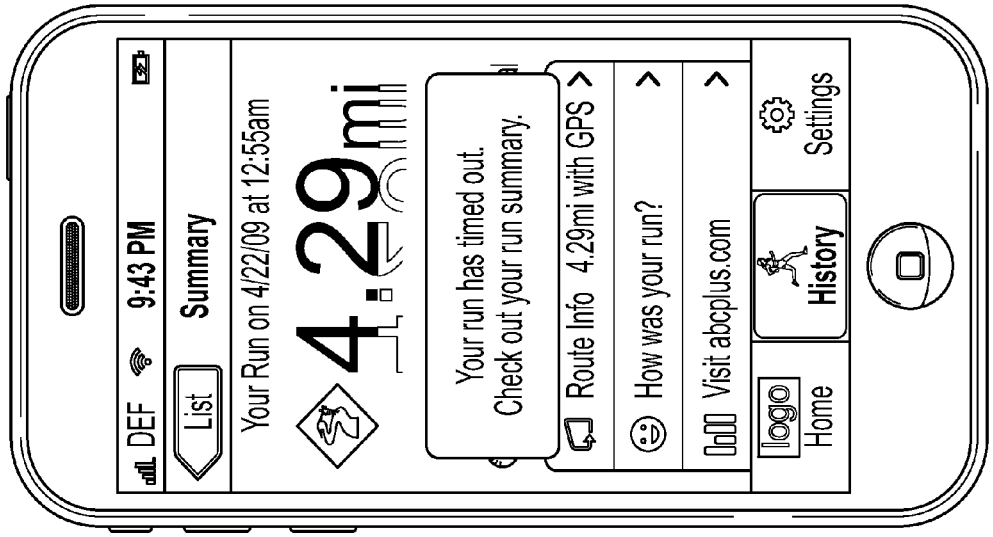
FIG. 43 illustrates an example interface with a message indicating that a workout has timed out according to one or more aspects described herein.

According to one or more aspects, if a run timed out instead of being completed, the user may be provided with an alert message with such a notification. FIG. 43 illustrates an interface with such a message. A run may time out if no athletic activity is detected for a specified amount of time. For example, if a user does not exhibit any athletic activity for 5 continuous minutes, 10 continuous minutes, 30 continuous minutes or the like, the device may automatically end the run and generate a workout summary with an alert message advising of the time out condition. According to one or more aspects, a point at which the run timed out may be displayed on a route map if the run was tracked using GPS or other location determination system. Other location determination systems may include triangulation using cellular signals, Wi-Fi (e.g., the user's location being equated to the location of a Wi-Fi service provider), determining a network service provider location and the like.

Audio messages may also be provided upon completion of a run. For example, the user may be congratulated for completing a longest workout (e.g., either in duration or distance). Other messages may be provided for accepting a mid-run challenge and meeting that challenge. Audio messages may be provided by an automated voice or by a celebrity or friend.

History

Figure 44B:
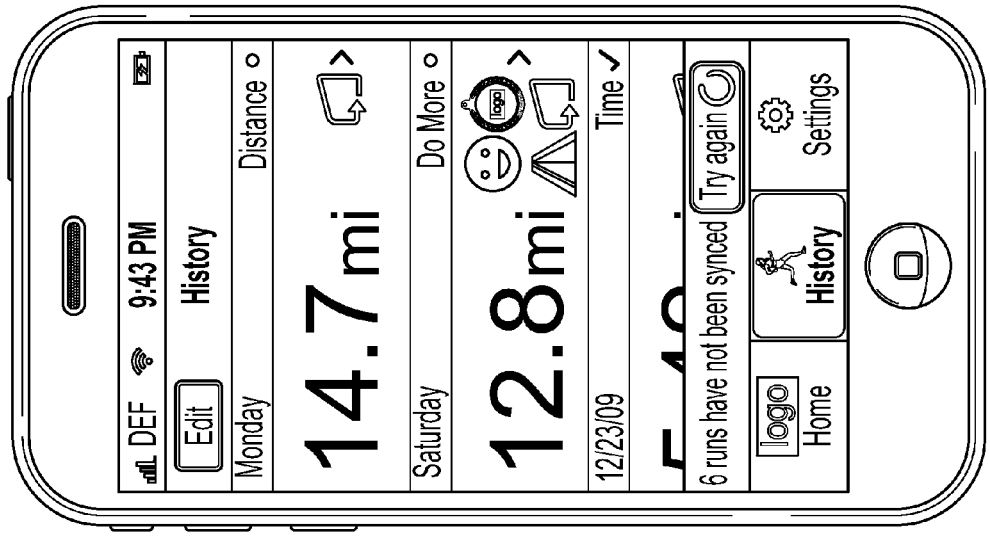
FIGS. 44A-44C illustrate a series of examples interfaces in which a synchronization process is performed according to one or more aspects described herein.
Figure 44A:
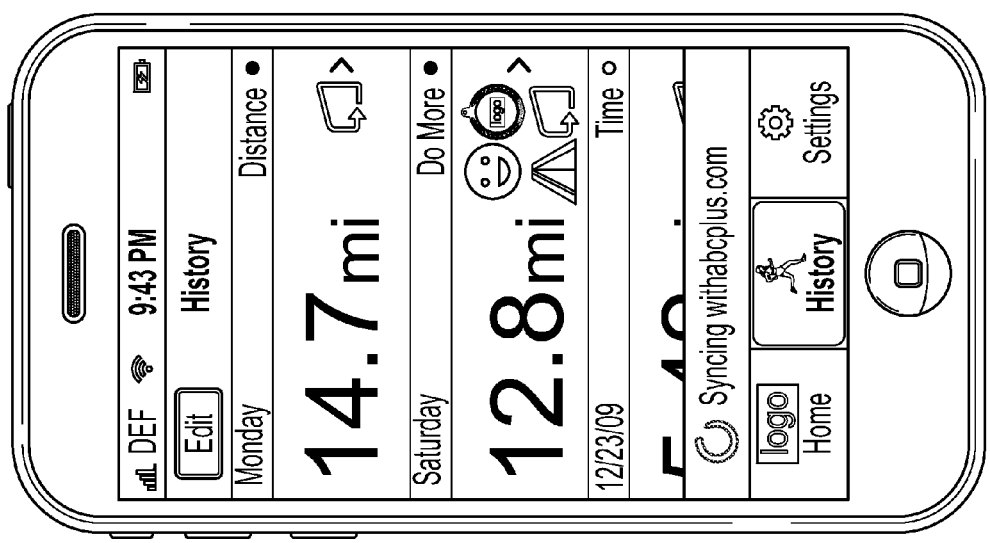
Figure 44C:
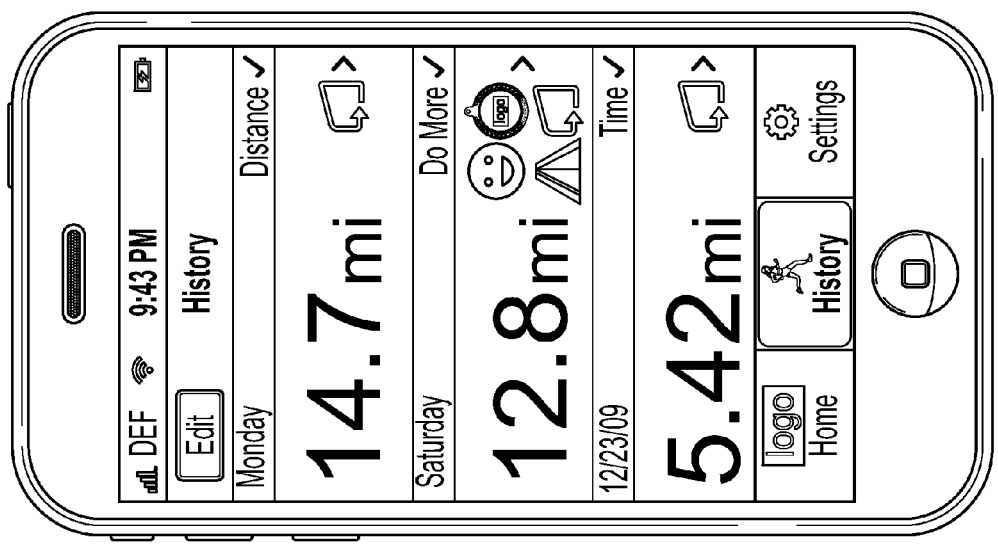

In a history list view, the user may be able to view details and summaries of workouts previously performed and recorded. Additionally or alternatively, the data may be synchronized with a service provider in the history view. FIGS. 44A-44C illustrates a series of interfaces illustrating the synchronization process. Synchronization may be automatic or may be triggered by a user command. If synchronization fails, the synchronization may be re-tried by a user command or automatically based on a predefined retry schedule. Synchronization may be performed each time the history view is loaded or when new workouts have been added since a previous synchronization time. A synchronization history may be stored to facilitate the scheduling of future synchronizations.

Figure 45A:
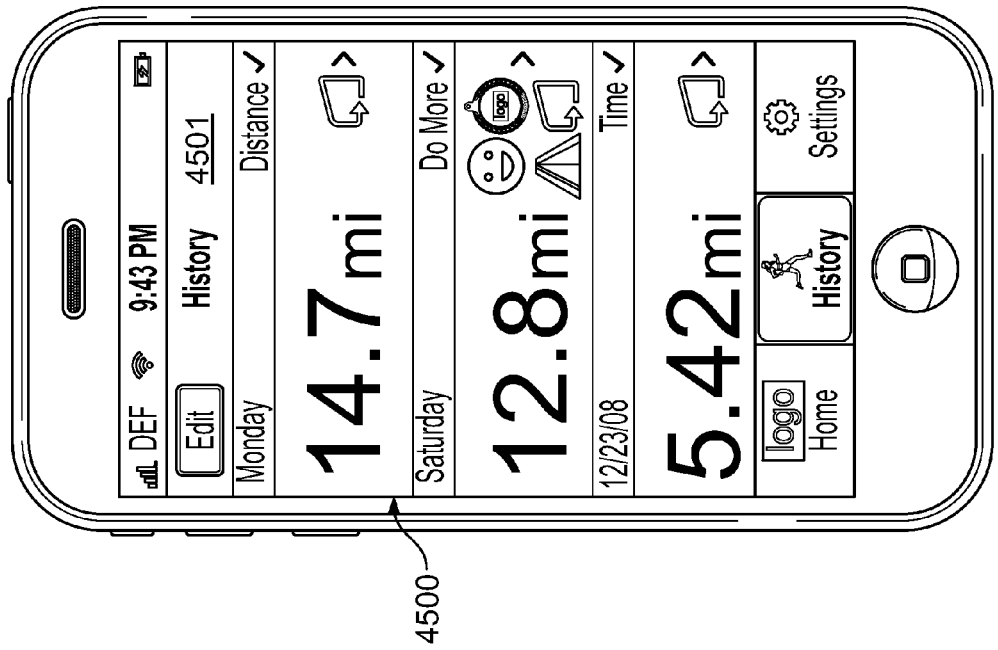
FIGS. 45A and 45B illustrate interfaces through which a user may delete entries from a workout history according to one or more aspects described herein.
Figure 45B:
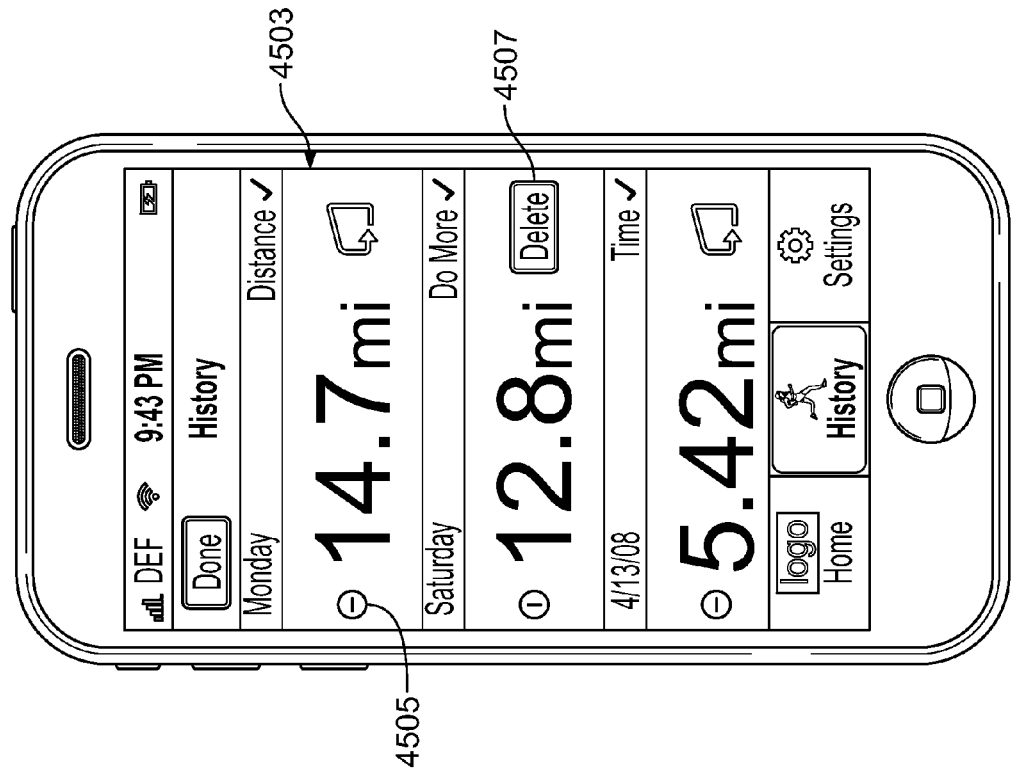

The user may further edit the history list to delete any undesired workout records. For example, in interface 4500 of FIG. 45A, the user may select edit option 01. Upon selecting edit option 4501, interface 4500 may change to provide deletion options. FIG. 45B illustrates a deletion interface 4503 through which a user may delete one or more entries. The user may use options 4505 to select the entries he or she wishes to delete. The user may be required to confirm the deletion by subsequently select a second deletion option 4507. Alternatively, the user may select option 4505 to mark the entries that are to be deleted. Upon selection a complete or confirm option 4509, the marked entries may be automatically deleted. The user may be required to confirm the deletions in either instance.

Figure 46A:
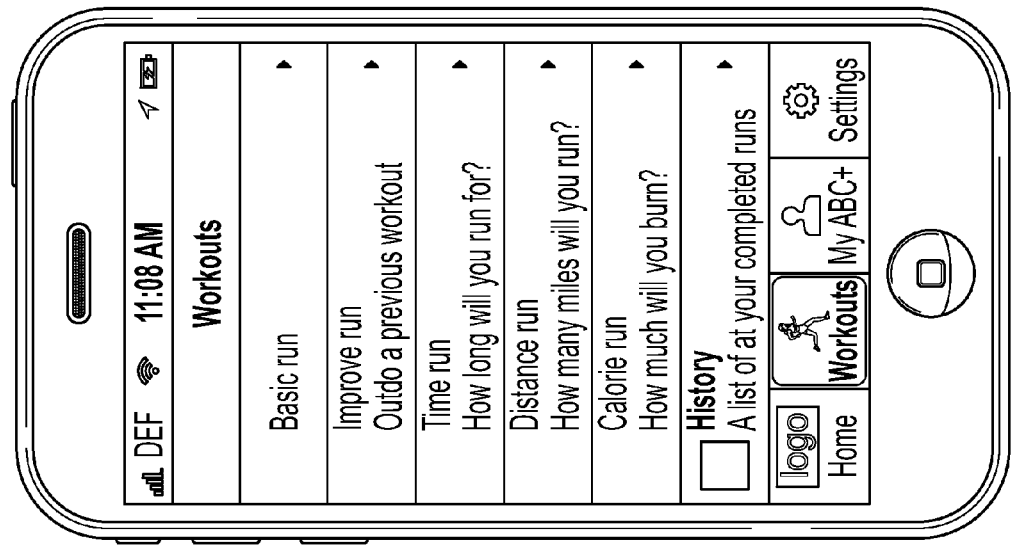
FIGS. 46A-46C illustrate additional example interfaces that may be displayed to convey history information to a user according to one or more aspects described herein.
Figure 46C:
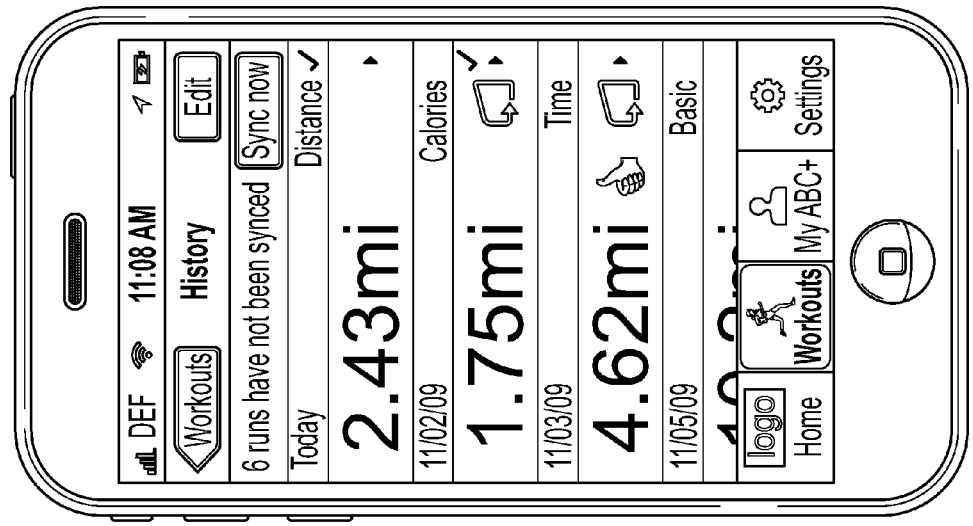
Figure 46B:
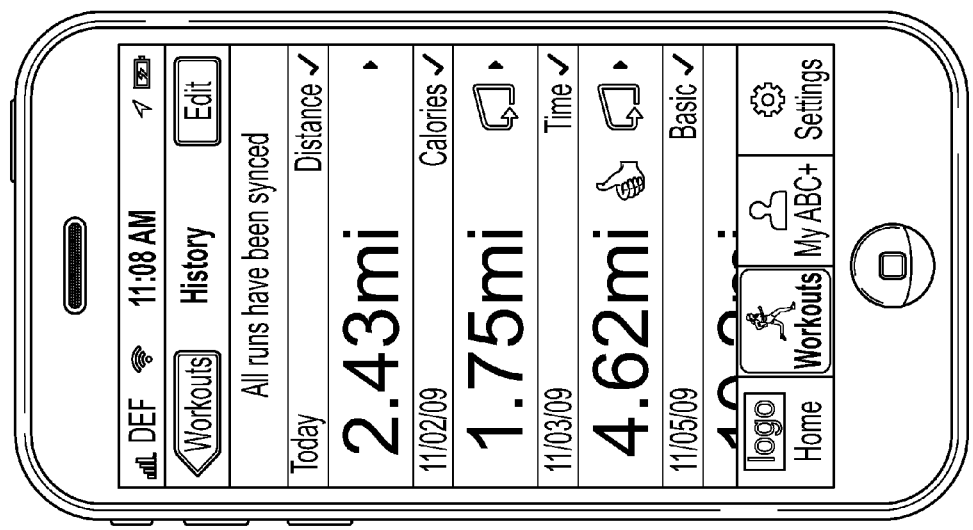

FIGS. 46A-46C illustrate additional example interfaces that may be displayed to convey history information to a user. In FIGS. 46B and 46C, for example, the interfaces may display an indicator or message that identifies whether any run information has not yet been synched with a service provider. If not, the interface may provide a synchronization option to allow the user to synchronize the data immediately (as shown in FIG. 46C). Alternatively or additionally, the user may schedule synchronization for a future date or time.

Settings

Figure 47B:
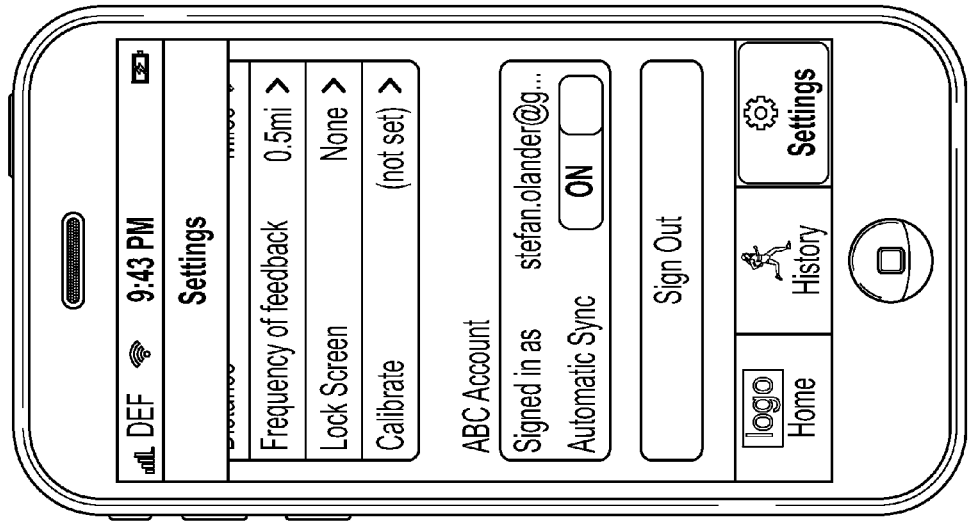
FIGS. 47A and 47B illustrate example portions of various settings interfaces for configuring an athletic activity monitoring device and application according to one or more aspects described herein.
Figure 47A:
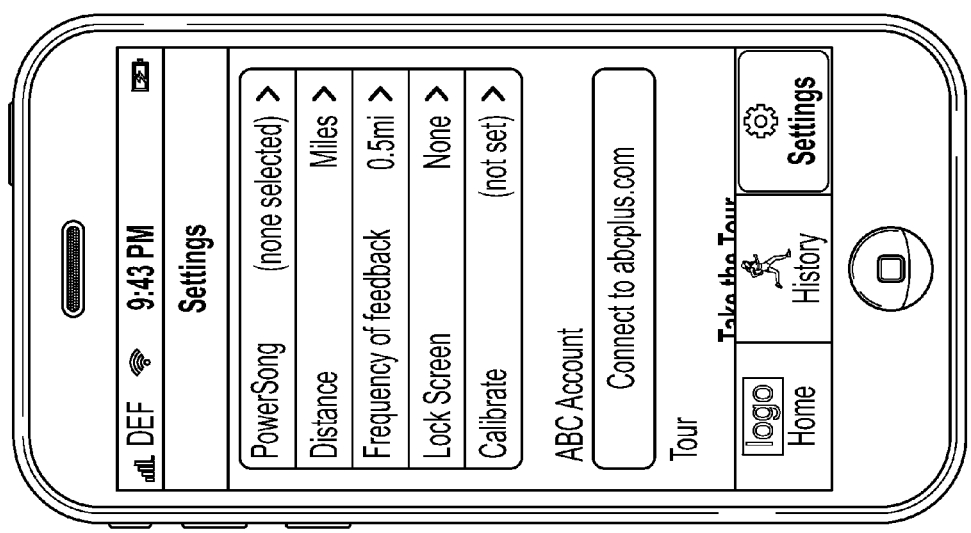
Figure 48B:
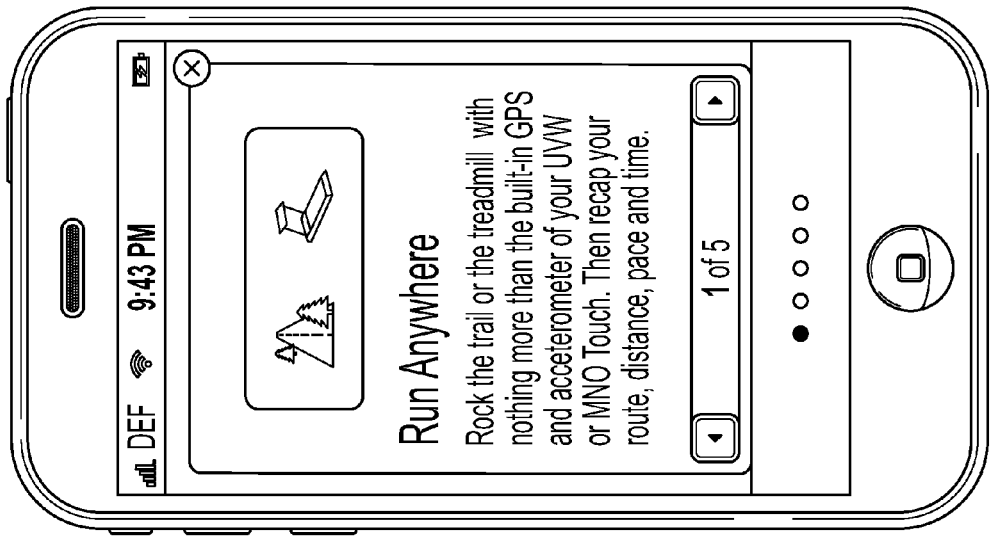
FIGS. 48A-48F illustrate example tour interfaces that provide detailed information describing the available features and functions according to one or more aspects described herein.
Figure 48A:
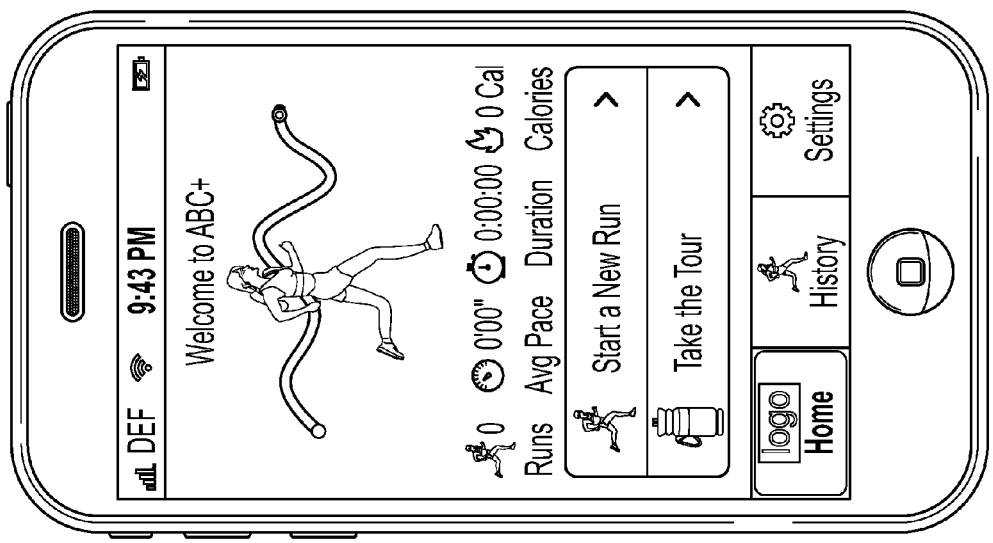
Figure 48D:
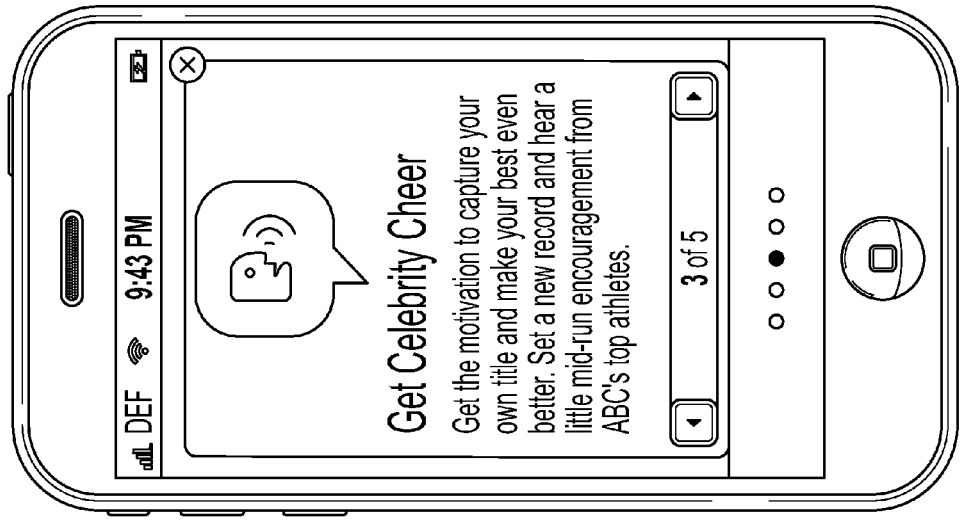
Figure 48C:
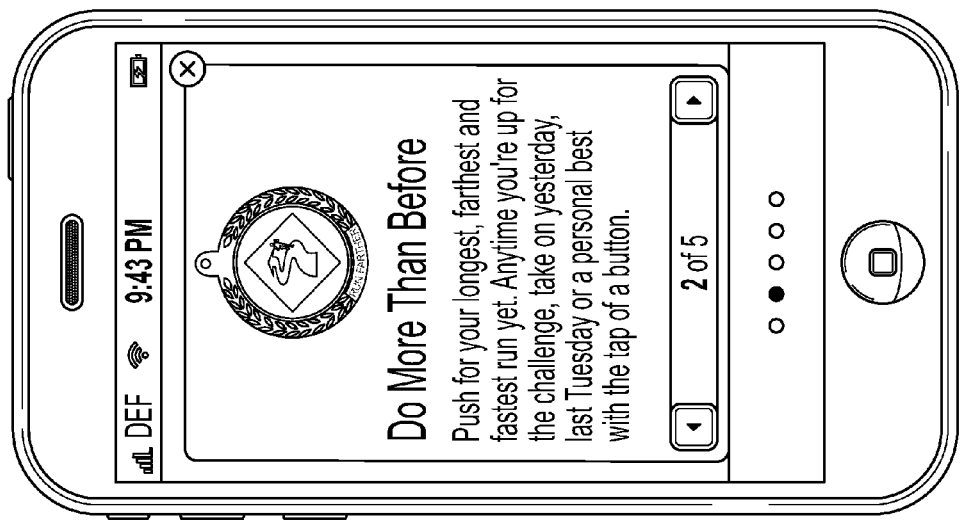
Figure 48F:
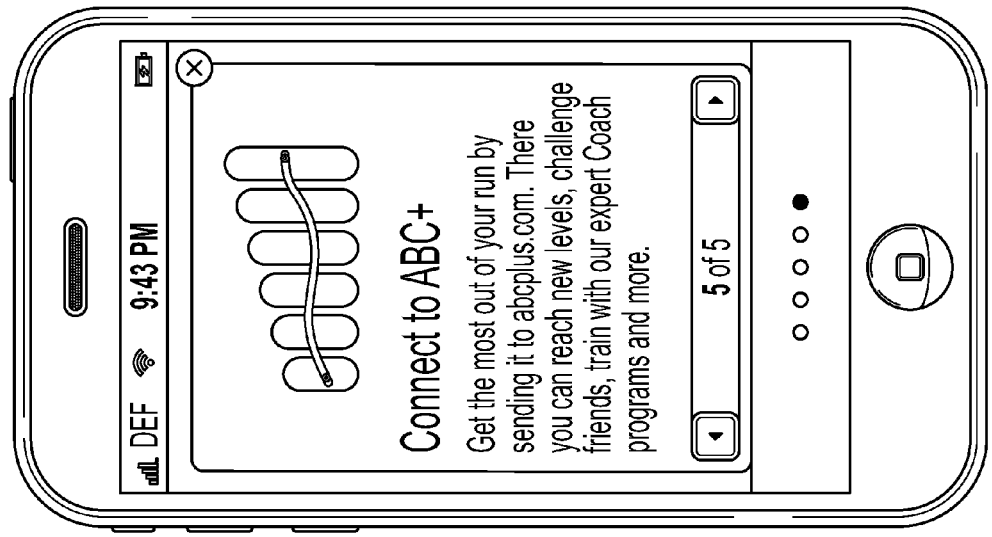
Figure 48E:
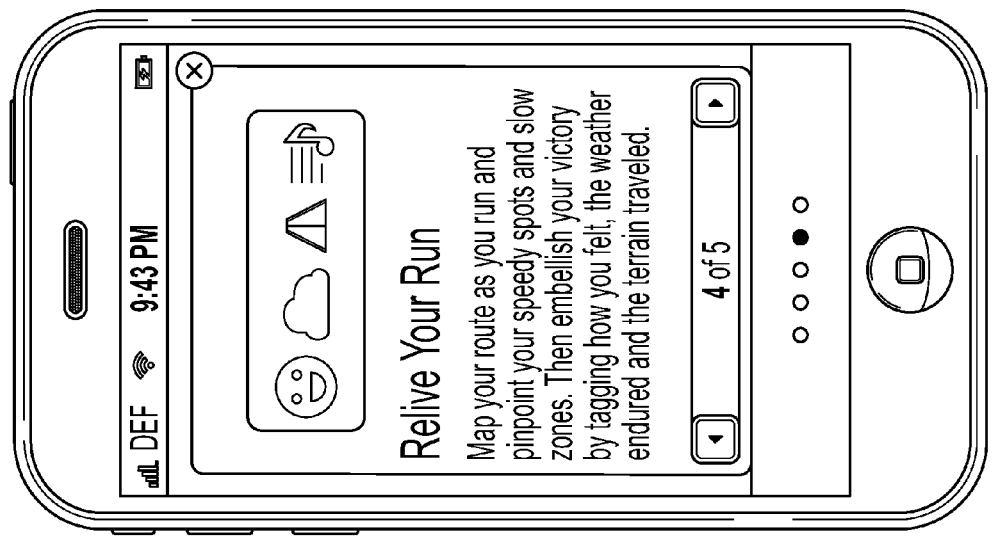
Figure 49B:
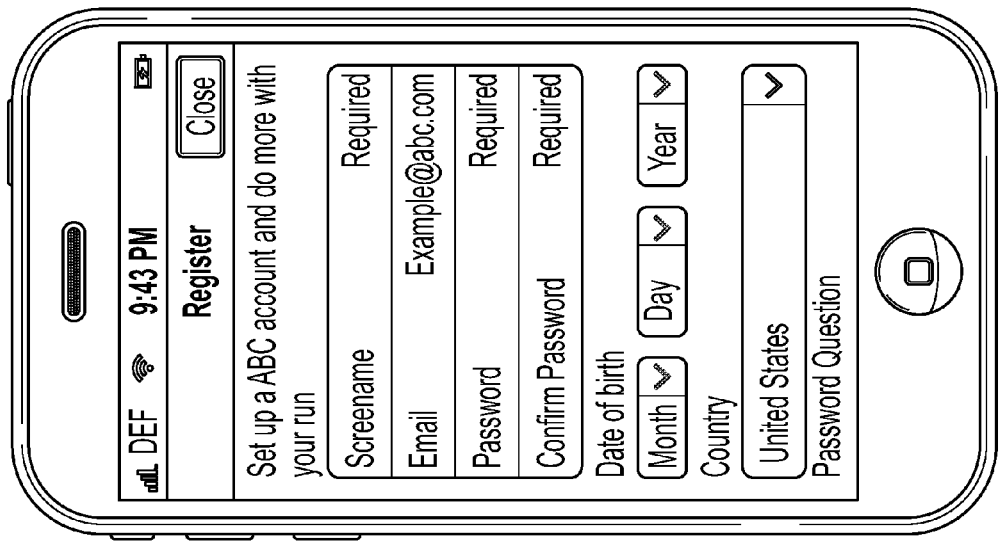
FIGS. 49A-49E illustrates a sequence of example interfaces through which a user may register with a service provider according to one or more aspects described herein.
Figure 49A:
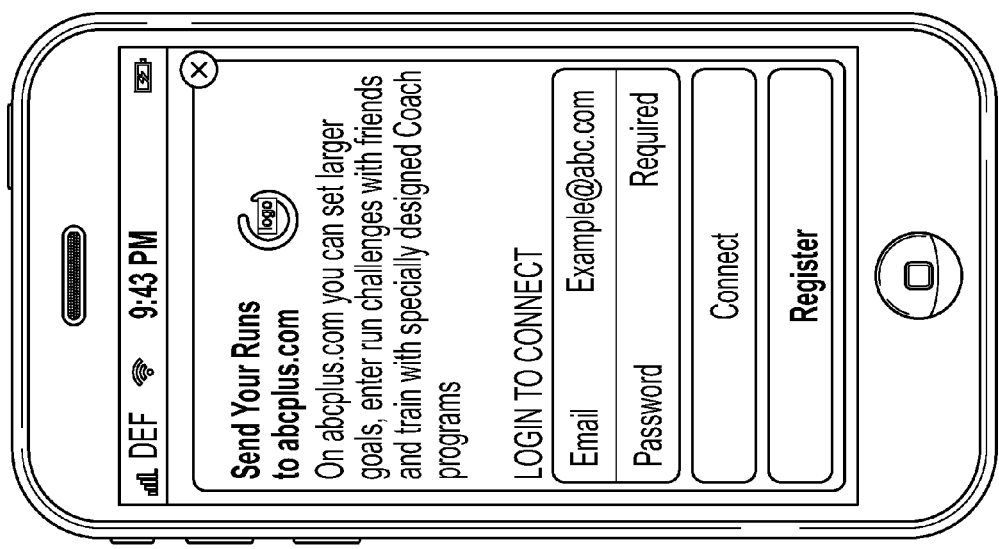
Figure 49D:
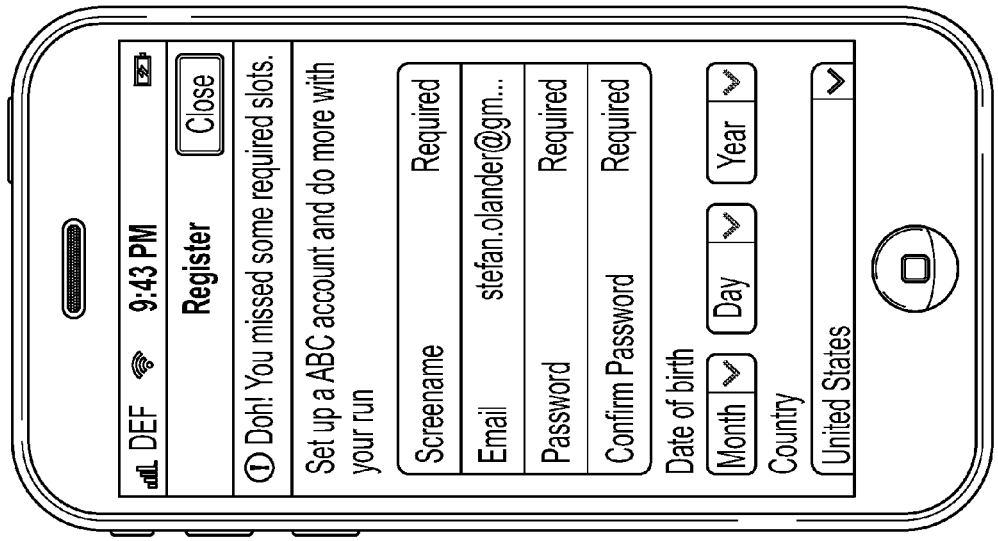
Figure 49C:
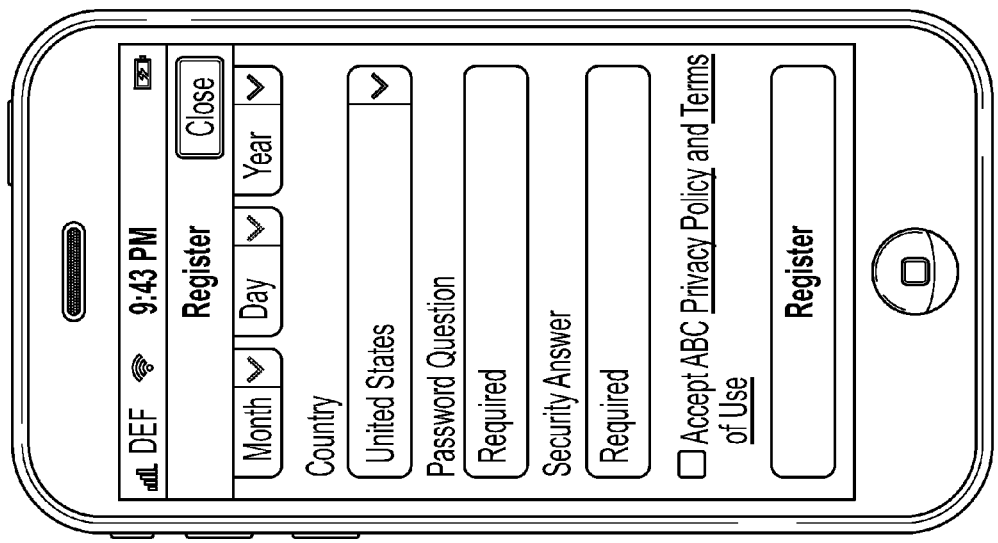

The user may define various settings that may affect the monitoring of a workout, recording of data and synchronization of data. FIGS. 47A and 47B illustrate example portions of various settings interfaces. FIG. 47A includes options allowing the user to define a distance metric (e.g., miles, feet, meters), frequency of feedback, whether the screen should be locked, calibration options and service provider account information (e.g., to allow for data synchronization). In FIG. 47A, the user has not defined or registered with the service provider. Accordingly, a tour option may also be included to allow the user to tour the features or services provided by the service provider upon the user registering.

Selection of the tour option may provide the user with additional information about the fitness monitoring and motivation features and functions of an underlying application and device. For example, FIGS. 48A-48F illustrate tour interfaces that provide detailed information describing the available features and functions.

FIG. 47B illustrates a settings interface portion that may be displayed if the user has provided service provider account information. By defining service provider account information, the user may be provided with a further option to define whether automatically synchronization should be performed. The tour option included in FIG. 47A might not be included in the interface of FIG. 47B. The user may also be provided with an option to sign out of the service provider. By signing out, the interface may change to the interface of FIG. 47A. Alternatively, the service provider account information may be stored and the sign out option replaced with a sign in option.

FIGS. 49A-49E illustrates a sequence of interfaces through which a user may register with a service provider. Some information may be required or optional including a username, an email, password, date of birth and the like.

Figure 50A:
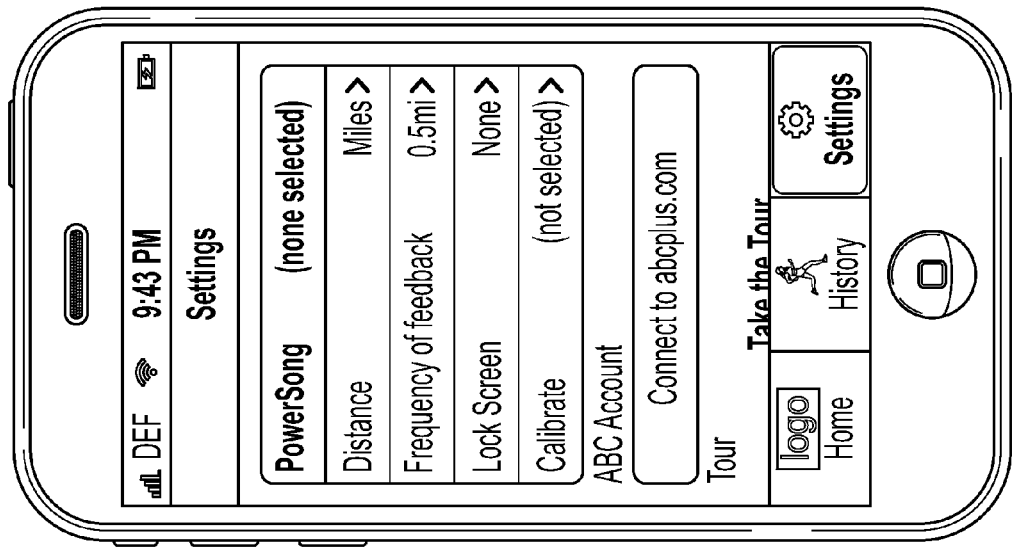
FIGS. 50A and 50B illustrate a sequence of example interfaces where a user may select a power song option and subsequently select a song from a song list according to one or more aspects described herein.
Figure 49E:
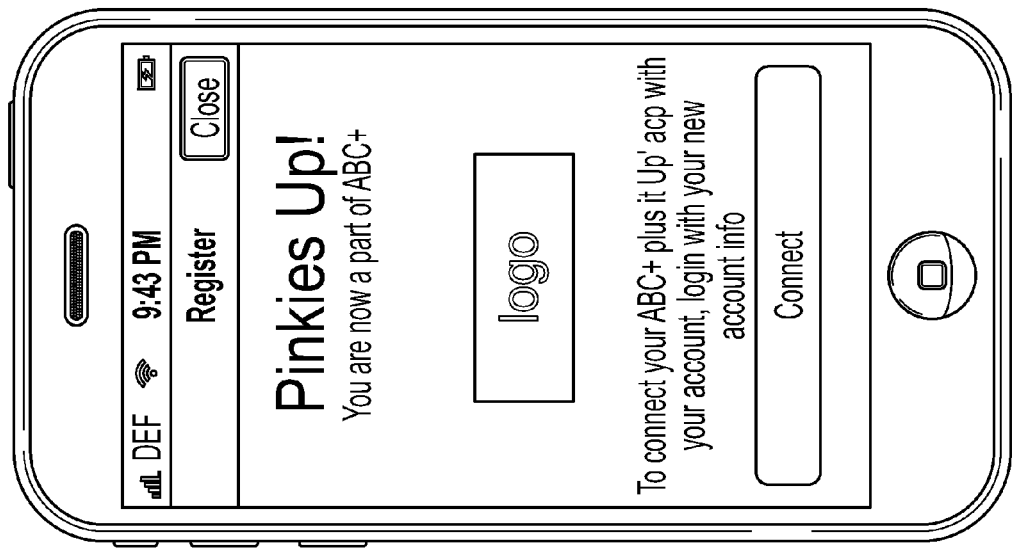
Figure 50B:
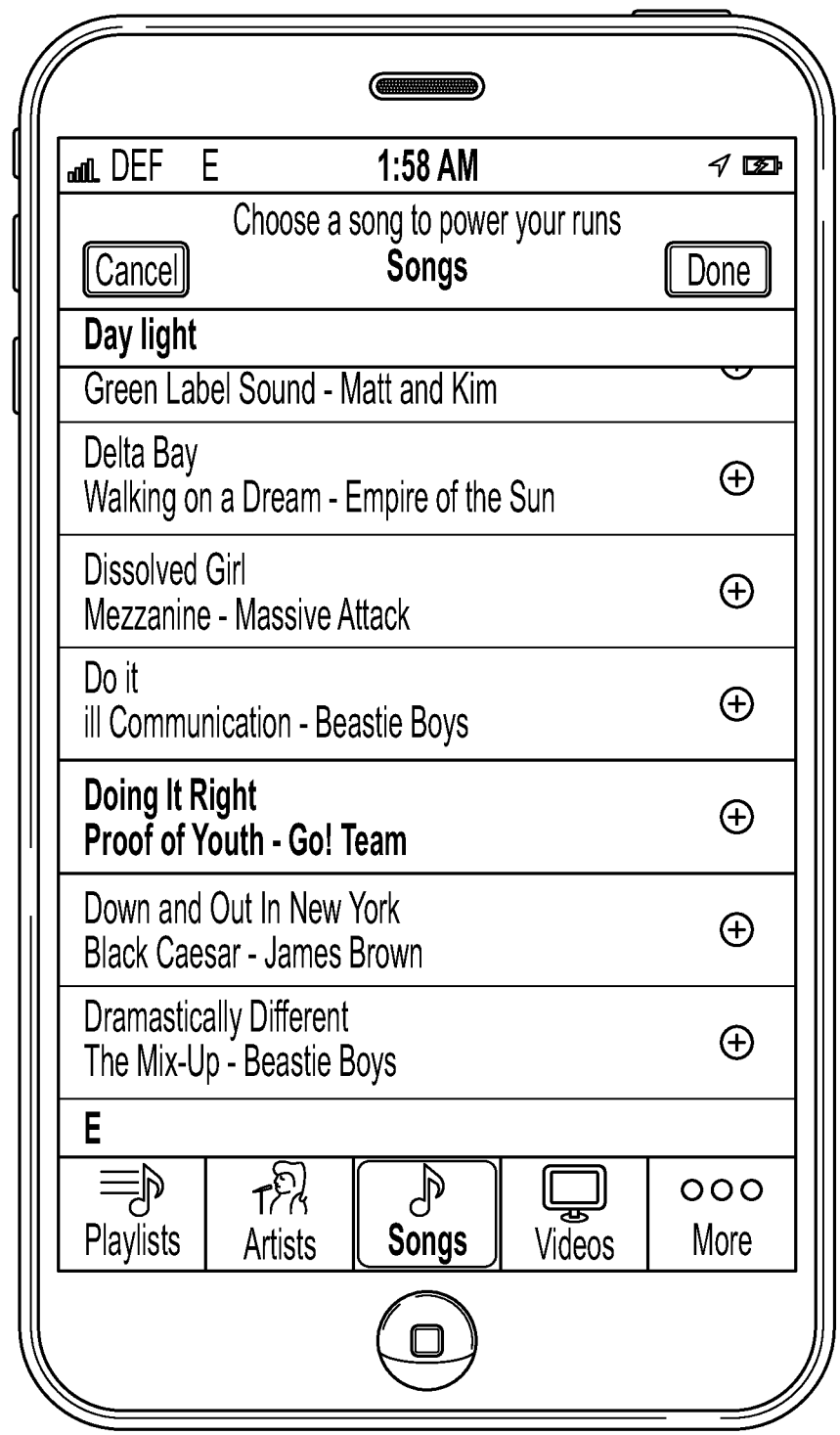

A user may be asked or allowed to choose a power song. A power song may correspond to audio content that the user finds particularly motivating. FIGS. 50A and 50B illustrate a sequence of interfaces where a user initially selects the power song option and subsequently selects a song from a song list. The song list may be a list of songs already owned by the user or may include songs available through an audio content provider. In FIG. 50A, if a power song is not selected, the power song option may indicate as much in a portion of the selection button. In contrast, if a power song is selected, the name of the power song may be displayed in the portion of the selection button.

Figure 51B:
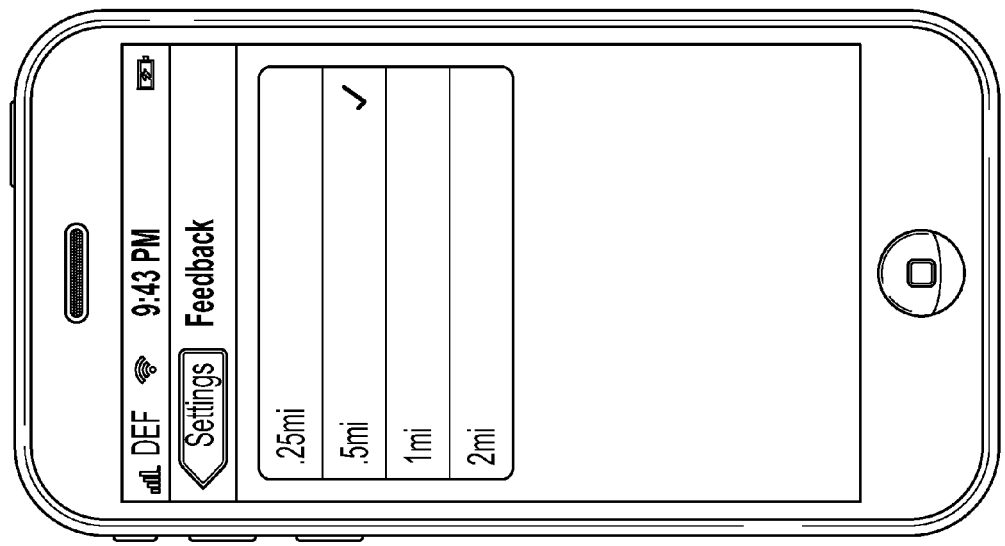
FIGS. 51A-51C illustrate example interfaces that allow the user to set the distance metric, a feedback frequency and a lock screen orientation, respectively, according to one or more aspects described herein.
Figure 51A:
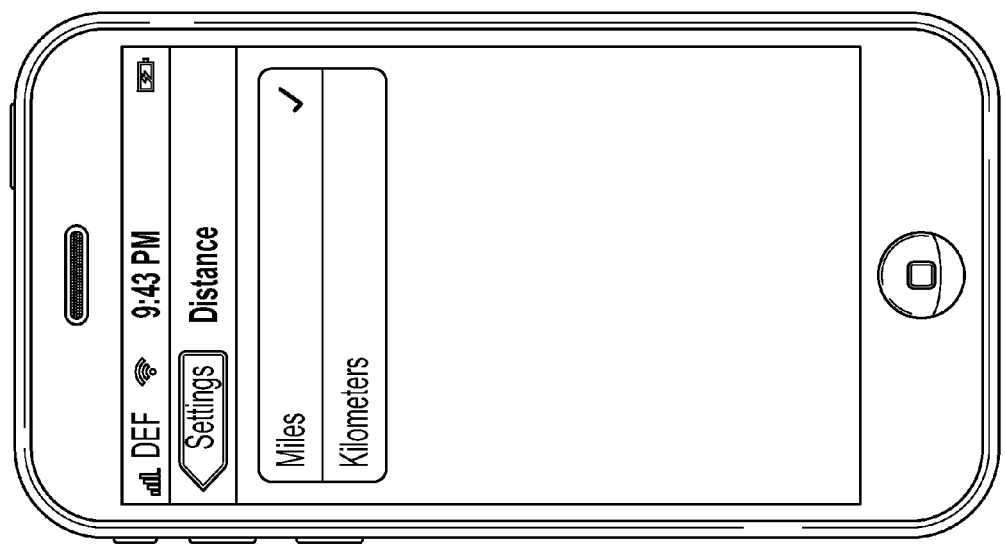
Figure 52A:
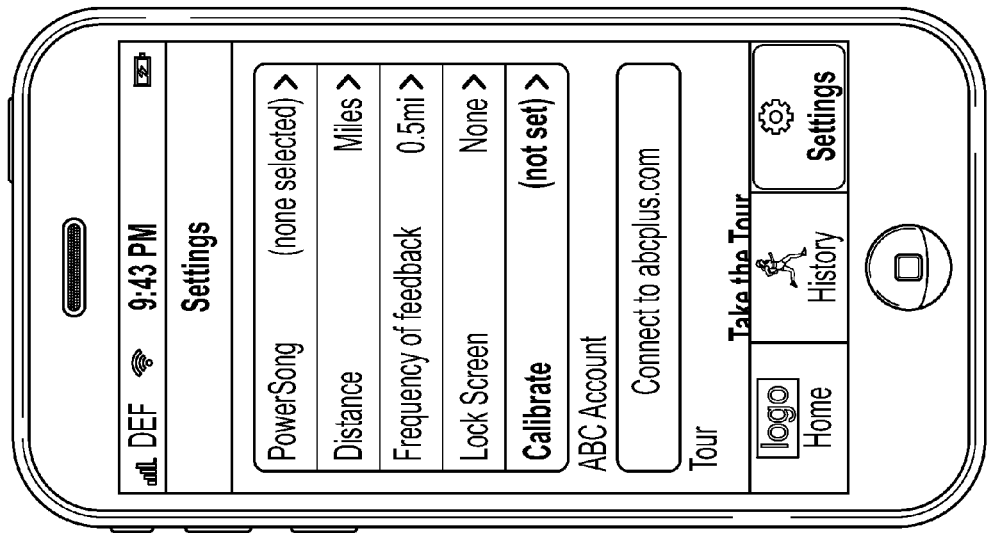
FIGS. 52A-52H illustrate example calibration interfaces for defining various user attributes and preferences that may enable more accurate monitoring and tracking of athletic activity statistics.
Figure 51C:
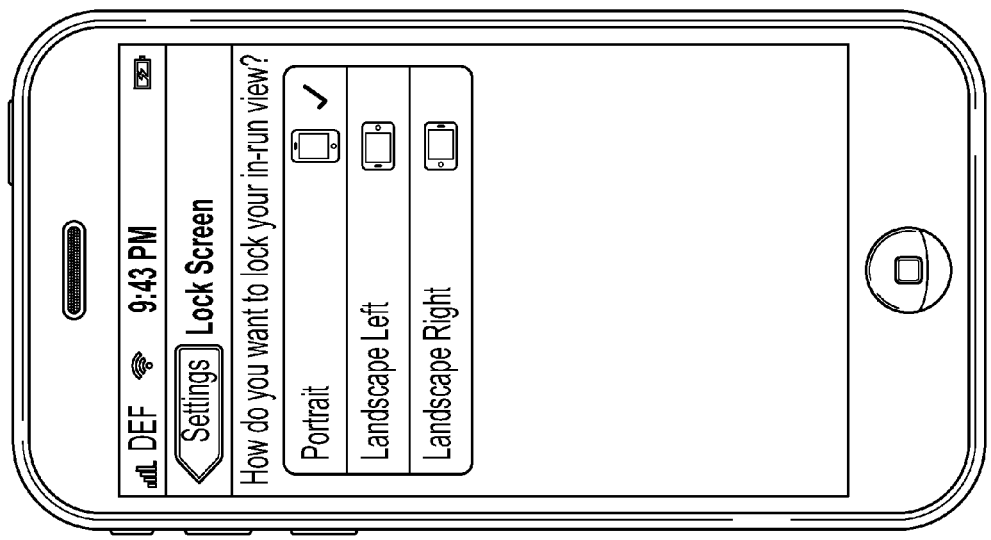
Figure 52C:
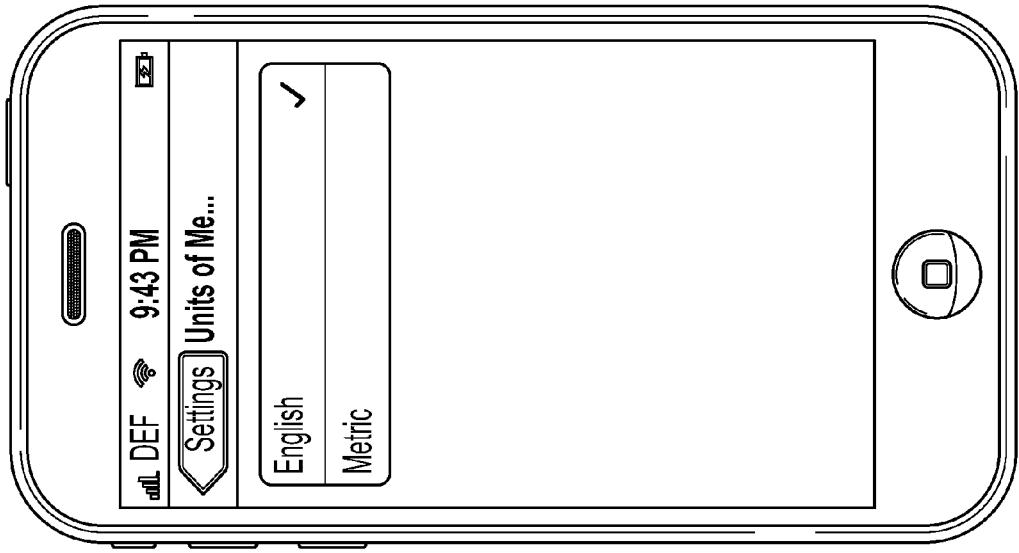
Figure 52B:
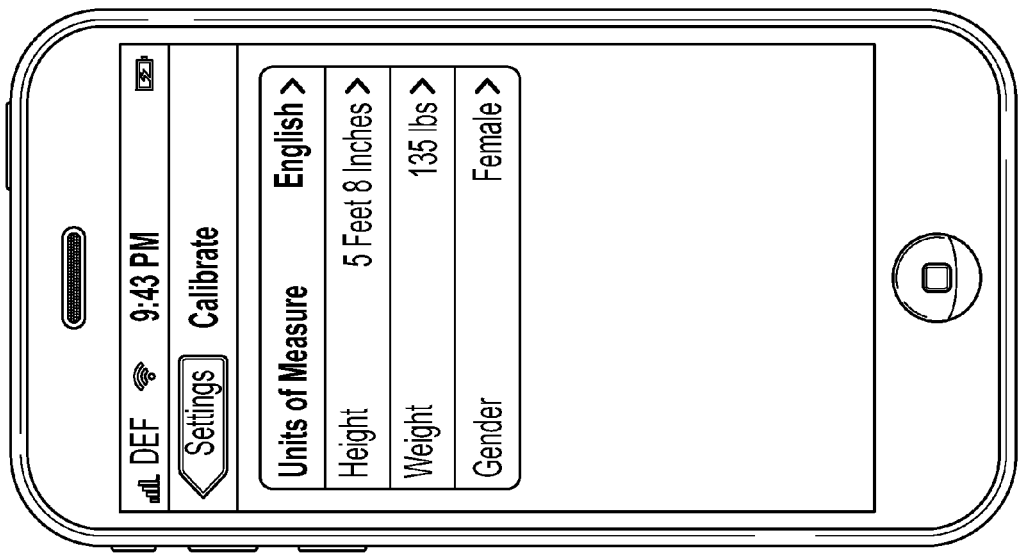
Figure 52E:
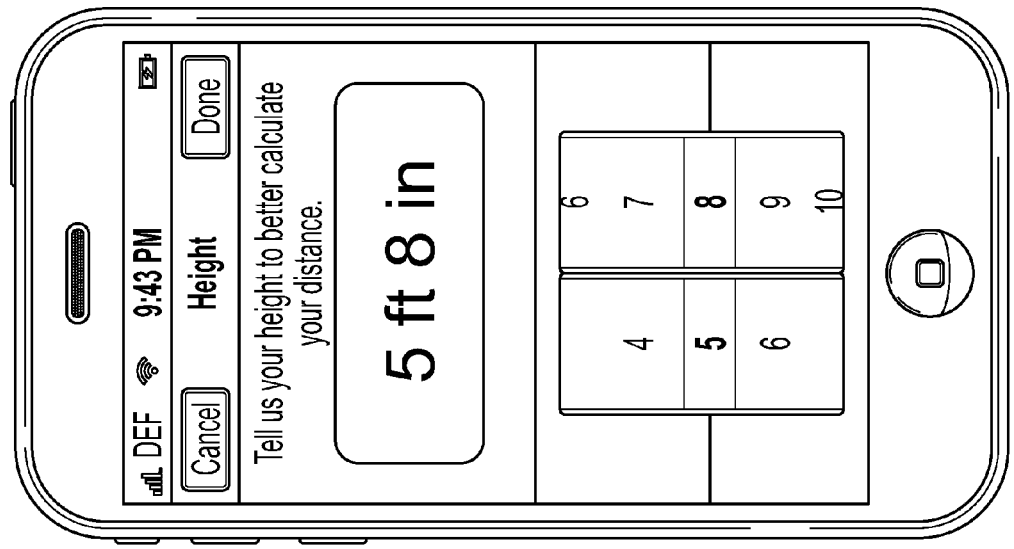
Figure 52D:
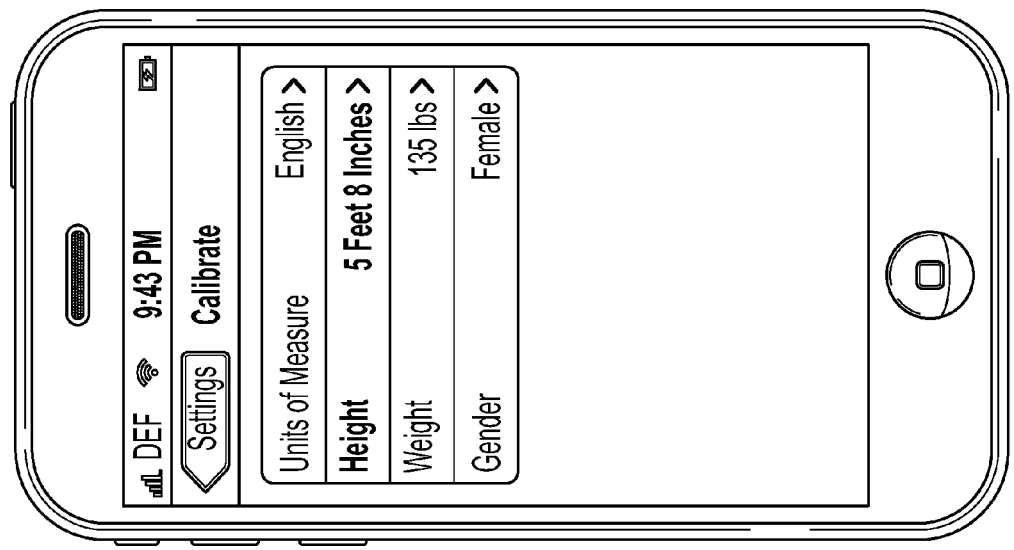
Figure 52G:
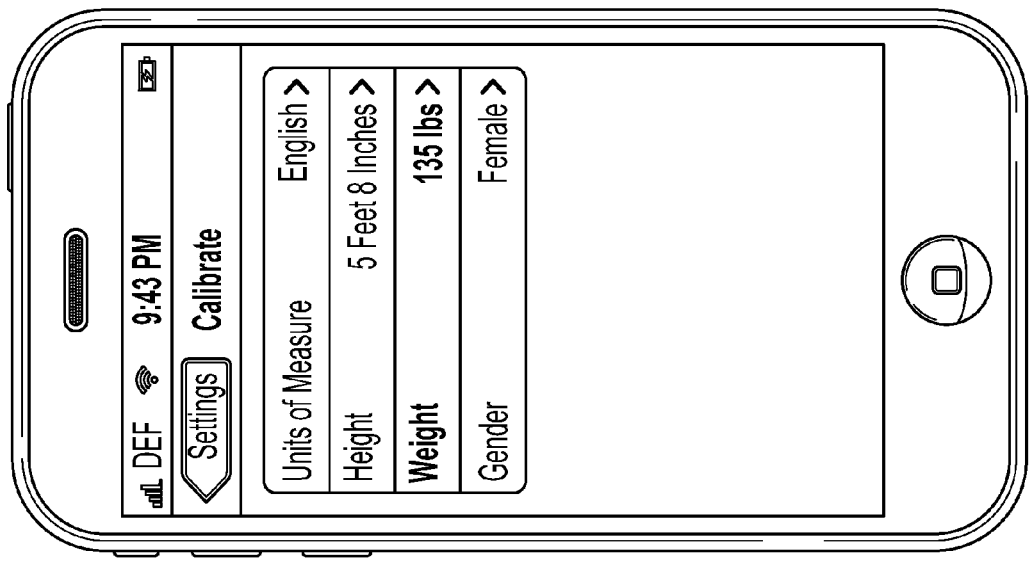
Figure 52F:
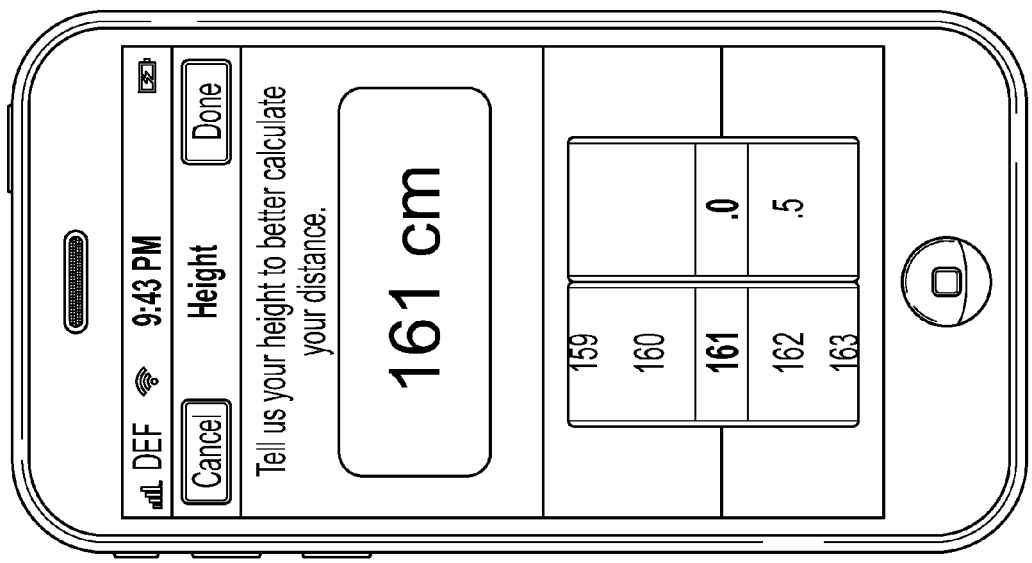

FIGS. 51A-51C illustrate interfaces that allow the user to set the distance metric, a feedback frequency and a lock screen orientation, respectively. For example, FIG. 51A illustrates an interface through which the user may select either miles or kilometers as the unit of measurement. FIG. 51B, on the other hand, allows the user to define how frequently to provide feedback (audio or visual). The frequency may be distance-based or time-based. FIG. 51C illustrates an interface that allows the user to define the orientation in which to lock the interface. For example, the user may select a portrait orientation or a landscape orientation. The selection may be made based on a user preference, an orientation of the device during the run and/or a combination thereof.

FIGS. 52A-52H illustrate calibration interfaces for defining various user attributes and preferences that may enable more accurate monitoring and tracking of athletic activity statistics. Through a calibration menu (e.g., as displayed in FIG. 52B), the user may select the units of measure, a user height, a user weight and the user's gender. The units of measure, for example, may be chosen from options including English and metric. Height and weight may be defined using scroll wheels and may allow selection from values of the selected unit of measure. The device may use this data to better determine the results of a user's athletic activity. For example, the accelerometer readings may be translated or converted into calories burned, or distance run using the user's weight, height and gender.

Figure 53A:
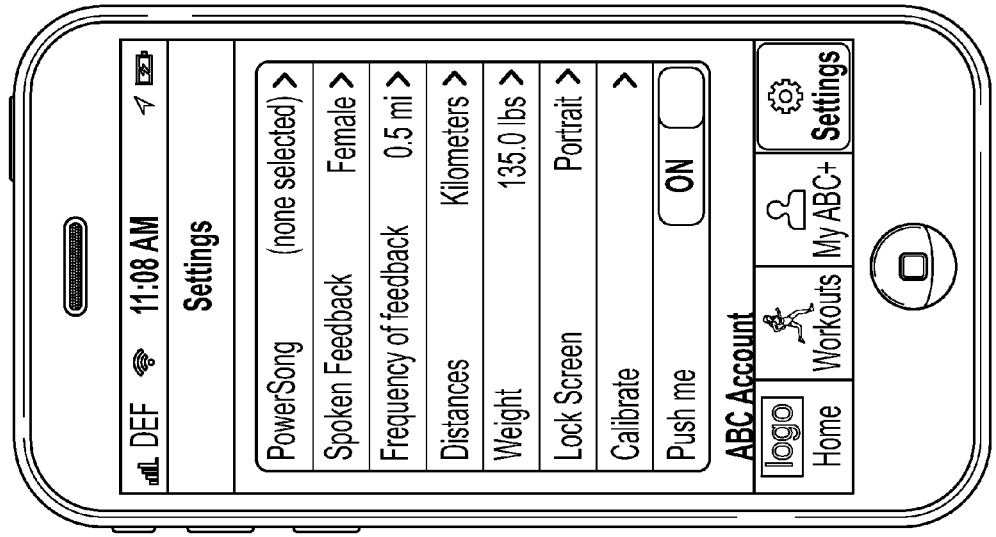
FIGS. 53A-53V illustrate alternative or additional settings interfaces that may be generated and displayed through the mobile fitness monitoring device
Figure 52H:
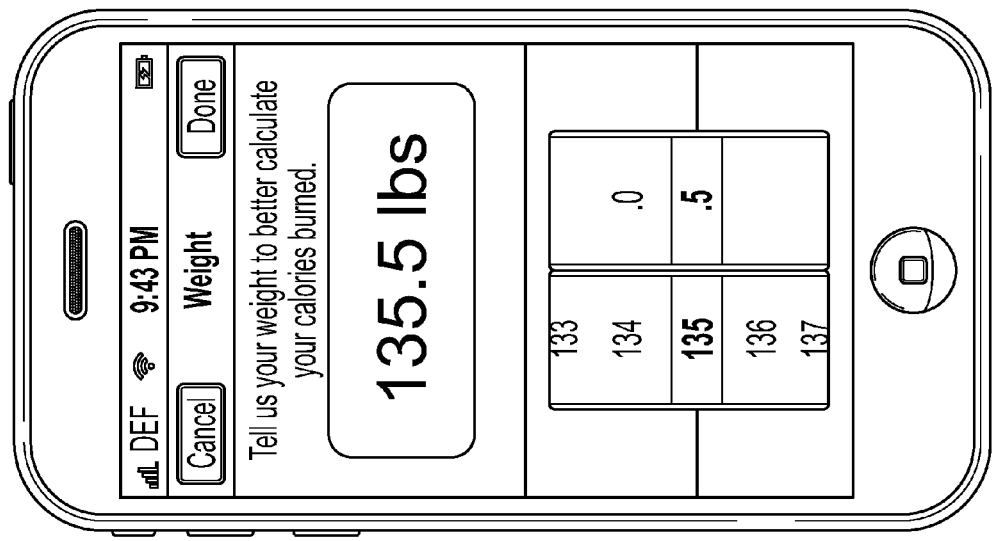
Figure 53C:
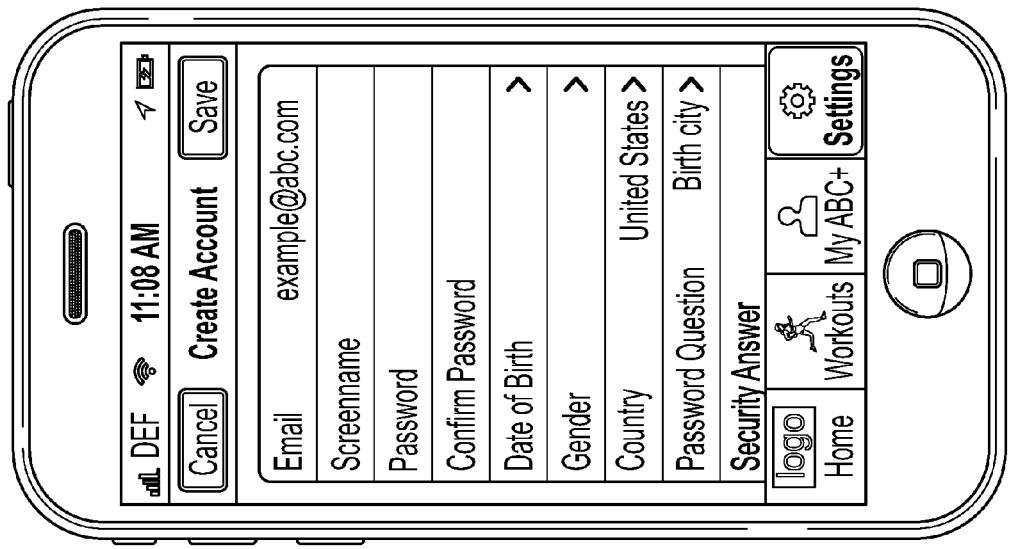
Figure 53B:
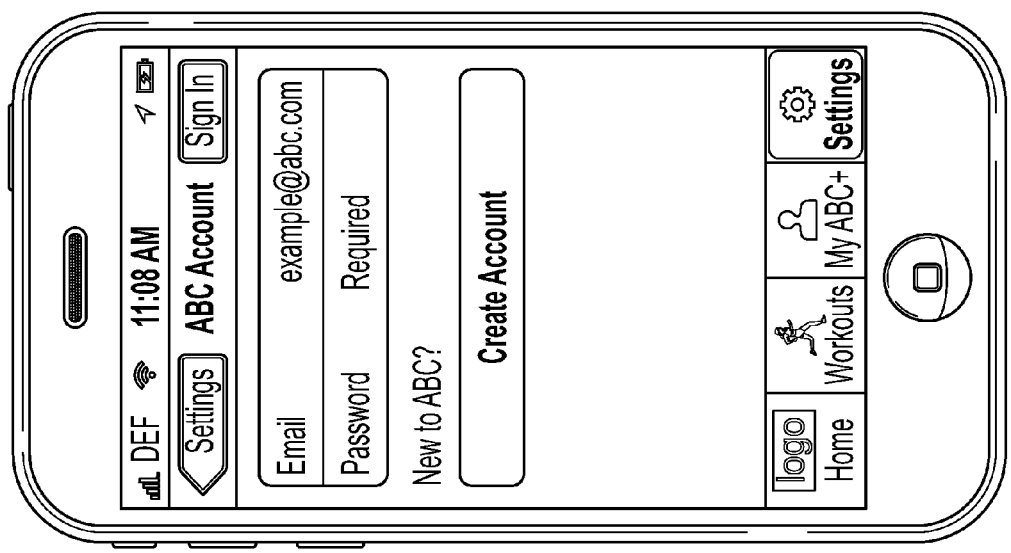
Figure 53E:
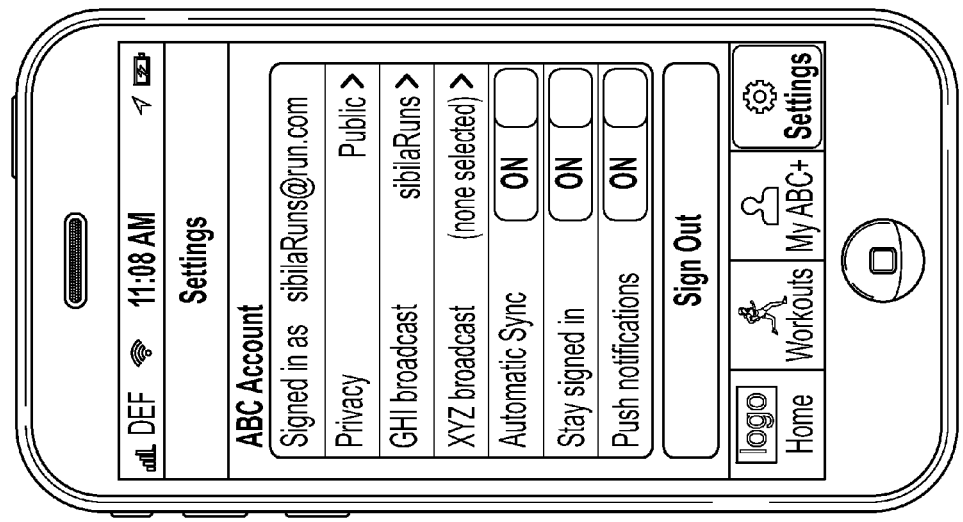
Figure 53D:
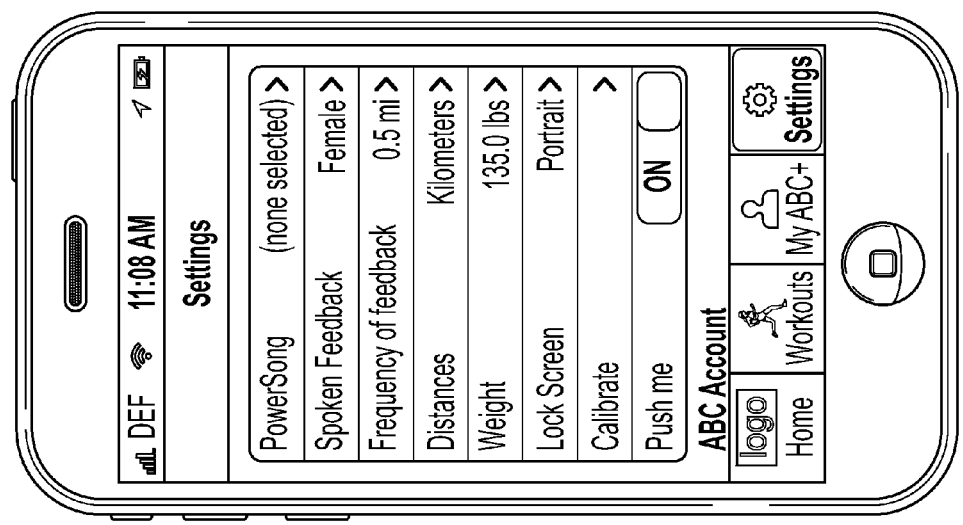
Figure 53F:
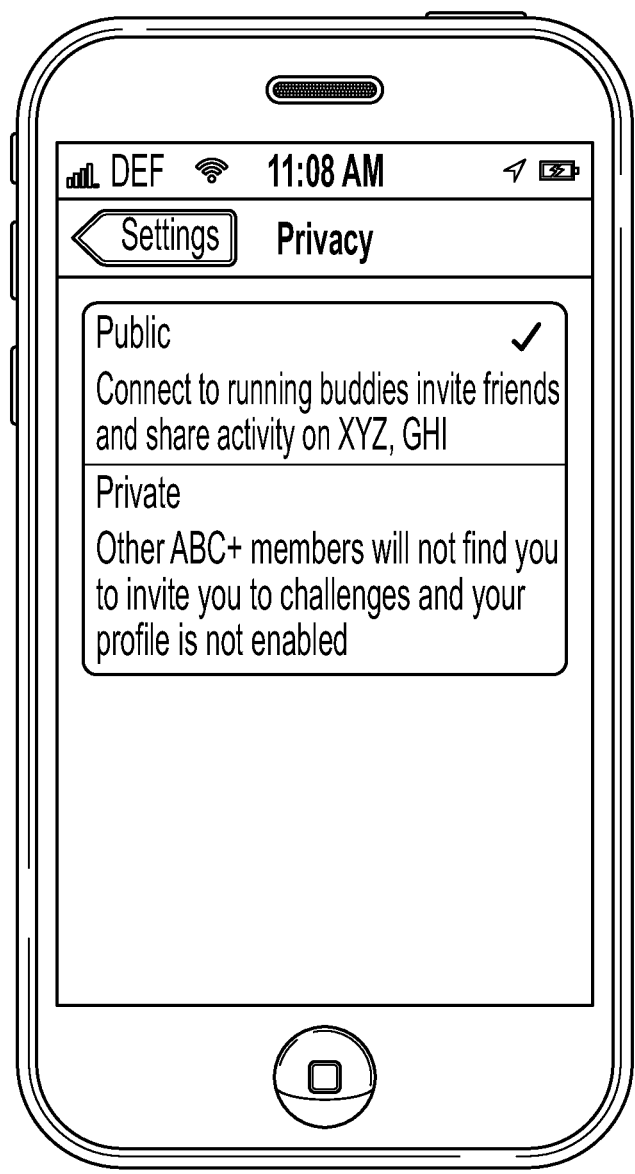
Figure 53G:
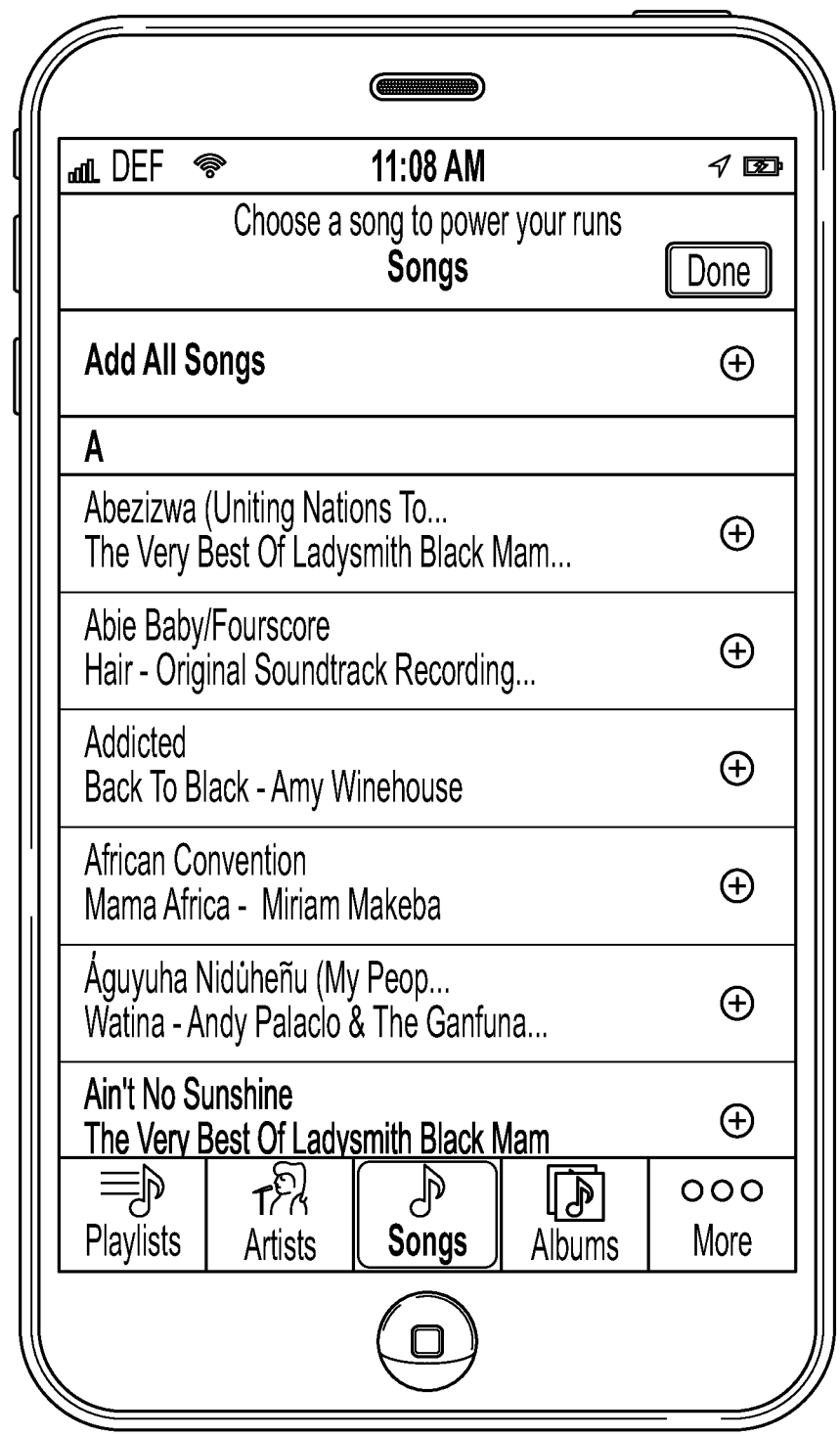
Figure 53I:
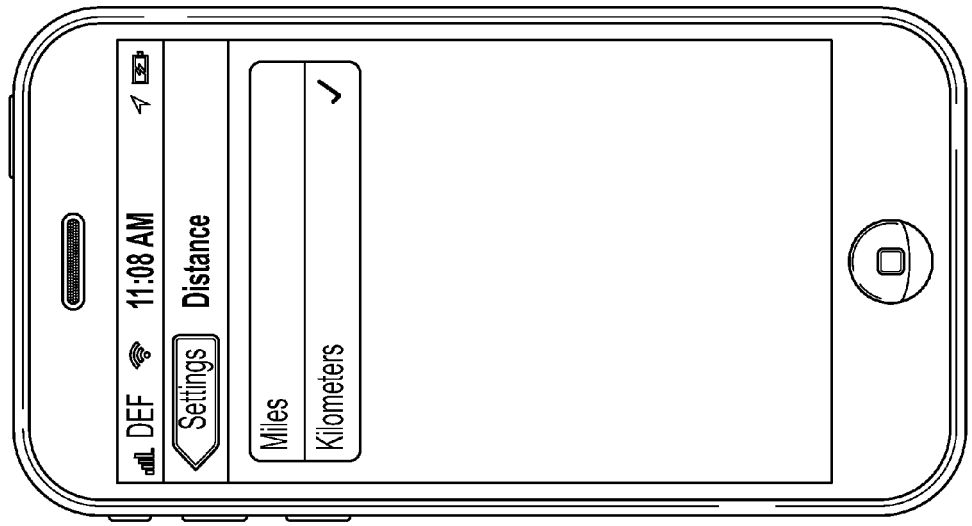
Figure 53H:
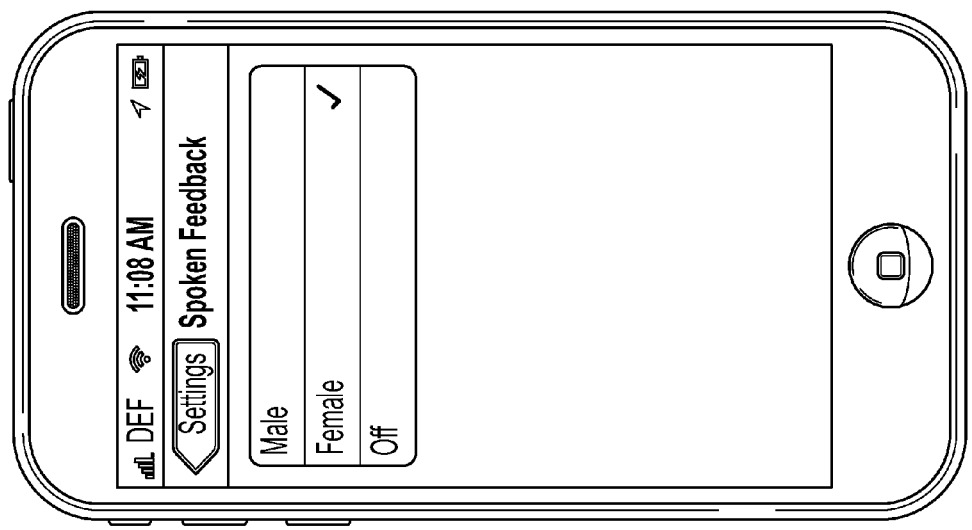
Figure 53K:
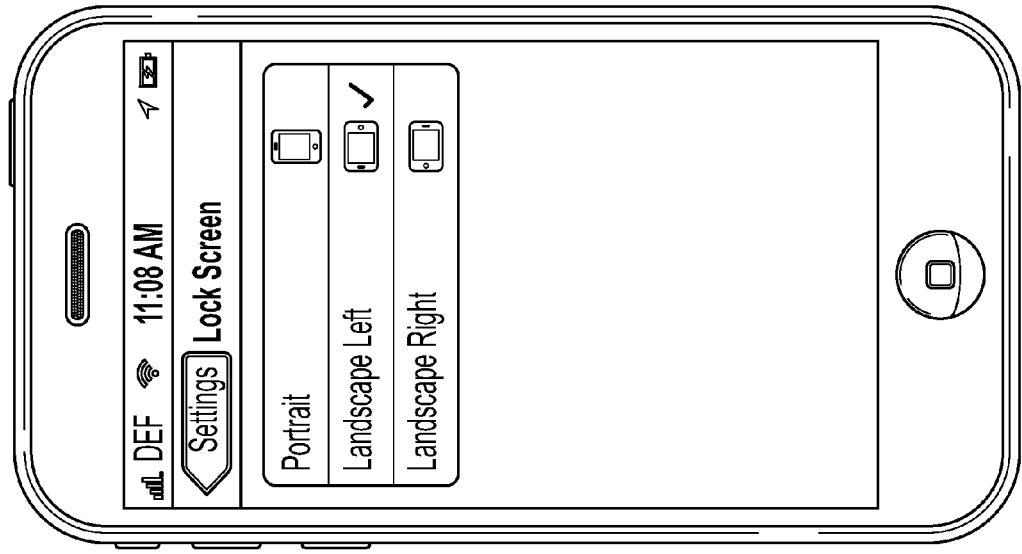
Figure 53J:
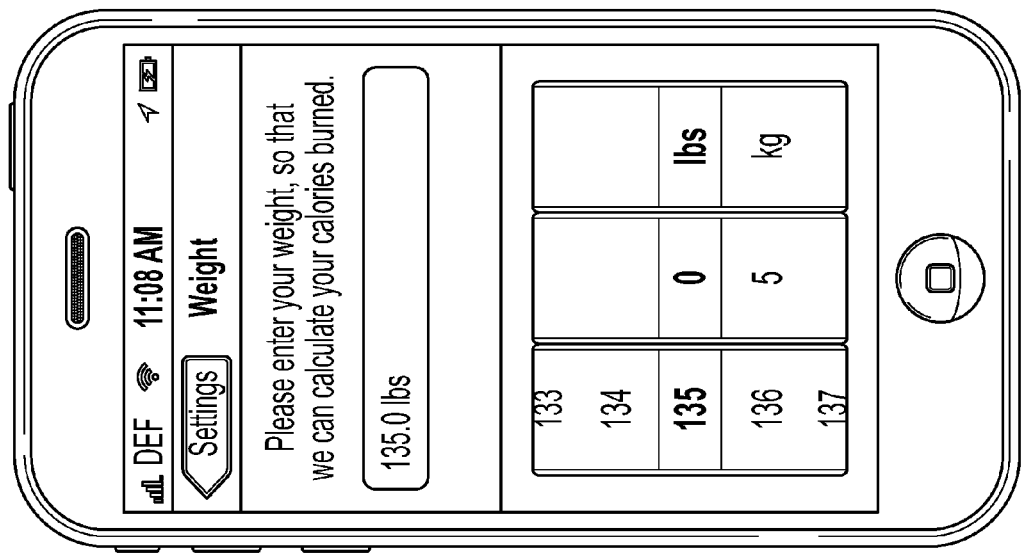
Figure 53M:
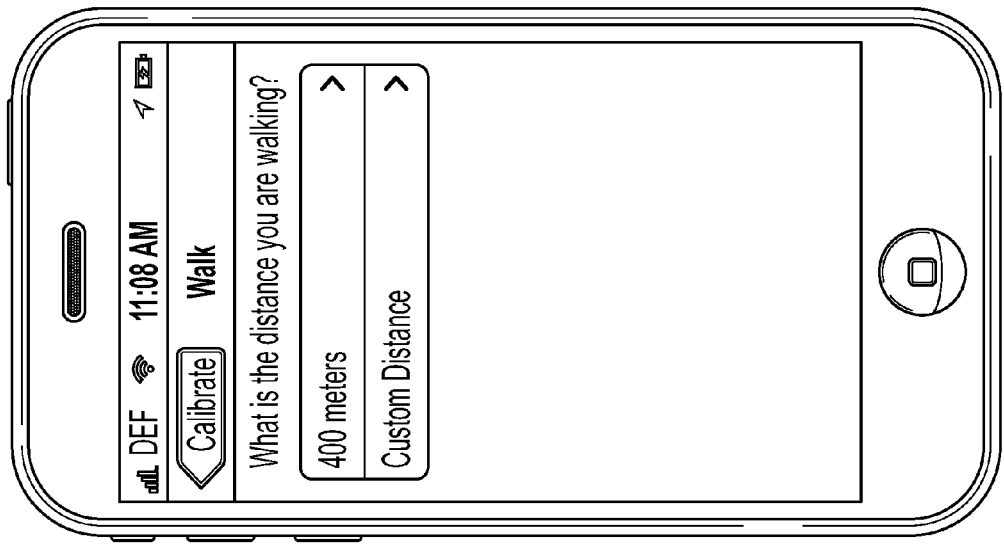
Figure 53L:
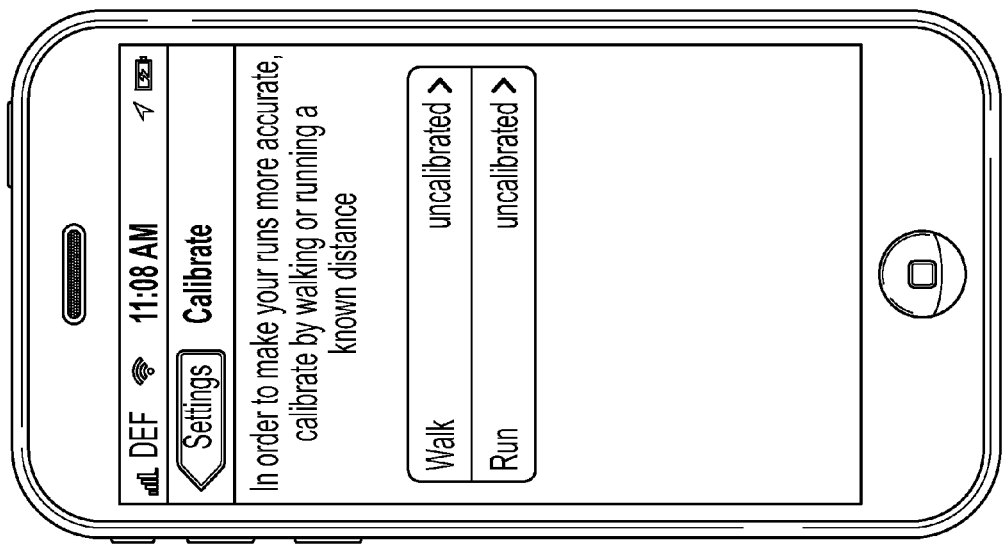
Figure 53N:
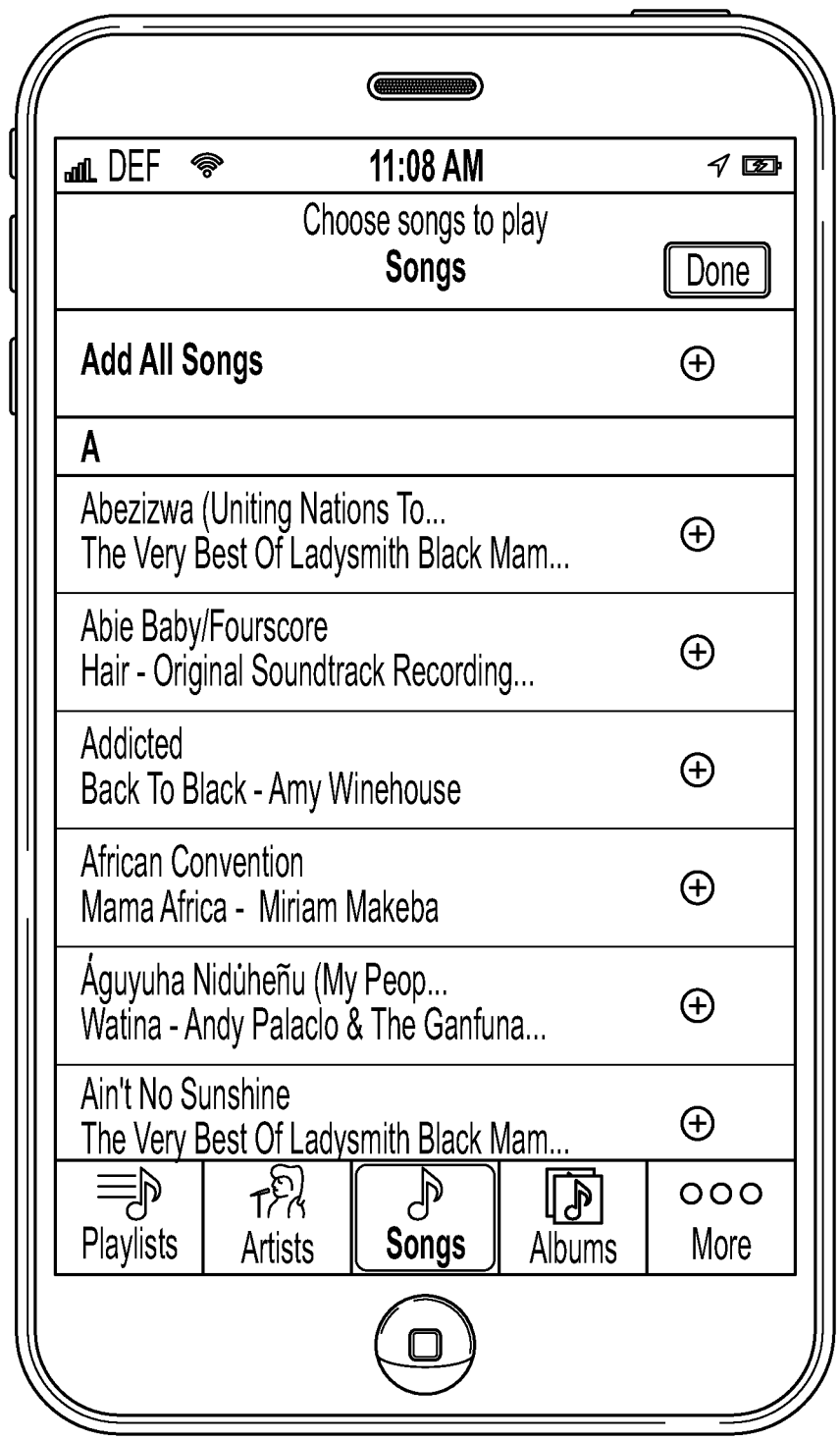
Figure 53P:
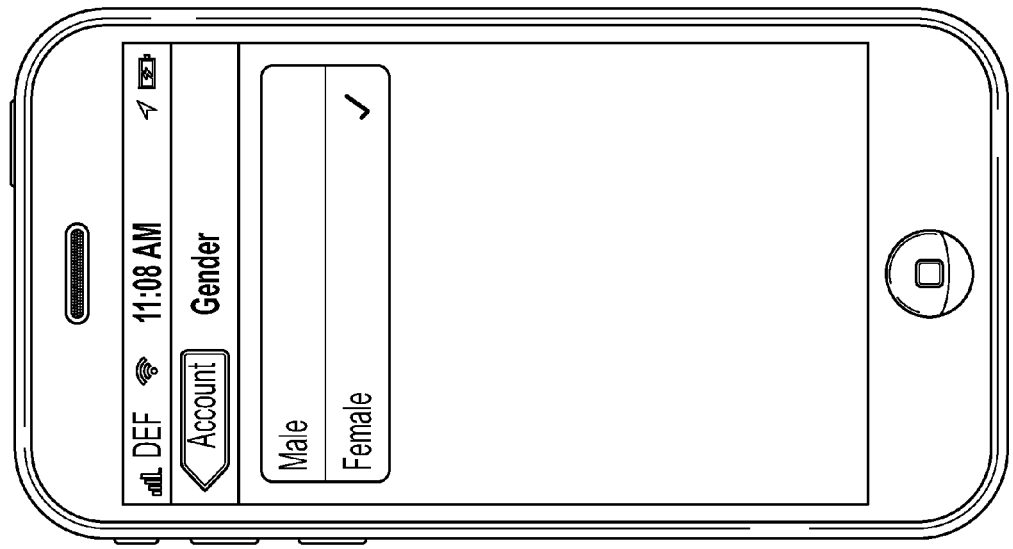
Figure 53O:
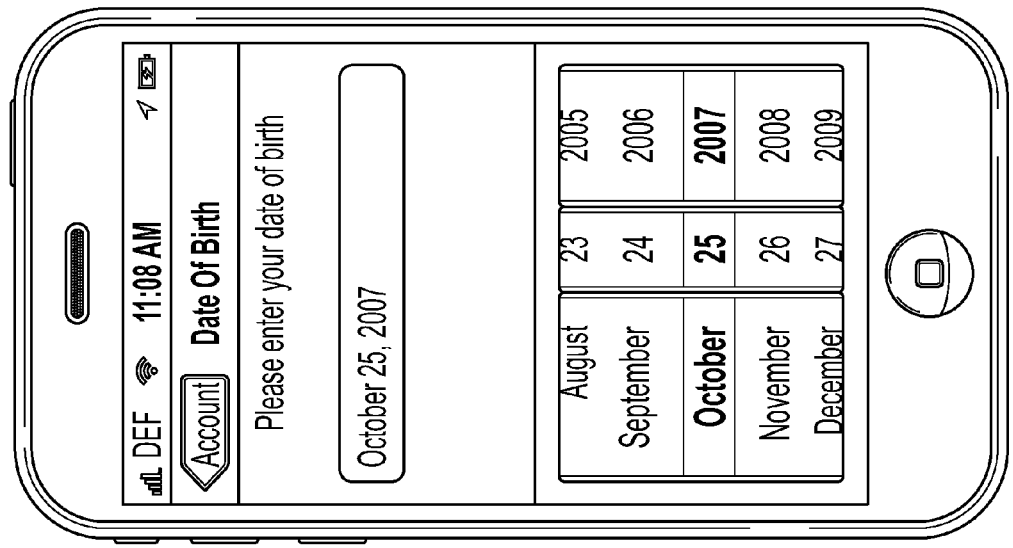
Figure 53R:
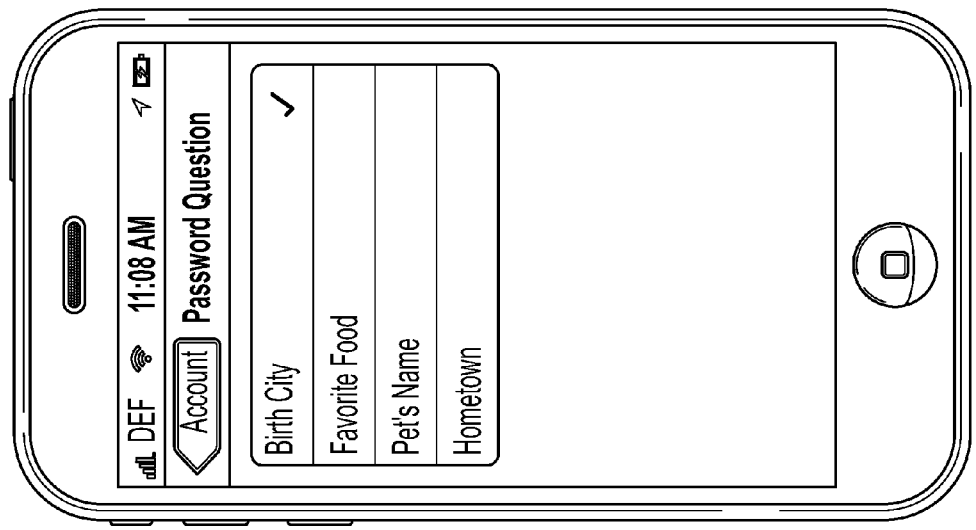
Figure 53Q:
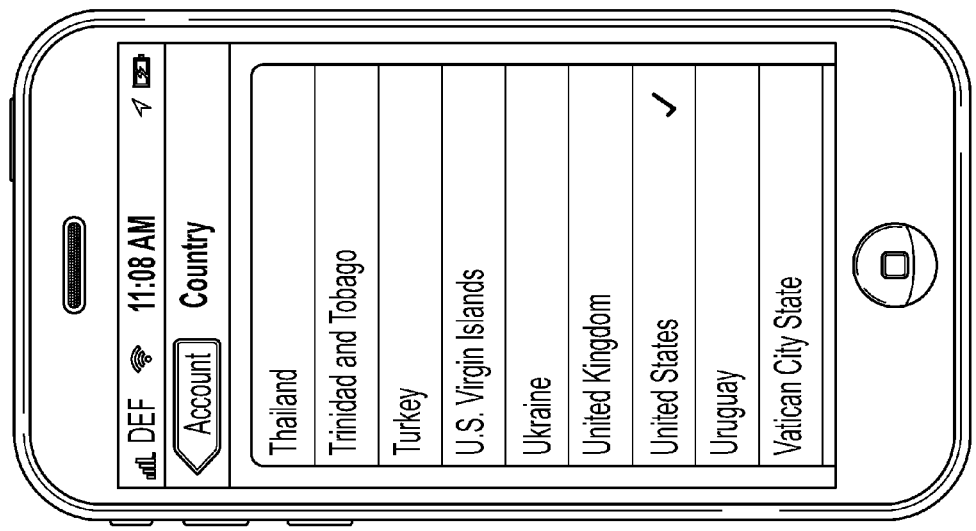
Figure 53T:
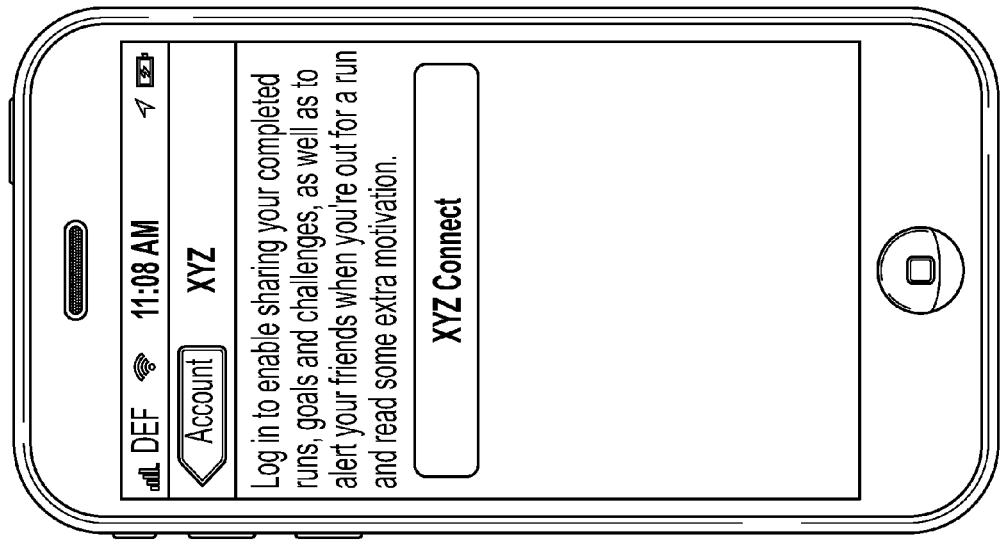
Figure 53S:
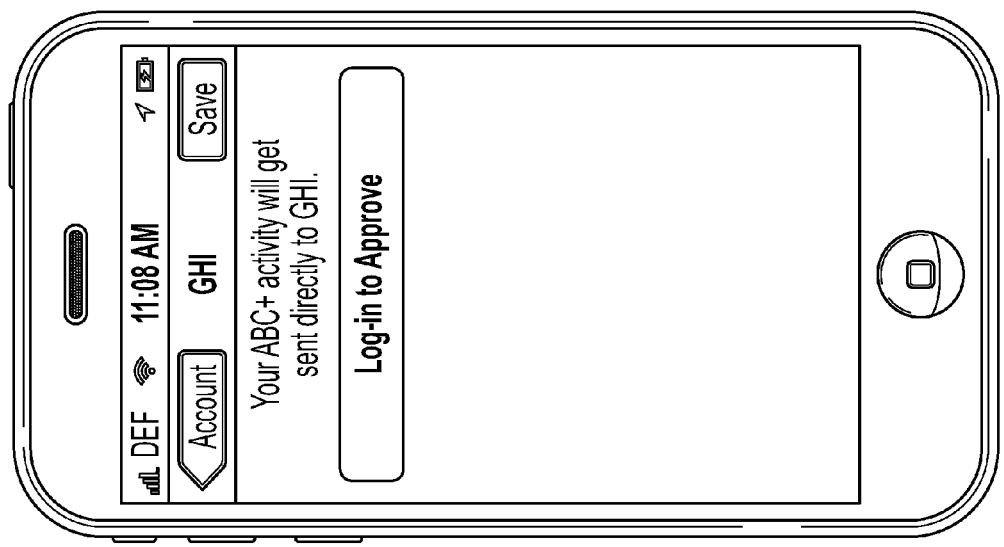
Figure 53V:
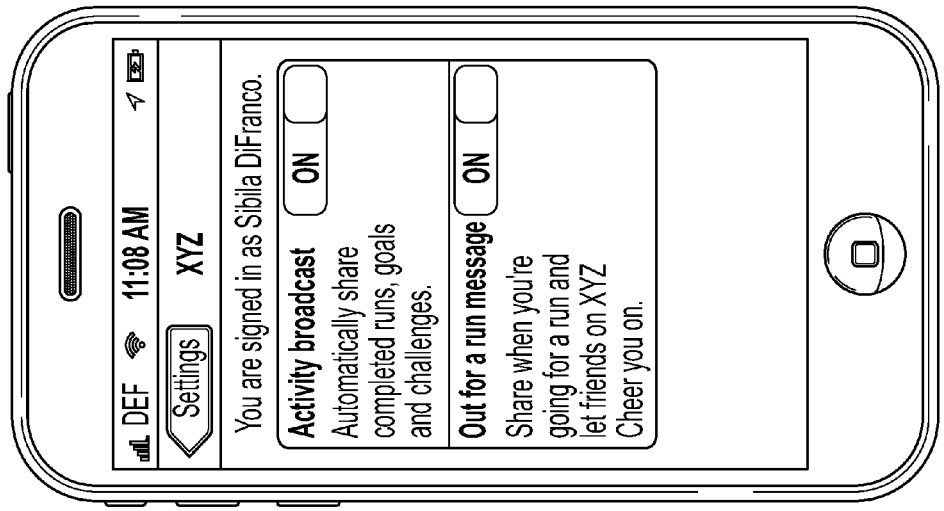
Figure 53U:
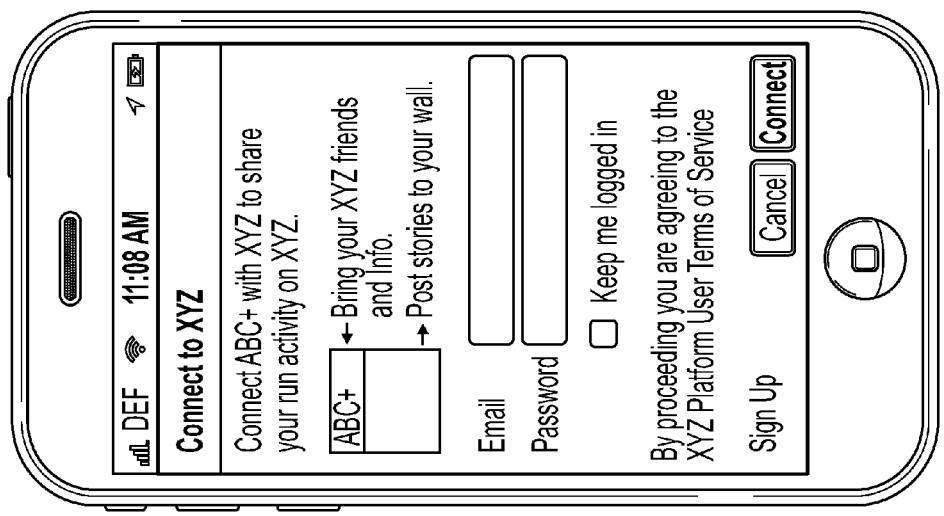

FIGS. 53A-53V illustrate alternative or additional setting interfaces that may be generated and displayed through the mobile fitness monitoring device. The interfaces of FIGS. 53A-53C may, in one or more examples, be configured for beginner users while the interfaces of FIGS. 53D-53F may be configured for more advanced or power users. Advanced or power users may include users that already have registered with a fitness monitoring service provider. Accordingly, FIG. 53E may include additional account and monitoring setting information that might not otherwise be displayed for non-registered users. Additionally, a user may be able to select privacy settings in the interface of FIG. 53F. If a user chooses a private setting, other users might not be able to find the user or view the user's information. If, on the other hand, a public setting is selected, other users may be able to publicly search for the user and view various information about the user. The public setting may also allow for sharing information on other sites such as social network sites and news feeds.

In other aspects, a user may define information sharing settings. For example, FIGS. 53S-53V illustrate various setting interfaces that may be used to configure information accounts and sharing settings. FIG. 53S illustrates that workout information may be sent directly to a news feed automatically upon the user logging into the news feed service. The logging into the news feed service may correspond to approval of the automatic sharing feature.

FIG. 53V, on the other hand, may allow the user to set various settings for information sharing on a network site such as a social network site like FACEBOOK. In particular, the user may be able to enable or disable activity broadcasts. Activity broadcasts may include the automatic sharing of completed runs, goals and challenges. Additionally or alternatively, the user may enable or disable a function that notifies other users (e.g., placing a post or status update on the user's network site page) whenever the user is on a run or other workout. This may enable other users to post messages of encouragement and to track the user's progress during the run. Workout data may also be posted to social network sites and social networking feeds mid-run and in real-time. Various other features and functions may also be configured by the user for sharing information.

Workout Sharing

Figure 54B:
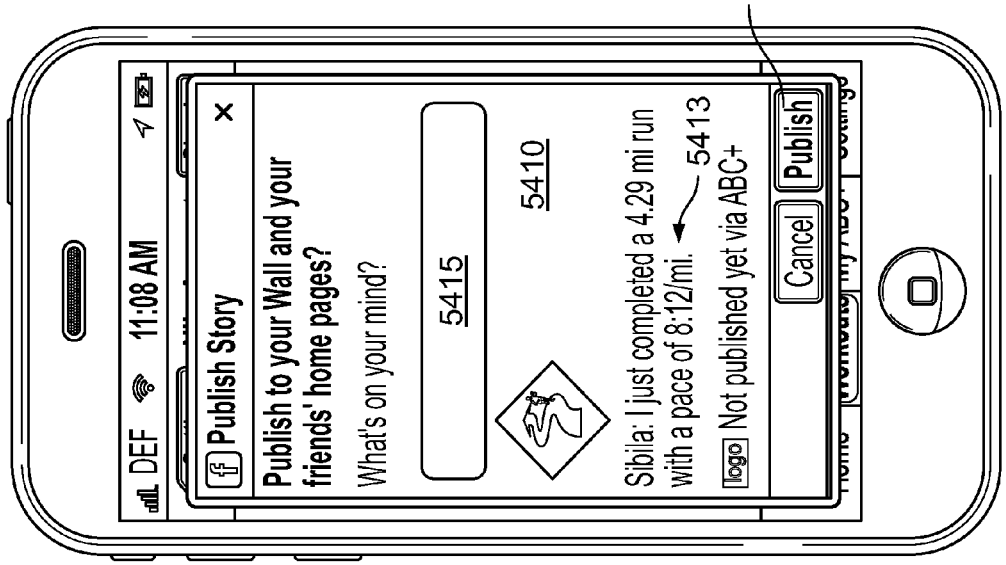
FIGS. 54A-54C illustrate example interfaces through which a user may share workout information on social networking sites and news feeds.
Figure 54A:
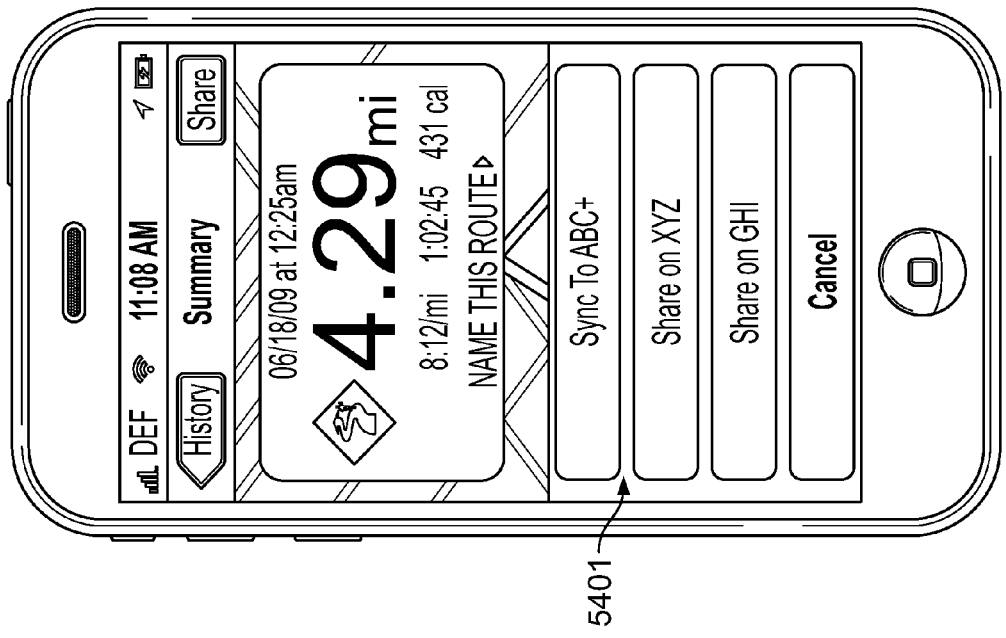
Figure 54C:
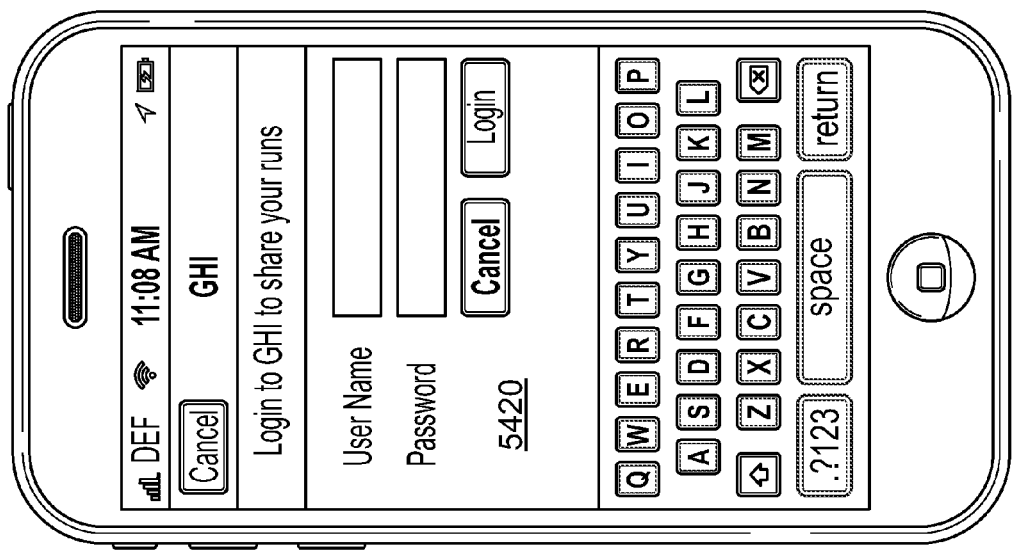

Users may choose to share workout information or portions thereof with one or more other users, friends or through a social networking site. FIGS. 54A-54C illustrate example interfaces through which a user may share workout information on social networking sites and news feeds. In FIG. 54A, the user may be presented with a share menu 5401 that includes multiple sharing outlets including FACEBOOK and TWITTER. Menu 5401 may also include an option to synchronize workout information with a fitness monitoring service provider.

If the user chooses to share workout data through a social network site such as FACEBOOK, an interface such as interface 5410 of FIG. 54B may be displayed. Interface 5410 may include an automatically generated workout update message 5413 and allow the user to include additional information or notes in form 5415. Upon approving the message, the user may publish the data to the social networking site by selecting publish option 5417.

Sharing workout data through a news feed service such as TWITTER may be performed through an interface such as interface 5420 of FIG. 54C. In particular, interface 5420 may require a user's login and password information to automatically access the news feed service. The news feed message may be an automatically generated message that includes workout and/or route information. The user may be allowed to edit the message and/or create his or her own.

Figure 55A:
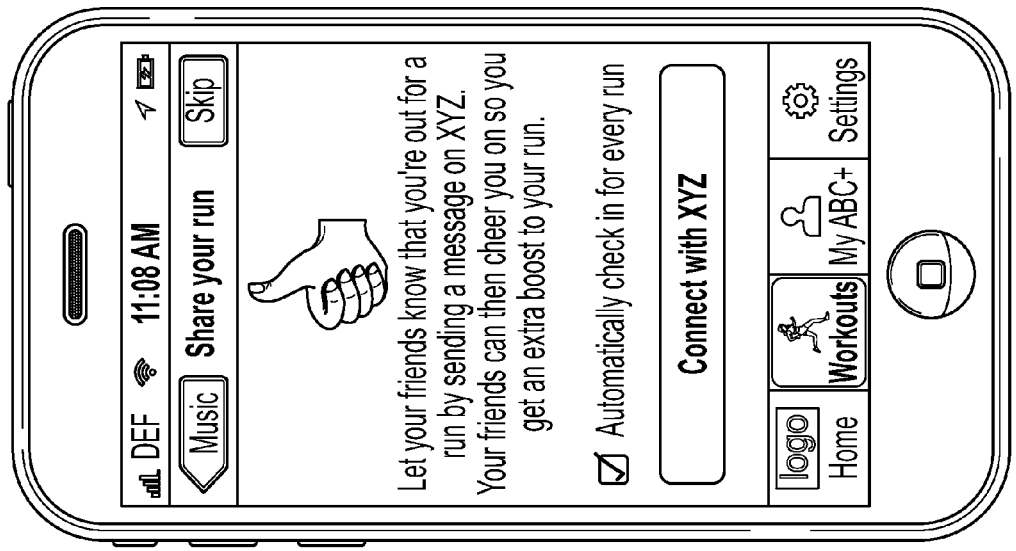
FIGS. 55A and 55B illustrate other example interfaces for sharing workout/run information.
Figure 55B:
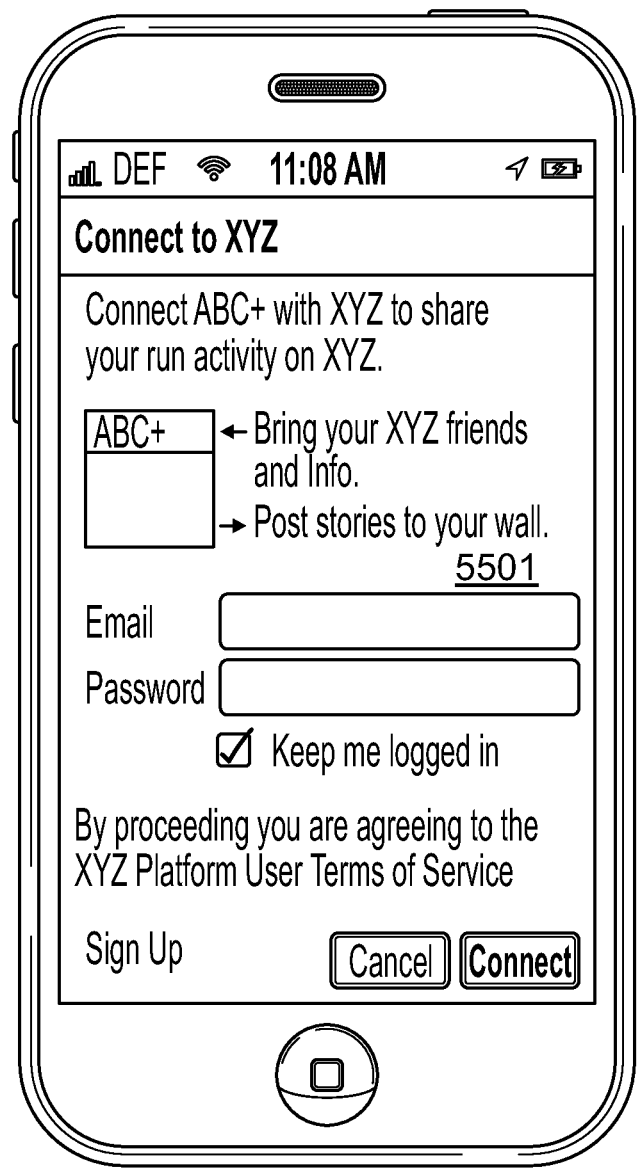

FIGS. 55A and 55B illustrate other example interfaces for sharing workout/run information. Interface 5501 of FIG. 55B, for example, allows the user to enter login information for a social networking site or other information outlet. The login information may be stored and used in association with a fitness monitoring service provider to synchronize and publish data automatically to the information outlet. Once the user is logged in, the system may automatically share new run information through the information outlet. In some arrangements, the information might only be shared in response to receiving a user command or confirmation.

Workout information may be shared through other channels including a fitness monitoring service provider site, a personal homepage and the like. In some arrangements, the user may be able to publish workout information to multiple sites or services simultaneously or non-simultaneously through a single sharing interface.

Figure 56:
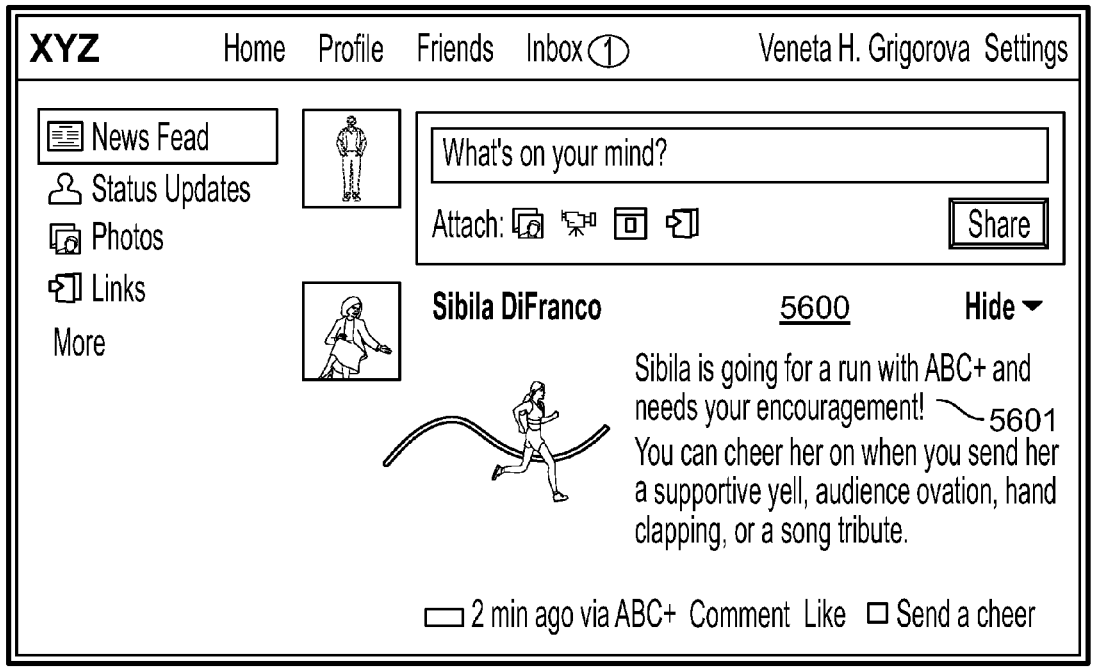
FIG. 56 illustrates an example social networking site interface in which workout information may be posted and conveyed.

FIG. 56 illustrates an example social networking site interface in which workout information may be posted and conveyed. Interface 5600 may correspond to a user's personal page and includes a status message 5601 that indicates the user is going for a run and encouraging other users to provide supportive comments.

Figure 57:
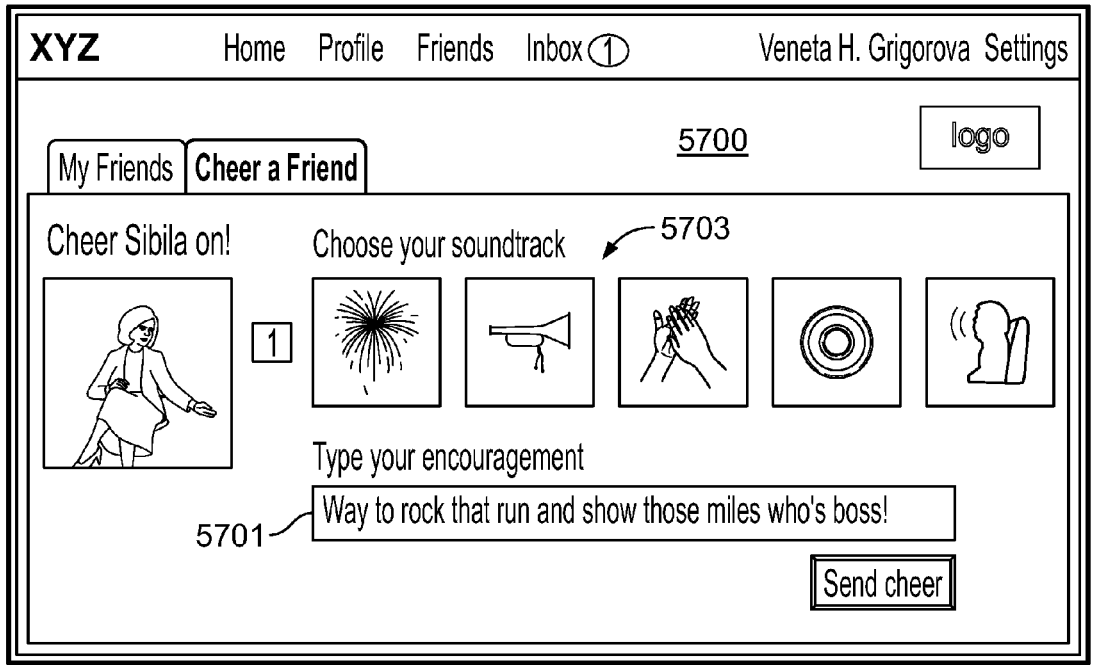
FIG. 57 illustrates an example message entry interface that allows a friend or other user to enter an encouragement message according to one or more aspects described herein.

FIG. 57 illustrates an example message entry interface 5700 that allows a friend or other user to enter an encouragement message in text entry form 5701. The user may also select audio content from a list of predefined sounds 5703.

Figure 58:
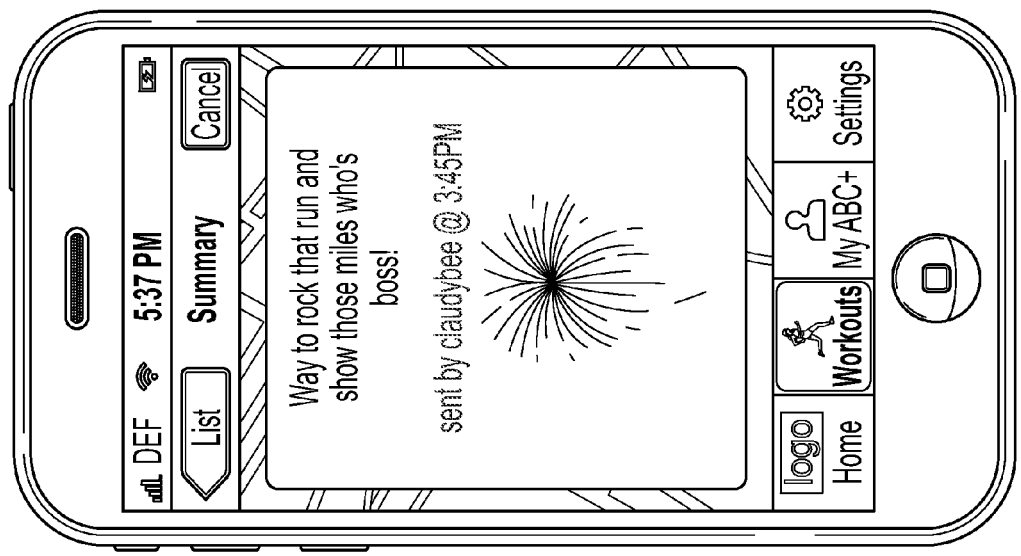
FIG. 58 illustrates an example mobile device interface displaying the message submitted through the interface of FIG. 57.

FIG. 58 illustrates the message submitted through interface 5700 of FIG. 57 and as displayed on a user's mobile device.

Figure 59:
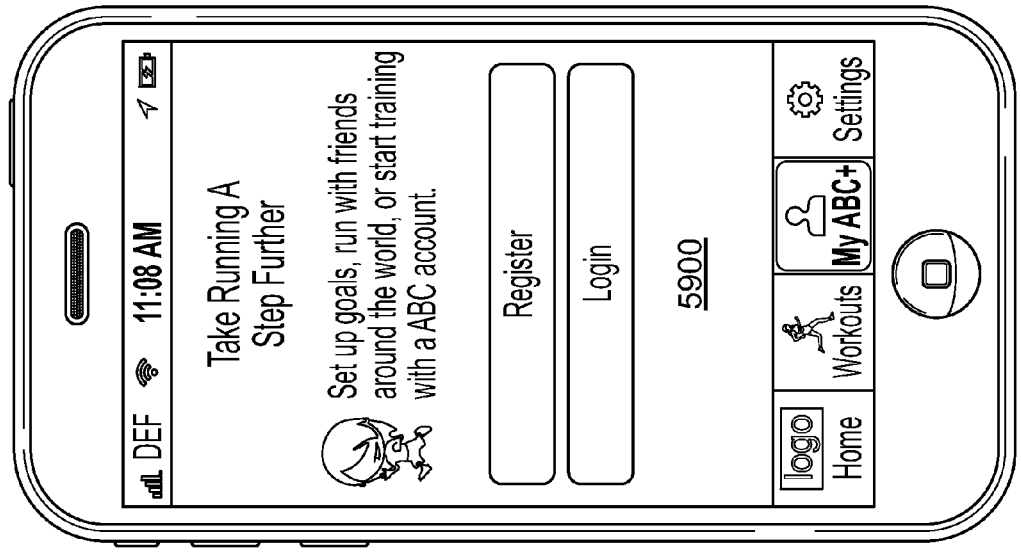
FIG. 59 illustrates a login interface for an athletic activity monitoring service according to one or more aspects described herein.

According to one or more arrangements, a user may further access a remote fitness monitoring service site and receive data through the mobile fitness monitoring device. For example, interfaces may be generated by the mobile monitoring device based on data received from the remote fitness monitoring site through a network. A user may login and/or register with the remote fitness monitoring service through an interface such as interface 5900 of FIG. 59.

Once a user has entered user information and/or login information, the user may navigate through various user interfaces displaying user athletic activity records, achievements, schedules, progress and the like. FIGS. 60A-60D illustrate example interfaces that may be used to navigate and view workout information that may at least partially be received from a remote fitness monitoring site. In FIG. 60A, a user may be informed of a number of runs or workouts that have not yet been synchronized with the remote site. The device may reconcile data between the device and a database of the remote site to identify those workouts or runs that still need to be synchronized. The synchronization message may be displayed as part of a summary of a number of awards and trophies that the user has achieved or earned. Synchronization of the runs may be automatically initiated or initiated through a manual command.

Figure 60B:
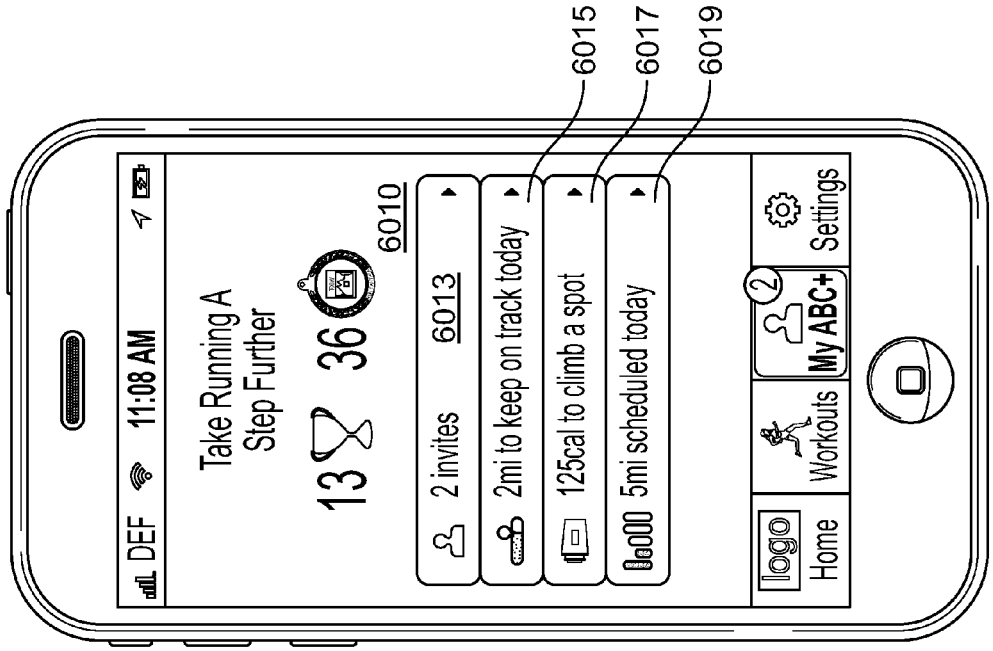
FIGS. 60A-60F illustrate example interfaces that may be used to navigate and view workout information that may at least partially be received from a remote fitness monitoring site according to one or more aspects described herein.
Figure 60A:
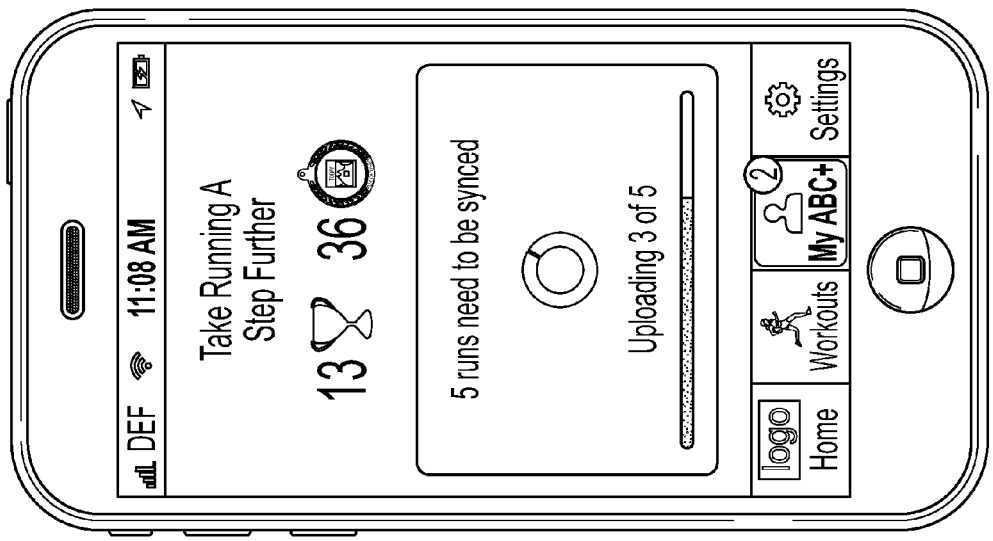

In FIG. 60B, interface 6010 may include a summary of various workout and user data including friend invitations 6013, a daily progress indicator 6015 and goal indicators 6017 and 6019. Friend invitations 6013 may allow for users of the athletic activity monitoring site to interact with one another. Friends may be provided different levels of privileges as opposed to non-friends. For examples, friends may be able to view photos, detailed workout information and other personal data about the user while non-friends might only be allowed to view generic profile data such a name, gender and a general activity level. Accordingly, a user may control who is classified as a friend by confirming or accepting friend requests. The daily progress indicator 6015 identifies an amount of additional athletic activity (e.g., a number of miles) that must still be completed to finish a daily goal such as daily goal 6019. In addition to daily goal, goal 6017 may be defined. Goal 6017 may correspond to another achievement that the user wishes to reach. Alternatively or additionally, goal 6017 may correspond to an elevation in predefined fitness levels or increase a user's ranking among multiple fitness users.

Figure 60D:
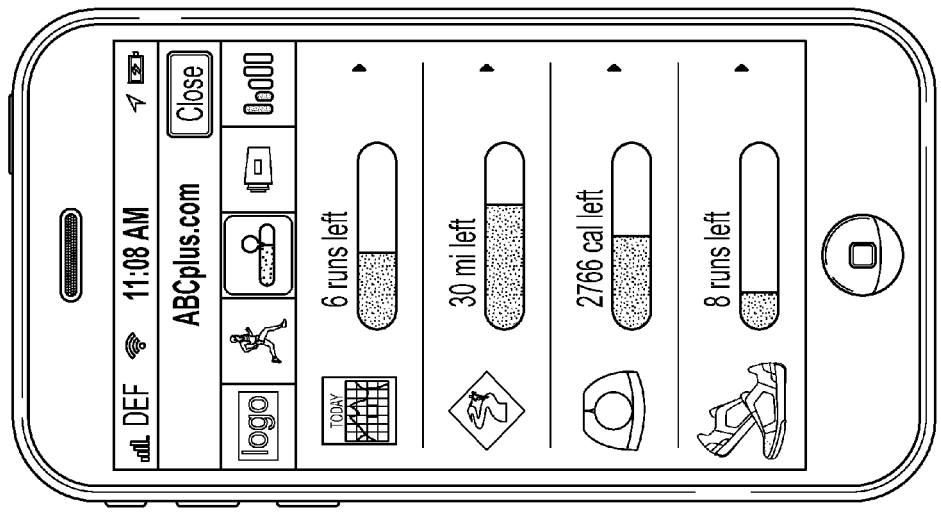
Figure 60C:
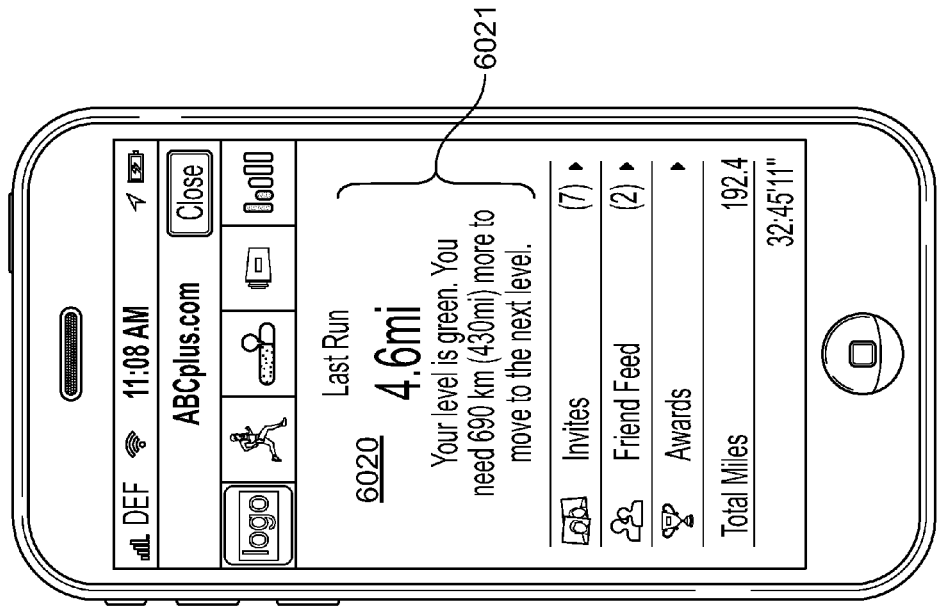

FIG. 60C illustrates an interface 6020 display another example workout data summary that may at least partially be received from and/or generated by a remote fitness monitoring service. For example, summary 6021 may include a summary of a last run (e.g., a number of miles run) in addition to a number of friend invites, a number updates in friend feeds and an award viewing option. Additionally or alternatively, summary 6021 may include the total number of miles that have been run and a total amount of time spent performing athletic activity. The friend need indicator may identify the number of updates that have been posted for the user's friend. For example, if a friend has completed a new run and the friend's profile has been updated with that information, the friend feed indicator may reflect that additional update. Feeds may also include manual posts (e.g., user comments or messages) in addition to automatic updates and posts. A user may use the award viewing option to view the accolades, accomplishments, achievements and goals the user has accumulated in his run history. By accessing data from the remote fitness monitoring site, the user may be able to view workout information and history not previously stored on the mobile monitoring device. Accordingly, the user may be able to view a full workout history and not just what is at that time on the mobile device.

Goals

Figure 61B:
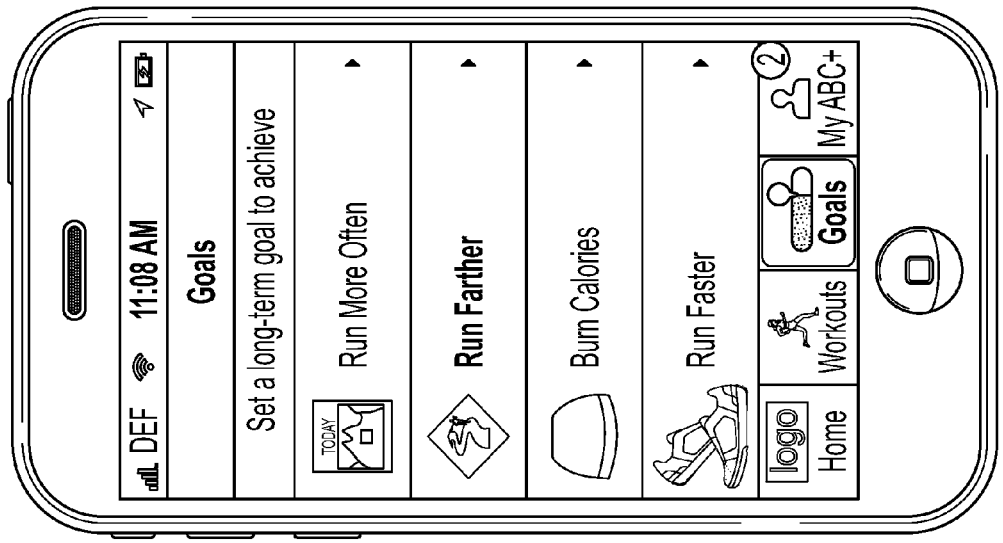
FIGS. 61A-61C illustrate example goal definition interfaces according to one or more aspects described herein.
Figure 61A:
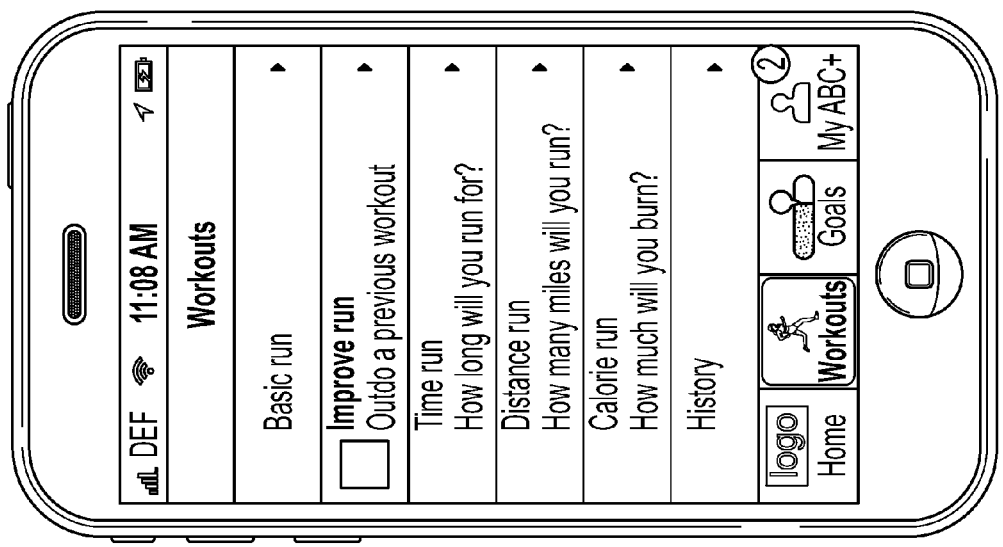
Figure 61C:
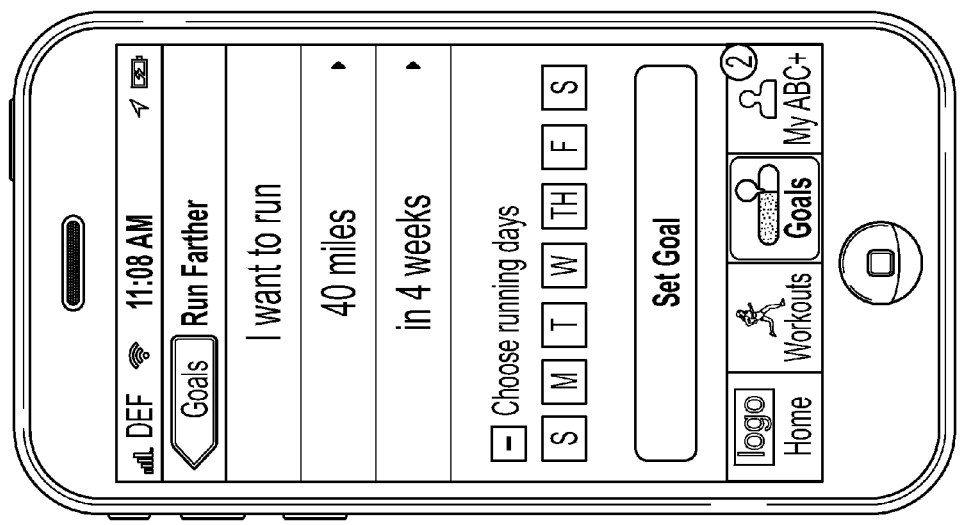

While a user may define an improvement run to set a goal for an immediate run, the user may also be allowed to select a long term goal that may span multiple runs. FIGS. 61A-61C illustrate example goal definition interfaces. In FIGS. 61A and 61B, the user may select an improvement option and subsequent a distance improvement option, respectively. In FIG. 61C, the user may then define the distance improvement goal by selecting an amount off distance the user wishes to run and a time period over which the distance is to be run. The user may also choose which days the user wishes to run in order to achieve the defined goal. Once the various parameters have been selected, the user may set or start the goal. Similar interfaces and options may be defined for other types of goals including time goals, pace goals, calorie goals and the like. The user may also define daily goals. For example, the user may specify how he or she wishes to accomplish the overall goal (e.g., running 40 miles in 4 weeks) on a day to day basis. Accordingly, the user may specify that he or she wishes to run 3 miles on Mondays and 5 miles on Wednesdays. Goals may also be combined. For example, the user may indicate that he or she wishes to run 40 miles in 4 weeks and achieve a pace of 8.5 ml/hour.

Progress towards one or more goals may be tracked in a variety of manners. FIG. 60D, for example, illustrates a goal tracking interface that displays a list of goals and a progress associated therewith. For example, a monthly goal indicates that there are 6 runs left for the months. A distance goal may indicate that there are 30 miles left to be run while a calories goal or objective may indicate that the user still needs to burn 2766 calories to complete the goal.

Figure 60F:
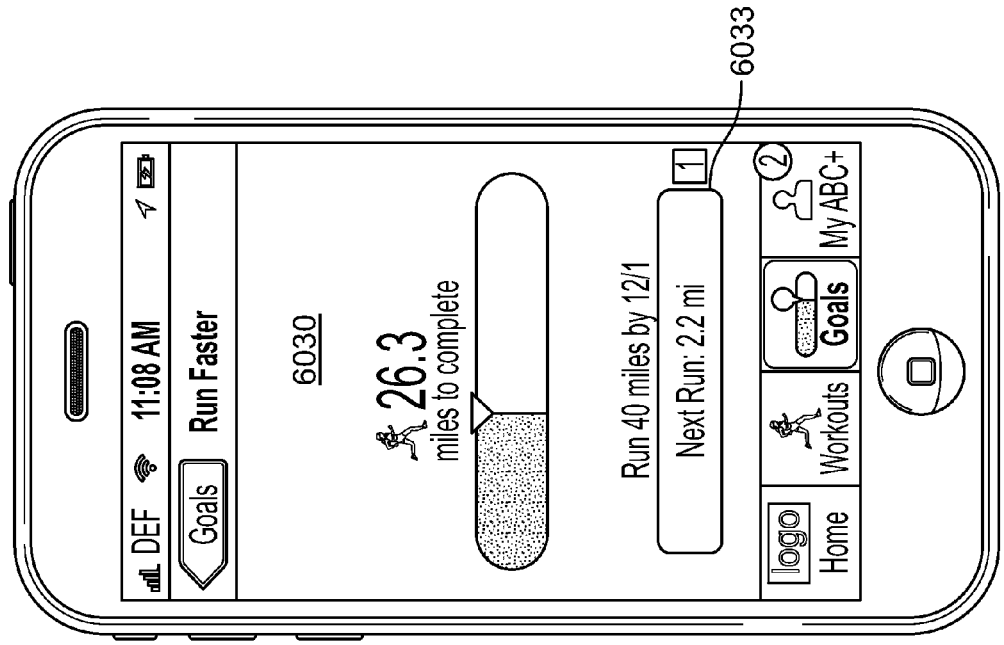
Figure 60E:
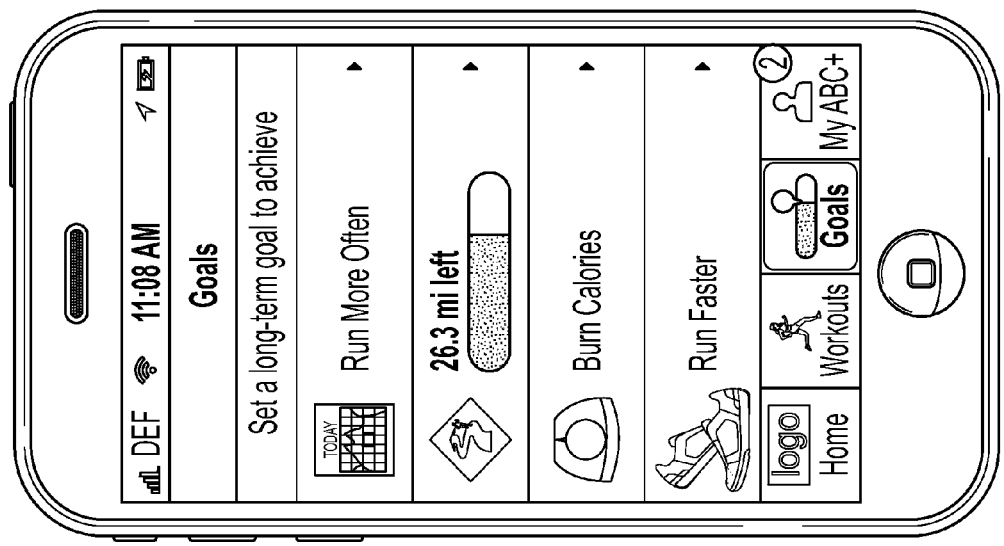

FIGS. 60E and 60F illustrate additional example goal tracking interfaces. For example, in FIG. 60E, a progress bar might not be displayed until the goal type or goal has been selected or the user has placed focus thereon. In FIG. 60F, the interface may display details of the goal and the goal progress. For example, interface 6030 illustrates that the user has 26.3 miles to complete the goal and indicate that the goal is to run 40 miles by December 1. Additionally, the user may be offered an option 6033 to proceed directly to a next workout (e.g., run 2.2 miles).

Figure 62A:
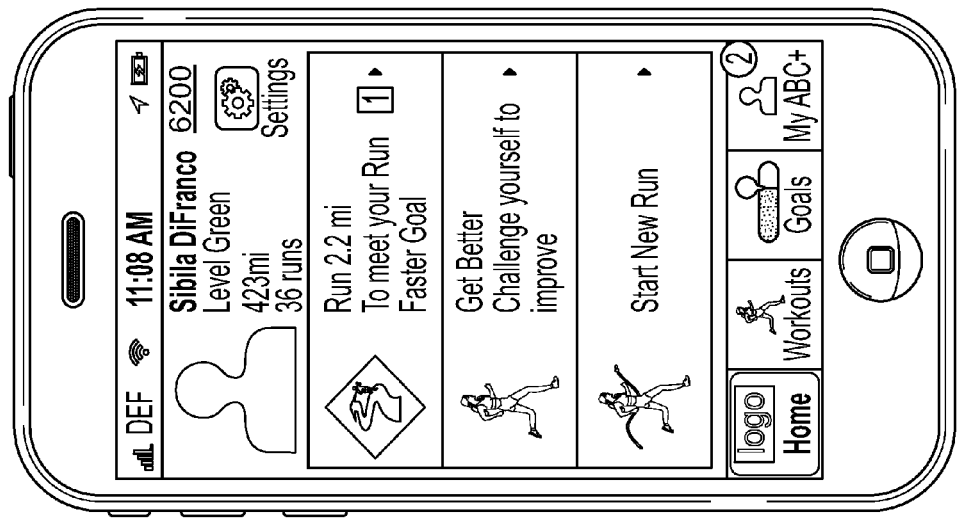
FIGS. 62A and 62B illustrate example interfaces for providing workout and goal reminders according to one or more aspects described herein.
Figure 62B:
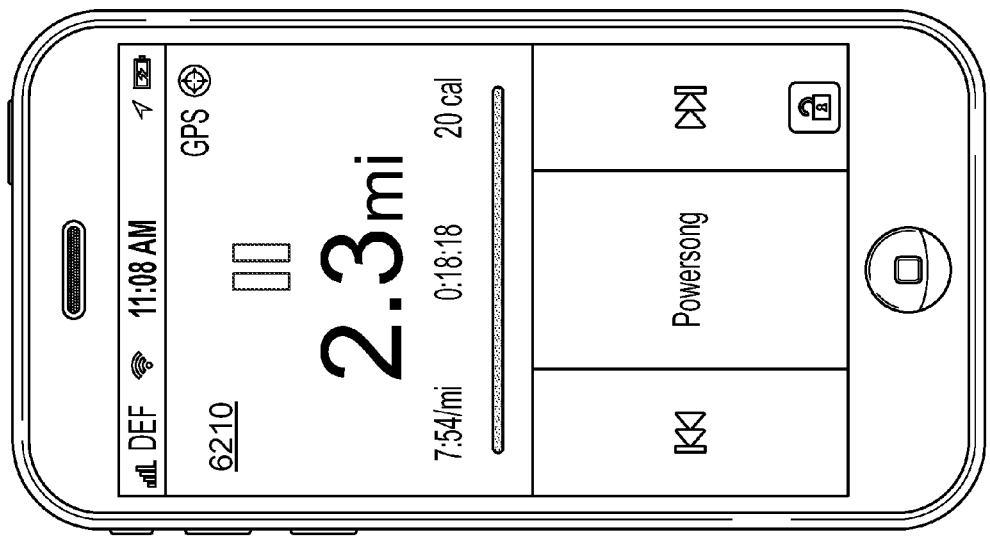

A user may be reminded of goals and workouts for achieving the goal through various interfaces. FIGS. 62A and 62B illustrate example interfaces for providing such reminders. In FIG. 62A, interface 6200 provides a notification that the user must run 2.2 miles to reach his or her predefined goal. In FIG. 62B, interface 6210 may provide various voice notifications during the run. The voice notifications may indicate to the user a progress made toward the goal. For example, the user may be provided with a message that indicates the current portion of the goal has been completed and that progress has been made to the overall goal. The message may, alternatively or additionally, be textual in nature and may further include reminder information such as "Your next run is 3 miles on Saturday" or "You have 5 more runs of 2.2 miles each before completing the goal!"

Celebrations

When a user completes a goal, reaches a milestone, completes an objective, makes progress or completes an improvement run, a user may be provided with encouraging or celebratory messages. Alternatively or additionally, cheers, words or encouragement and other messages may be provided pre- or mid-run. These messages may include audio, video, images, animated images, tactile or haptic feedback (e.g., vibrations) and the like. In one or more arrangements, the celebratory messages may include a celebrity. The user may be allowed to configure when such messages are to be rendered. For example, the user might not want celebratory messages during the run and thus, may indicate a preference that all messages be played after a workout or during non-workout times.

Figure 63A:
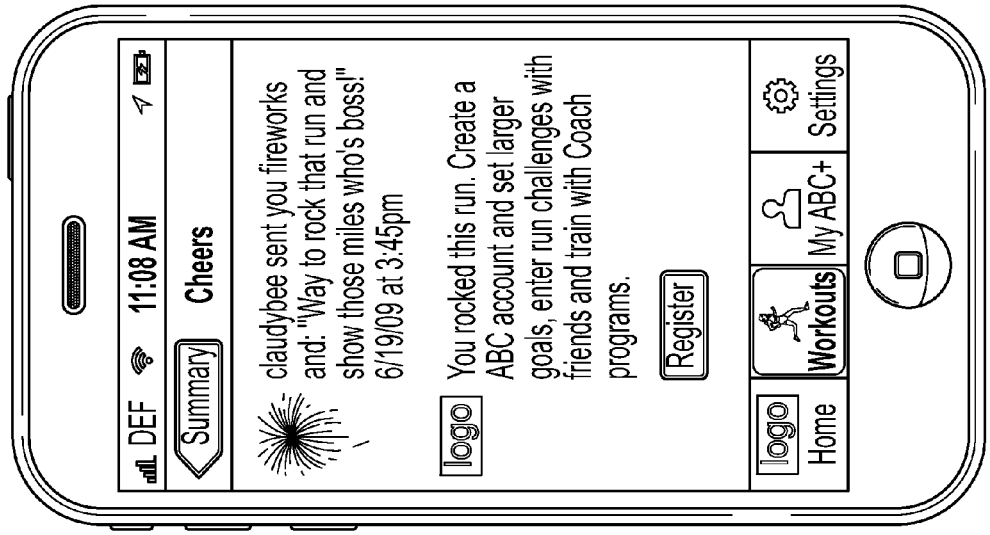
FIGS. 63A-63C illustrate example celebratory interfaces in which one or more congratulatory or motivating messages may be displayed in a list according to one or more aspects described herein.
Figure 63C:
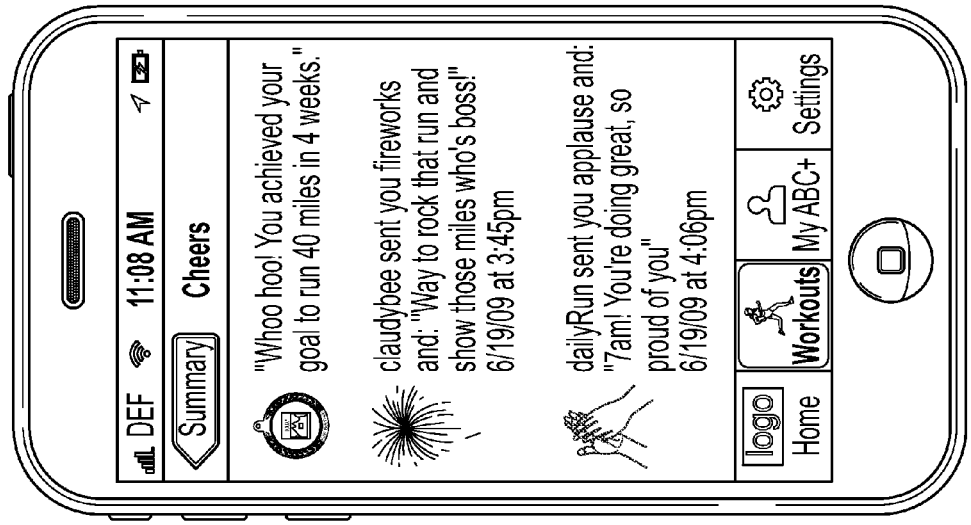
Figure 63B:
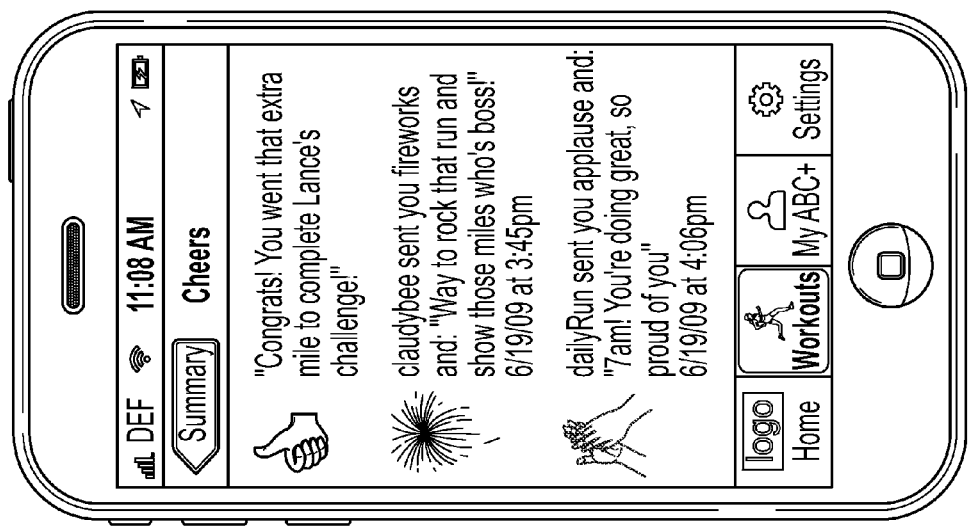
Figure 64B:
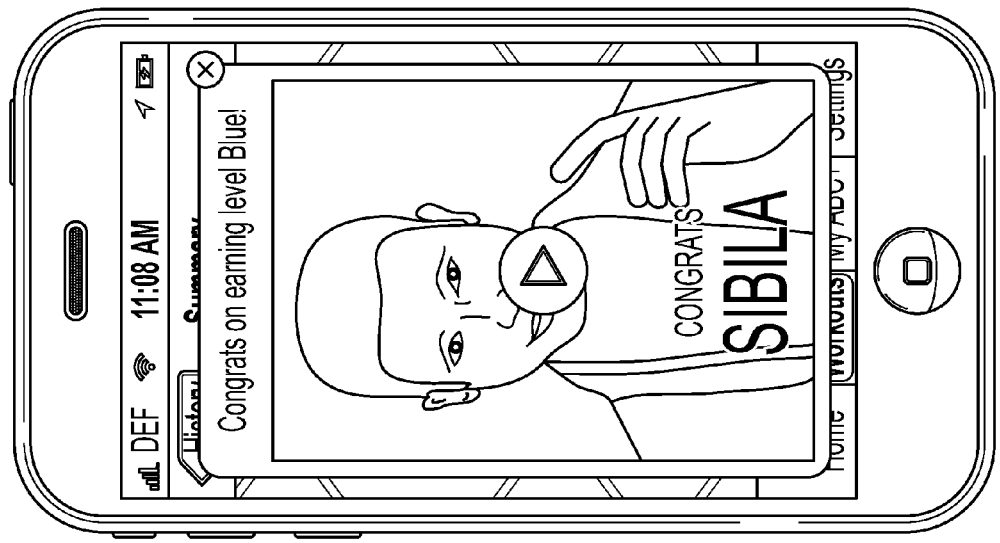
FIGS. 64A-64E illustrate example congratulatory interfaces that include celebrity messages according to one or more aspects described herein.
Figure 64A:
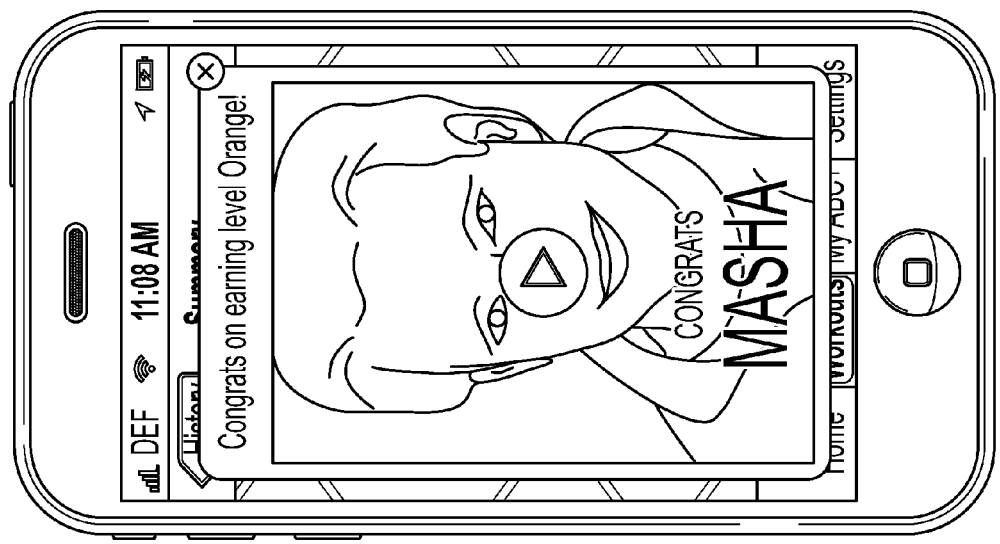
Figure 64D:
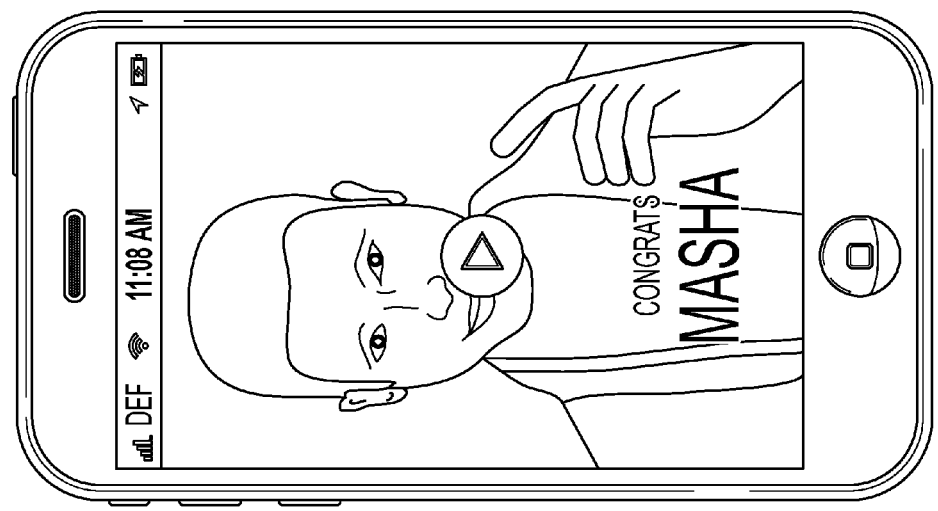
Figure 64C:
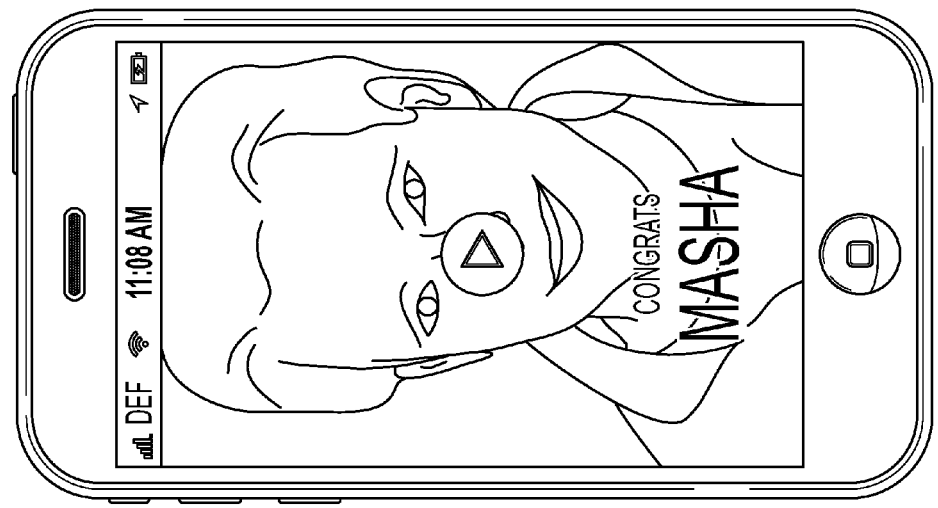
Figure 64E:
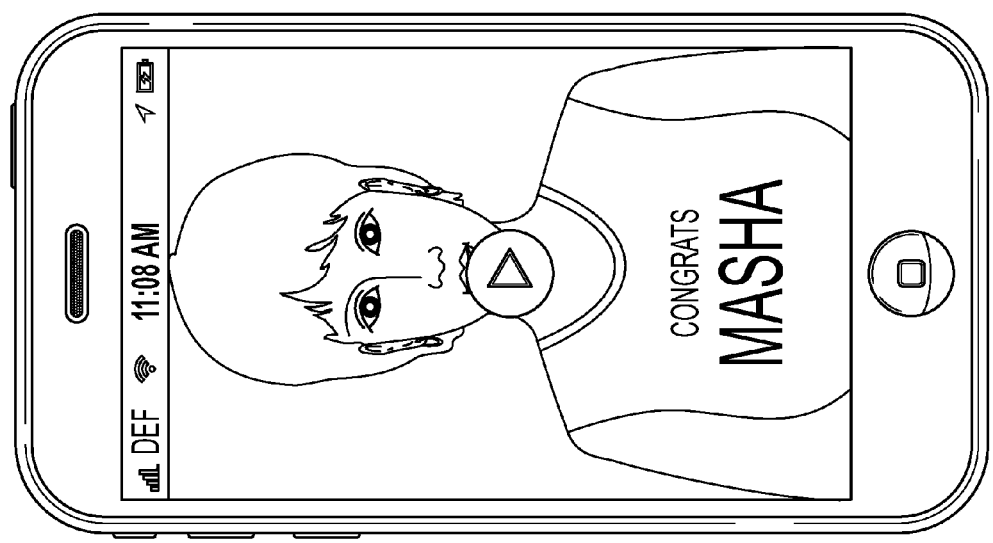

FIGS. 63A-63C illustrate example celebratory interfaces in which one or more congratulatory or motivating messages may be displayed in a list. Some messages may be generated by the mobile device while other messages may be received from other users. In one or more examples, the messages may be converted using text-to-speech systems and played through an audio output device. Alternatively or additionally, other users may send audio and/or video messages. A sender of the message may indicate a triggering event for when the message is to be conveyed to the user. For example, the sender may specify that the message is to be displayed or played to the user when the user reaches a 5 mile mark during a single workout.

In some examples, a user may be congratulated by a celebrity. FIGS. 64A-64E illustrate example congratulatory interfaces that include celebrity messages. The messages may include audio and/or video. The messages may be conveyed for various achievements such as completing an improvement run, reaching a milestone (e.g., 25 miles in a week), setting a fastest pace, fastest distance or fastest pace. In one or more arrangements, an achievement may include reaching different fitness levels. For example, running 5 miles or less in a week may be considered to be a first fitness level while running more than 5 miles but less than 10 miles a week may be considered a second fitness level. Additional fitness levels may be defined and various awards or privileges may be associated therewith. For example, the user may receive access to different workouts, receive various awards (e.g., music, products, services), earn recognition through various public channels (e.g., on a fitness monitoring site's main page) and the like.

Display of Athletic Activity Information

Athletic activity information and information generated therefrom (e.g., statistics, trends, recommendations, etc.) may be displayed in one or more interfaces as described herein. In one arrangement, a user may access a remote network site that generates and displays athletic activity information for a user registered with an athletic activity monitoring service. In one or more arrangements, the information displays and interfaces may be accessed through the mobile device and/or a fitness monitoring application executing thereon. Alternatively, the user may access the information displays through another computing device. Because in some arrangements, the information displays are generated and provided by a remote fitness monitoring server, the user may access the workout information from a variety of locations and devices without having to synchronize or transfer data to each of those devices or locations.

Figure 65A:
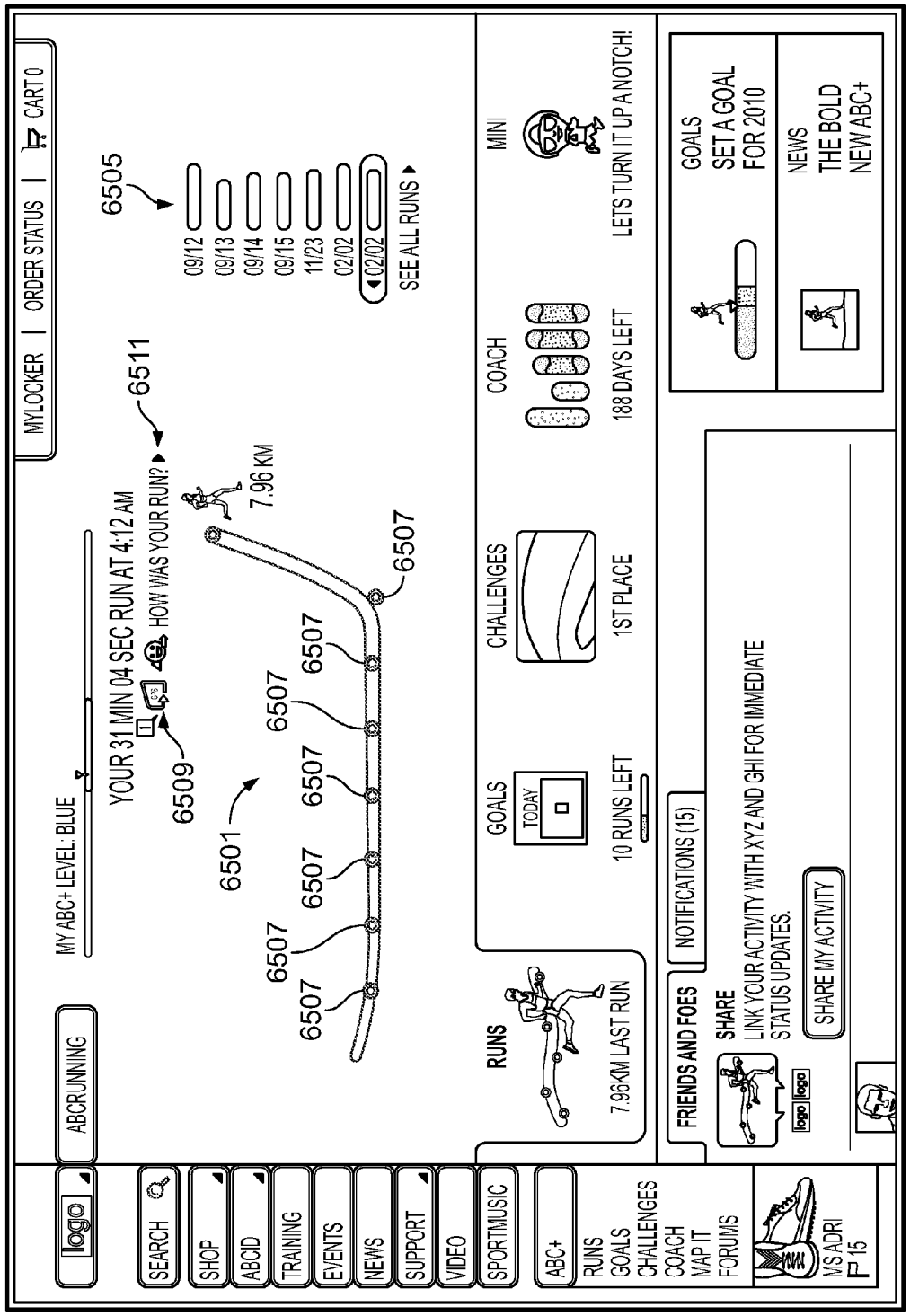
Figure 65B:
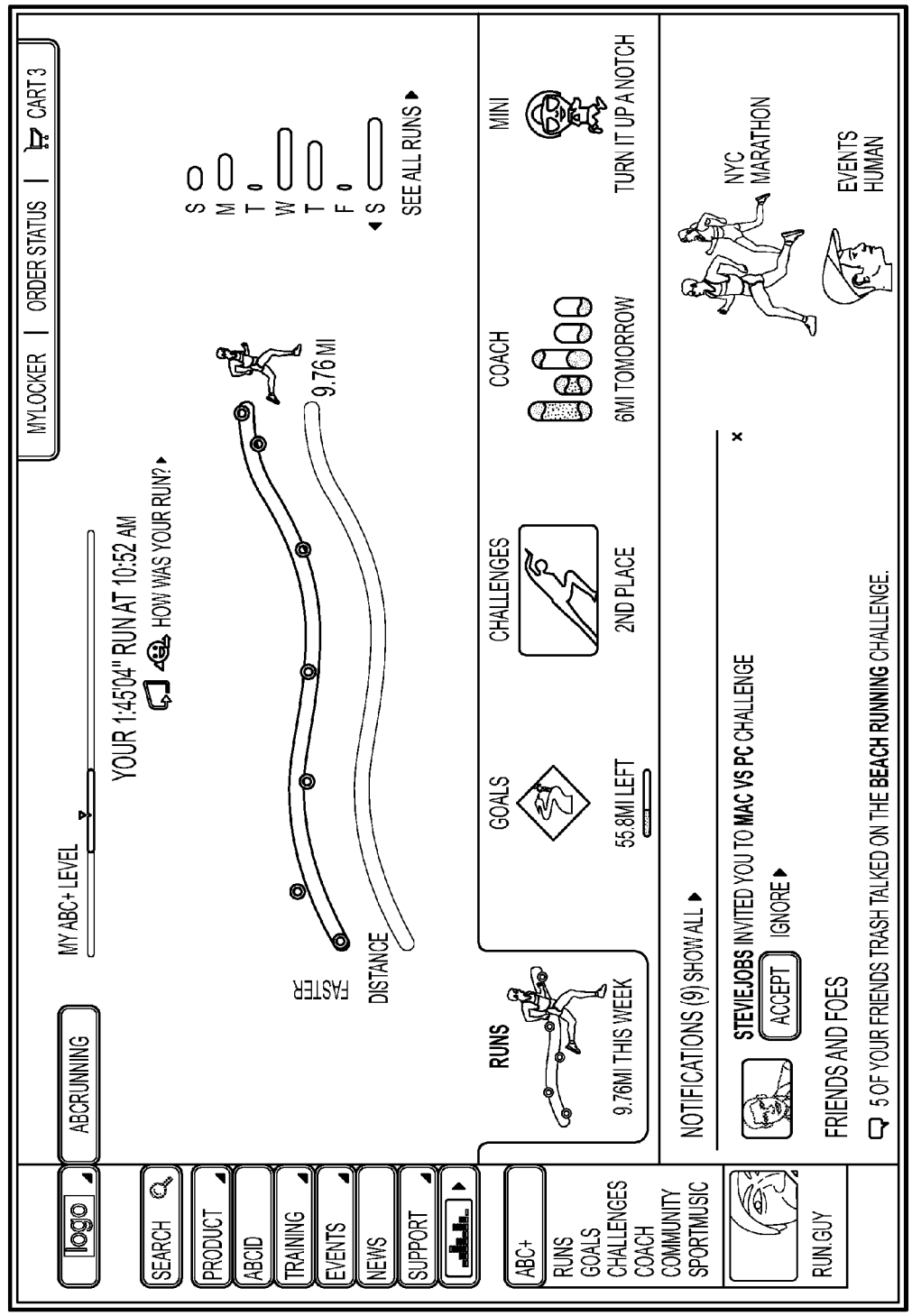

FIGS. 65A and 65B illustrate example interfaces that include a workout review. The workout review may include a graph 6501 of the user's pace over the entire distance run for a selected run. A user may select different runs to view from a workout list such as list 6505. List 6505 may include a predefined number of most recent workouts. Graph 6501 may include indicators or markers 6507 that identify points in the run that correspond to a distance increment such as 1 mile, 1 kilometer, 0.5 miles and the like. The workout review interface may further include workout attribute indicators such as a GPS indicator 6509. GPS indicator 6509 may signify that the workout was recorded with GPS information. Accordingly, a user's route may have been recorded as part of the workout information. Additionally, a user may add further attributes or parameters to the workout. For example, the user may select mood selector option 6511 to enter a mood of the user after the run. The mood may include how the user emotionally and/or physically felt after completing the workout. Other information may also be included in the workout review including news or message feeds, a brief summary of a last run, a goal progress (or an amount left to complete to reach the goal), a challenge progress or position and the like.

Figure 65C:
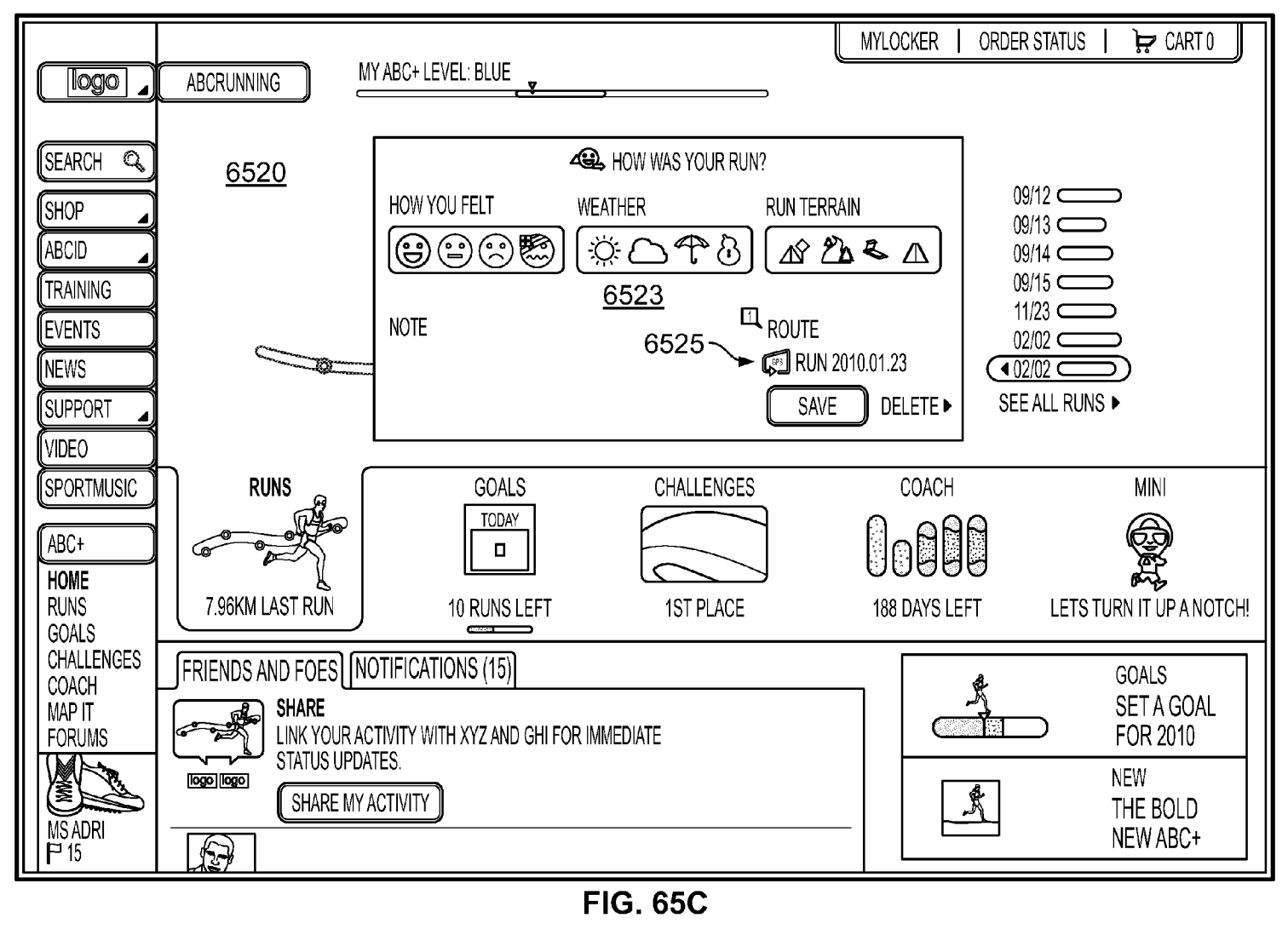
Figure 65D:
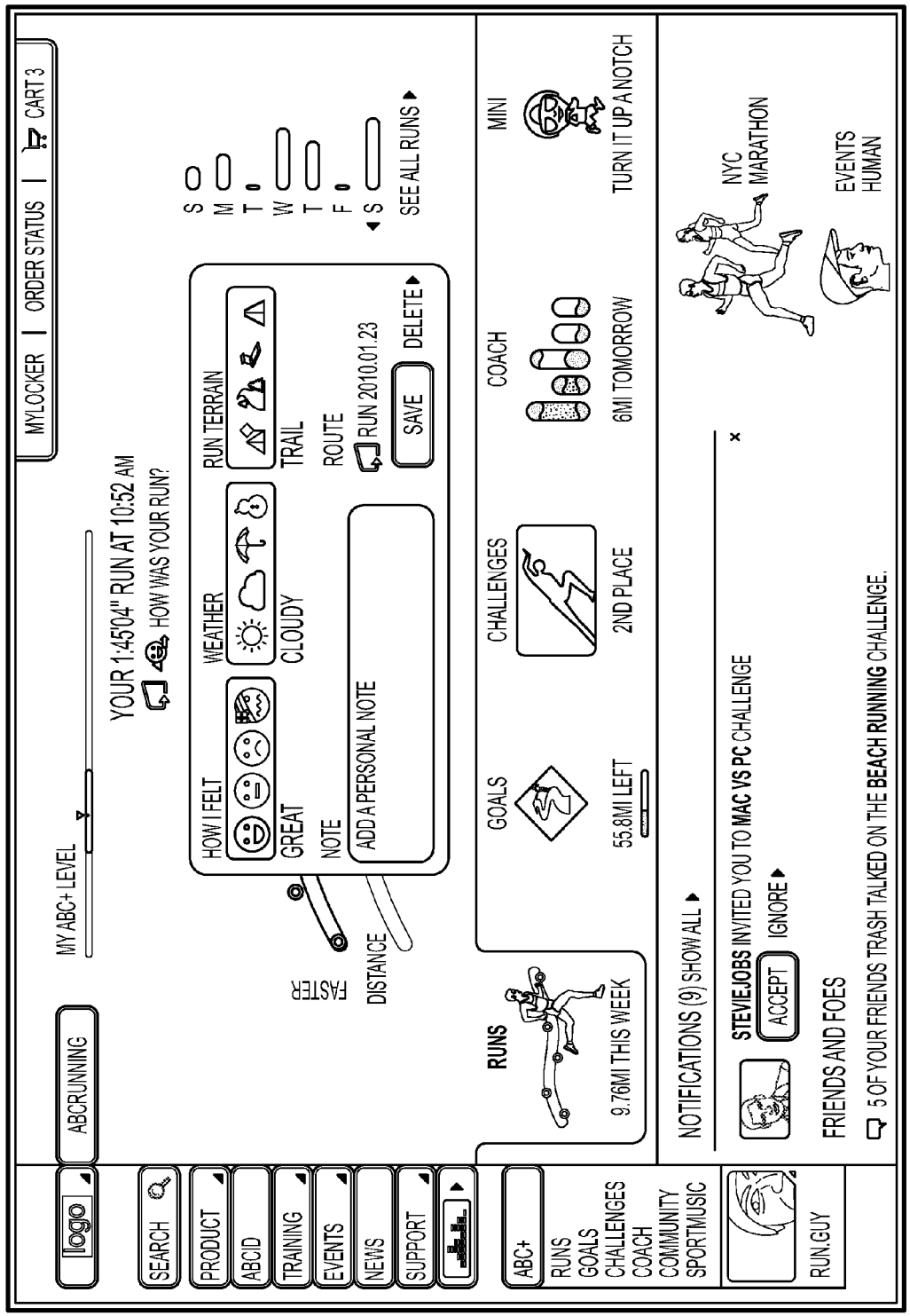

FIGS. 65C and 65D illustrate interfaces for entering attributes of a run or workout. For example, interface 6520 includes an input window 6523 for specifying a user's mood, a weather condition and a terrain. Window 6523 may further provide a text entry form configured to receive additional user comments about the workout. In one or more arrangements, window 6523 may display an indicator 6525 if the workout was recorded using location determination systems such as a GPS device.

Figure 65E:
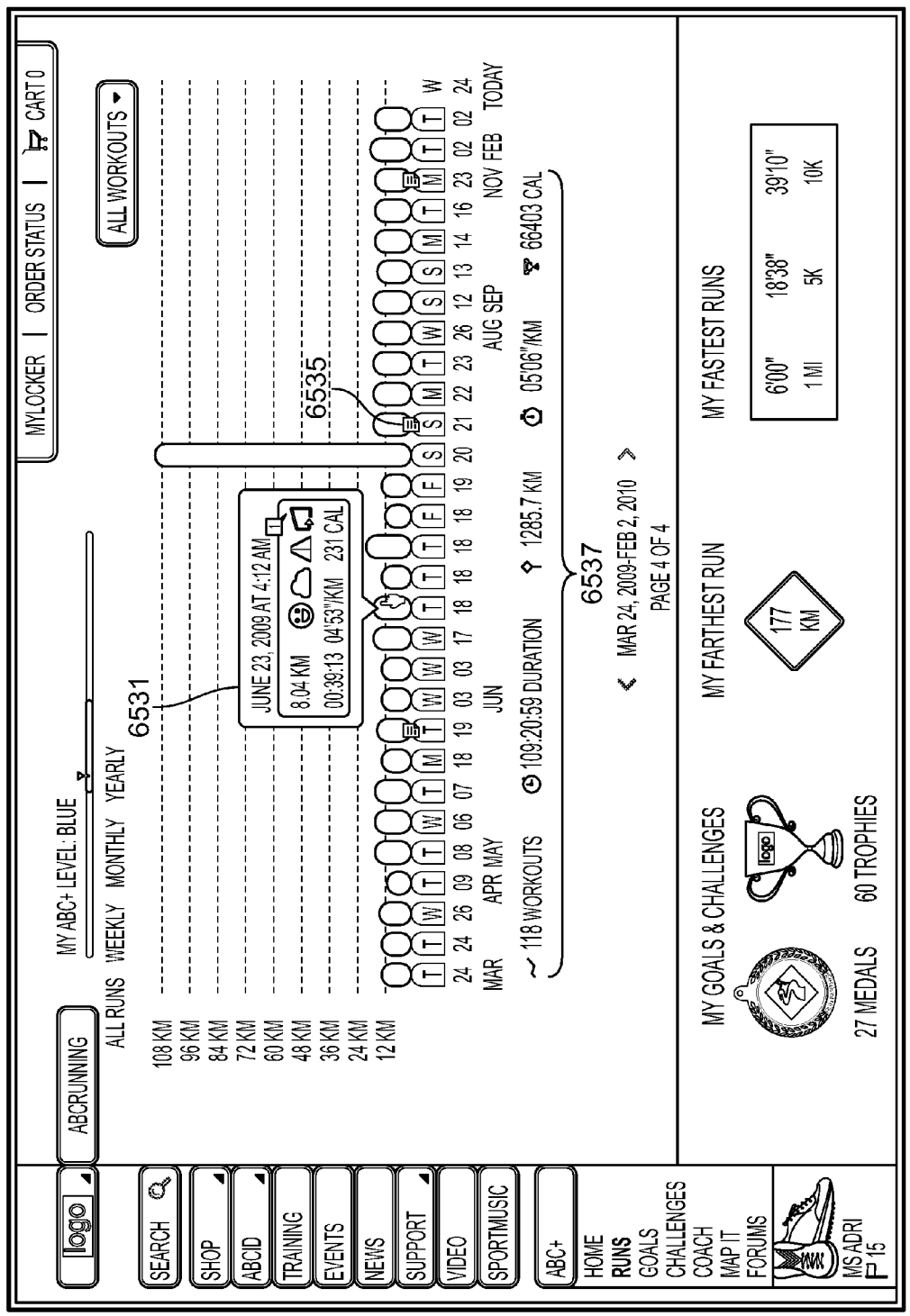
Figure 65F:
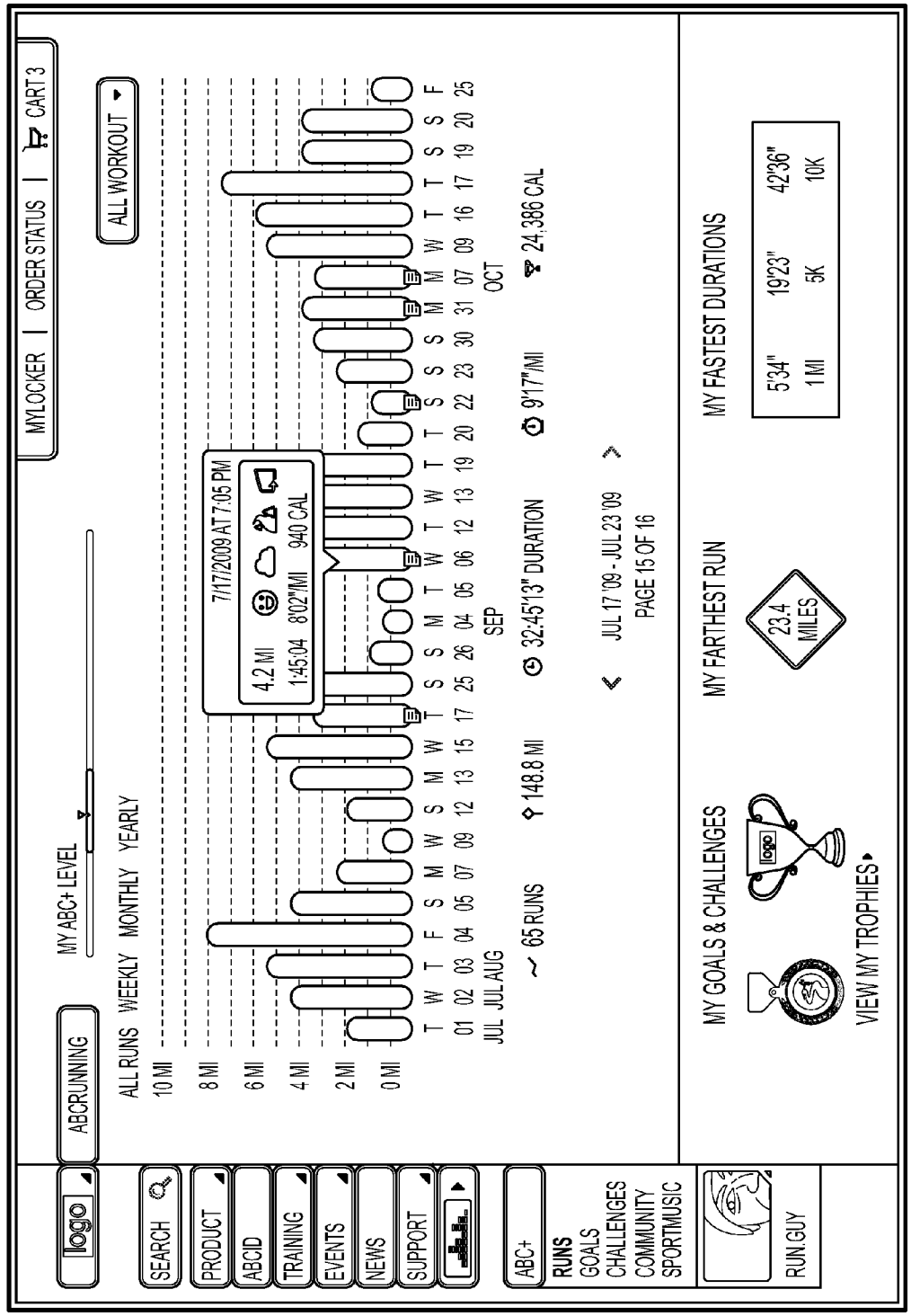

FIGS. 65E and 65F illustrate calendar or timeline views of a workout summary for multiple workouts. Each day may include a bar graph that indicates a distance run on that day (or other time unit such as hour, week, month, etc.). Hovering over or otherwise interacting with each bar graph may cause a detail window such as window 6531 to be displayed with additional information about the run. For example, window 6531 may indicate the user's mood after the run, a weather condition, a terrain and whether the workout includes location and route information. If a user has entered a manual or custom note, a note icon 6535 may be displayed in association with bar graphs representing to the corresponding workout. Summary data 6537 may also be displayed for indicating a total amount of time, workouts, distance and calories burned for all workouts in the currently displayed timeframe.

Figure 65G:
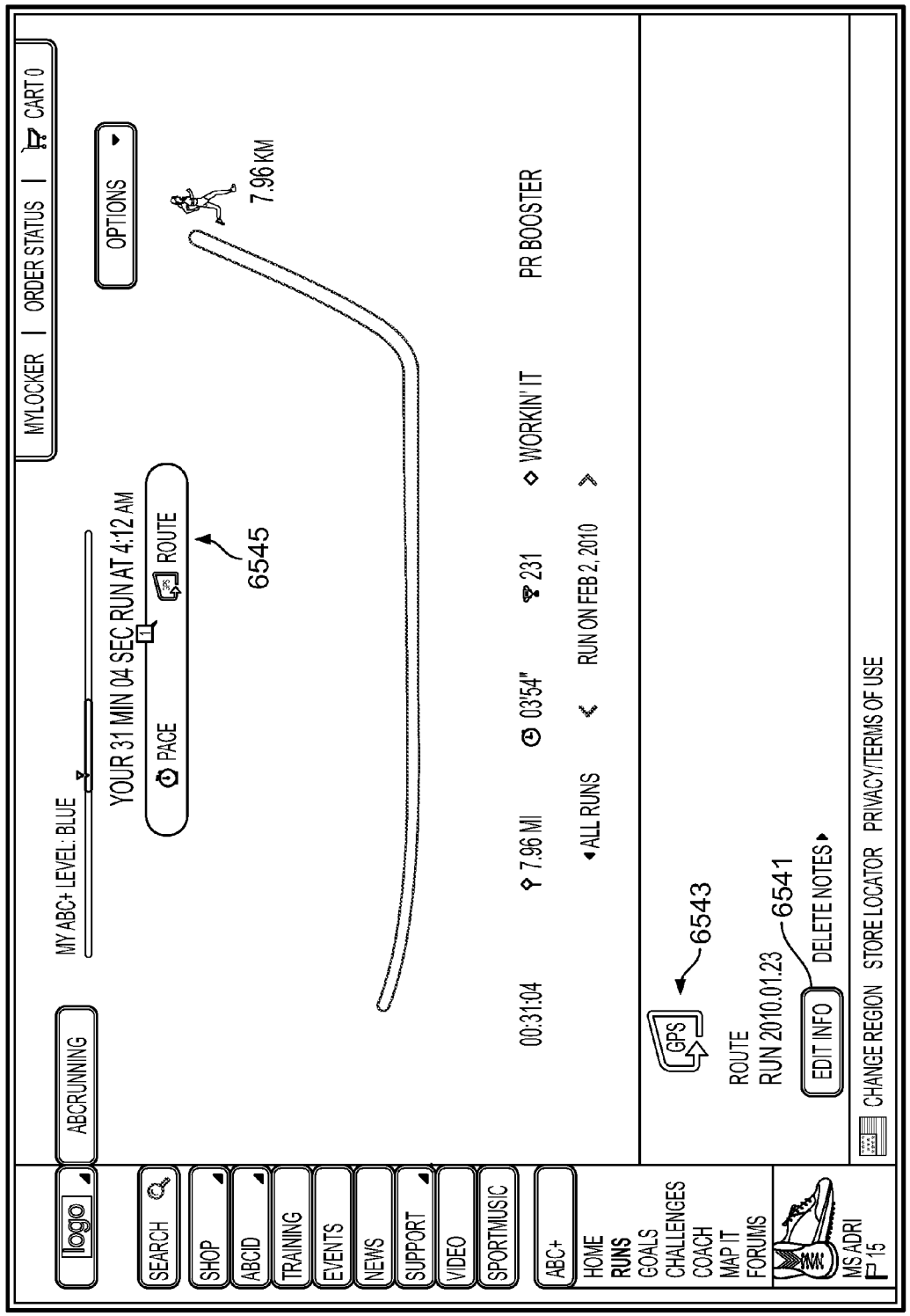
Figure 65H:
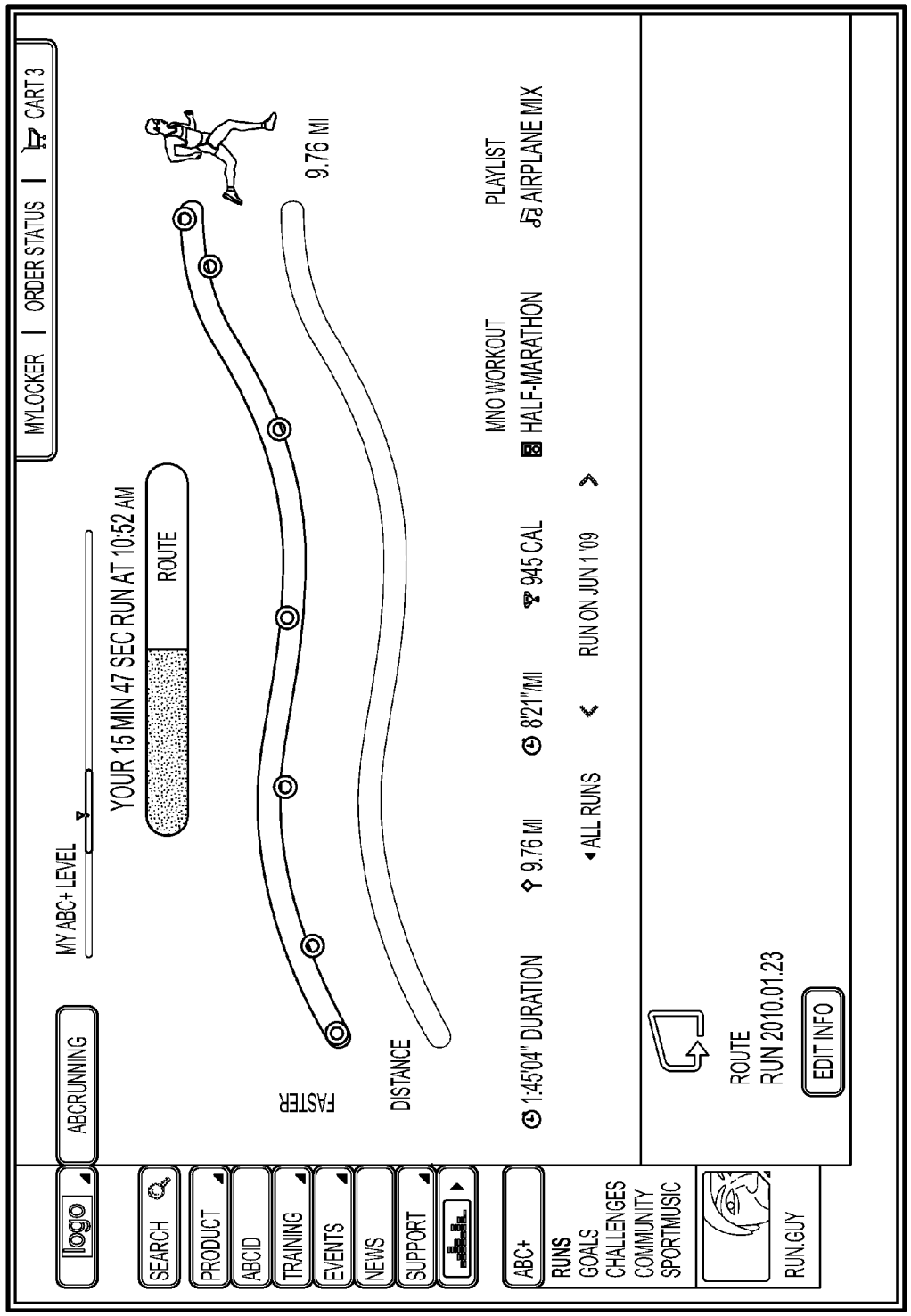

Upon selecting a particular workout to view and/or analyze, the user may be presented with an interface that provides details for the selected workout. FIGS. 65G and 65H illustrate an example run details page that provides a summary of the statistics recorded for the run. The user may be allowed to edit various parameters stored for the workout using edit option 6541. In some arrangements, some parameters might not be changeable such as the distance and time run and/or calories burned. If the run was recorded with a GPS device or other location positioning system, the run details interface may include a GPS indicator 6543. Additionally, the interface may display a route view option 6545 if the run was recorded with location information. Routes and route information is further described in detailed below.

Figure 65I:
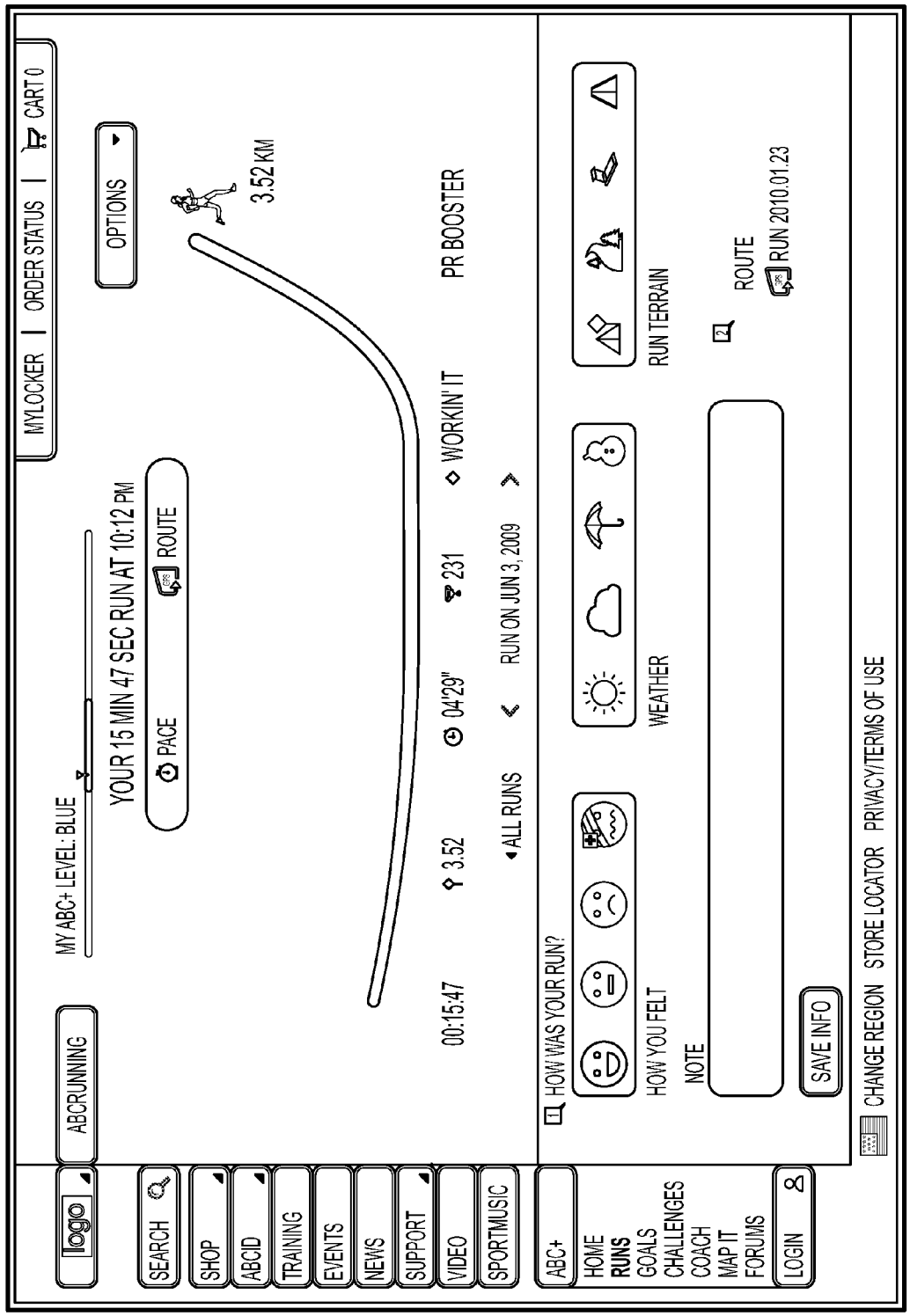
Figure 65J:
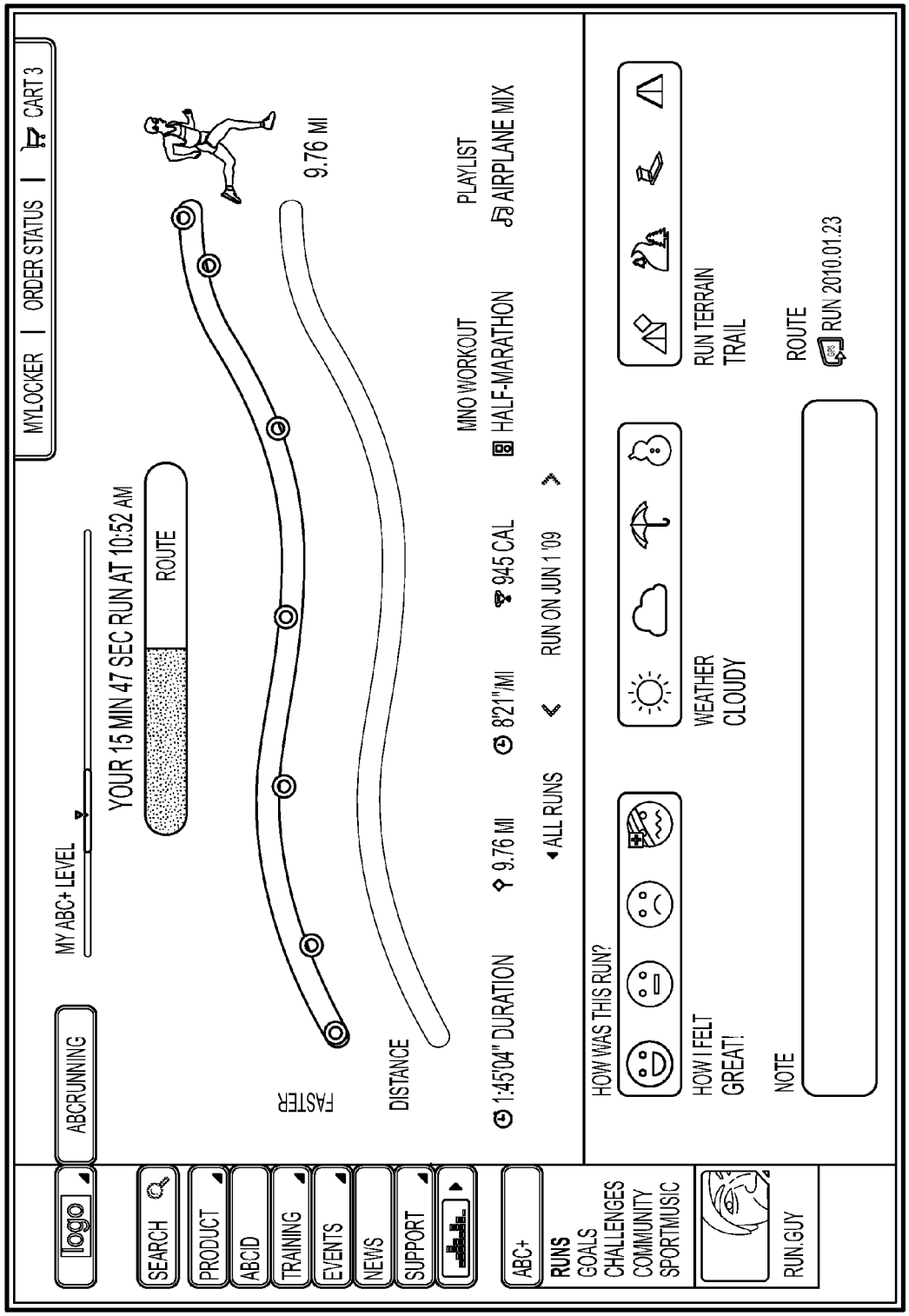

FIGS. 65I and 65J illustrate edit interfaces for modifying one or more parameters of the recorded workout information. For example, the user may be provided with options to modify the user's mood after the run, the weather conditions, the terrain and a note. Other parameters may also be modified depending on user preferences, service provider requirements and rules and the like.

Route Tracking, Display and Creation

As described herein, in some arrangements, a user's workout may be recorded with location determination systems. Accordingly, the user's route may be recorded and stored as part of the workout data. Upon retrieval of the workout data, the route may be displayed for the user's review.

FIGS. 66A-66G illustrate a series of route detail interfaces in which route information may be displayed. For example, in interface 6600 of FIG. 6A, the user's route 6601 may be drawn in an animated fashion on a map. Icon 6603 representing the user may be animated and move in accordance with the route of the run. The route may be indicated by preliminary route line 6605 followed by a secondary route line 6607 once icon 6603 has traversed a portion of the route. Icon 6603 may be animated in accordance with a speed of the user along the route. For example, icon 6603 may move slower during portions of route 6601 where the user exhibited a slower pace and faster during portions of route 6601 where the user exhibited a faster pace. The movement animation may be proportional to the user's pace and may be calculated using an algorithm that is based on the user's pace (e.g., mile per hour may be converted to pixels per second). Interface 6600 may further include distance markers 6609 along the route to identify the distance increments (e.g., 1 mile, 1 kilometer, 0.5 mile, etc.). Pace markers 6611 may also be included to indicate the points on the route where the user exhibited the fastest pace and slowest pace. Elevation information may also be provided using elevation markers 6613 to identify the point of highest elevation.

In portion 6615, interface 6600 may include graph 6617 of the user's pace and altitude versus time. Lines 6619 and 6621 may change in appearance (e.g., in animated fashion) as the animation of the user's run using icon 6603 proceeds. For example, portion 6623 of line 6619 may appear bolder indicating that the animation has traversed that portion of the route. Marker 6625 indicates the animations current position in the route. Detailed information relating to that position including distance, time, pace and elevation may be provided as well. A replay option 6627 may be selected to have the animation replayed. A replay may, in one or more arrangements, play the animation at a slower pace as compared to a pace at which the animation is shown on initial load of the run and route details. Legend 6629 may provide explanations for each of markers 6609, 6611 and 6613 as well as corresponding workout data. For example, the pace of the best and worst miles may be displayed while the fastest and slowest pace information may also be provided. Elevation data corresponding to highest elevation marker 6613 may further be displayed. Users may also manually create their own markers to help associate a particular location along the run or workout with a set of performance statistics.

Figure 66A:
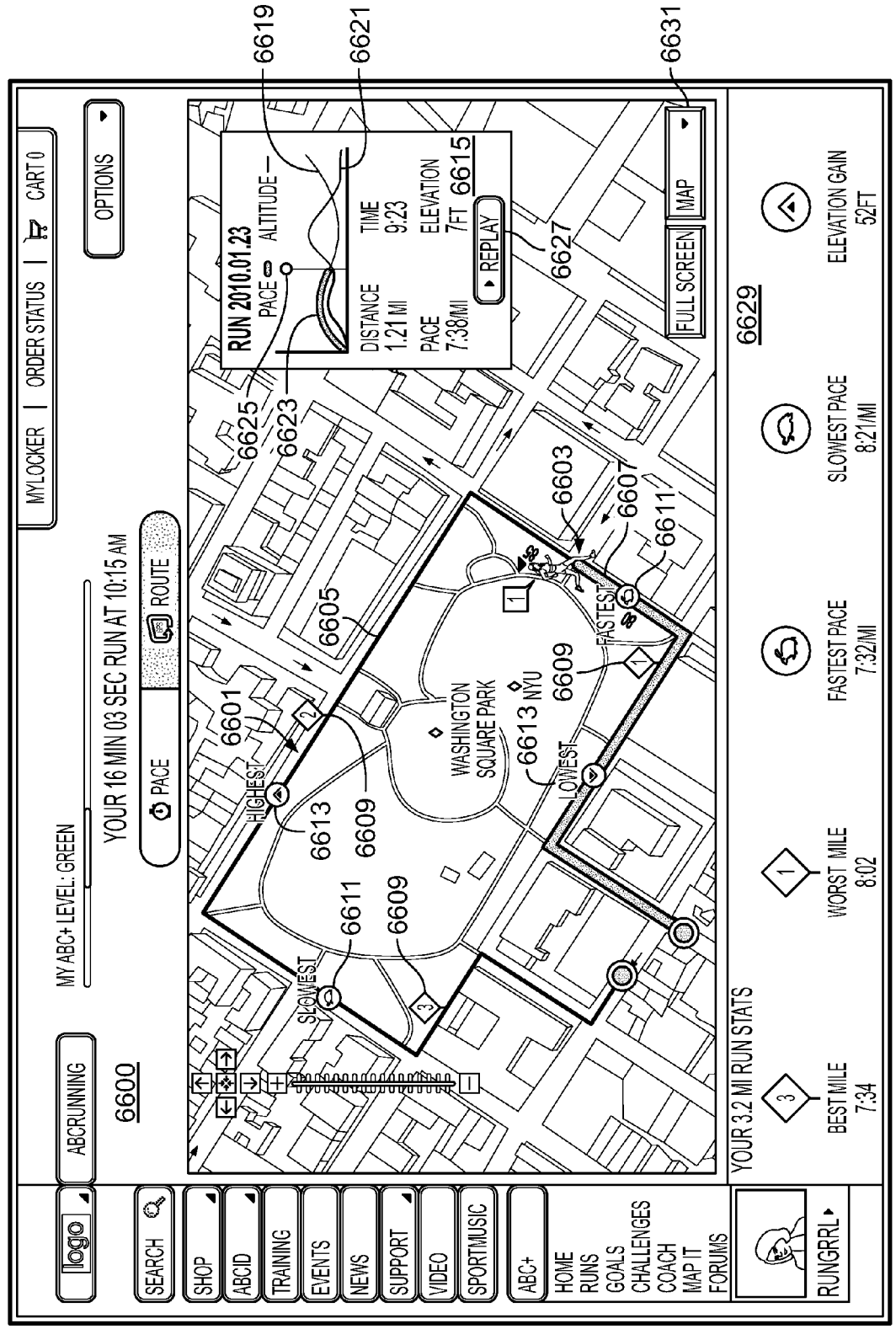
FIGS. 66A-66G illustrate a series of example route detail interfaces in which route information may be displayed according to one or more aspects described herein.
Figure 66B:
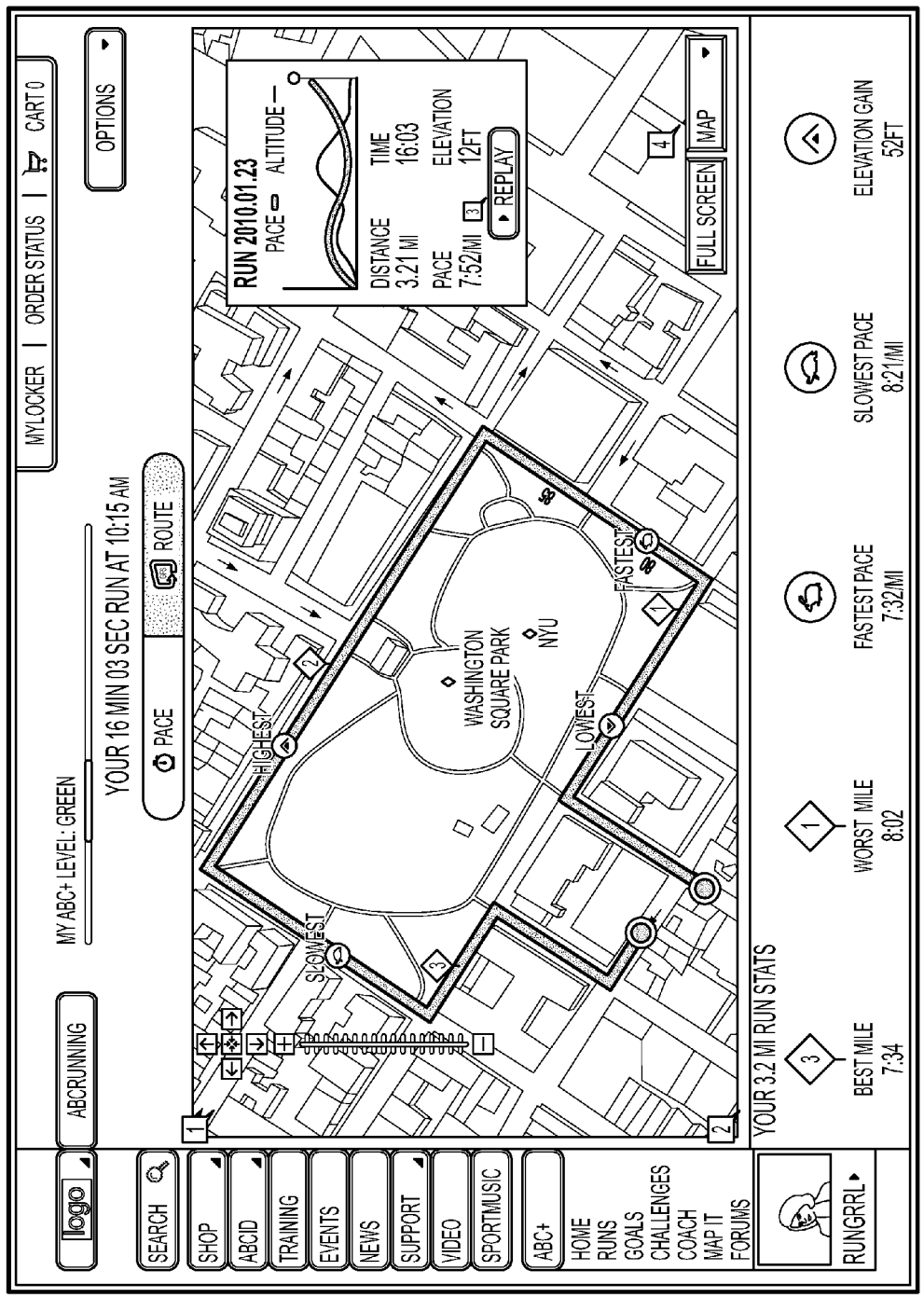
Figure 66C:
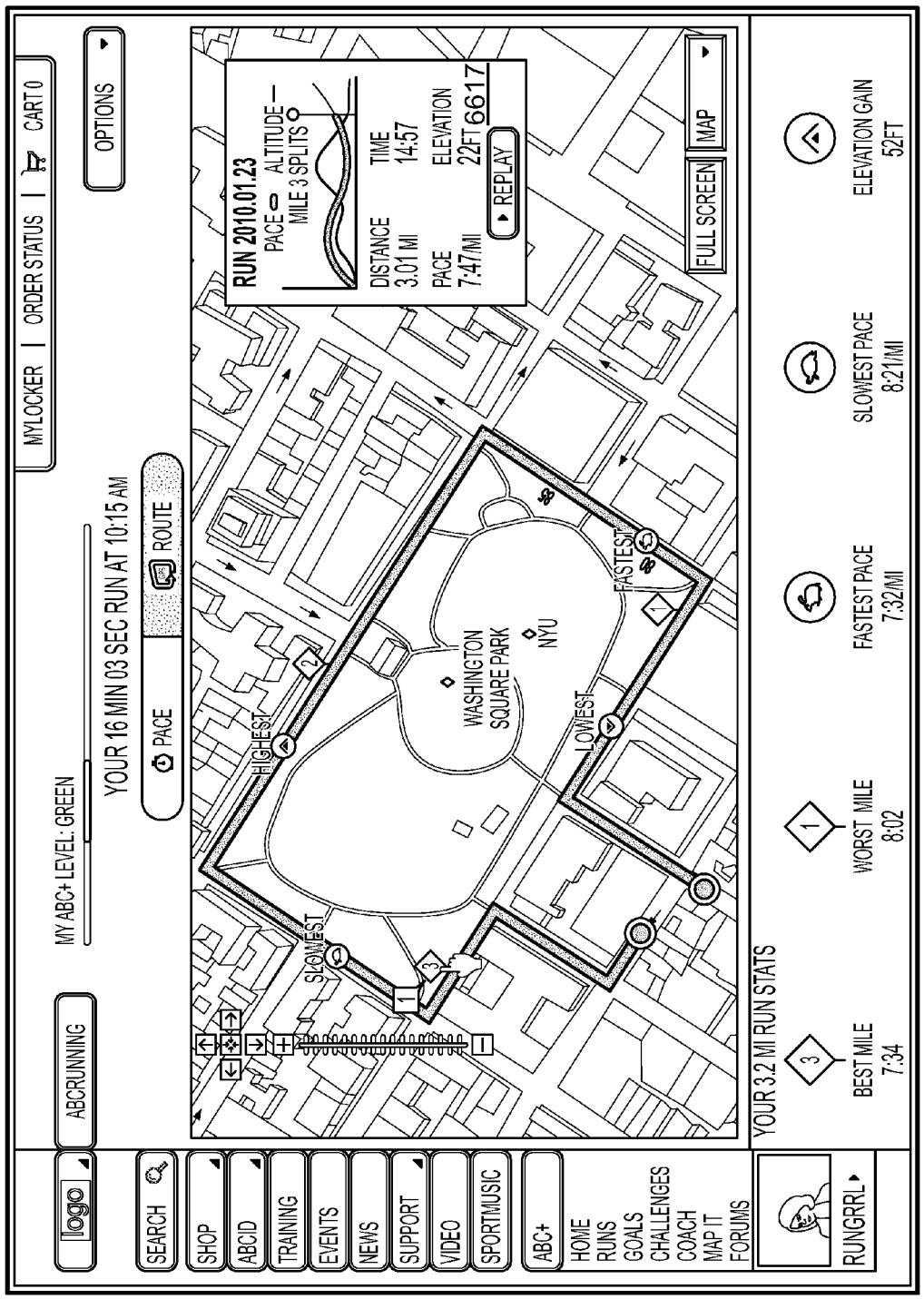
Figure 66D:
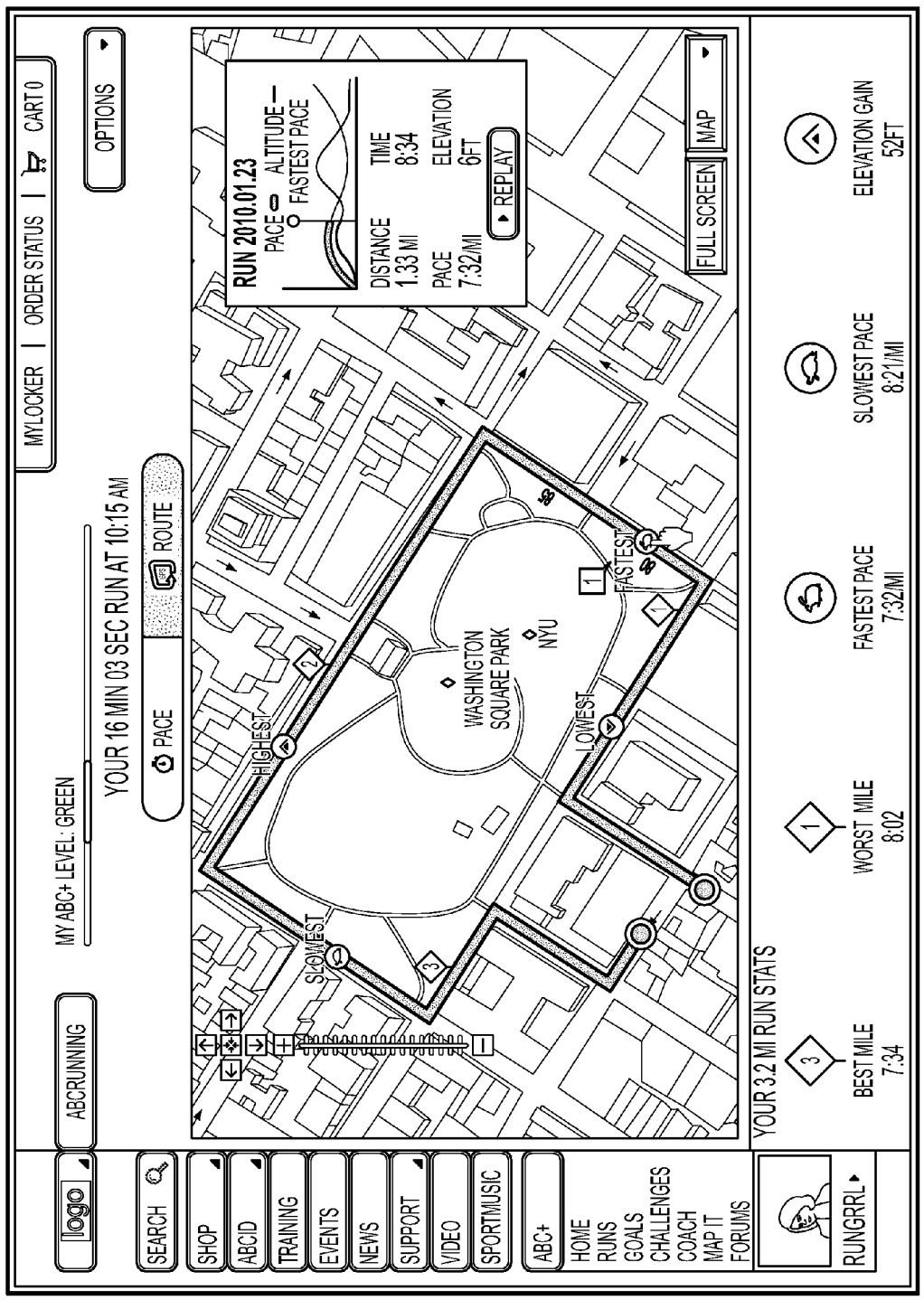
Figure 66E:
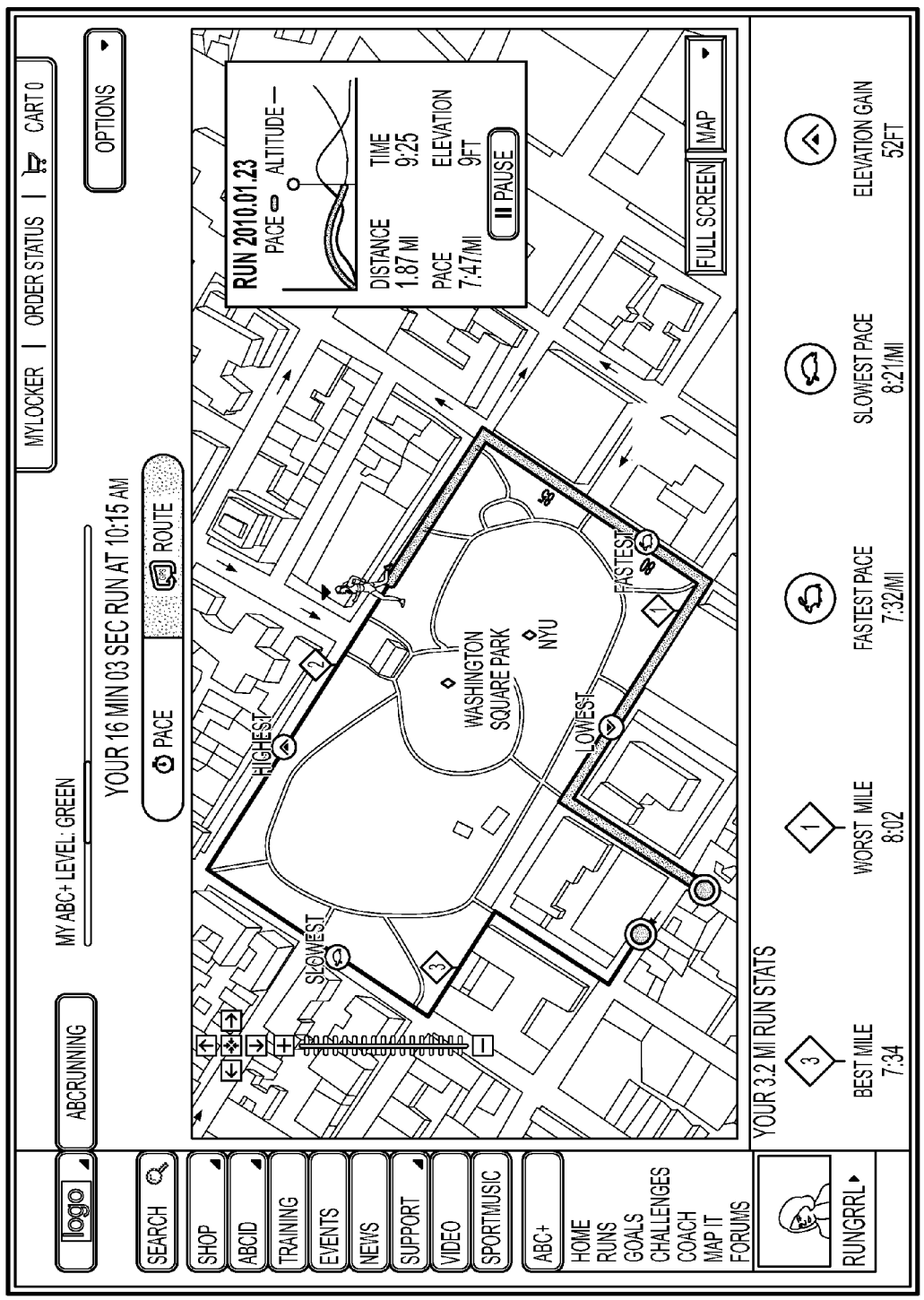

Interacting with one or more of markers 6609, 6611 and 6613 may cause the corresponding workout data to be displayed for that particular point of the user's workout. FIG. 66C illustrates an example interface when a user selects marker 6613. In response to the section, graph 6617 may be modified accordingly to display the corresponding data. In one or more arrangements, the user's icon (e.g., icon 6603 of FIG. 66A) may be moved immediately to the selected location. Additionally or alternatively, the displayed route may also be modified to reflect the position of the user's icon (e.g., the portion of the route up to the selected point may be changed to reflect traversal). Non-marked portions may also be selectable to view workout data. Legend 6629 may also be updated upon selection of a marker or other point on the route.

Figure 66F:
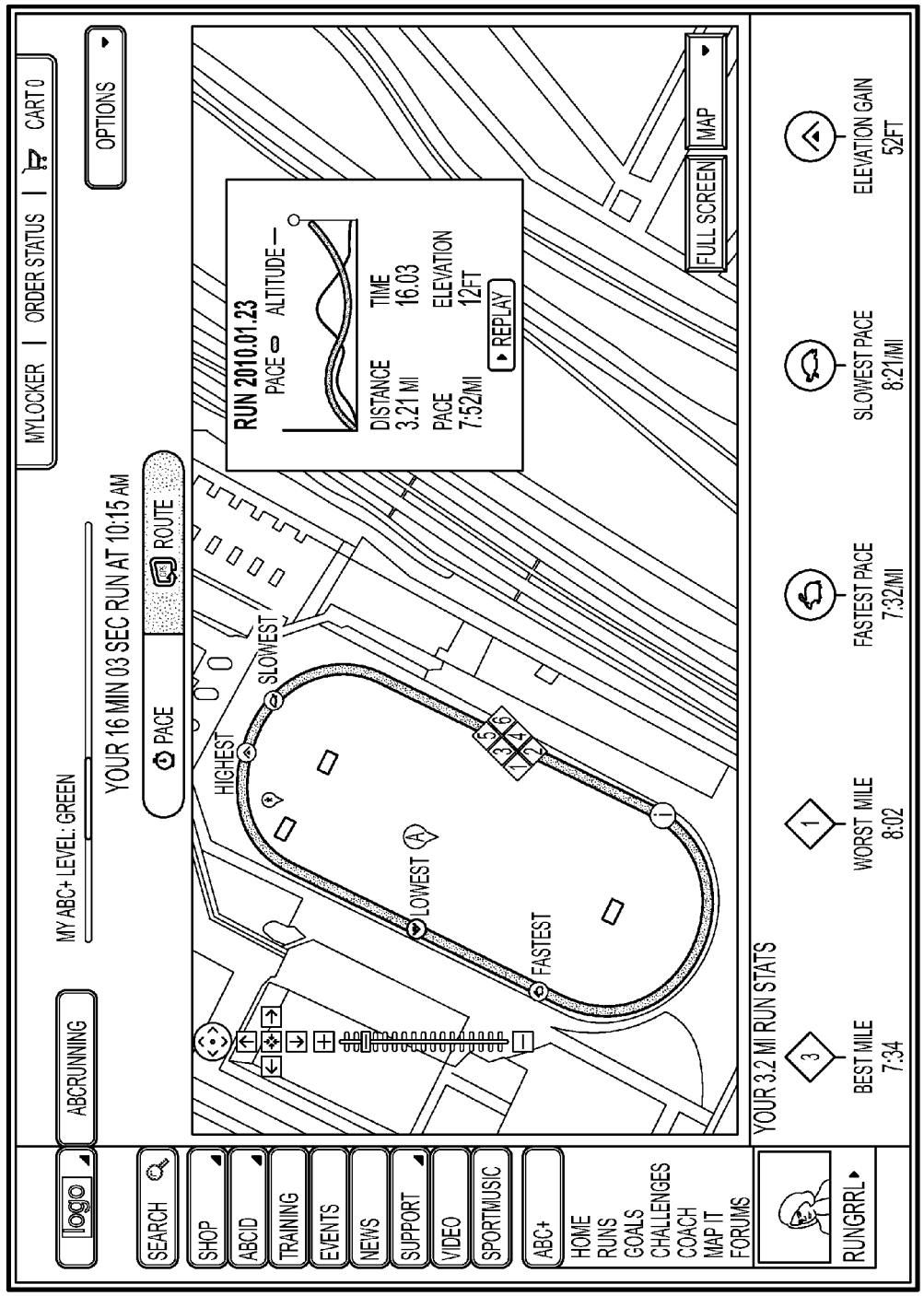

According to one or more additional aspects, map drop-down menu option 6631 that may display various options for the underlying map. For example, the user may be able to alter the appearance of the map to display a satellite image, a computer generated representation (as shown in FIG. 66A), a terrain image and/or a hybrid image combining satellite and terrain. FIG. 66F illustrates a route on a map in satellite image mode.

Figure 66G:
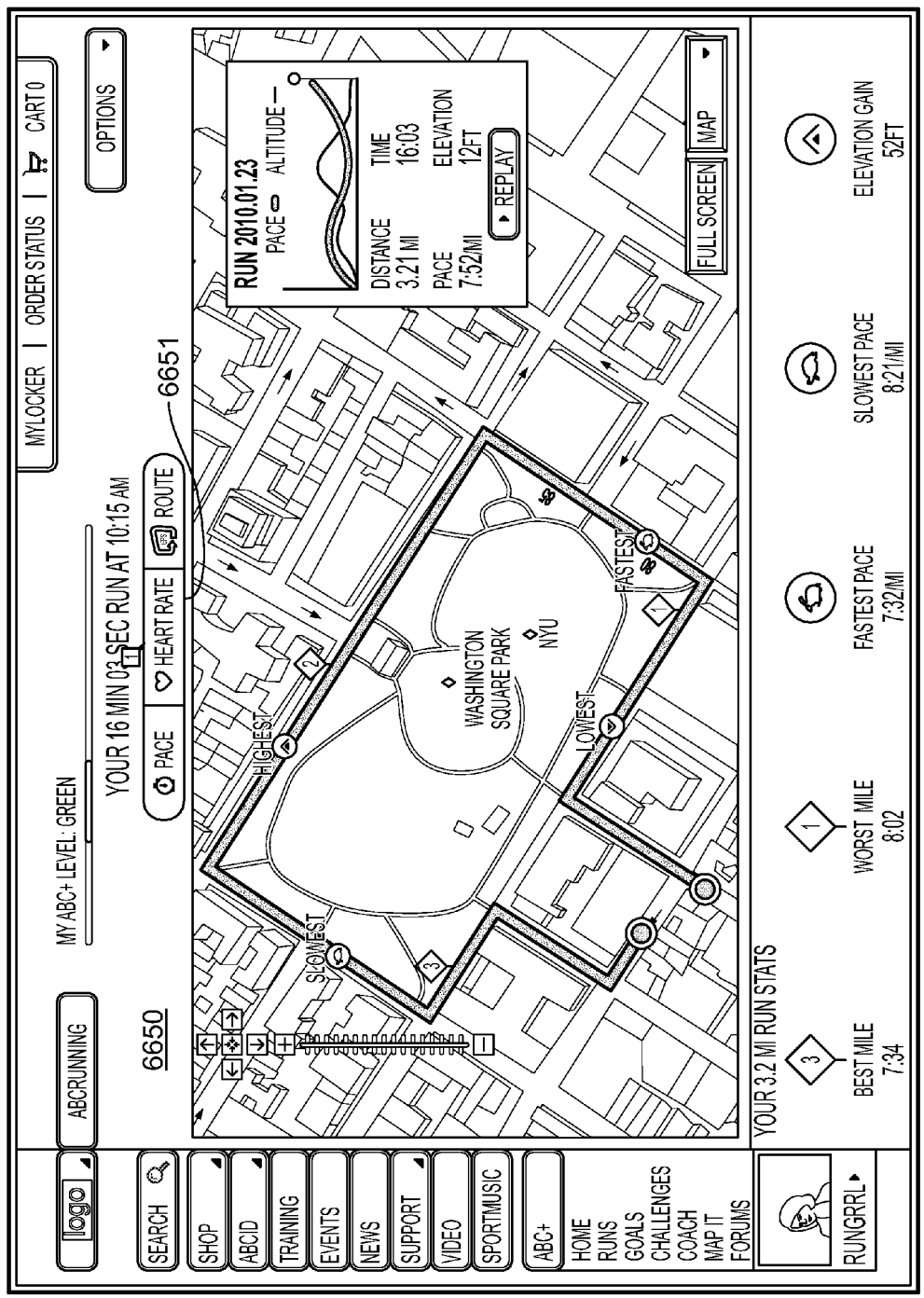

FIG. 66G illustrates a route information interface 6650 in which a heart rate tab 6651 is displayed if heart rate information is available. Selection heart rate tab 6651 may cause a graph to be displaying that graphs heart rate versus time or distance or pace. If heart rate information is available, route information and details may also be supplemented with this data. For example, highest and lowest heart rate markers may be displayed on the route.

Figure 67A:
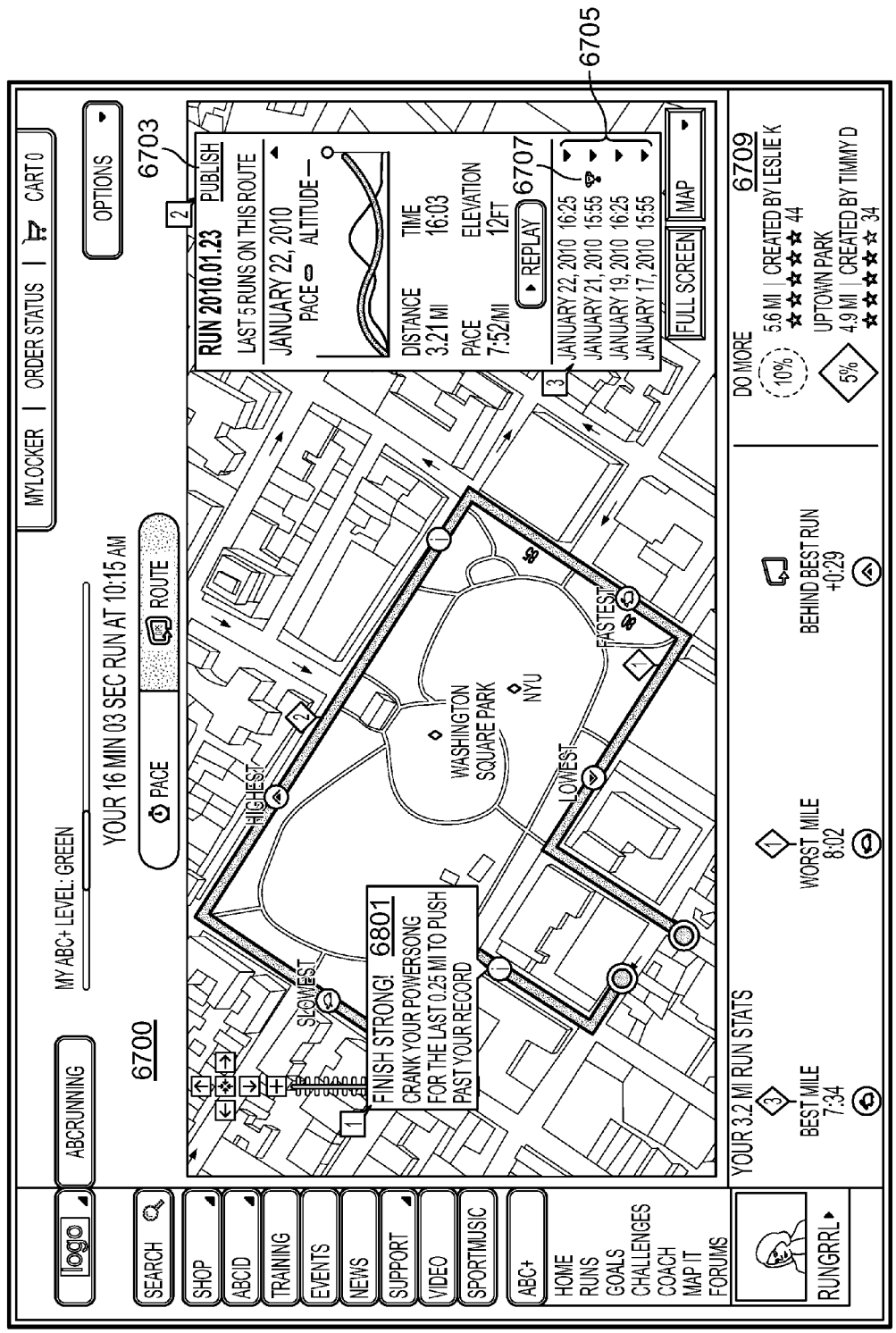
FIG. 67A illustrates another example route detail interface according to one or more aspects described herein.

FIG. 67A illustrates another example route detail interface 6700. Interface 6700 may include additional information such as run insights or suggestions such as suggestion 6701 which recommends playing a power song for a last 0.25 miles to set a new time record for the route. The suggestions may be generated based on various algorithms and parameters and, in one example, may include identifying a portion of the run where the user had the slowest pace and suggesting playing a motivation song to increase that pace. In another example, if a user appears to be exerting significant effort in a first portion of the run/route (e.g., based on heart rate information), the system may suggest that the user run at a slower pace during that first portion so as not to become exhausted for a remaining portion of the route.

Route information may be published in one or more arrangements by selection of publish option 6703. A user may publish information to various outlets including FACEBOOK, TWITTER and/or other social networking sites and news feed services. A menu (not shown) for specifying account information and publication options may be displayed upon selection of publish option 6703.

Interface 6700 may further include a listing 6705 of previous workouts for the same or a similar route. Listing 6705 may include one or more entries may include a brief summary of workout details including, for example, a run time and whether any achievements were recorded. For example, if the user ran the route in the fastest time on January 21, that entry may include a trophy icon 6707 as an indicator of that achievement or significance. Further, interface 6700 may provide improvement run suggestions in portion 6709. In particular, interface 6700 may display other routes that improve on the current route by a predefined amount of distance. The route suggestions may be generated based on routes the user has run in the past or routes that other users have run.

Figure 67B:
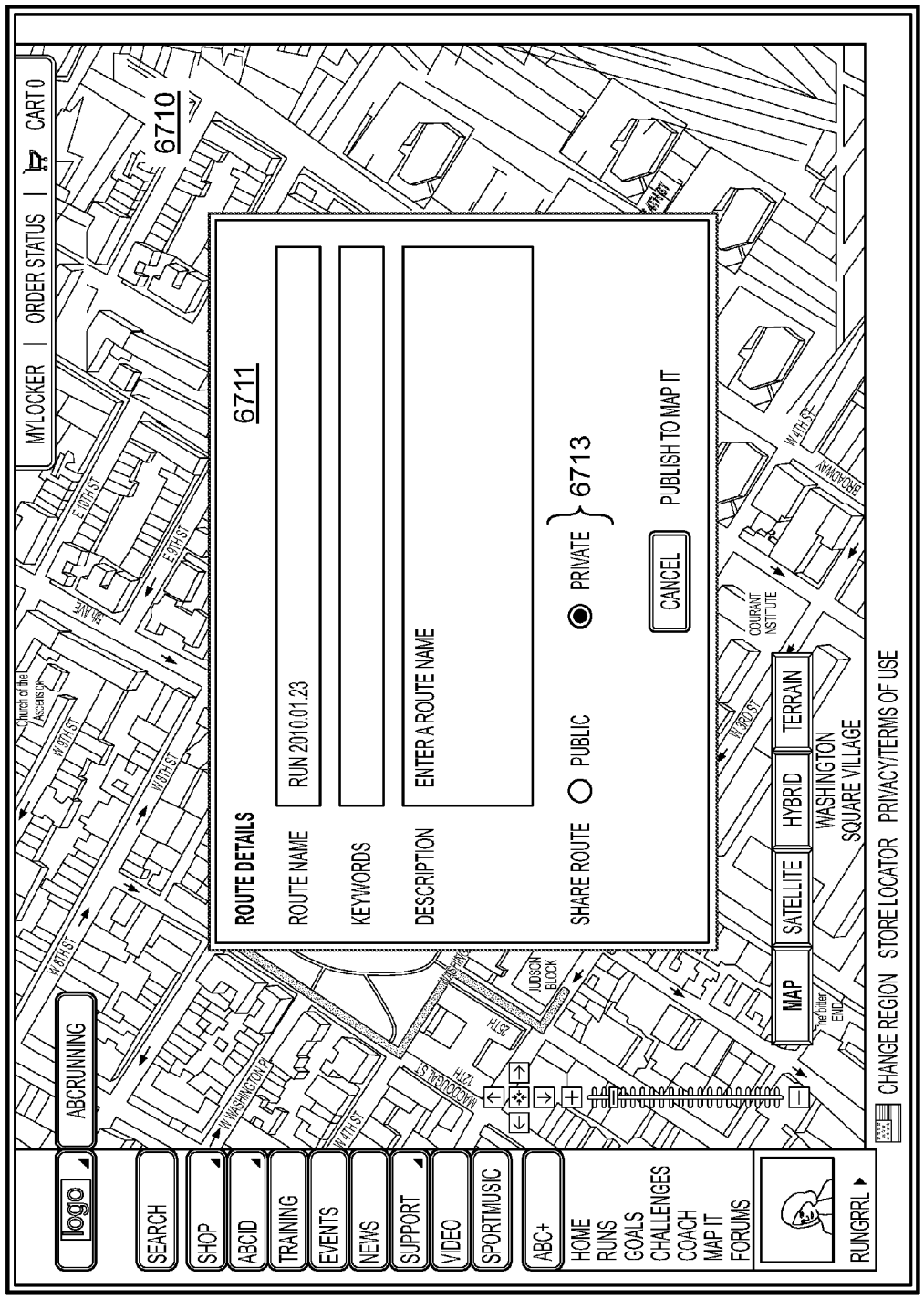
FIG. 67B illustrates an example interface through which a user may save a route and add route details.

FIG. 67B illustrates an interface where a user may save a route and add route details. Interface 6710 includes a prompt 6711 in which a route name may be specified in addition to keywords and a description. Keywords may include one or more words that may be used as search terms so that the user or other users may more easily find the route from a database of routes. The description may include a lengthier discussion of the route including scenery, terrain, difficulty, weather, traffic, noise, and the like. The user may further select a privacy of the route using options 6713. For example, by setting the route to private, other users might not be able to find or view the route. Additional privacy parameters and settings may be provided including options for selecting particular individuals or groups of individuals that are permitted to find and/or view the route. Other options may include defining what viewing and access privileges are allowed for each individual or group of individual.

Figure 68A:
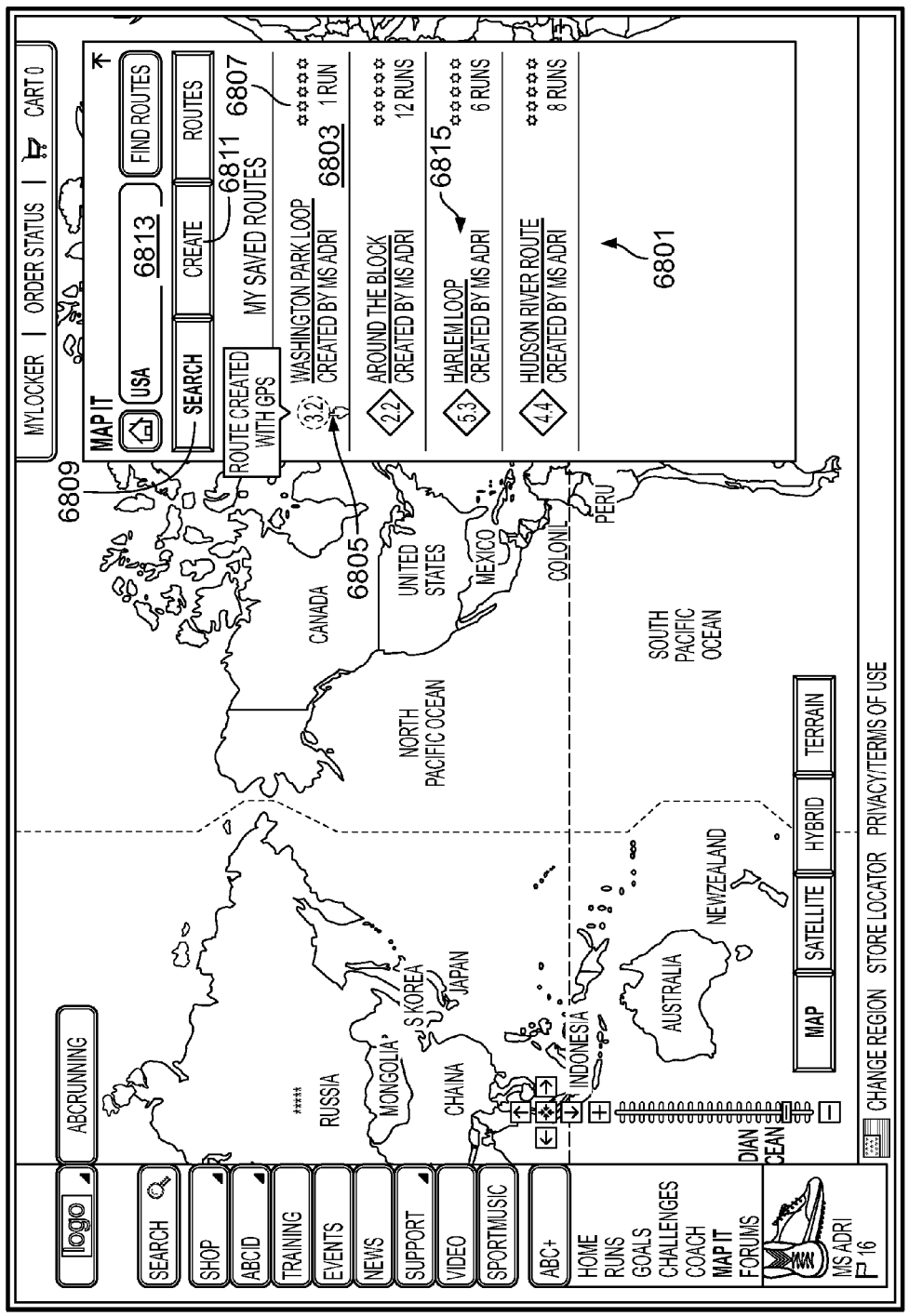
FIG. 68A illustrates an example saved routes interface listing the various routes that a user has run, created and/or saved.

FIG. 68A illustrates a saved routes interface listing the various routes that a user has run, created and/or saved. For example, routes list 6801 includes 4 different routes saved by the user. Routes that were created/recorded using GPS such as route 6803 may include one or more indicators or displayed in a different manner. For example, the distance indicator 6805 may appear differently than for non-GPS created routes such as route 6805. The saved routes list 6801 may be displayed against a backdrop of a map. The map may include one or more markers identifying the location of the routes and routes in the list 6801 may be numbered or otherwise identified to correspond to the markers. Routes may also be rated by the user or other users that have run the route. The rating may be reflected or indicated by ratings indicator 6807, for example. Other tabs in the interface may include a search tab 6809 and a create tab 6811 for searching a database or list of routes and for creating a route, respectively. Additionally, a quick search bar 6813 may be used for keywords searches while search tab 6809 may provide advanced search options such as distance, terrain, weather and the like.

Figure 68B:
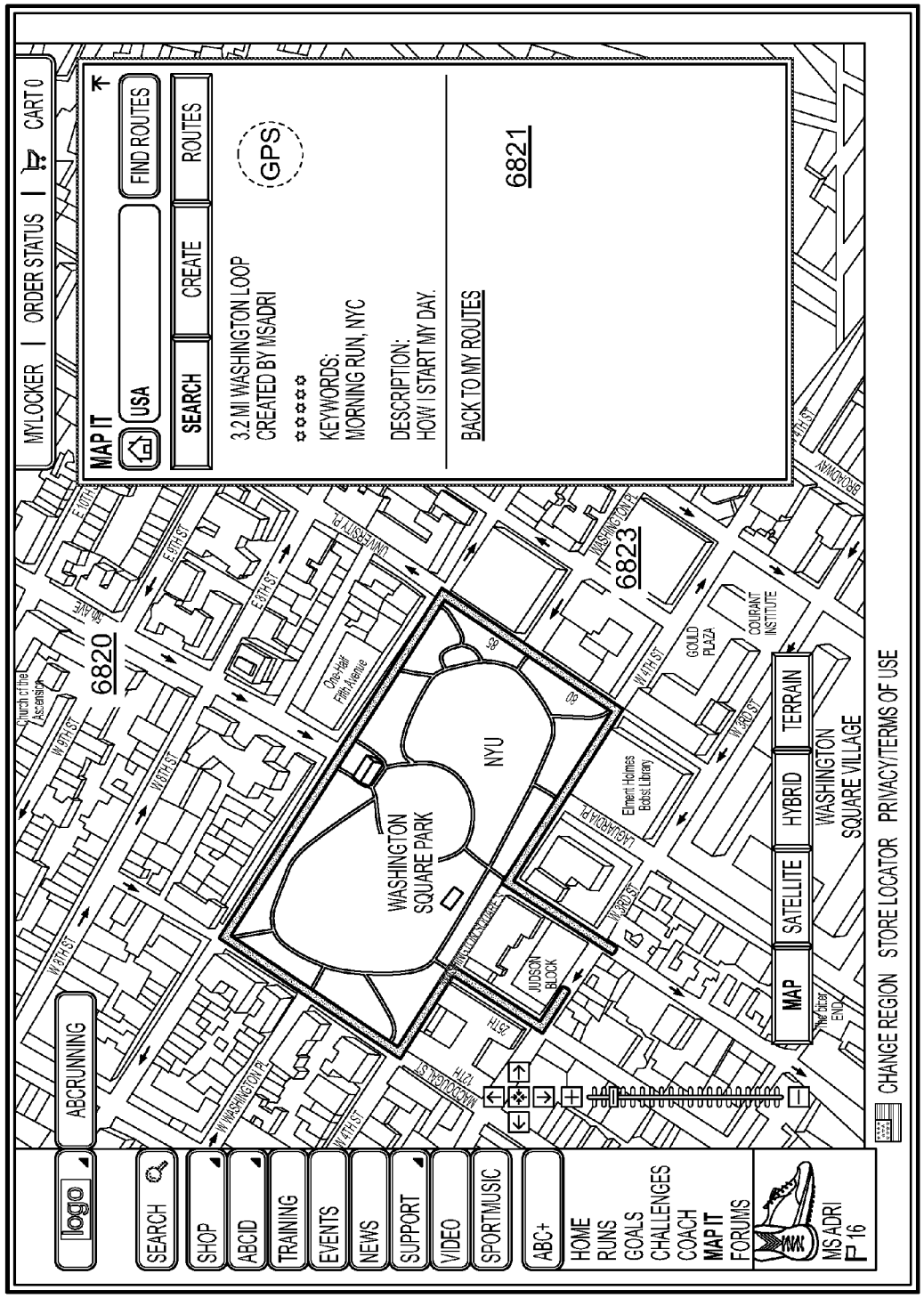
FIG. 68B illustrates an example route interface that may be displayed upon a user selecting a route from a route list.

FIG. 68B illustrates a route interface 6820 that may be displayed upon a user selecting a route (e.g., route 6805 of FIG. 68A) from a route list (e.g., route list 6801 of FIG. 68A). Upon selection of a route, route listing 6821 might only display the selected route and provide additional details beyond what was displayed in a route list including multiple routes (e.g., route list 6801 of FIG. 68A). The additional details may include keywords stored in association with the route and a description. The information may further indicate a creator of the route. Underlying map 6823 may also change to display the route at a scale where each portion of the route is discernible. In one example, map 6823 may display an area that is a predefined amount larger than the boundaries of the route. For example, the displayed area of map 6823 may be defined such that the route occupies 60%, 75%, 90% of the displayed area.

Figure 69A:
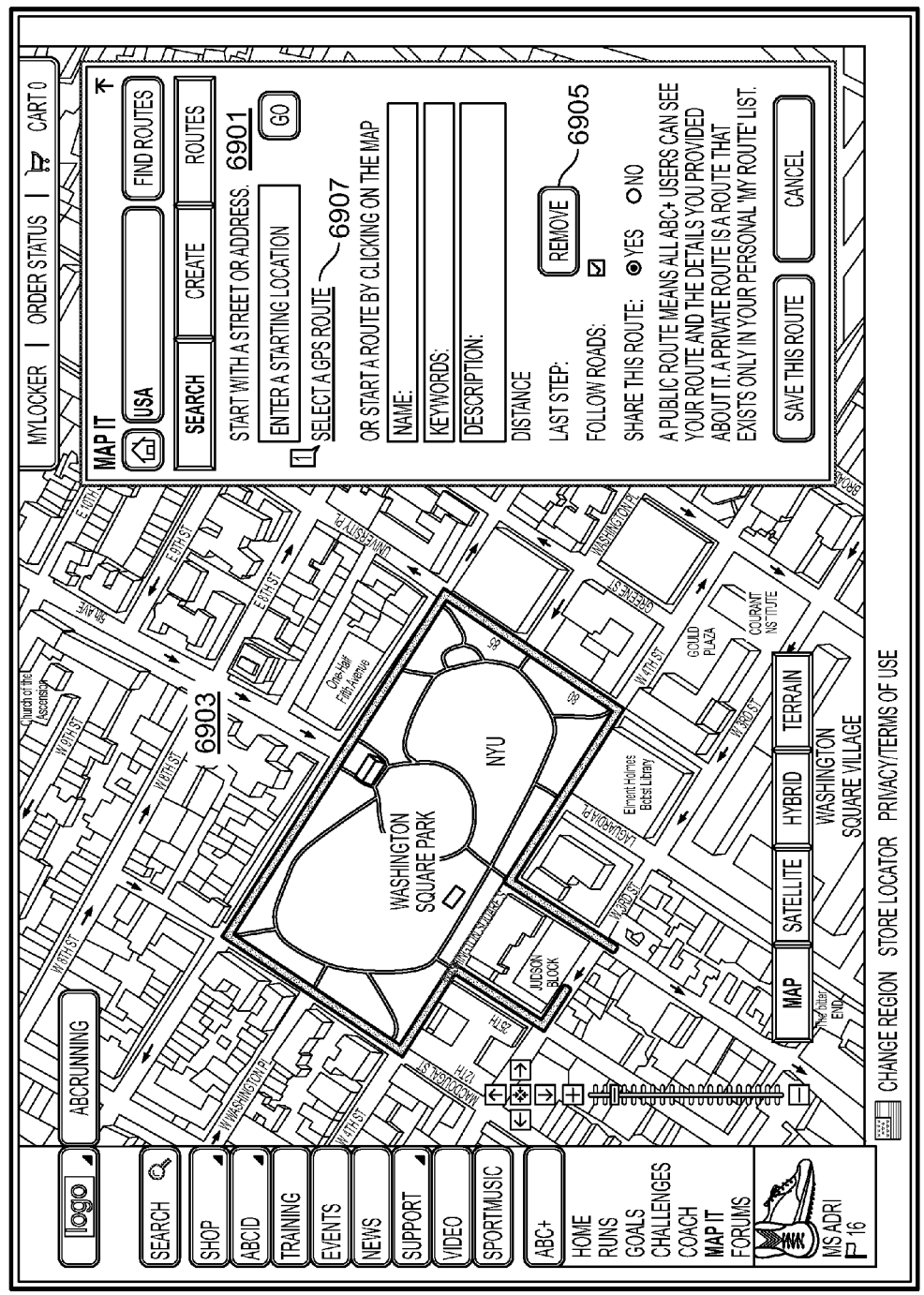
FIG. 69A illustrates an example route creation interface through which a user may define a new route.

FIG. 69A illustrate a route creation interface through which a user may define a new route. To create a new route, the user may define a starting location through form 6901. Alternatively, the user may base the route on a recorded GPS route. The user may further specify a name, keywords (e.g., for searching), a description and whether the route is to be shared. Upon selecting a start location, an ending location form (not shown) may be displayed. Starting and ending locations may be selected by interacting with map 6903 or by entering an address. In one or more arrangements, the user may further specify intermediate points that the user wishes to traverse during the run. The user may further specify a distance he or she wishes to run and whether the run should follow roads. Based on these parameters, the system and interface may generate suggested routes and display such routes on map 6903. A user may modify the routes by interacting with the route lines displayed on map 6903, including additional intermediate points, adjusting the distance, modifying the start and end points and the like. The user may further use option 6905 to remove a previous step or steps taken. For example, if the user is creating the route by initially running or walking the route while the creation interface is active and the user makes a mistake in his or her path, the user may pause to remove the last portion of the path.

Figure 69B:
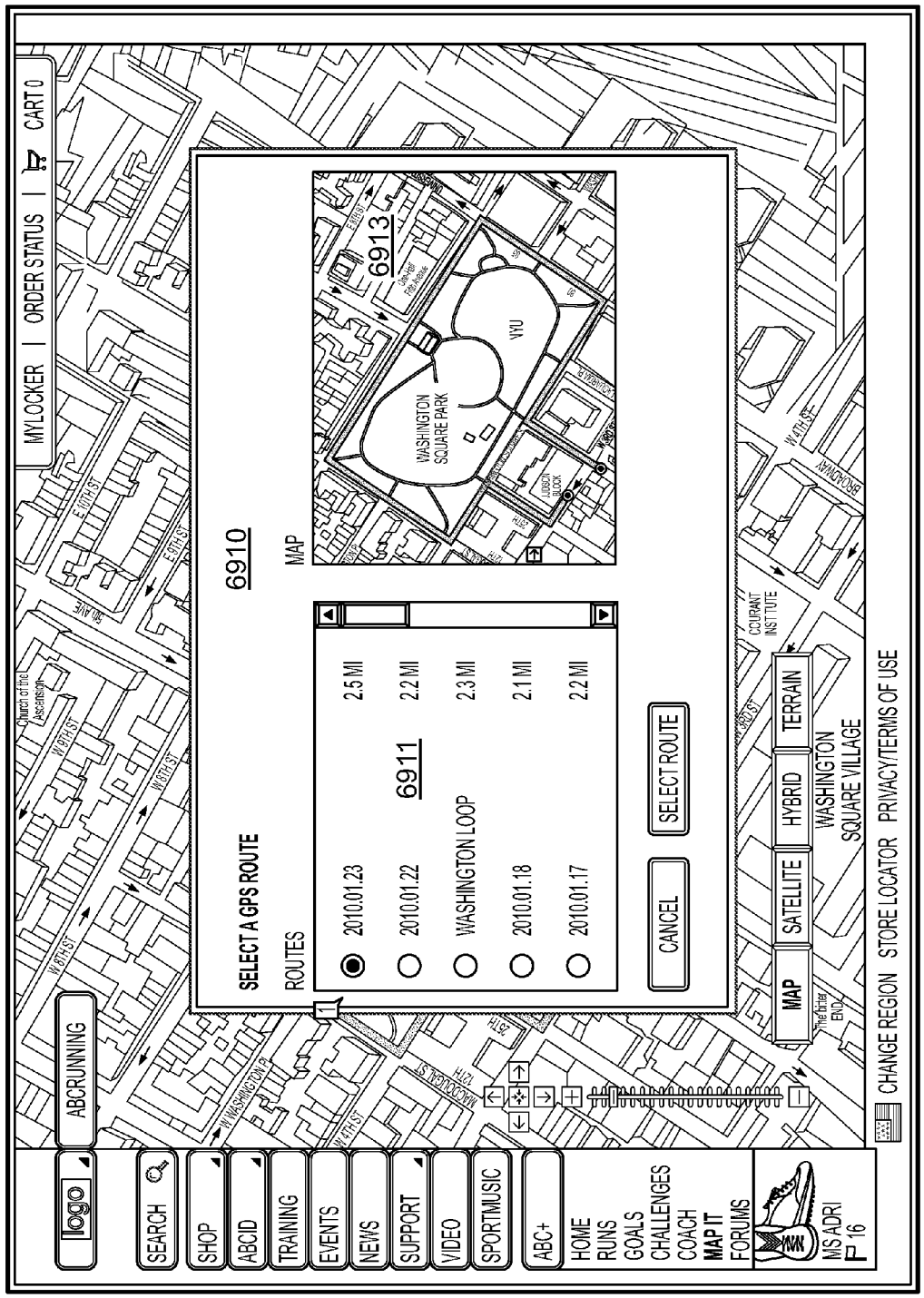
FIG. 69B illustrates an example selection menu where multiple previously recorded routes are displayed.

Alternatively, a user may create a route by retrieving a previously recorded GPS route from a database. For example, the user may select option 6907 to retrieve a GPS route. FIG. 69B illustrates selection menu 6910 where multiple previously recorded routes are displayed in list 6911. A mini-map

6913 may be displayed to provide a general overview of the shape and location of the route. List 6911 may be displayed in reverse chronological order, by alphabetical order, by distance or the like.

Figure 69C:
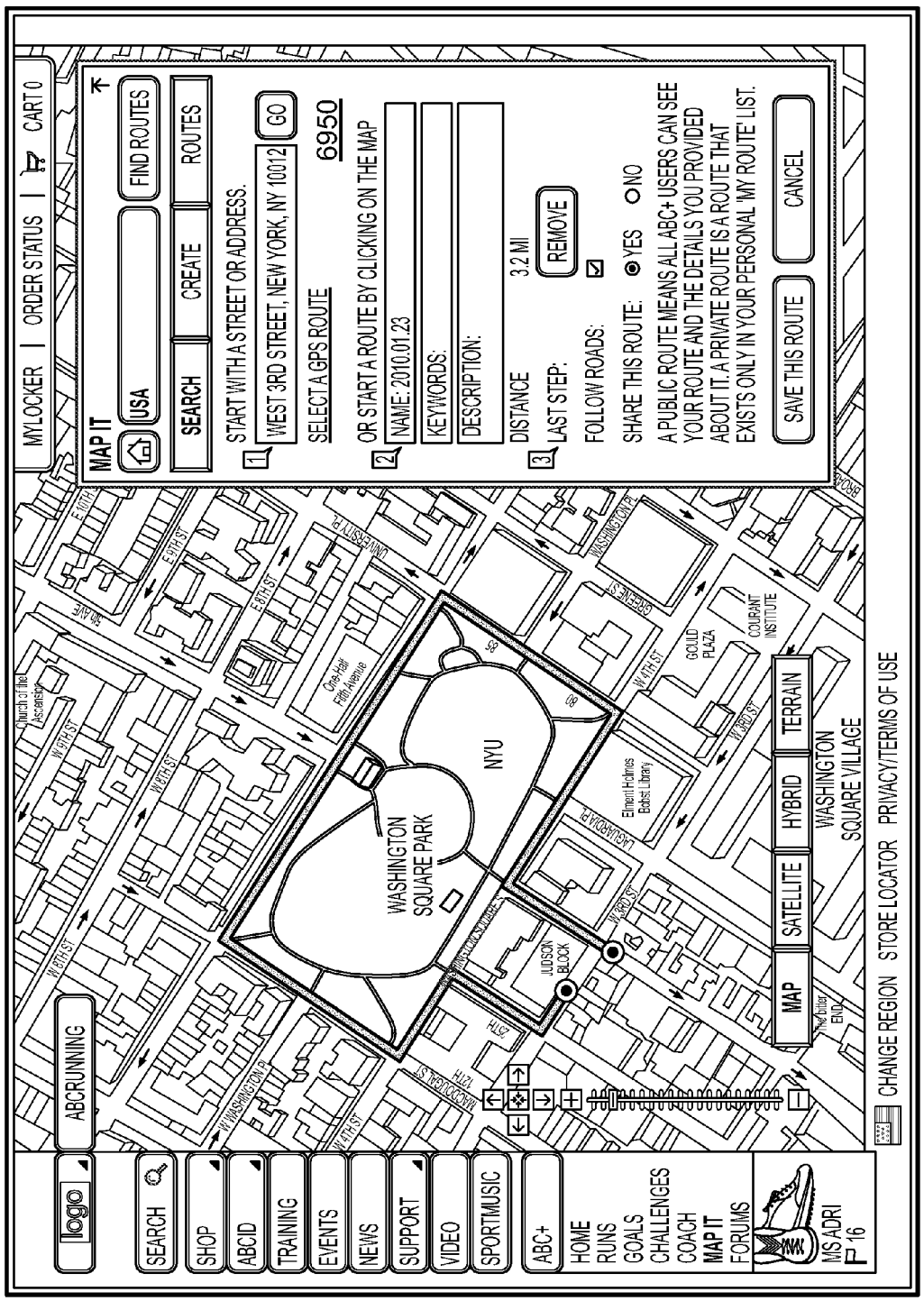
FIG. 69C illustrates an example route creation interface in which various fields have been pre-populated.

If a user selects a previously recorded GPS route, various fields in a route creation interface may be automatically populated. For example, in FIG. 69C, creation interface 6950 has pre-populated the starting address, distance and the name of the route. If keywords or a description were stored with the selected route, those fields might also be automatically pre-populated. Because the route was generated as using a GPS device, the last step and follow roads options may be deactivated. Alternatively, the options may remain active to allow the user to modify the route recorded by the GPS device.

Figure 70A:
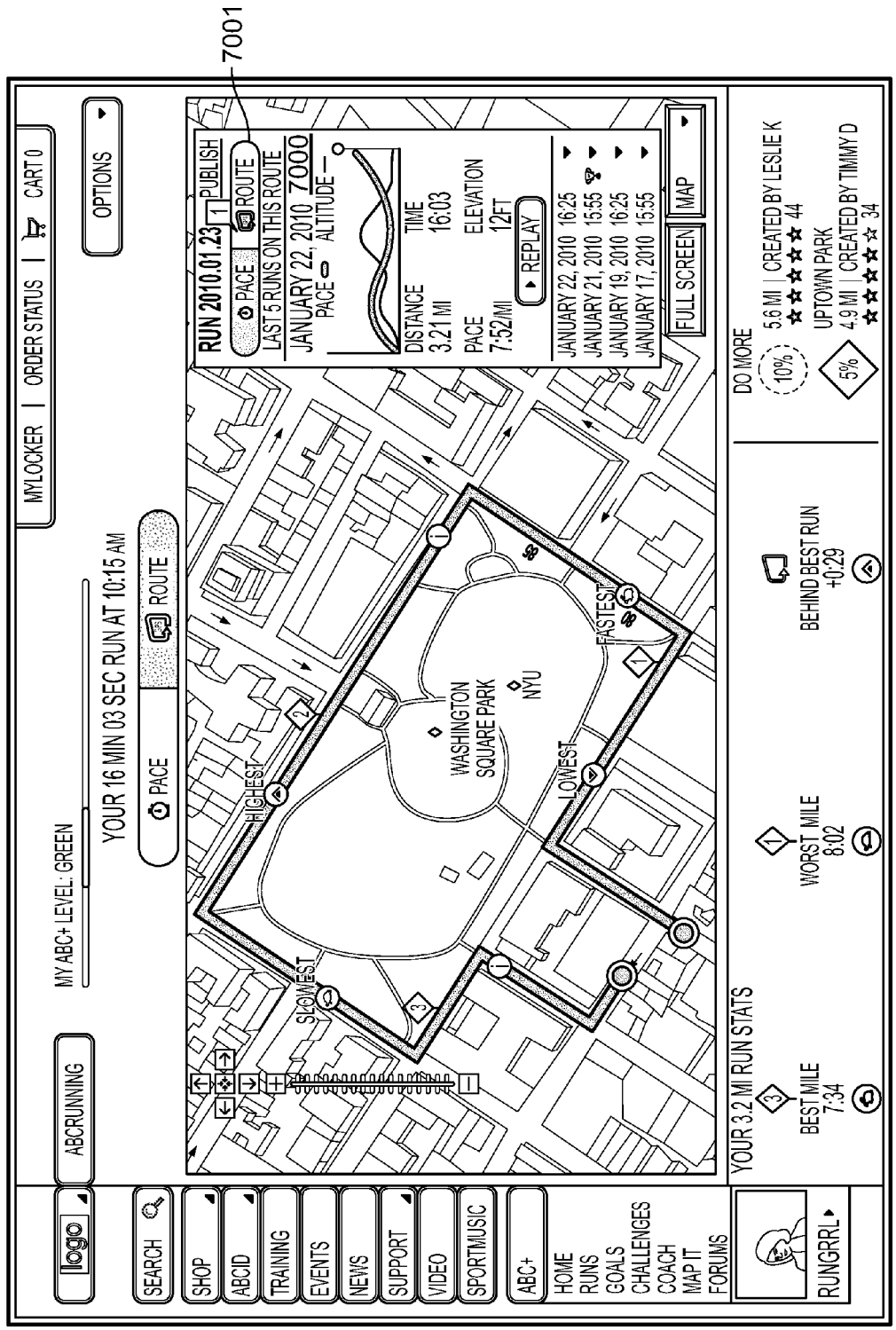
FIGS. 70A and 70B illustrate further example interfaces for viewing route information.
Figure 70B:
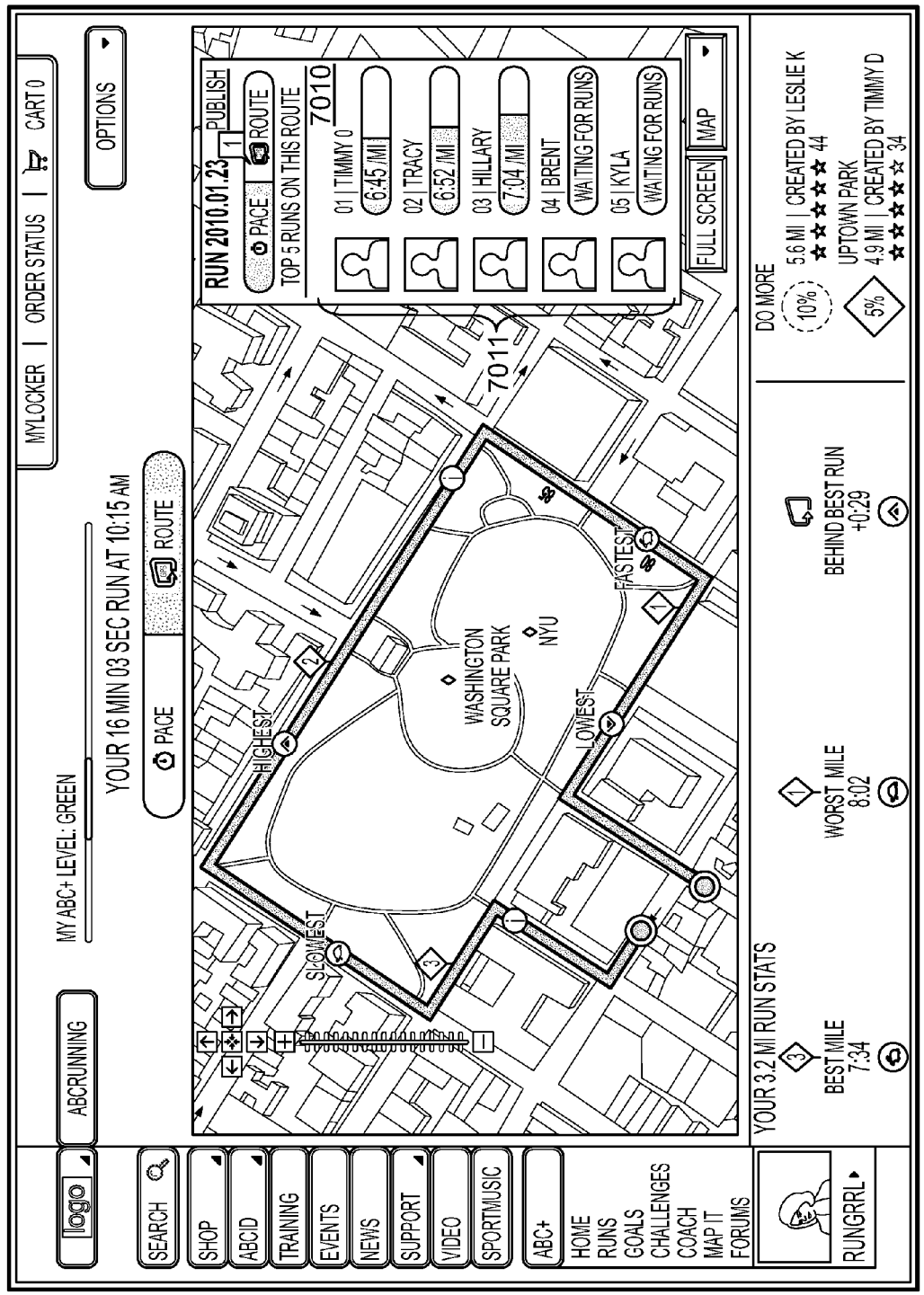
Figure 71A:
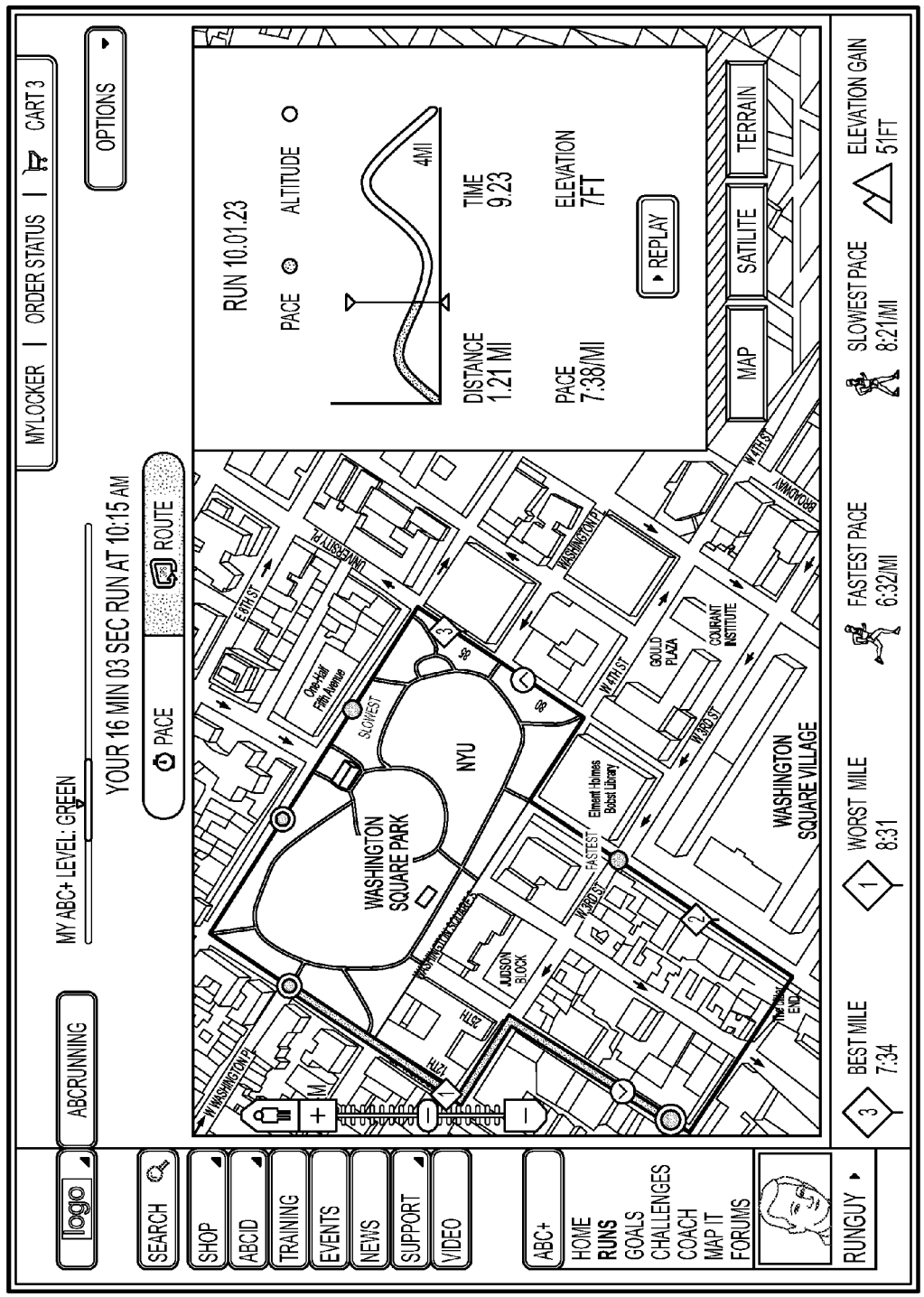
FIGS. 71A-71F illustrate further example route tracking and viewing interfaces.
Figure 71B:
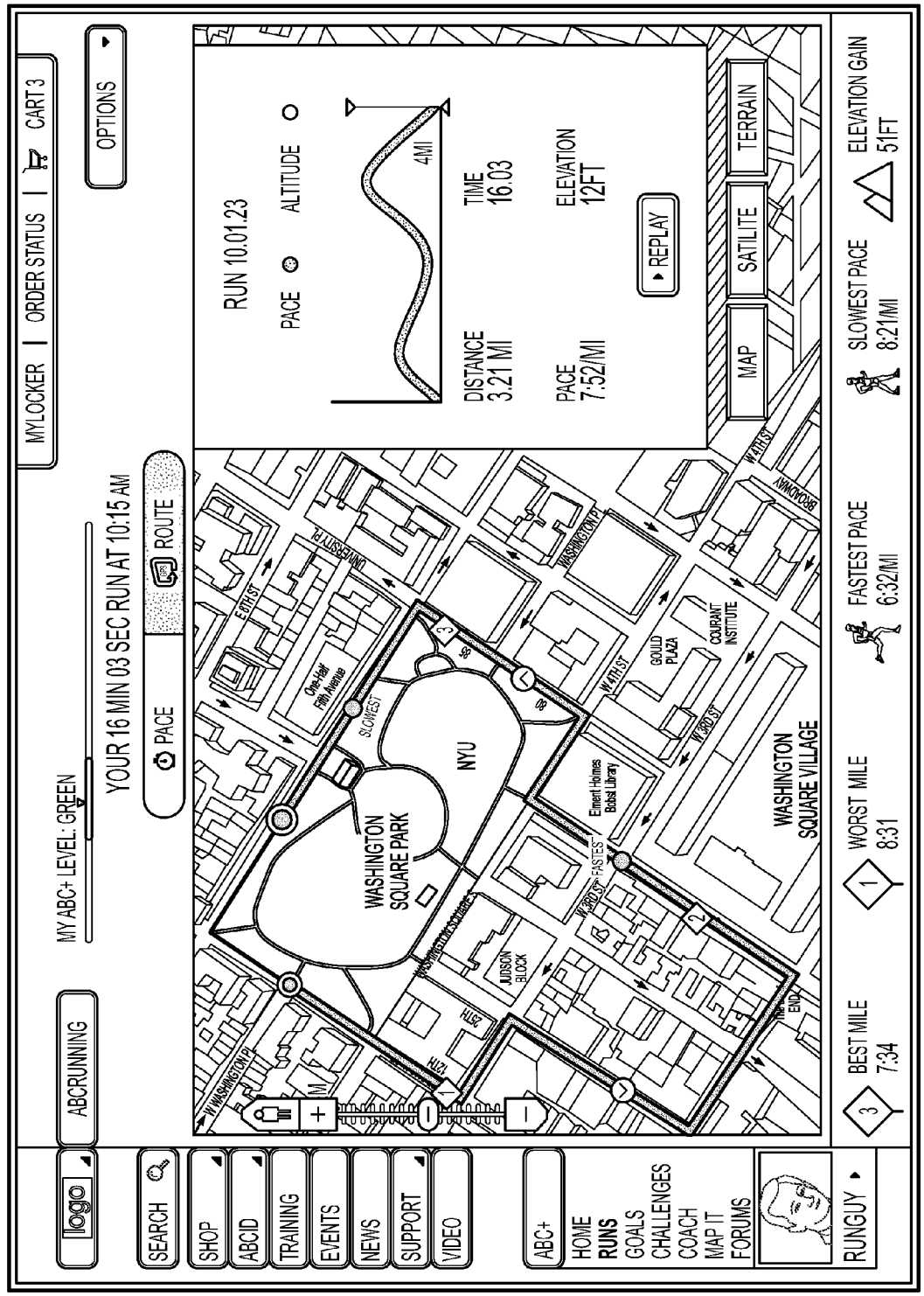
Figure 71C:
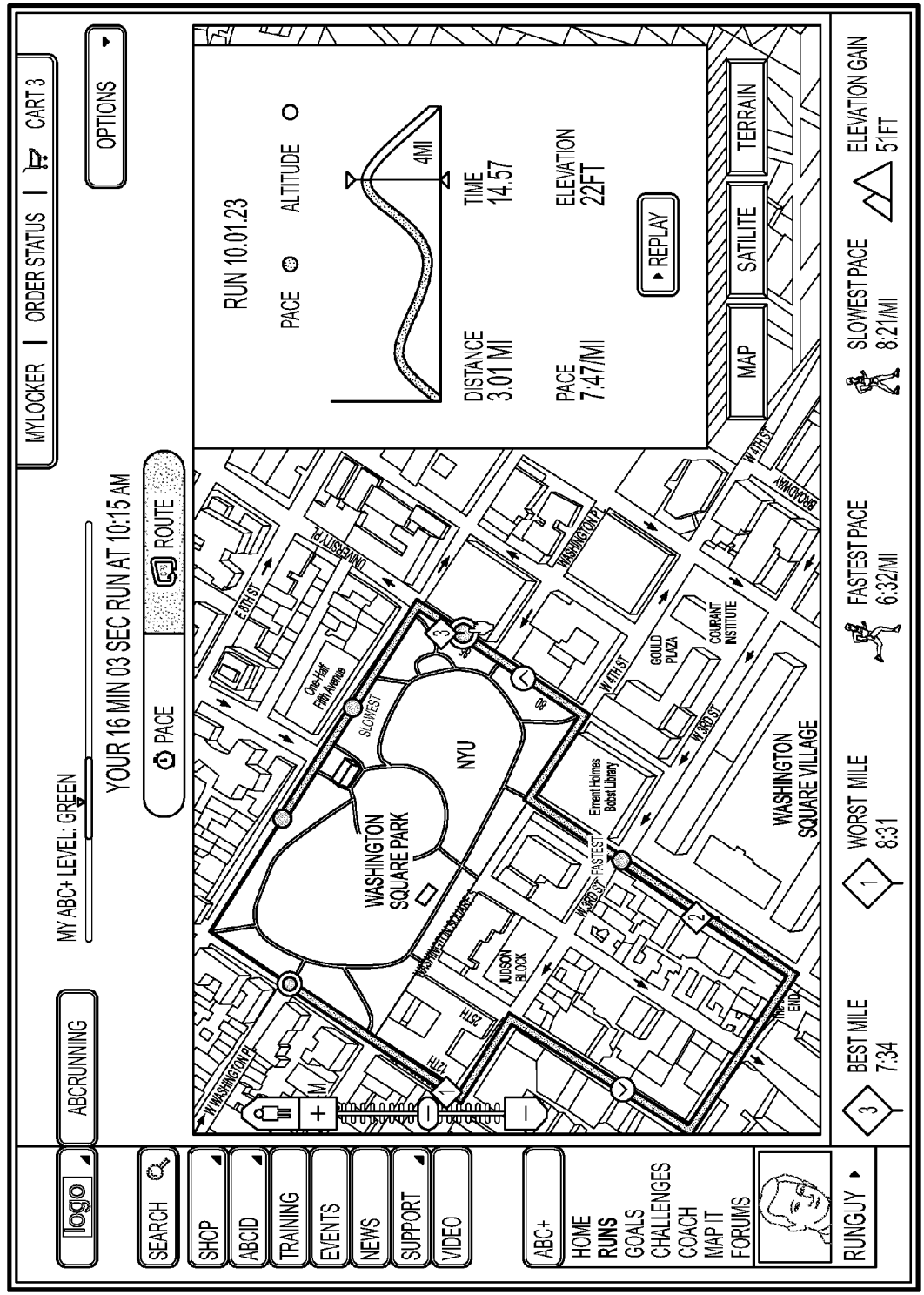
Figure 71D:
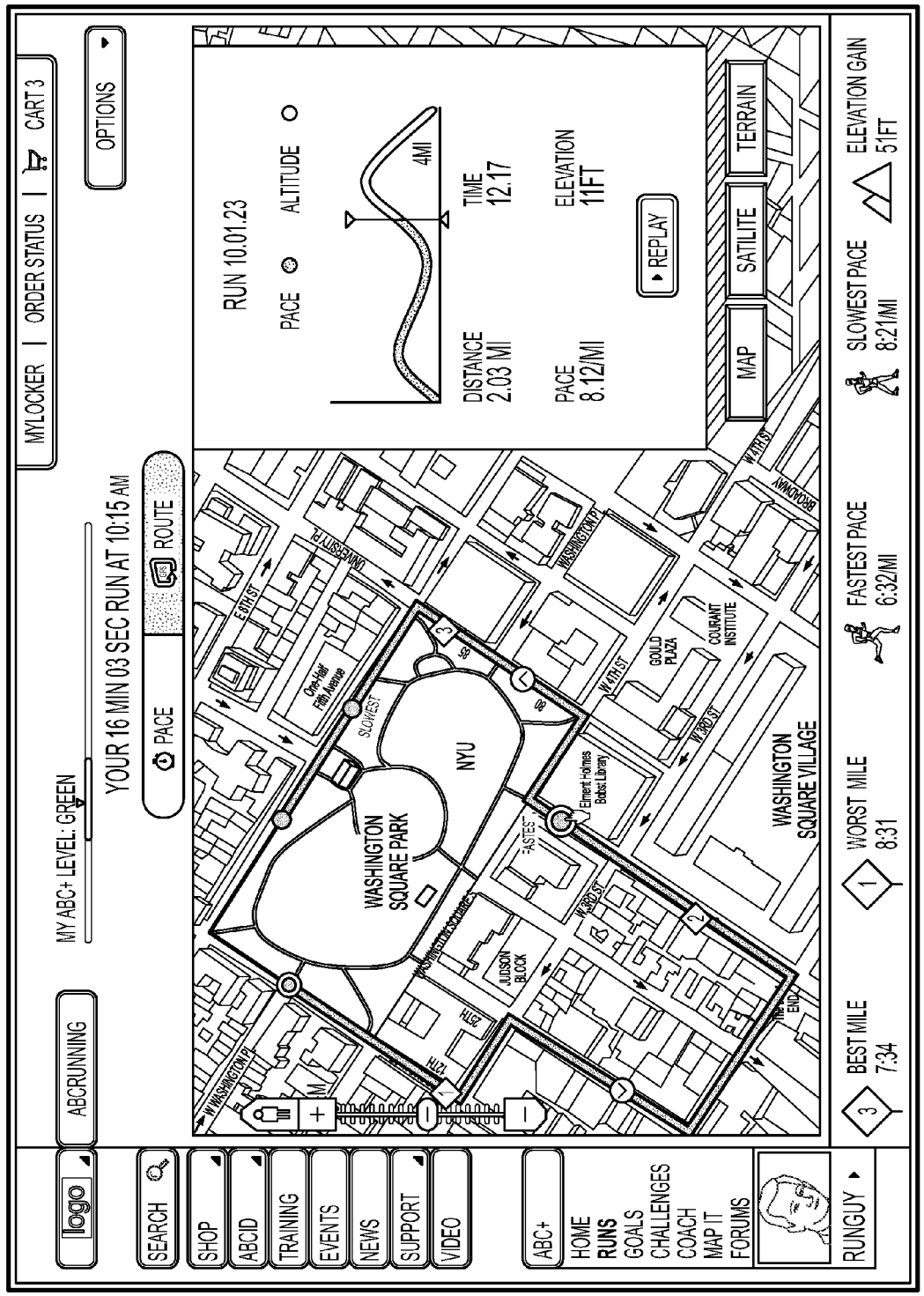
Figure 71E:
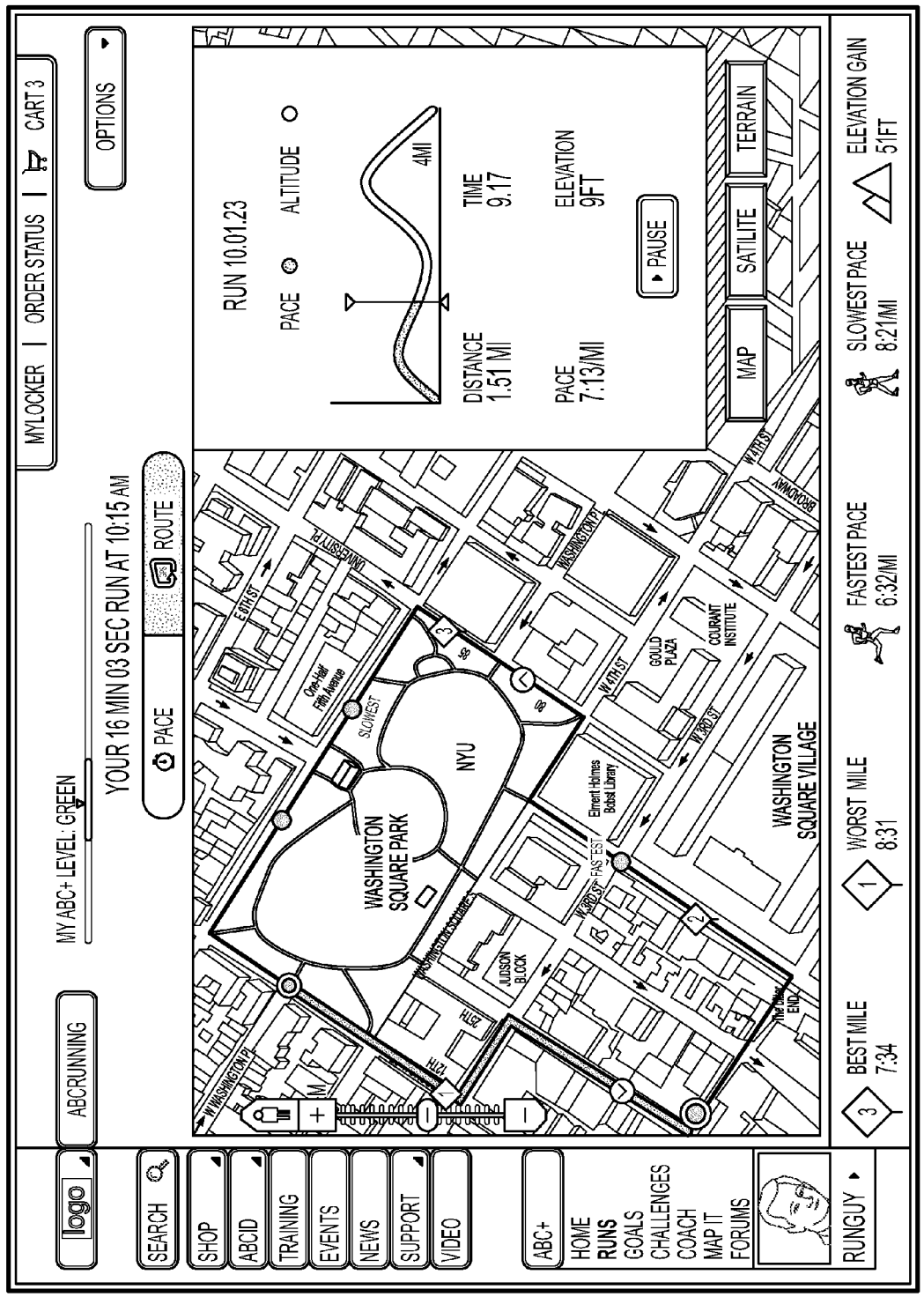
Figure 71F:
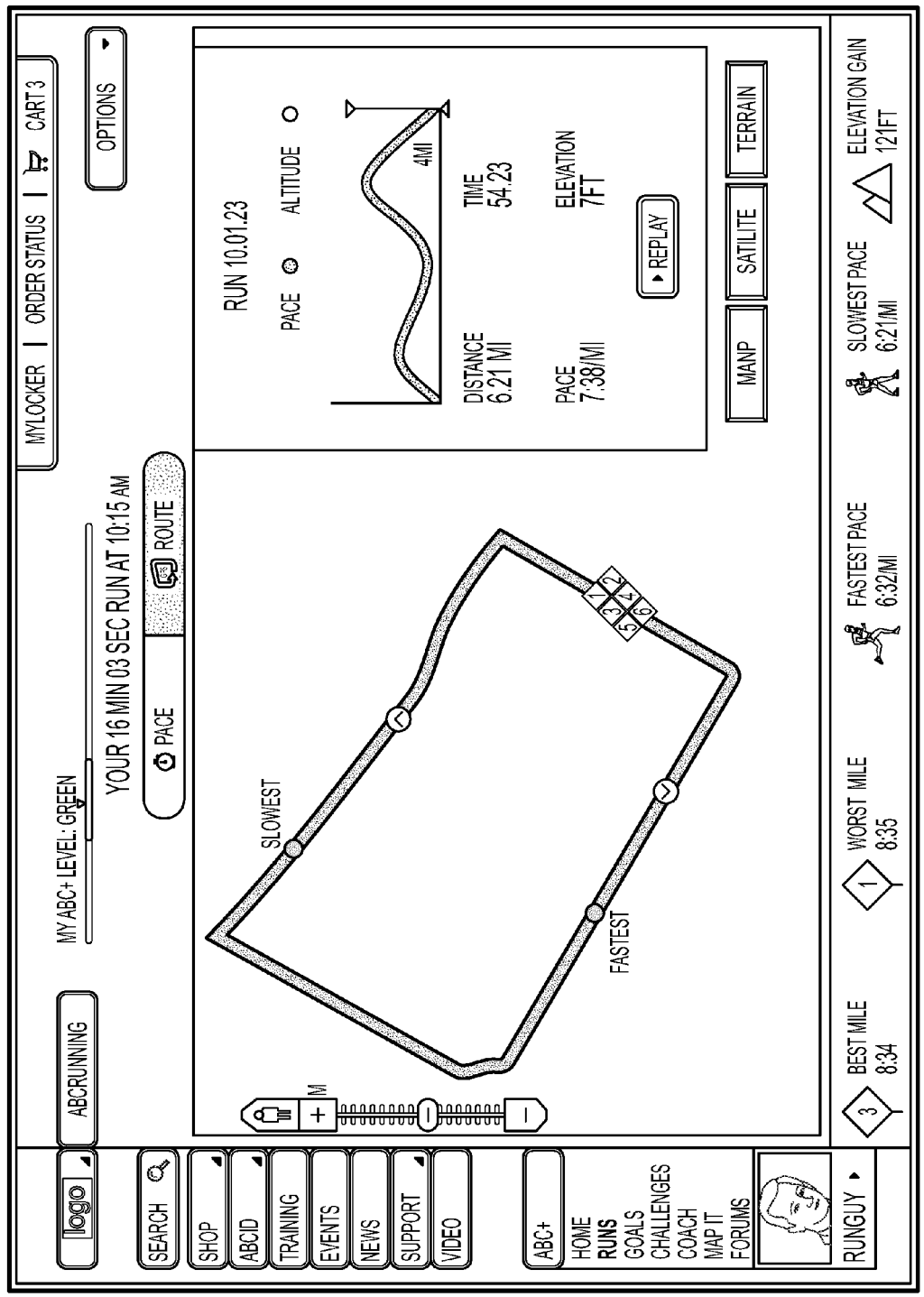

FIGS. 70A and 70B illustrate further example interfaces for viewing route information. In FIG. 70A, route information display 7000 may include a friends tab 7001 that allows the user to view a list of friends that are running or have run the same or a similar route. FIG. 70B illustrates friends list display 7010 in which friends 7011 are displayed in an order indicating a current standing for a challenge associated with the route. For example, a pace challenge may be defined for the route and thus, list display 7010 may list the friends in an order of fastest to slowest pace. Those without pace data may be listed at the bottom in alphabetical order. Friends may also be displayed according to other orders including alphabetical, age, number of times the route has been run by the user, pace and the like.

FIGS. 71A-71F illustrate further example route tracking and viewing interfaces. In one more arrangements, route tracking may include an option for tagging the route with personal information, automatically determined information and/or user entered information. For example, a user may tag the route with how he or she felt while exercising along the route, a name of the route, a route rating (e.g., how much the user enjoyed the route, scenery rating, noise rating, terrain rating), music suggestions, landmarks or interesting places along the route and the like. This information may then be shared with other individuals that are seeking a route to use. Different users may tag the route so that the route may be displayed with multiple tags.

Live Challenges

Figure 72:
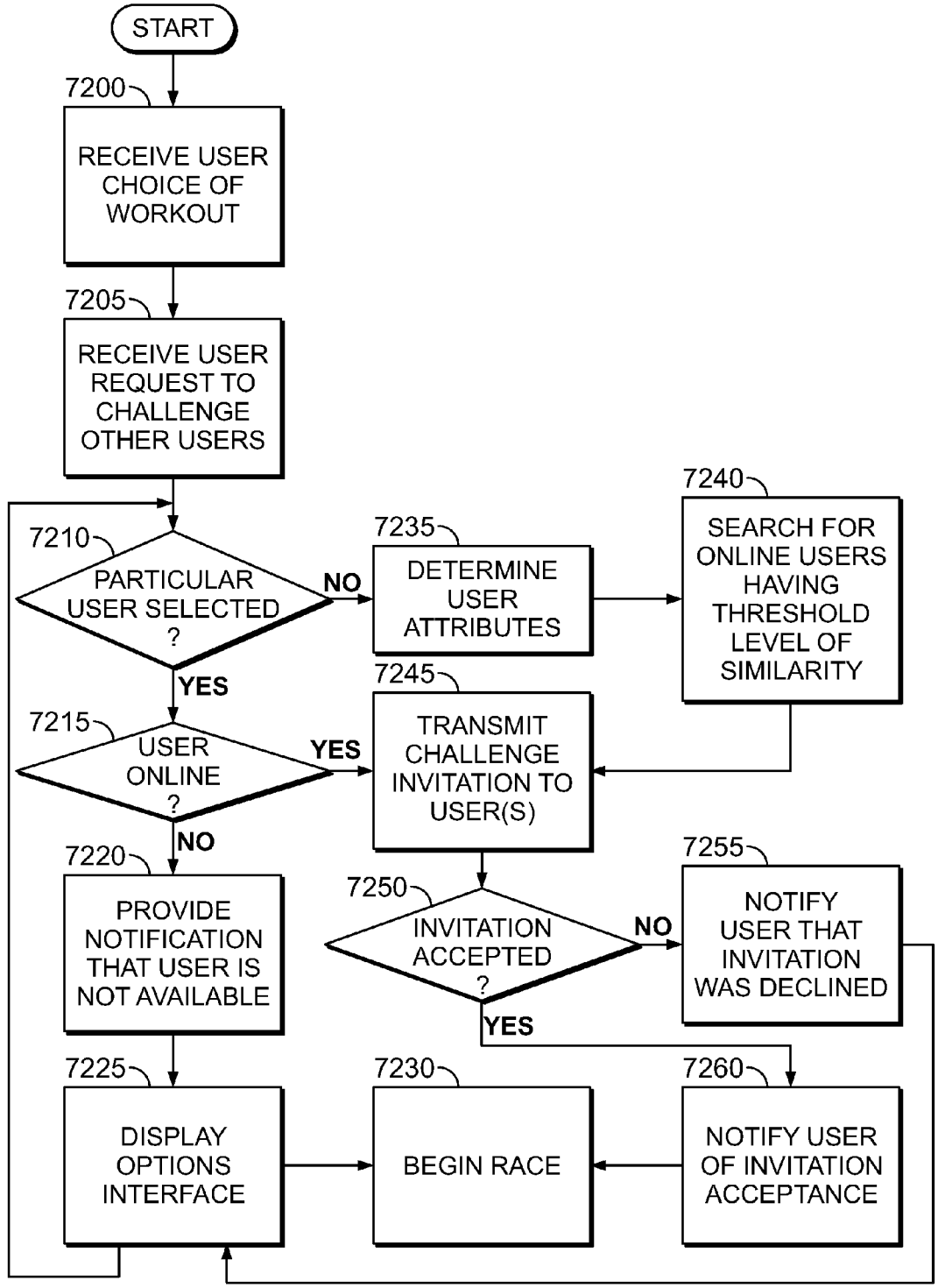
FIG. 72 illustrates an example method for generating and processing a live challenge.

According to one or more additional or alternative aspects, a monitoring device and/or service provider may facilitate the matching of a user to a competitor in a live challenge environment. FIG. 72 illustrates an example method for generating and processing a live challenge. For example, in step 7200, a user may choose to a workout such as a 1K run. The workout may be defined and initiated through a device such as a mobile fitness monitoring device. The user may select a predefined run type/configuration or may customize his or her own run. Subsequently, in step 7205, the user may initiate a challenge for the 1K run to one or more other users. In step 7210, a challenge matching system may determine whether the user has specified a particular user to challenge. For example, the user may have selected a friend to challenge. If so, the system may determine if the selected user is currently online with an athletic activity service associated with the matching system in step 7215. For example, if the user is not signed on to the service, the user may be determined to be offline. Alternatively, if the user is online, the user may be deemed to be online. In one or more arrangements, being online may further include an active data communication connection with the user. Thus, if an active data connection is not available with the selected user, the user may be deemed to be offline. If the selected user is determined to be offline, the system may transmit a message indicating that the selected user is not available in step 7220. The system may subsequently display an interface allowing the user to challenge another user or to proceed directly to the run in step 7225. The system may return to step 7210 if the user choose to challenge another user. Alternatively, the system may proceed to step 7230 where the run may be initiated without the challenge component.

If the user has not selected a particular user to challenge, the system may automatically identify and select one or more users. For example, in step 7235, the system may identify one or more attributes of the present user initiating the run. The attributes may include age, weight, height, fitness level, resting heart rate and the like. In step 7240, the system may search for online users that may have a threshold level of similarity to the present user. The system may subsequently transmit a challenge invitation to each of the matching online users in step 7245. In some arrangements, the matching system may filter out users that are currently performing athletic activity (e.g., as not to interrupt those users). In other arrangements, the matching system may identify users that are within vicinity of the same path or route or a similar route (e.g., of a similar distance). Various other matching parameters and algorithms may be used to find other users to challenge. For example, in some instances, the search scope may be limited to a list of the user's friends rather than all users of the service.

In step 7250, the matching system may determine whether the invited users have accepted the challenge. If not, the system may notify the user that the user's challenge invitation has been declined in step 7255. The system may then display a menu such as that generated and displayed in step 7225. If one or more of the invited users has accepted the challenge, the present user may be notified of the acceptance in step 7260. The workout may then be initiated in step 7230 as a challenge between the accepted participants.

In one or more arrangements, a participant may increase the challenge by selecting an option to increase the goal amount (e.g., distance, calories burned, pace) during the challenge (e.g., mid-run). A notification may then be transmitted to the other participants to ask if they agree to the modification in the challenge. The challenge may then be automatically and immediately modified on the fly if a predefined number of participants agree. For example, the challenge might only be modified if a majority of the participants agree or at least 75% of the participants agree or all participants agree (or some other threshold or rule is met). In other examples, the challenge may be modified for agreeing participants but not participants that do not agree to the modification in the challenge. In such cases, two separate challenges may be created mid-run: one corresponding to the original goal/challenge and another corresponding to the modified goal/challenge. Participants of the modified goal/challenge may also remain participants of the original goal/challenge if the modified goal/challenge is greater than the original.

At the conclusion of the challenge, the users' results may be compared and a winner may be declared. In some arrangements, the service provider may award the winner with an accolade, virtual medal, virtual currency or other prize. Additionally or alternatively, the system may prompt the challenge participants to engage in another run at another scheduled time to further encourage the participants to engage in athletic activity.

Multi-User Games and Other Activities

In one example of a motivating multi-user activity, a user device may be configured to support a multi-user physical activity game in which users avoid satisfying a predefined condition used to identify a loser or losers of the activity game (e.g., finishing last or being the slowest). If a user's level of activity corresponds to the predefined losing condition, one or more consequences may be applied to the user. For example, such consequences may include becoming "tagged" (such as in a game of physical activity tag) or otherwise labeled, having to treat others to a meal, monetary compensation or punishment, having to perform a specific type and/or amount of physical activity and the like. To avoid the specified consequences (e.g., a tagged label), users may be required to perform an athletic activity in competition with others without losing as defined by one or more predetermined conditions. In one particular example, a user may initiate an athletic activity game such as a tag game in which the last user to finish a specified athletic activity, such as running 20 miles or walking 30000 steps, will be labeled with a predefined tag such as "IT." In another example, a tag game may involve performing an athletic activity (e.g., running 3 miles) in the shortest amount of time (e.g., fastest pace). The slowest competitor may thus be labeled with a predefined losing tag. In yet another example, the tag game may involve performing as much of an athletic activity as possible within a given amount of time. One or more users with the lowest level of athletic activity (e.g., based on a distance metric, time metric, or the like) may be identified as losers of the game.

In order for the user to remove the "IT" tag and/or to remove the adverse consequences, the user may be required to start a new game and/or to finish a new athletic activity game without losing (e.g., by avoiding the specified losing conditions for the new game). In some arrangements, a user may be able to remove adverse consequences of losing by meeting other types of removal conditions in a subsequent athletic activity game. For example, the removal conditions may include running within a range of paces, finishing the subsequent game ranked within a certain range of places (e.g., top 25%, top 10%, etc.), improving upon the user's performance in the game in which the user lost and the like and/or combinations thereof. In some examples, the removal condition may correspond to the punishment. In a particular example, if the punishment is to run 4 miles, a "loser" tag and/or the requirement to run 4 miles may be removed once the user has run the 4 miles. Various other types of objectives, tags and/or consequences may be defined as desired.

According to one or more aspects, winners or a number of non-losing users of a game may be rewarded. Thus, in contrast to losers of a game (as defined by the predetermined conditions), one or more non-losing users may be provided with a reward. Such rewards may include virtual items, monetary rewards, products, services, discounts, tickets and the like. Moreover, a bottom number of competitors (e.g., losers) may have different levels of punishments or consequences applied to them. For example, the last place competitor may be subject to the most severe consequences while a second to last place competitor may be subject to consequences that are less severe than those applied to the last place competitor. In a particular example, the last place competitor may be required to start a new game and to finish the new game without losing in order to remove a loser label and/or other adverse effects of losing a previous game. The second to last place competitor, on the other hand, may be required to start a new game to remove a loser label and/or other adverse effects of losing (e.g., without having to finish the new game without losing). Additionally or alternatively, the last place competitor may receive a more significant loser label such as "IT" or "LOSER," while the second to last place competitor may receive a less significant loser label such as "SLOWPOKE" or "ALMOST IT."

The athletic activity game may further include multiple parts such that each part, upon completion, is scored to determine one or more losers or winners. The determined losers may be eliminated from the game and subject to one or more adverse consequences. Winners (or non-losing/non-eliminated players), on the other hand, may move on to the next part of the game. The various parts of the game may be configured to determine one or more ultimate winners as specified in the rules of the game. In some instances, eliminated losers may be allowed to choose a type of athletic activity to be performed for the next part of the game. In other examples, one or more of the winners (or non-eliminated players) may be allowed to choose the type of athletic activity to be performed for the subsequent part of the game. Accordingly, each part of the game may include different rewards, different types of athletic activity, different objectives and different losing and/or winning conditions. A loser may, in some configurations, be allowed to rejoin a competition or game (e.g., a subsequent part of the game) upon completion of a certain rejoining condition. For example, a user may be required or allowed to participate in the next part of the game even after losing a previous part of the game. However, the user's results for the next part might not apply to the overall game results unless the user satisfies a predefined rejoining condition such as winning that next part. Various other rejoining conditions may be defined as desired.

The activity game may be conducted over a network (e.g., wireless or wired) using applications or apps executing on various electronic devices including wireless telecommunication devices, laptop computers, tablet computers, athletic sensor systems, athletic performance monitoring devices, audio and video content rendering devices and the like. In one example, real-time athletic performance data may be transmitted via a wireless and/or cellular network to other participating users on their devices. Additionally or alternatively, athletic activity data may also be provided to an athletic performance monitoring site or service.

Figure 73:
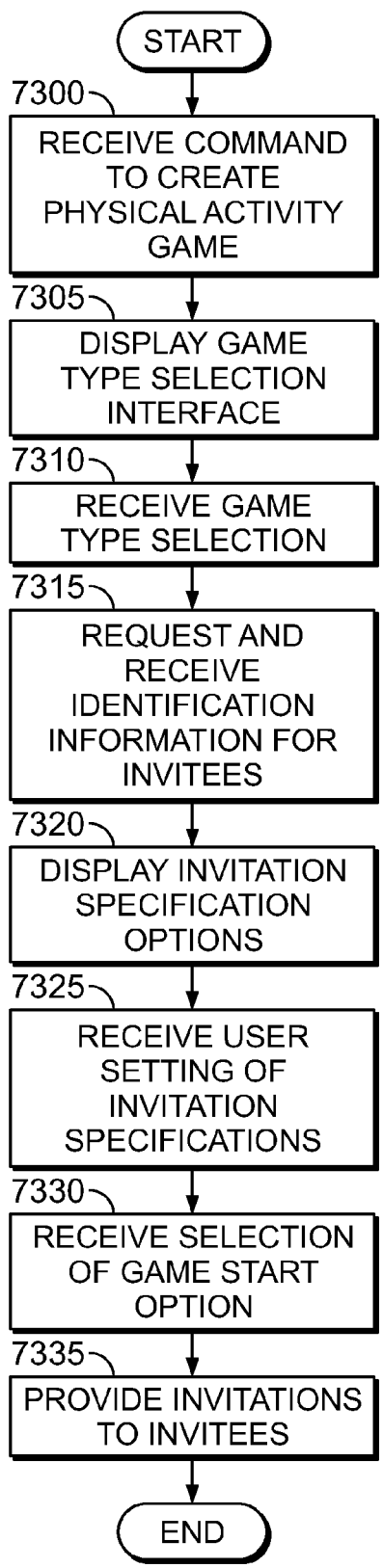
FIG. 73 illustrates an example method for creating a multi-user athletic activity game according to one or more aspects described herein.

FIG. 73 is a flowchart illustrating a method for creating a physical activity game. In step 7300, an athletic performance monitoring device (e.g., laptop computer, wearable sensor or digital content player, mobile telecommunication device, etc.) may receive a user command to create a physical activity game. The command or options may be displayed in a user interface, for example, after a user completes a workout or in a home screen of an athletic activity monitoring application or program. Upon receiving the user command to create a new athletic activity game, the device may display multiple game types for the user's further selection in step 7305. The various types of games may include a distance-based competition, a time-based challenge or a last-to-finish event. In one or more configurations, a last-to-finish game may include a random start time within a predefined range of time. For example, a random start time may be chosen within a predefined window of time of the game creation (e.g., 3 days, 1 weeks, 24 hours, 36 hours, 48 hours, etc.). In a distance-based competition, for instance, the user who completes (e.g., run, walk) the least amount of distance in the allotted time is labeled as the loser and must endure the consequences. In a time-based challenge, the user who performs a physical activity (e.g., run, walk, play basketball) for the least amount of time may be required to endure the consequences. In a last-to-finish event, the last person to finish the objectives may be identified as the loser. Another example type of game may be a last-to-compete in which users must reach a certain activity threshold to be considered in "competition" status. Accordingly, a last-to-compete game type may define a sub-game or part of another game type such as last to finish. Thus, if a user joins a last to finish game with a last to compete portion, the user may be identified as a loser with respect to the last to compete portion if the user is the last person to reach a certain amount of activity (e.g., less than the overall objective). The user may be allowed to continue to participate in the game, and may still be considered a winner or non-loser of the overall game.

In some examples, a user may use a previously created game (either by the user or by another user) to define a new game. For example, all parameters such as objectives, losing conditions, winning conditions, consequences and the like may be replicated from the previously created game for the new game. The user may still be provided with options to change these parameters after the initial parameters for the new game have been defined based on the previously created game. Games may be shared between users. For example, games may be e-mailed, sent over short or multimedia messaging, uploaded/downloaded over a community website or network and the like.

Various other types of events may be defined and selected including heart rate based competitions where the user who achieves the lowest average heart rate receives a certain punishment. A lowest average heart rate may be measured in absolute terms or lowest after scaling the average heart rate. Scaling the average heart rate may be performed based on a user's resting heart rate, a typical heart rate for a particular type of individual (e.g., height, weight, BMI, etc.), a heart rate average among all players of the game, an average heart rate among all individuals or a specified group of individuals with similar demographics. In another example, a calories burned competition may define consequences based on caloric objectives (e.g., burning the most calories). Additionally or alternatively, winners of the game may be rewarded in some manner. For example, the winners may receive a virtual item, a real-life physical reward (e.g., discounts, trophies, apparel, other products, services, etc.), bragging items and the like.

Once the user enters a game type selection in step 7310, the device may then request and receive identification information for game invitees (or potential participants) in step 7315. Although illustrated as a single step 7315, in other examples, the steps of requesting and receiving may be performed as two or more separate and distinct steps. In one example, the device may offer the user a variety of options for selecting invitees including a community list of friends, a list of contacts defined in a mobile communication device or e-mail addresses. Alternatively or additionally, contacts may be retrieved from social networking sites such as FACEBOOK, TWITTER, gaming networks, corporate directories and the like. Invitees that have been selected may be displayed simultaneously with the various invitee adding options. In some examples, the selection of invitees may be performed automatically based on configuration options set by the user upon registering such as inviting a first predefined group of individuals for all running type athletic activity games and inviting a second predefined group of individuals for all walking type athletic activity games. Accordingly, the user's selection of invitees may be configured prior to game creation. In yet other examples, the system may automatically select invitees without a user's input. If a user copies a game previously created by another user, for instance, the system may automatically invite all participants or invitees of the previous instance of the game. In yet another example, the system may match the user with other users based on profile information such as age, gender, previously activity metrics, location, fitness level and the like. The other users may be identified through one or more community networks or sites. The system, device or application may also limit the number of invitees or number of participants for the game. Thus, while a user may invite 50 players, only 25 may participate. Accordingly, the first 25 acceptees may participate. In another example, the user may choose from all acceptees based on the limit. In yet other examples, the user might only be allowed to invite a number of people equal to the maximum number of participants allowed. Participants may further be selected from invitees who responded positively based on other parameters such as frequency of participation of the invitee in games (overall or with the game creator), various metrics (e.g., within a certain range of the creator's metrics to insure a competitive game), location, time zones and/or combinations thereof.

The device may then display invitation specification options in step 7320. In one example, the display of the invitation specification options might only be provided upon the user finishing adding invitees. Invitation specifications may include customized messages/notes to be sent in the invitations, a blind invitation option (e.g., the sender and/or other invitees/participants remain anonymous) and the like. Other customization options may include color, sounds, animations and the like. Additionally or alternatively, users may be able to select and/or define a duration for the game (e.g., a number of hours, days, weeks, etc.), consequences (e.g., select a type of punishment or consequence that is applied to the loser), one or more rules for selecting the loser, an objective of the game (e.g., defining a particular distance that must be run) and/or combinations thereof. In one example, a user may define a rule for selecting the loser such that the second to last person to finish is identified as the loser. In another example, the user may define the rule for selecting the loser based on a lowest average distance run per session. Customization of an objective may include defining the goal or requirement of the game as, for example, running 10 miles or burning the most calories.

Once the options and specifications for the game have been finalized in step 7325, the user may then start the game by selecting a start option in step 7330. The device may then cause invitations to be sent to the invitees in step 7335. The game monitoring system may then monitor and facilitate the game. For example, the device may transmit e-mails, social networking messages, text messages, multimedia messages and the like upon the user initiating the start option. Additionally or alternatively, the system may enforce invitee or participant limits. The system may further monitor user athletic activity performances and provide feedback as to current player rankings to the participants. In some arrangements, the user may delay start of the game by setting a date and time (or an amount of delay) for the start of the game. Thus, the user may specify that invitations are to be sent out in 30 minutes, 1 hour, 2 hours, 9 hours, 3 days, etc. The user may also specify a specific date and time for the transmission of the invitations. Still further, the user may specify when the game will begin. The time and/or date at which the game begins may be different from the date and/or time at which invitations are sent out and may be defined separately. In other examples, these times may be the same and defined together. Additionally or alternatively, the user's device (e.g., if created through a user's athletic performance monitoring device or other personal device) may transmit game registration information to a central game monitoring system.

Figure 74B:
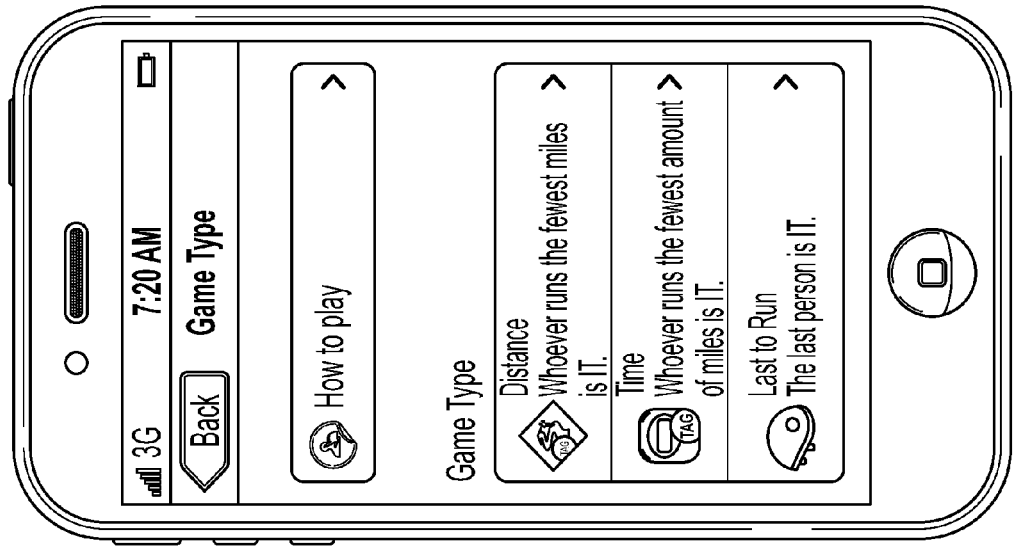
FIGS. 74A-74D illustrate example interfaces for creating a multi-user athletic activity game according to one or more aspects described herein.
Figure 74A:
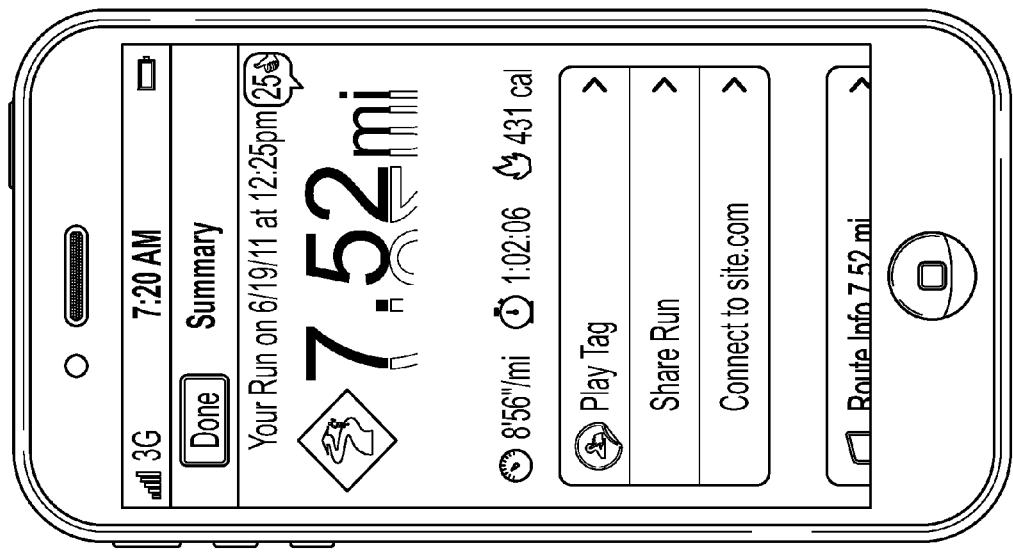
Figure 74D:
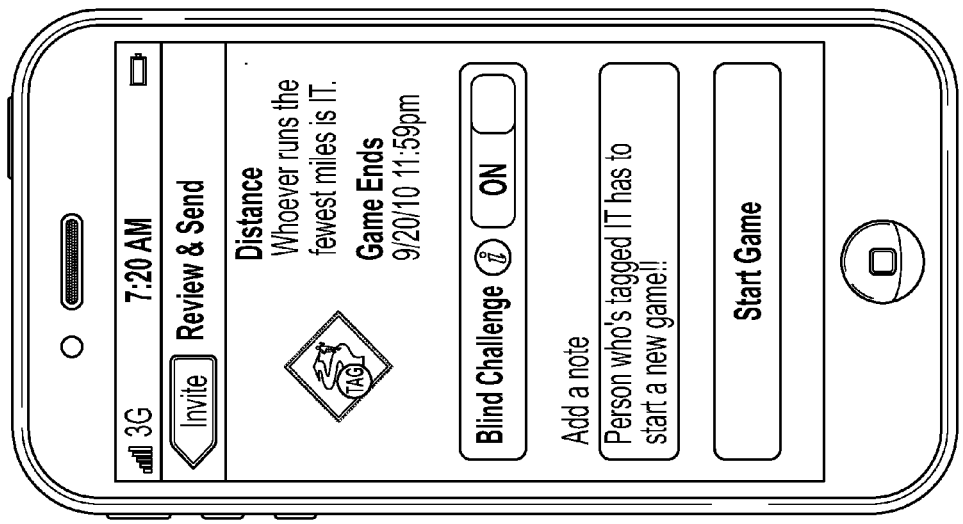

FIGS. 74A-74D illustrate a series of example interfaces through which a game may be defined and initiated. FIG. 74A, for example, illustrates a run summary page for a run that has just been completed. In the summary page, in addition to run statistics, an option to initiate a multi-user game or activity challenge may be displayed to motivate the user to exercise again. Upon selection of the game option, game types may be displayed in a subsequent interface as shown in FIG. 74B. An explanation of each game type may be provided in association with each game type option. Additionally, an option (not shown) for a customized or manually defined game type may be provided as well. In some arrangements, predefined game types may also include an option to modify one or more aspects of the predefined attributes of those game types. For example, a user may modify the consequences or punishment for a loser of the distance game type. In another example, a user may modify the objective of a time-based challenge so that the loser corresponds to the participants with the shortest amount of exercise time per day or per workout session (rather than, for instance, an absolute total amount of exercise over the game duration). As noted herein, other types of games may also be selected and defined including games that have multiple parts, where each part includes a different goal or objective. Additionally, one or more of the multiple game parts may include a different rule for identifying one or more losers and a different consequence for the one or more losers. In one example, a consequence for losing a first part of the game may be more severe than a consequence for losing a last part of the game. Various customizations may be applied to game creation.

Figure 74C:
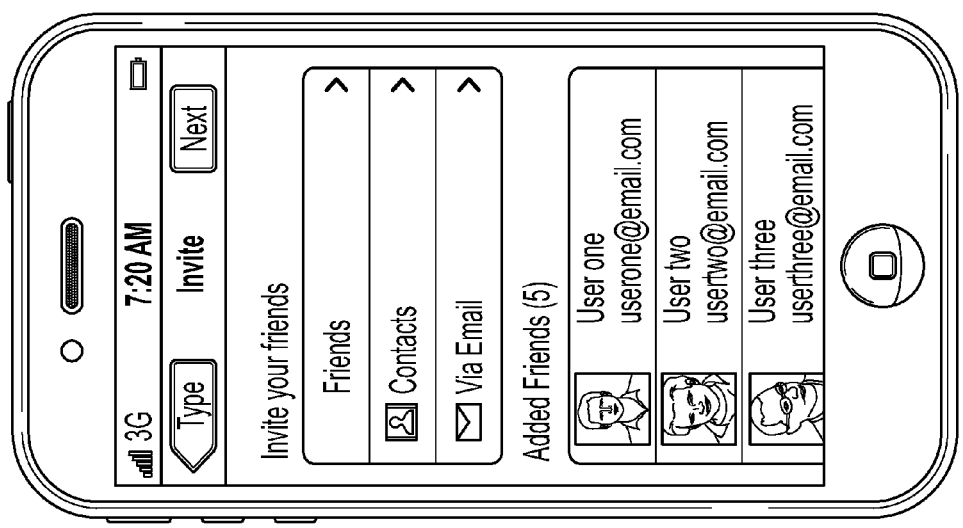

FIG. 74C illustrates example invitation options. The user may, for example, select invitees from a community site (e.g., FACEBOOK, or an athletic performance monitoring site/service), contacts stored in a device running the application or stored elsewhere, and/or e-mail addresses (e.g., entering specific e-mail addresses). Invitees may be displayed in a further portion of the interface for reference. Once the invitees have been selected, the user may then review and send the invitations through an interface, such as the interface illustrated in FIG. 74D. As noted above, a user may make the invitation and/or game a blind invitation or game, respectively, and/or include a customized or personalized message.

Figure 75:
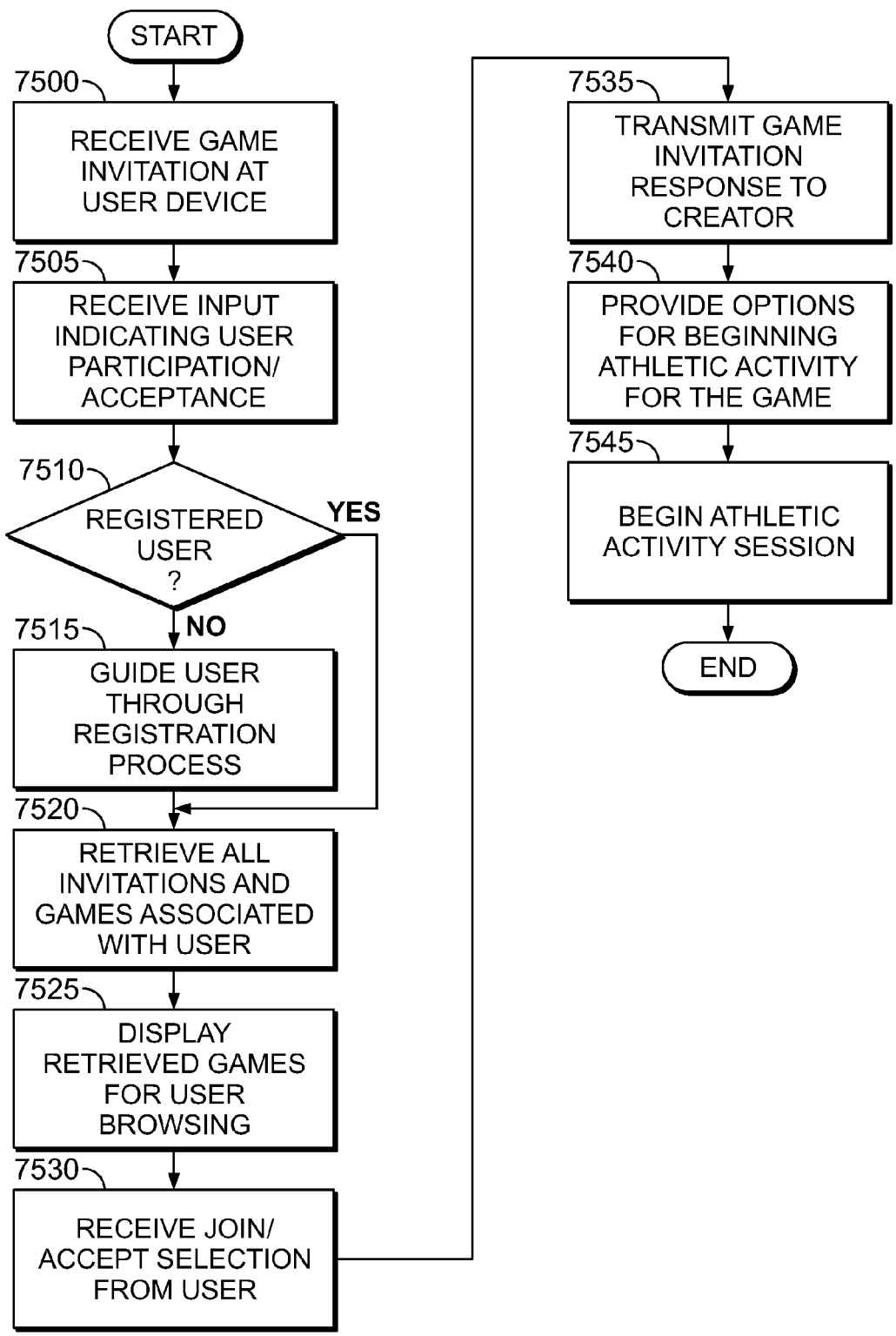
FIG. 75 illustrates an example method for receiving and responding to a game invitation according to one or more aspects described herein.
Figure 77B:
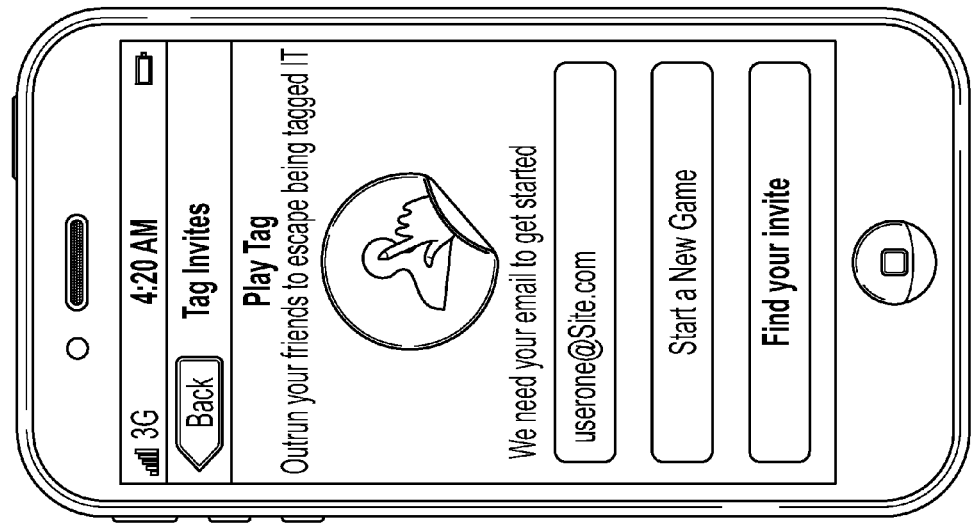
FIGS. 77A-77D illustrate example interfaces through which a user may register and accept an invitation according to one or more aspects described herein.
Figure 77A:
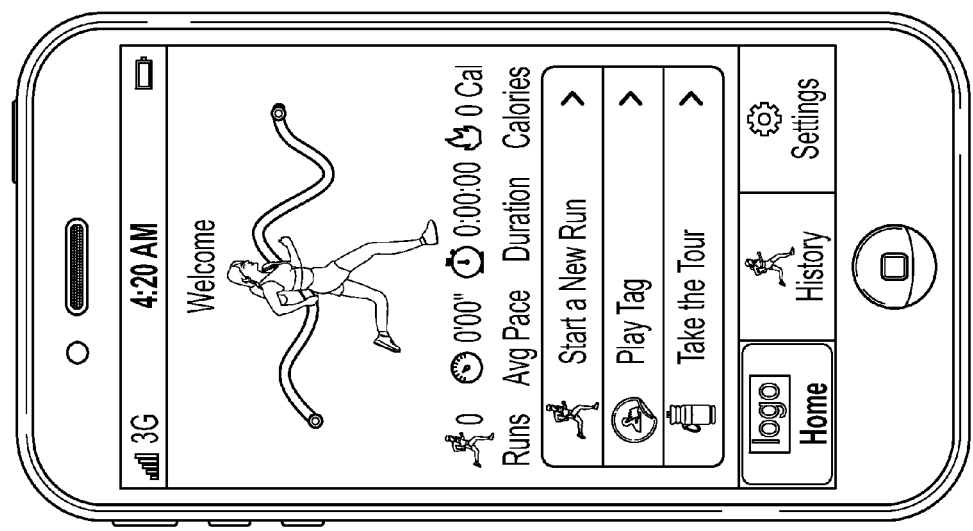
Figure 77D:
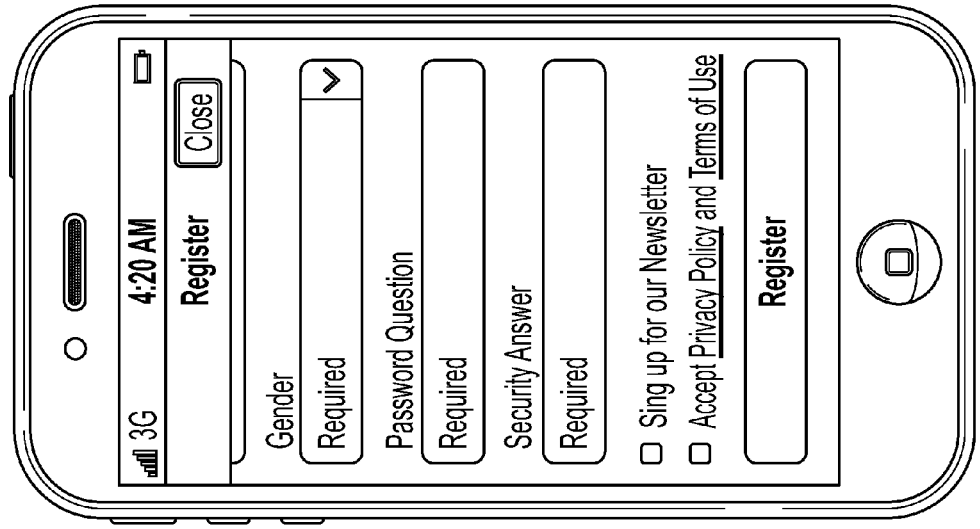
Figure 77C:
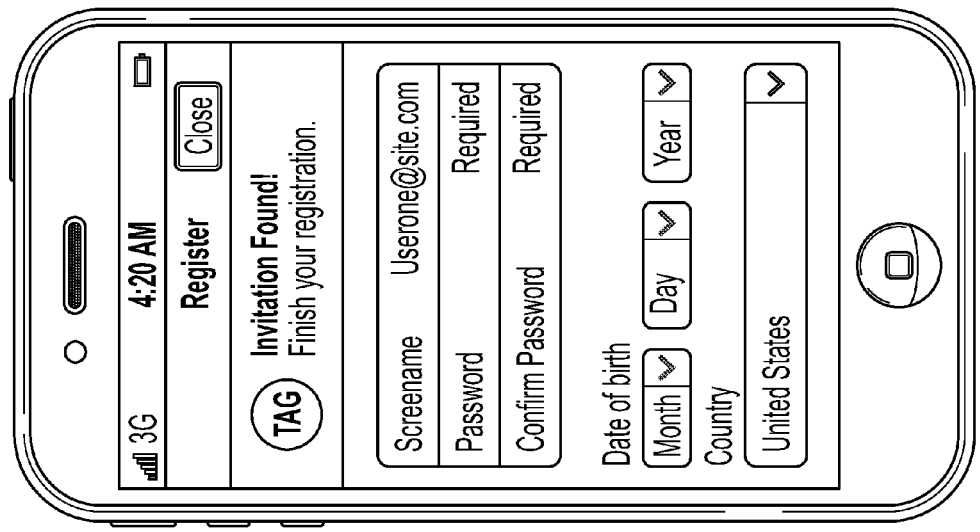

FIG. 75 illustrates an example method by which a user may accept an invitation and/or participate in an athletic activity game. In step 7500, for example, a user may receive an e-mail or other type of electronic message (e.g., SMS or MMS, message through an application) at a user device such as a mobile communication device or an athletic performance monitoring sensor or device. The message may include details of the game and/or instructions for accepting the invitation, joining the game and/or downloading an application for participating in the game.

FIG. 76 illustrates an example message that may be provided to invitees.

Referring again to FIG. 75, in step 7505, the user device may receive input indicating that the user wishes to join or participate in the game (e.g., acceptance of the invitation). In step 7510, the device may subsequently determine whether the user is registered. For example, the device may make such a determination by querying a registered user database for an entered username or e-mail address. Alternatively, a user may simply indicate that he or she has not yet registered with the service or site through which the game is hosted or otherwise facilitated. If the user is not registered, the user may be guided through a registration process in step 7515.

FIGS. 77A-77D illustrates example interfaces of a registration process. For example, a user may select a link provided in a message as illustrated in FIG. 76. Upon selection of the link, the user may be required to download an athletic monitoring application. Additionally, the user may be asked to provide an e-mail address or to sign in to their account. In some instances, the e-mail address may be automatically populated based on the address to which the e-mail was sent. The user may then provide registration information in the interfaces of FIGS. 77C and 77D. According to one or more arrangements, a registration interface may indicate whether game invitations were found upon a user entering an e-mail address (e.g., as in FIG. 77B) and selecting a find your invitation option.

Continuing with FIG. 75, once the user has been registered and/or a registered user has signed-in, the device may retrieve all invitations, active games and/or inactive games associated with the user (e.g., to which the user was invited, that the user accepted or declined) for display in step 7520. The retrieval may be performed through a central database of an athletic activity performance monitoring service. The invitations, active or inactive games and other activity data may be keyed using the user's e-mail address or username. In other examples, the device may perform selective retrieval and/or selective display of data based on user configurations (e.g., retrieve/display only new games or new notifications, retrieve and/or display based on level of importance). Other contact information or identification data may also be used to search for invitations and games. In step 7525, the retrieved games may be displayed in an interface for a user to browse. A user may also select individual games to view detailed information. For example, a user may view an invitation list (if allowed), objectives, consequences, current progress of each invitee, whether an invitee declined or accepted or has not yet responded and the like. In some arrangements, if a creator of the game has set the game to blind or otherwise specified anonymity for one or more aspects of the game, some information might not be viewable by the participants. For example, participants or invitees might not be able to view an invitation list or a status of each participant.

The device may receive a selection of a game to join in step 7530. The device may then send a corresponding game invitation response to the game creator in step 7535. For example, if the individual accepted the invitation, the response may indicate that the user accepted the user's invitation to the game. The response, in one or more arrangements, may also be transmitted to a central game monitoring system. Alternatively, if the user declines the invitation, a corresponding response may also be provided to the game creator. Accepting an invitation may also cause the accepting user's device to be automatically reconfigured according to the specifications provided in the invitation. For example, the invitation may include device setting parameters such as run-only. Thus, if a user attempts to record a walking exercise for credit toward the game, the device may automatically reject the walking exercise as a valid athletic activity session for that particular game. However, the user may still credit the walking exercise to another game or for general tracking. Such parameters may also affect the type of data interpretation profile that is used to detect a user's pace or distance. For example, walking may have a different speed to contact time profile than running. Accordingly, if the invitation indicates a run-only game, the device may be reconfigured to the running profile. In another example, the device setting may control which sensors are activated and/or used in measuring athletic performance during the game.

Additionally, in some arrangements, a device, application or system may automatically determine games and/or game types to which a particular athletic activity may be applicable and provide a user with a list of valid games to which the workout session may be applied. In another example, the application, device or system may automatically select the game or games to which the athletic activity for the workout session is applied. Athletic activity for a single workout session may be applied to multiple different games either in whole or in part (as described herein).

According to one or more arrangements, the device may further provide options for beginning an athletic activity (e.g., running) corresponding to the joined/selected game and game type in step 7540. For example, a user may be able to select music for an athletic activity or workout session for the selected/join game, a location of the workout session and whether the user wishes to receive messages (e.g., words of encouragement, cheers, etc.) from other users. The user may then begin the workout session once the parameters have been set in step 7545. According to one or more aspects, when a user defines a new workout session after selecting a particular game or game type, the workout session initiation/definition screen might only provide parameter selections (e.g., music lists or types, workout type, terrain type, threshold speed, threshold distance, etc.) that are allowed by the game or game type. Accordingly, in the above example involving a game that only allows run workouts, walking exercises might not be selectable or even available (e.g., displayed) under a workout type selection menu. In another example, the device may require that one or more types of metrics be recorded (e.g., time for time-based games, distance for distance-based games, calories for calorie-based games). In yet another example, a device may automatically activate or deactivate various sensors depending on the game specifications (e.g., activation of GPS for distance-based games).

In some arrangements, cheers or encouragement may be provided based on messages from other users. In one particular example, upon a user beginning a workout or activity session, a post may be automatically (or manually) posted to a social networking site indicating that the user is beginning the activity session. The post may include an invitation to comment (e.g., encourage) on the user's athletic activity. If another user responds to the post, the social networking site and system may transmit a notification of the response to an athletic activity monitoring site and/or an athletic activity monitoring device of the user. In response to the notification, the athletic activity monitoring device of the user may convey a predefined sound, message, image, haptic feedback and the like. In some examples, the sound may include the sound of cheering. In other examples, the sound may include an audio rendering of the message submitted in response to the post. In another example, an intensity (e.g., loudness, brightness, strength of haptic feedback) of the predefined sound, message, image and/or haptic feedback may depend on a number of responses or an activity level of the responding users. Various other parameters may also be used to determine an intensity of the feedback.

Figure 78B:
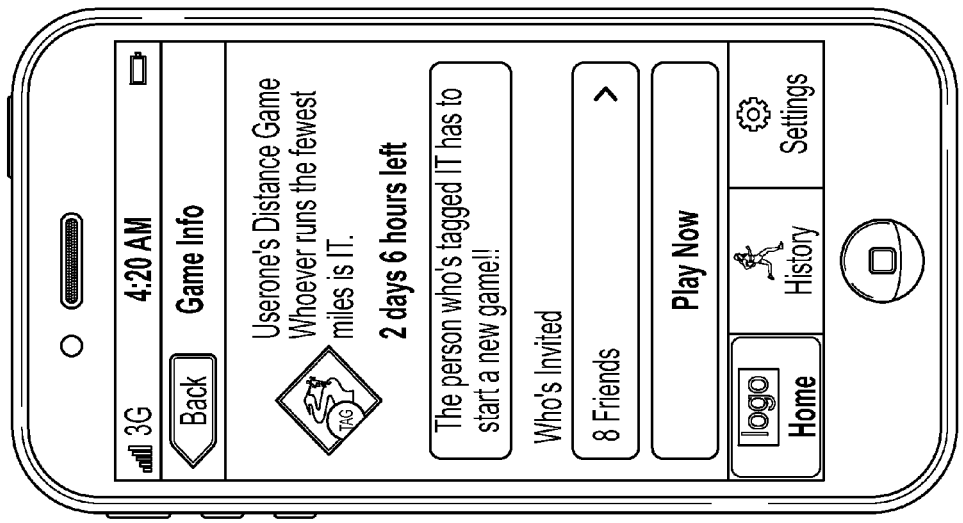
FIGS. 78A-78D illustrate example interfaces for viewing and joining a multi-user athletic activity game according to one or more aspects described herein.
Figure 78A:
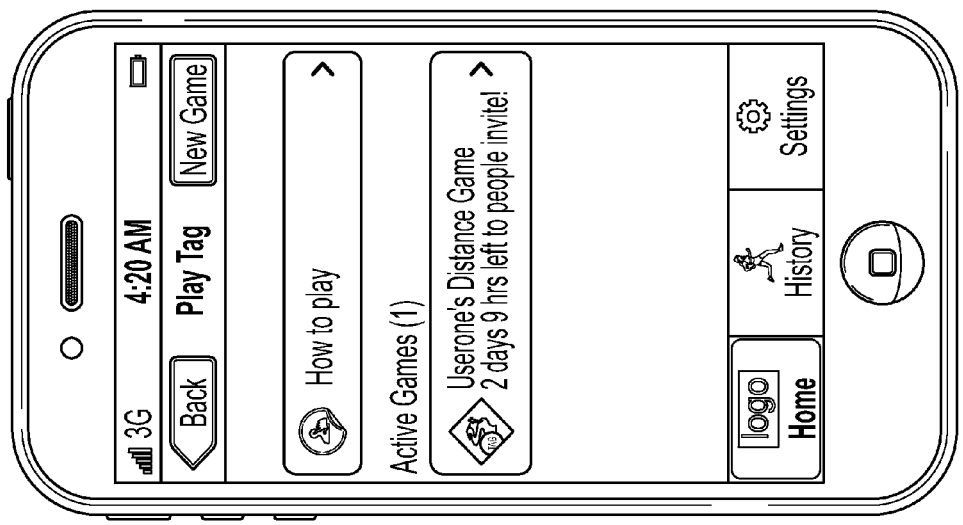

FIGS. 78A-78D illustrate an example series of interfaces through which a user may view a list of games to which he or she has been invited and initiate a workout session for one of the games. FIG. 78A, for example, illustrates an interface listing a single available game. The interface may display a breakdown of the games based on a variety of factors including a user's response (e.g., acceptance, not yet responded, declined), a status of the game (completed, in progress, not yet started), a user's current status (e.g., a user's current progress, a current place in the competition, etc.) and the like. In one example, games in which the user is currently in last place or in a "losing" position may be displayed in a separate category or identified differently based on color, pattern, font size, etc.

Figure 78D:
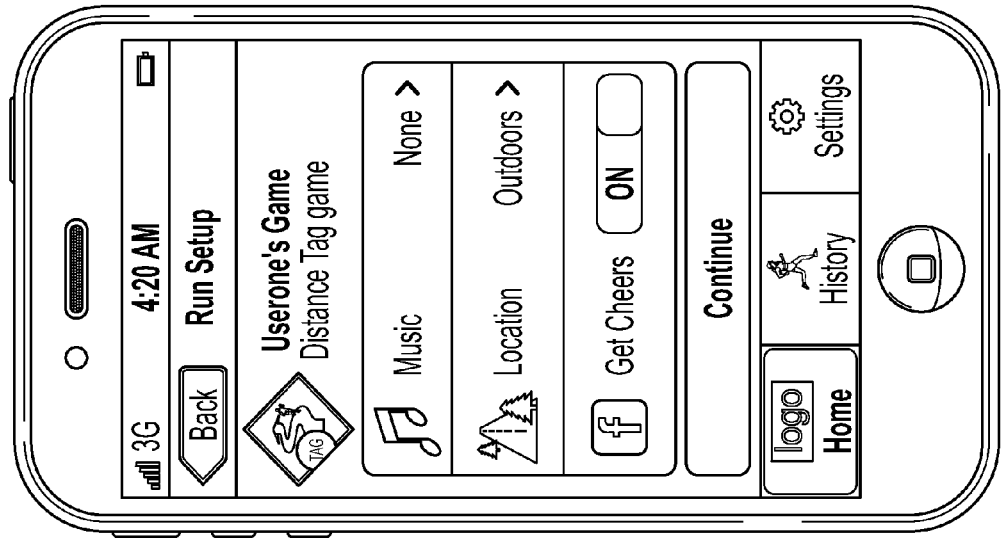
Figure 78C:
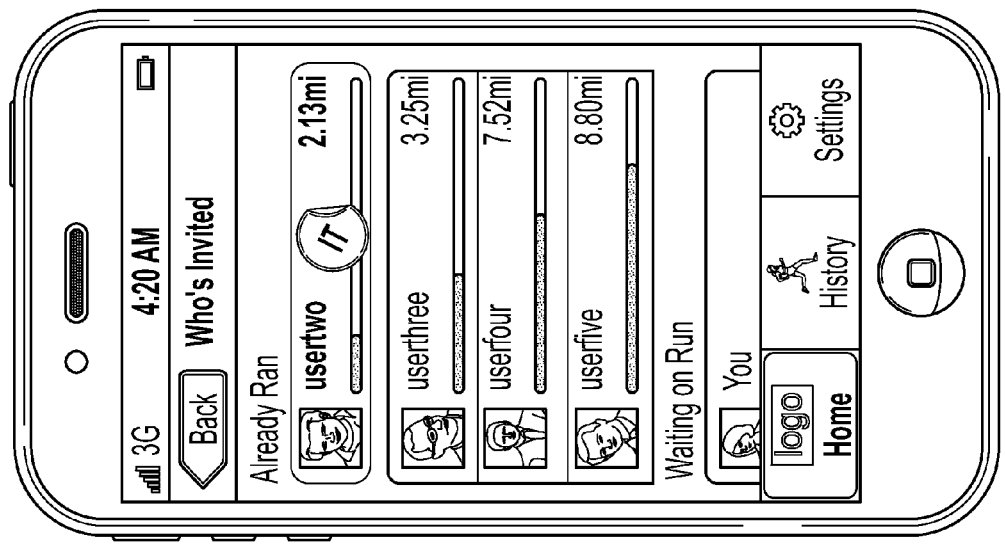

FIG. 78B illustrates example details for a particular game while FIG. 78C illustrates an invitation list of users. In FIG. 78C, progress for each user may also be displayed in the list. Users that are already participating in the game versus those who have not yet responded or not yet registered a first activity session may be displayed in one or more other categories. FIG. 78D illustrates an interface through which a user may select workout parameters upon choosing to begin a workout session for a selected game (e.g., the game displayed in FIGS. 78B and 78C).

Figure 79:
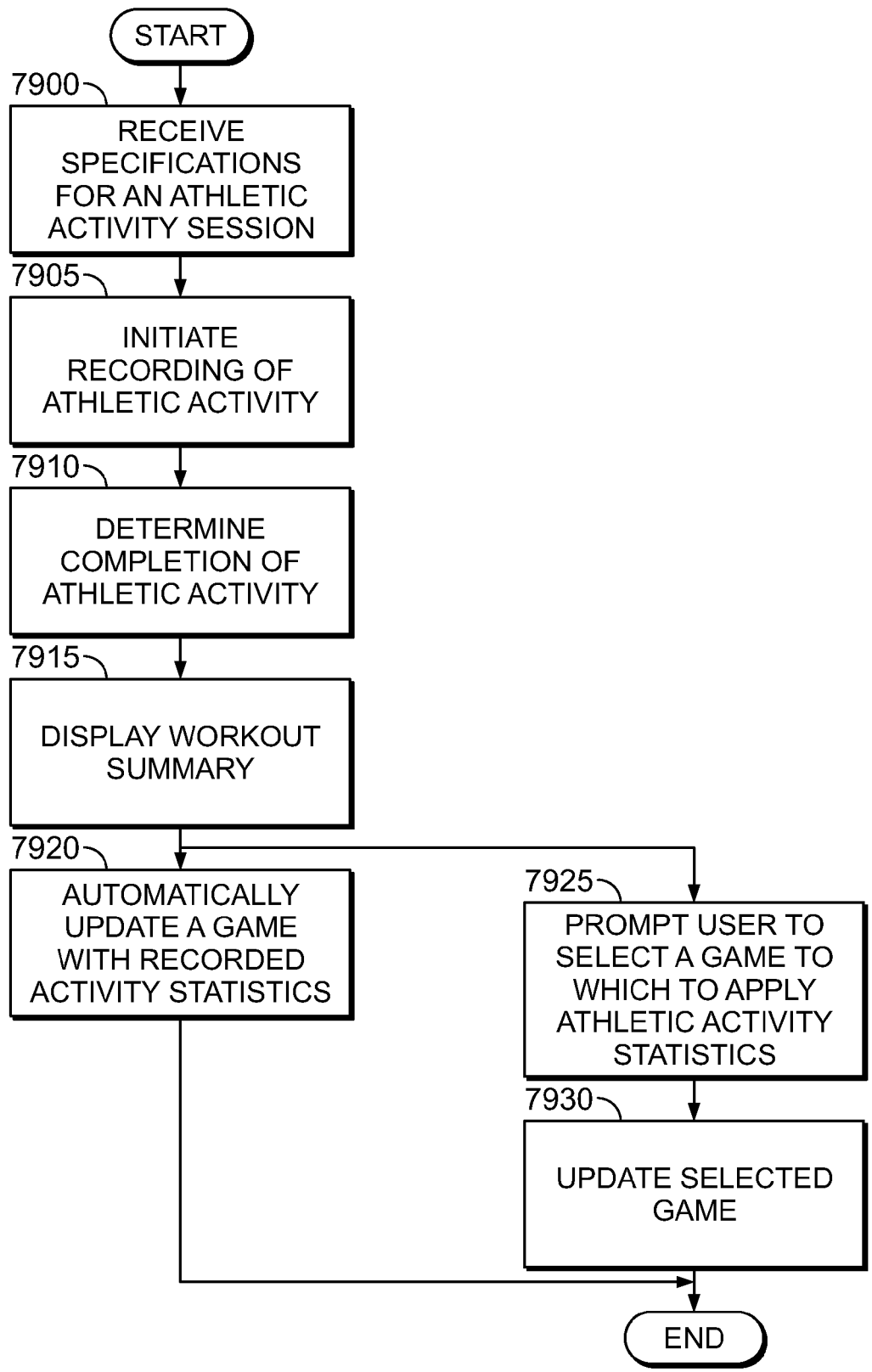
FIG. 79 illustrates an example method for collecting athletic activity data and crediting the athletic activity to one or more games according to one or more aspects described herein.

FIG. 79 illustrates an example method by which a user may record athletic activity to a game. In step 7900, an athletic performance monitoring device may receive specifications for an athletic activity session. As discussed herein, a user may initiate an athletic activity session in a variety of ways including by specifying music to be played, types of athletic metrics to be recorded, location types, coaching parameters and the like. In step 7905, the device may subsequently initiate recording of the athletic activity in response to user initiation (e.g., selecting a start option) or automatically upon detecting user movement or other type of physical activity. In step 7910, the device may determine that the user has completed the athletic activity. The determination may be based on user input such as selecting a complete or stop option or automatically based on time, amount of movement (e.g., number of laps in swimming or repetitions in weight lifting), distance (e.g., predefined run distance or distance of a particular course) or the like.

Upon detecting that the user has completed the athletic activity, the device may display a workout summary including various statistics in step 7915. The device may further automatically update a game in step 7920 if the user selected a game prior to initiating the workout or if there is only one game available (e.g., a game selection step (not shown) occurring prior to receiving specifications for the athletic activity session in step 7900). If the user did not select a game or initiate the athletic activity session through a particular game, the athletic activity data might not be automatically updated to a particular game. Alternatively, the device may prompt the user to select a game to update with the workout information (e.g., after the workout is completed) in step 7925. Once selected, the device may update the game in step 7930. For example, the device may transmit the workout statistics to a game monitoring system or site with the game selections. In one or more arrangements, the device may allow a user to divide a workout session among multiple games. For example, a user may direct 5 miles of a 10 mile run to a first game and another 5 miles to a second game. In other examples, different metrics recorded for a workout session may be assigned or applied to different games. For example, a first game may have a heart rate criterion while a second game may be a time duration criteria. Accordingly, a workout session where a user recorded both heart rate information and time duration information may be divided into the heart rate data and the time duration data, where each of the types of data are applied to the first or second game as appropriate. This division of information may also be transmitted to the game monitoring system.

Figure 80B:
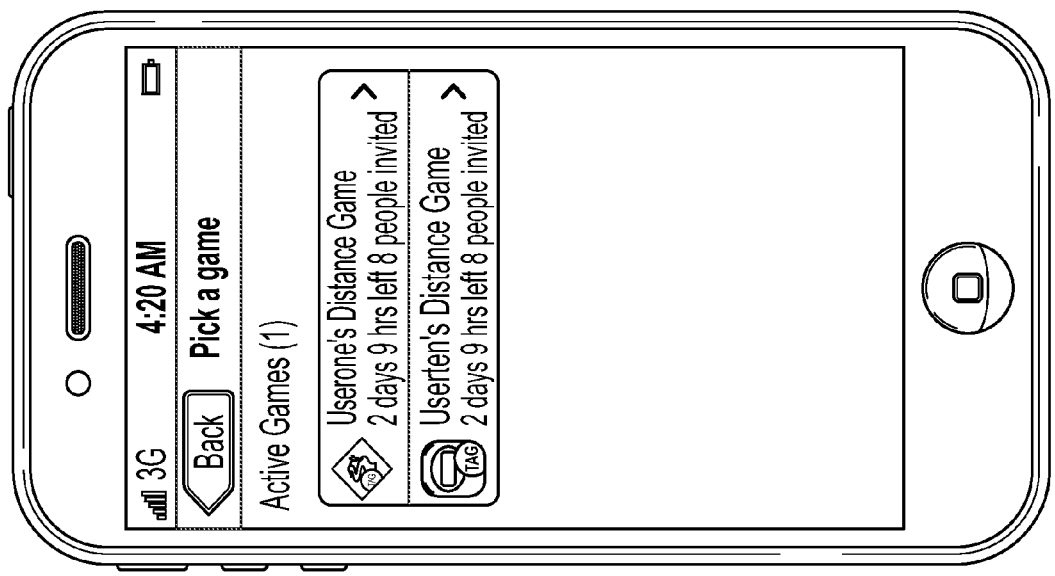
FIGS. 80A-80C illustrate example interfaces through which a user may select one or more games to which to credit athletic activity according to one or more aspects described herein.
Figure 80A:
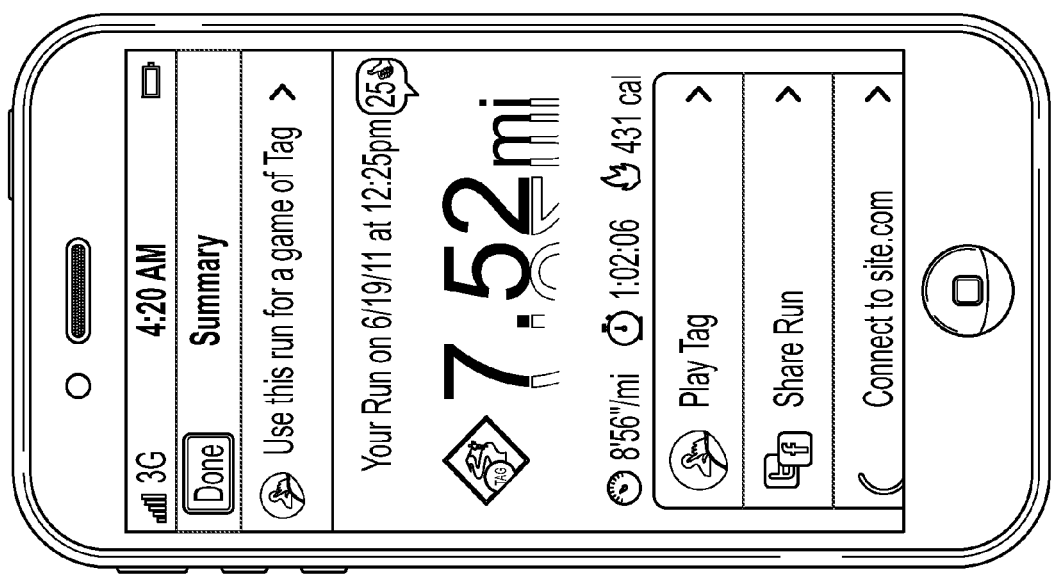
Figure 80C:

FIGS. 80A-80C illustrate example interfaces through which a user may select a game to which to apply a completed run.

Figure 81B:
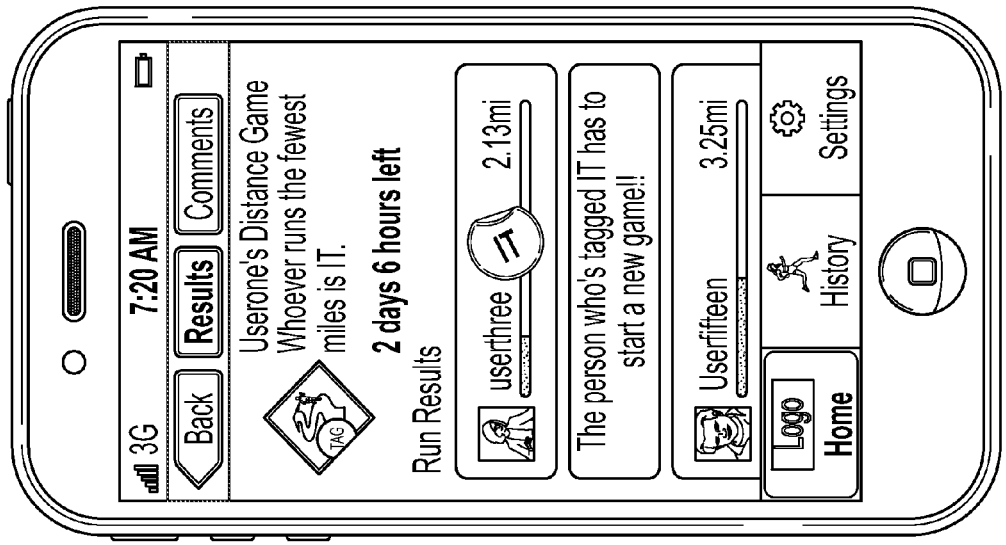
FIGS. 81A-81D illustrate example interfaces through which a user may view game progress and send messages to other game participants according to one or more aspects described herein.
Figure 81A:
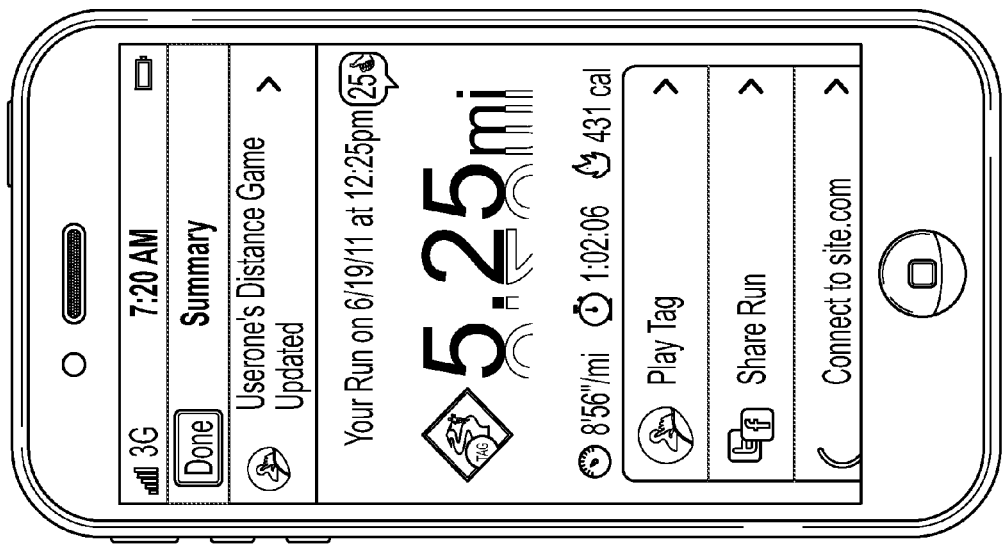
Figure 81D:
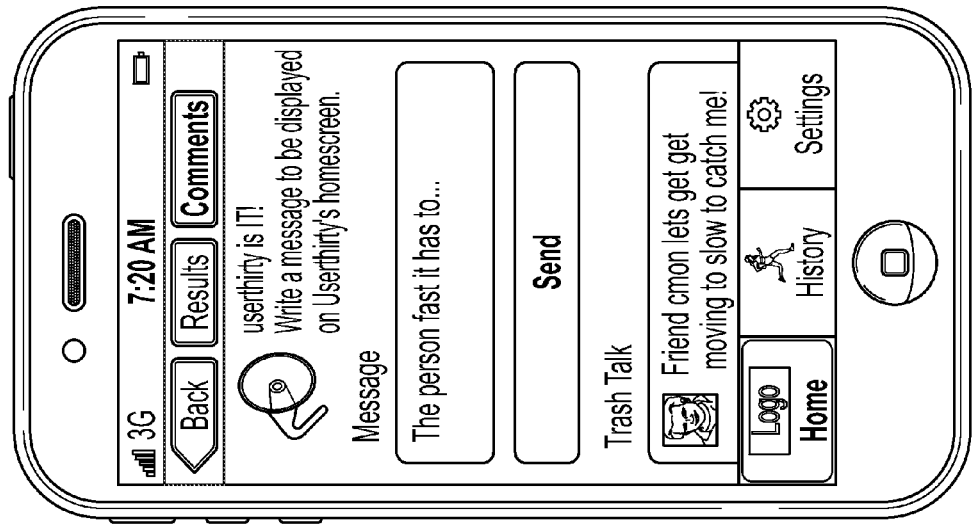
Figure 81C:
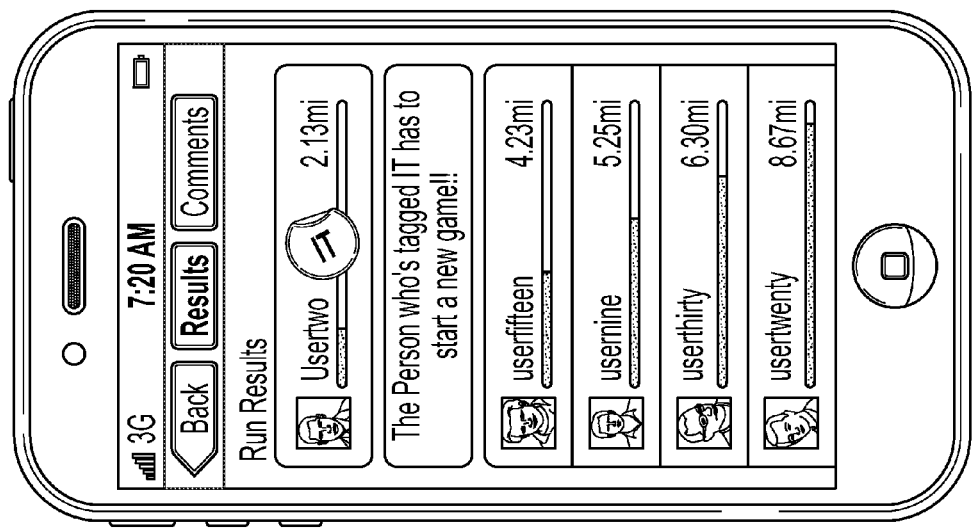

FIGS. 81A-81D illustrates a series of example interfaces in which a user may view a workout summary and update one or more games using the results of the workout. For example, FIG. 81A illustrates an interface displaying workout results for a most recent athletic activity session. The interface includes a notification bar indicating that a particular game has been updated with the workout activity data. By selecting the notification bar or an element thereof, the user may subsequently view a current status of the game as illustrated in FIGS. 81B and 81C. For example, the game status interface may display a current progress of each user and a currently "tagged" user. The currently tagged user may correspond to the game creator. In particular, the game creator may have been previously tagged for losing a previous game. The tag may carry over into the new game that the user is required to start and win, place better than last or otherwise not lose in order to get rid of the tag. Accordingly, the user may maintain the tag or status label until the game finishes and the user is determined to not have lost. If the user loses the new game, the user may maintain the status label or tag for a predefined amount of time or until the user is able to win or not lose a game. FIG. 81D illustrates an example interface through which a user may post or transmit messages to a losing participant of the game.

Figure 82:
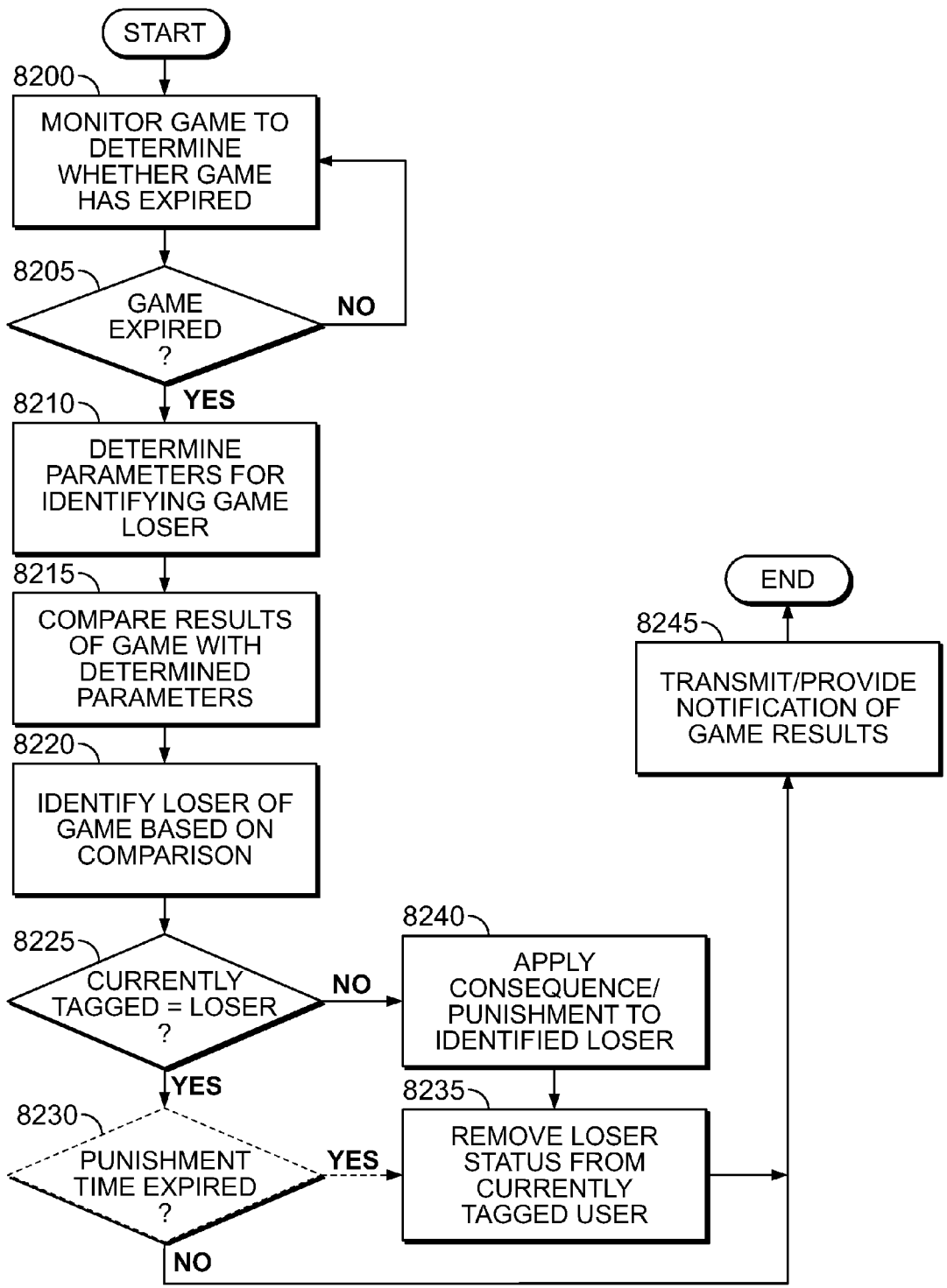
FIG. 82 illustrates an example method for determining a loser of a game and applying one or more consequences/punishments to the loser according to one or more aspects described herein.

FIG. 82 is a flowchart illustrating an example method for determining a loser of a game and applying a consequence of losing the game. In step 8200, for example, a system may monitor the game to determine whether the game time has expired or game expiration terms have been met. The type of game expiration term may depend on the type of game or may be the same for all game types. For example, in distance and time based games, the expiration term may be a period of time or a specified date and time. In another example, in last-to-complete games, the expiration term may correspond to when all but one participant (or all participants) have completed the predefined objective. In yet another example, all game types may expire based on a predefined time period. In step 8205, the system may determine whether the game has expired. If not, the system may return to monitoring the game in step 8200.

If the game term has expired, the system may determine the predefined parameters for determining a game loser in step 8210. In one example, the game loser parameters may be defined in the game invitation. In step 8215, the system may further compare the results of the game with the game loser parameters to determine the game loser. Upon comparing the results and the game loser parameters, the system may identify a loser of the game in step 8220. For example, the game loser parameters may indicate that the last person to complete a particular run is the loser. In another example, the person to run the shortest amount of time in the game period may be labeled as the loser.

Once the loser has been identified, the system may determine whether the currently tagged user is the game loser in step 8225. If so, the system may optionally determine whether a punishment or consequence period has expired in step 8230. If so, the system may remove the punishment (in this case, the label or tag) from the currently tagged user in step 8235. If, however, the punishment period has not expired, the system may allow the tag or punishment to remain. In some instances, losing of another new game may re-start a punishment or consequence expiration period. Accordingly, the system might not need to make the determination of step 8230.

If the currently tagged user is not the loser of the game, the system may apply a consequence or punishment to the identified game loser in step 8240. The consequence or punishment may be retrieved from the game definition parameters (e.g., defined through the invitation or from game parameters stored in a central game database). In one example, the game loser may be tagged with an "IT" label and be required to start and complete a new game without losing to remove the tag. Alternatively, the user may have to wait a specified period of time (e.g., 3 days, 1 week, 1 month, etc.) for the punishment or tag to expire. Upon applying the consequence or punishment to the identified game loser, the punishment of the previously tagged user may be removed as in step 8235. Additionally or alternatively, notifications of a user's game result and standing may be provided to each of the participants in step 8245. For example, a system may transmit an e-mail, SMS or MMS to each of the participants indicating whether identifying the user's placement in the game (e.g., $1^{st}$, $2^{nd}$, last, loser, etc.).

In some arrangements, a user's loser status might not be removed until the user completes a game without losing. Accordingly, no punishment/consequence expiration period may be defined or used. For example, step 8230 may be optional and might not be performed if a user's loser status does not expire based on time. Thus, in a particular arrangement, the only way the user may remove a loser status may be to complete a game without losing.

The game may be monitored by a central performance monitoring system or by a user's device or both. For example, performance statistics of each participant may be transmitted to a central server or system for recordkeeping and for determining a winner and/or loser at the end of the game. The central server system may also determine an expiration time of the game and transmit instructions for applying a punishment. In one or more arrangements, the server or game monitoring system may transmit notifications and updates before, during and after the game. For example, a reminder to respond to an invitation may be issued before the game, while updates on progress and/or standings may be transmitted to each participant during the game. As noted above, each of these functionalities may also be performed by a user's own device rather than or in addition to a central system.

Figure 83B:
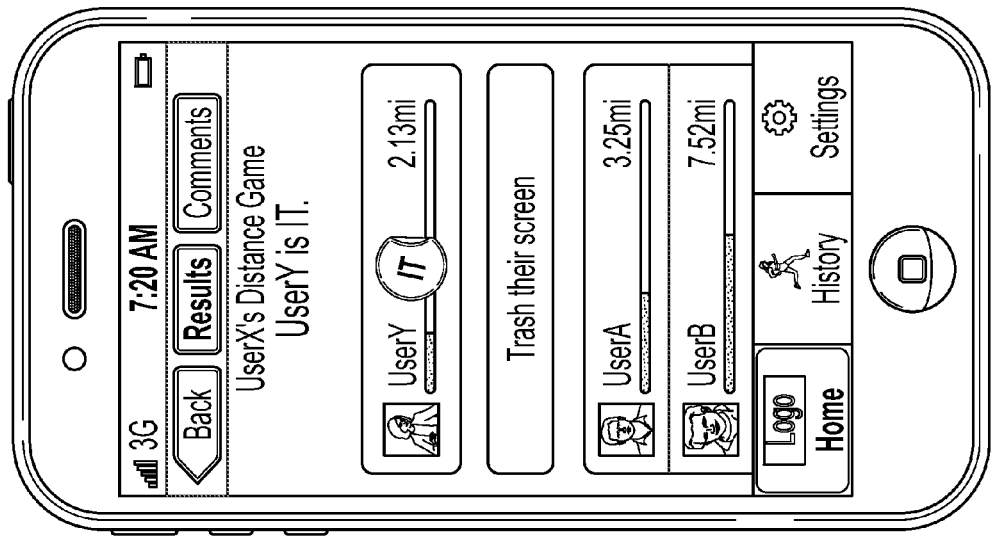
FIGS. 83A-83C illustrate example interfaces that may be provided upon completion of a game when the user has not lost according to one or more aspects described herein.
Figure 83A:
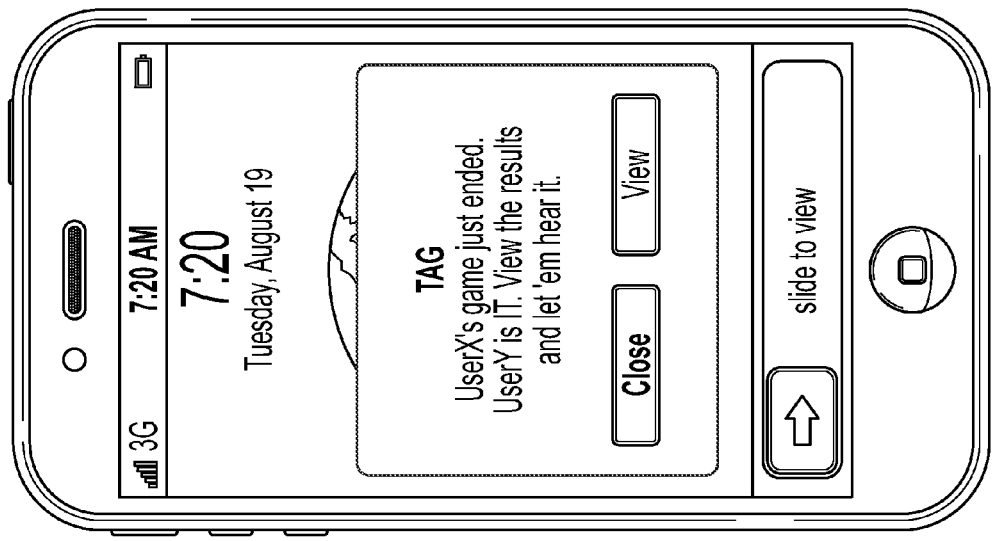
Figure 83C:
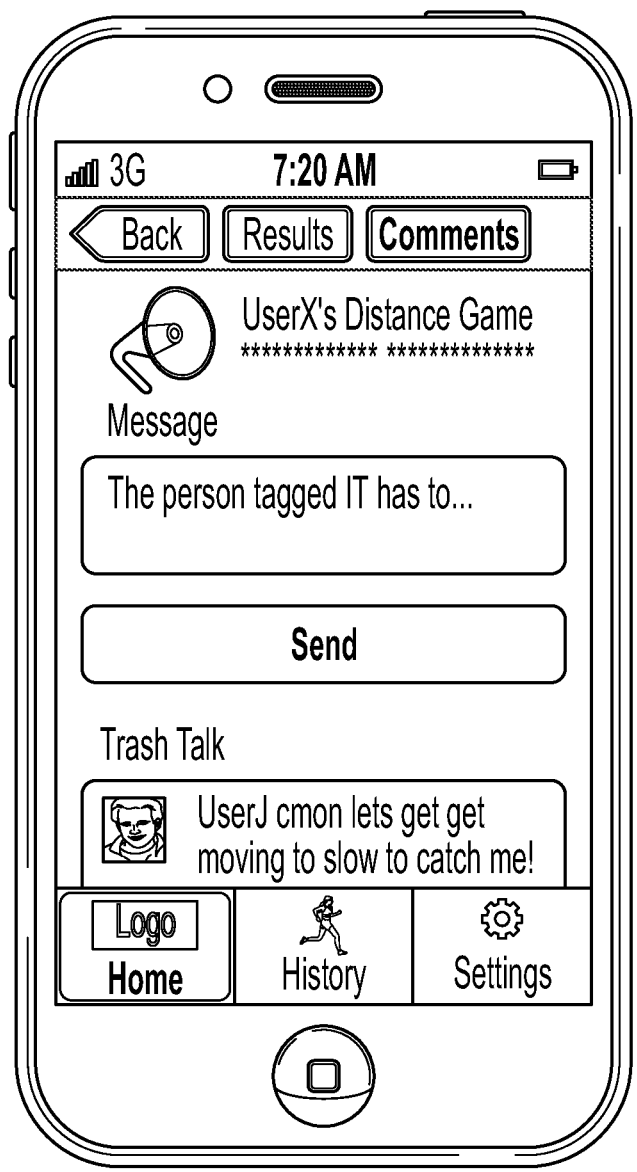

FIGS. 83A-83C illustrate a series of example user interfaces that may be displayed to a user that was not identified as the loser of the game. A notification prompt may be displayed as in FIG. 83A and a user may select an option or link to view the results of the game. The notification may indicate that the user has not lost. Alternatively, if the notification does not indicate that the user has lost, the user may assume that he or she has not lost the game. Alternatively or additionally, the notification may indicate that the user's previous loser status or punishment has been removed for not losing the presently completed game. Selecting the result view option may display a detailed view of the game results as shown in FIG. 83B. The interface may identify the loser of the game as well as provide a list of each user's standing and an amount of athletic activity performed for the game. Additionally or alternatively, a user may be presented with an option to cause a visual or functional effect on the losing participant's application or device (e.g., "Trash their screen" option in FIG. 83B). For example, the user may select a fog effect or a screen breaking effect to have activated on the losing participant's application or device. Identification of the selected effect may be transmitted to the losing user's device and the device may activate the selected effect in response thereto.

A user may also be allowed to send a message to one of the participants such as the loser of the game. FIG. 83C illustrates an example messaging interface through which the user may post or send a message to the loser.

FIGS. 84A-84D illustrate a series of example interfaces that may be displayed or available to a user when a user has lost the game. The notification message shown in FIG. 84A may indicate that the user has lost the game and has suffered a consequence such as being tagged. The user may further be required to start and complete a new game without losing in order to have the tag removed.

Figure 84B:
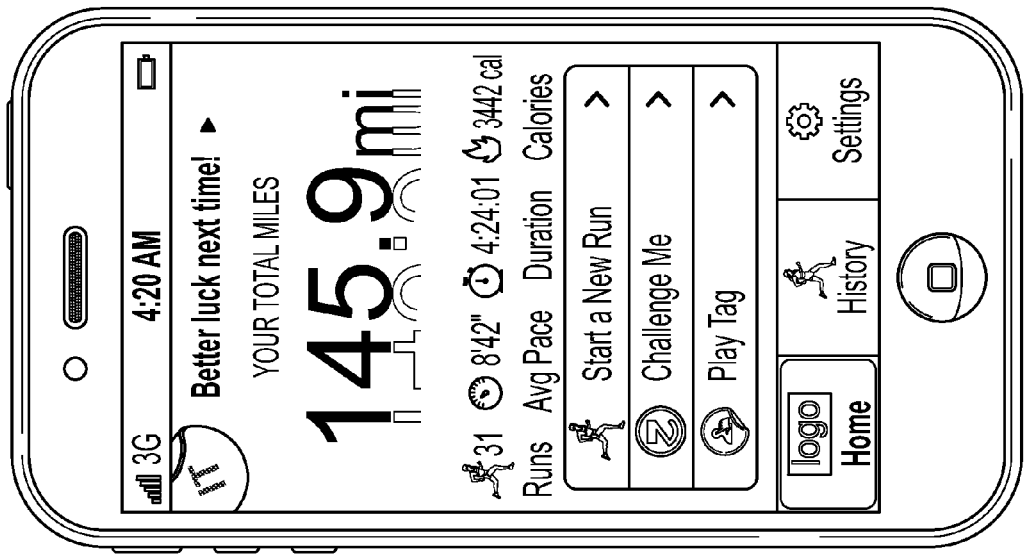
FIGS. 84A-84D illustrate example interfaces that may be provided upon completion of a game when a user has lost according to one or more aspects described herein.
Figure 84A:
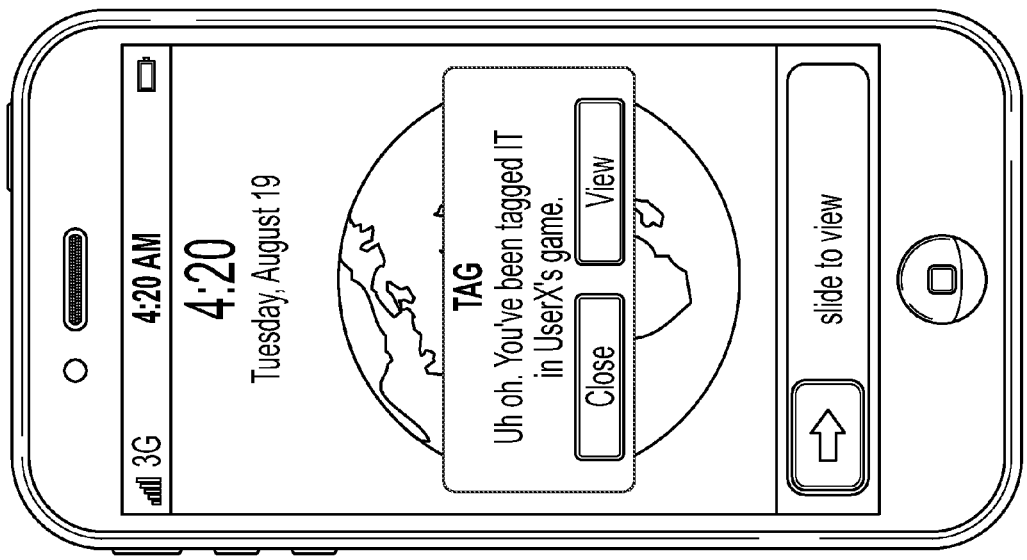
Figure 84D:
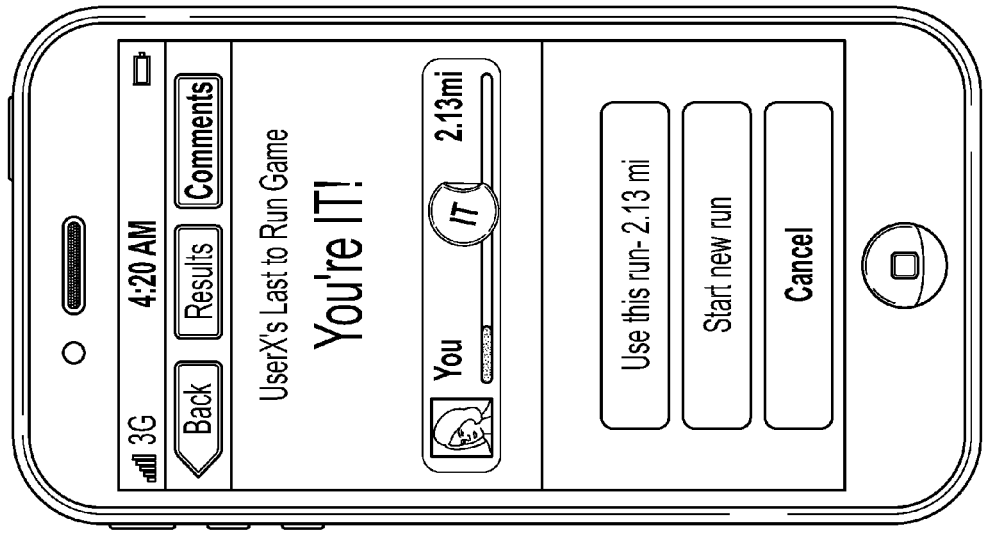
Figure 84C:
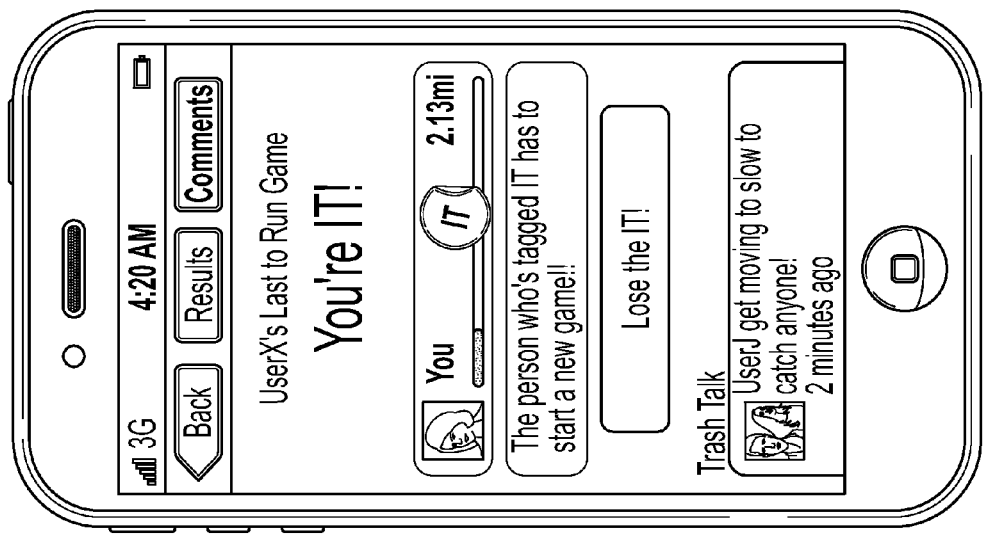

To notify and remind the user of the loss and his or her tagged status, the user may be presented with the interface of FIG. 84B where the user is presented with his or her overall performance metrics (e.g., metrics that are not limited to just the game). In addition, the interface of FIG. 84B may include a visual indicator such as an "IT" label to signify that the user has lost a game and the corresponding punishment or consequence is still active. FIG. 84C illustrates an interface through which a user may view his or her performance during the game. The interface of FIG. 84C further provides a predefined option that may be selected to remove the tag or other punishment that has been applied for losing the game. In one example, the predefined option may correspond to creating and participating in a new game without losing. FIG. 84D, for example, illustrates options for creating a new game. In this particular example, the user is permitted to use a previous run to begin a new game or to start a new run entirely.

Figure 85B:
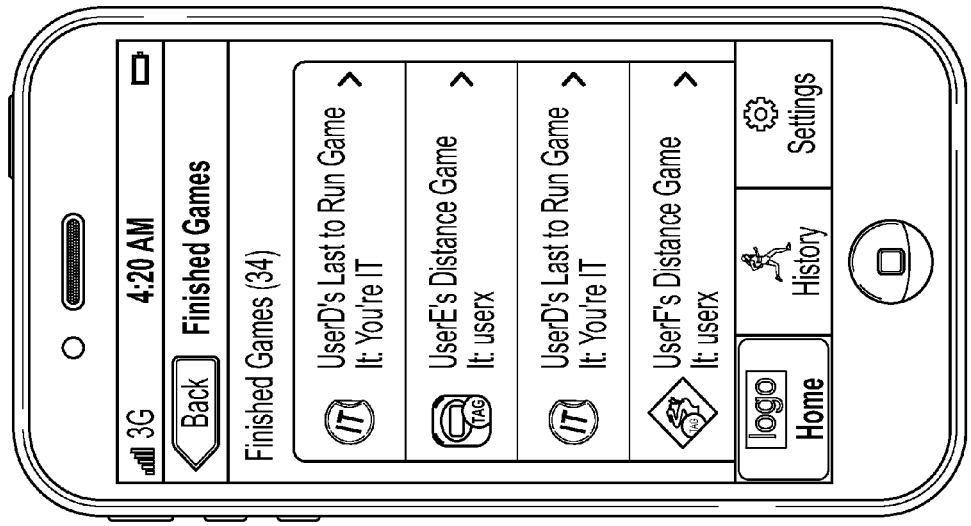
FIGS. 85A and 85B illustrate example interfaces displaying a user's scoreboard and history of games according to one or more aspects described herein.
Figure 85A:
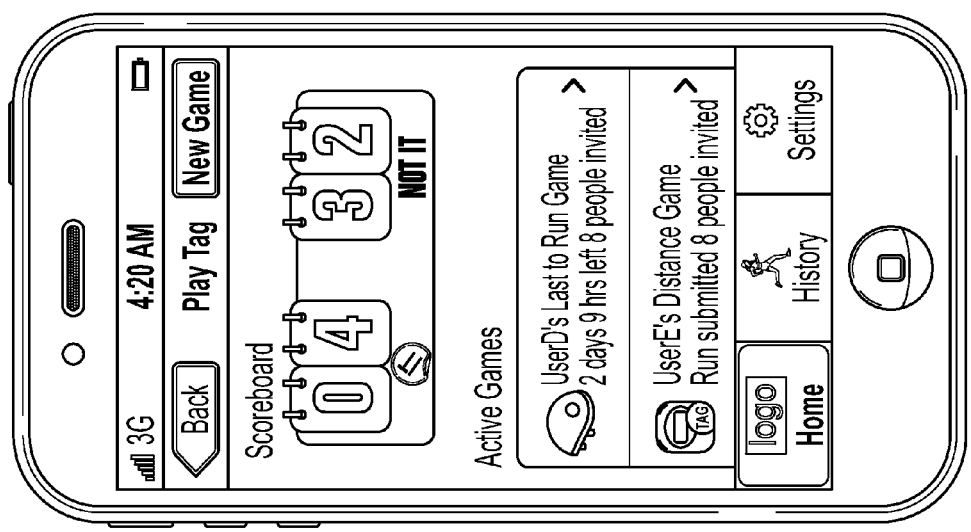

FIGS. 85A and 85B illustrate example scoreboard interfaces displaying a user's track record for previously played games. For example, in the interface of FIG. 85A, the scoreboard may indicate a number of games lost and a number of games not lost. The interface in FIG. 85A may further display the currently active games to remind the user to continue progress in those games to avoid losing. A user may also view a list of finished games through the interface of FIG. 85B. The track record may also indicate a number of games won (not shown).

Figure 86:
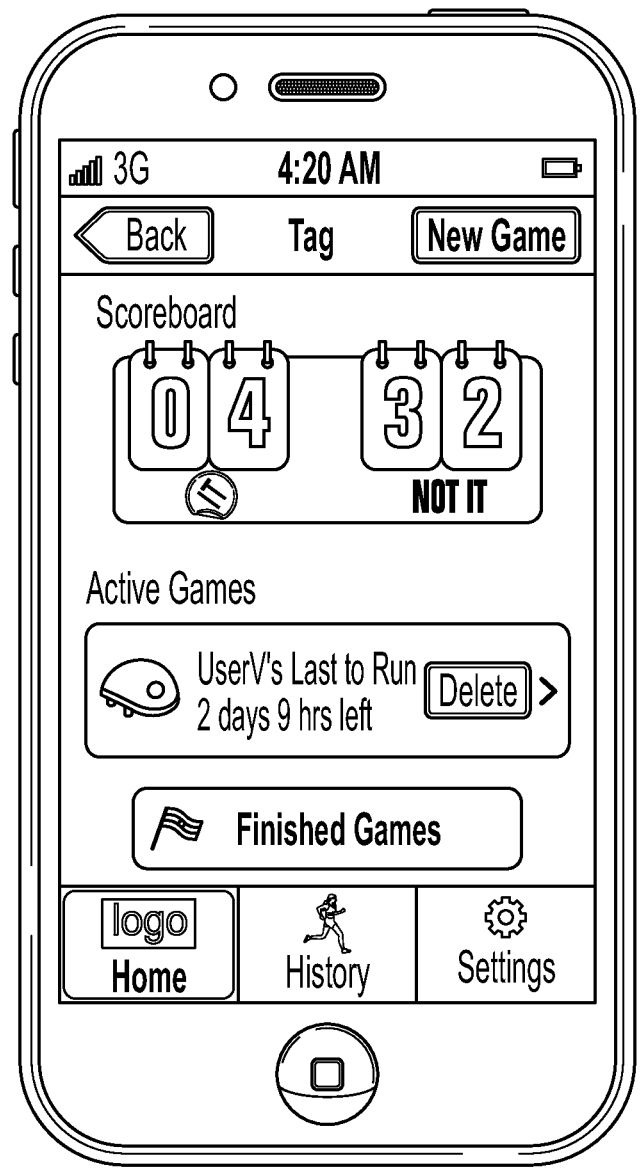
FIG. 86 illustrates an example interface including a delete option that may be used to remove or reject a game or game invitation according to one or more aspects described herein.

In one or more arrangements, a user may also reject an invitation or quit a game by deleting the corresponding invitation or game. For example, FIG. 86 illustrates a delete option that may be displayed in association with an active game selection bar or element. Upon deleting the game, the user may be notified that he or she has quit the game or rejected the invitation. The user will then be protected from losing the game which the user quit or to which he or she was invited.

Figure 87B:
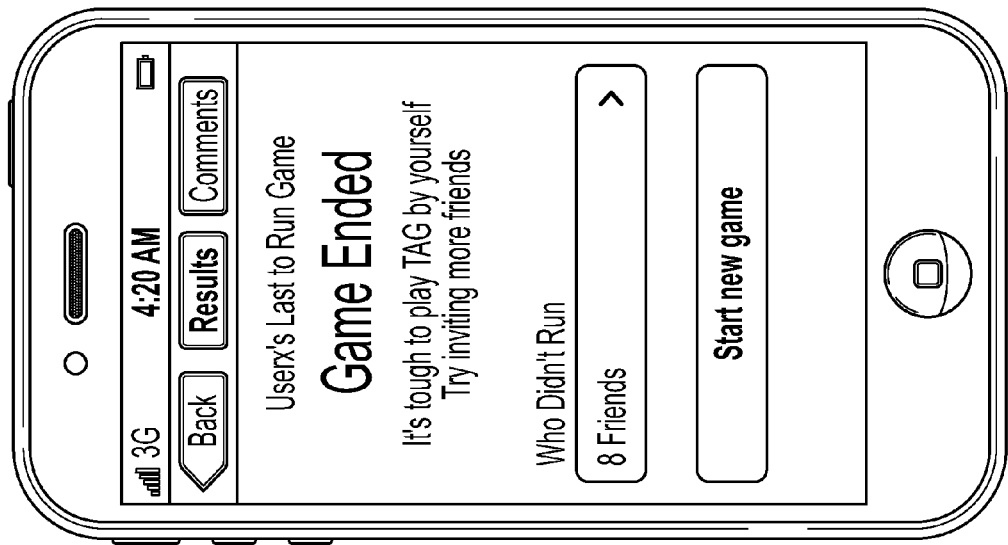
FIGS. 87A-87C illustrate example interfaces that may be generated and provided upon a game being cancelled due to non-participation according to one or more aspects described herein.
Figure 87A:
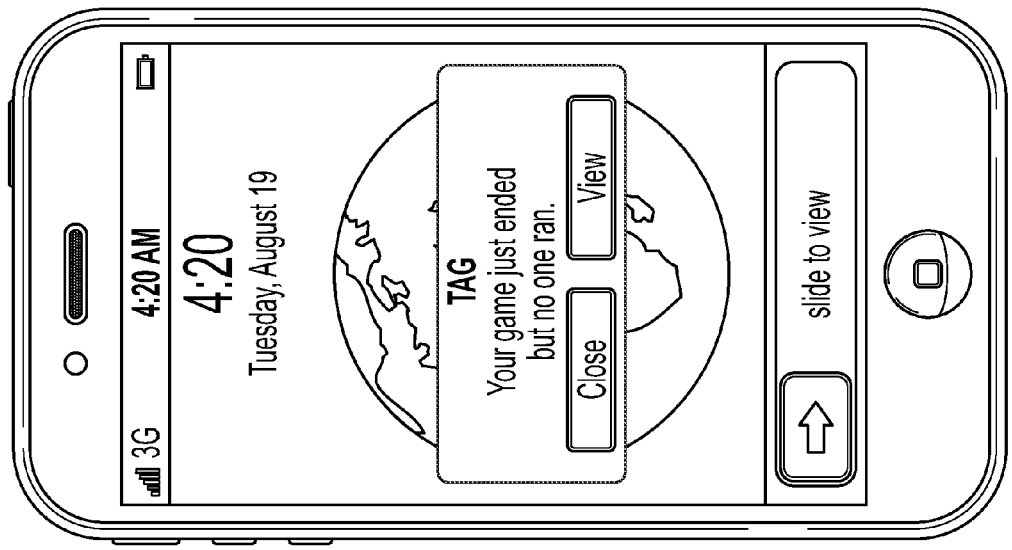
Figure 87C:

If none of the invited users accepted a game invitation or an insufficient number of invited users accepted the game invitation, the game may automatically be ended or deleted. FIG. 87A illustrates an example notification message that may be generated and provided to a game creator upon determining that an insufficient number of users accepted the game invitation. The user may further be brought to the interface of FIG. 87B to provide additional information about the ended game and to allow the user to try again by starting a new game. Upon selecting the option to start a new game, the user may be provided with further game start options including using a previous run or starting a new run for run-based games as shown in FIG. 87C.

Initiating a game using a previous run or other athletic activity allows a user to register the previous run as the user's entry in the new game. Thus, the user's previous run will be compared to runs of other participants when determining a loser of the game. In one example, the previous run may correspond to the run with which the user lost the previous game and gained the loser status. In another example, the user may be permitted to choose any previous run. In yet another example, the previous run may be a most recently completed run. The above game initiation options and parameters may also be used for other types of athletic activity including walking, weigh-lifting, swimming, using exercise machines, jumping rope, and the like.

The option to initiate a new game using a previous activity session might not be available for some game types such as last-to-finish games. By allowing the user to use a previous run in last-to-finish games, the user may gain an unfair advantage (e.g., the user cannot lose since the user is the game creator).

Figure 88B:
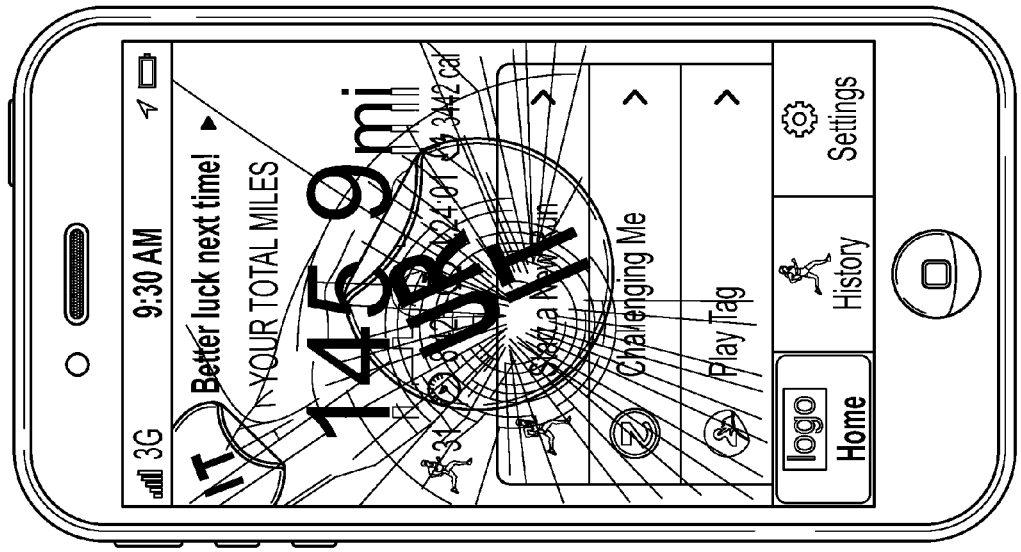
FIGS. 88A and 88B illustrate example interface effects that may be applied to a game loser's display according to one or more aspects described herein.
Figure 88A:
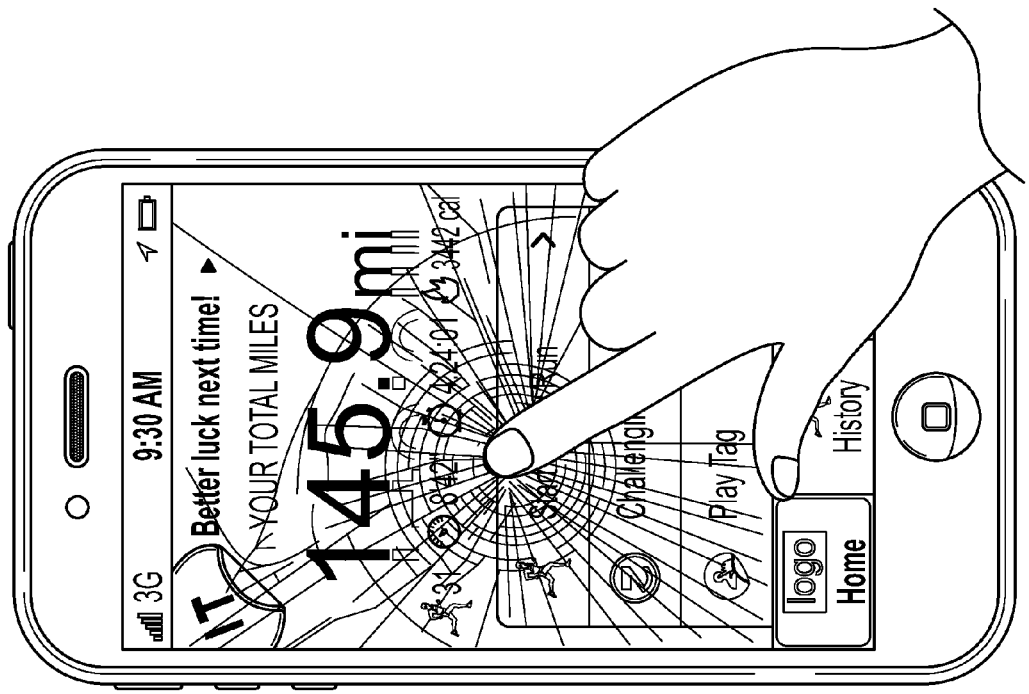

In addition to displaying a tag on a user's athletic activity monitoring home screen or other interfaces and requiring the user to complete a new game without losing, losing a game may cause other effects. For example, FIGS. 88A and 88B illustrate example interfaces that may be displayed for a user that has lost a game. In FIG. 88A, for example, a user's interface may include a simulated shattered screen to remind the user that he or she lost a previous game. The screen shattering point may correspond to a point at which the user touches the screen and may, in some arrangements, move in accordance with a user's finger as it moves along the screen while in contact with the screen. Additionally or alternatively, other visual effects such as a large label or other graphic with the words "U R IT" may be displayed overlaying elements of the display, as illustrated in FIG. 88B. In one particular example, the adverse visual effect or other adverse effects might only be applied once, e.g., the first time the user accesses the athletic activity application after losing a game. In other examples, the adverse effect may be applied each time the athletic activity application is activated or when a user's device is activated from a sleeping or off state or when the user navigates to a particular section of the application. The creator of the game and/or the loser of the game may customize, define or select the conditions under which the adverse effect is activated. Such effects may motivate the user to start and complete a new game without losing in order to remove the effects. By having to start and complete a new game to remove the loser status, the user is also motivated to complete additional physical activity.

Figure 89B:
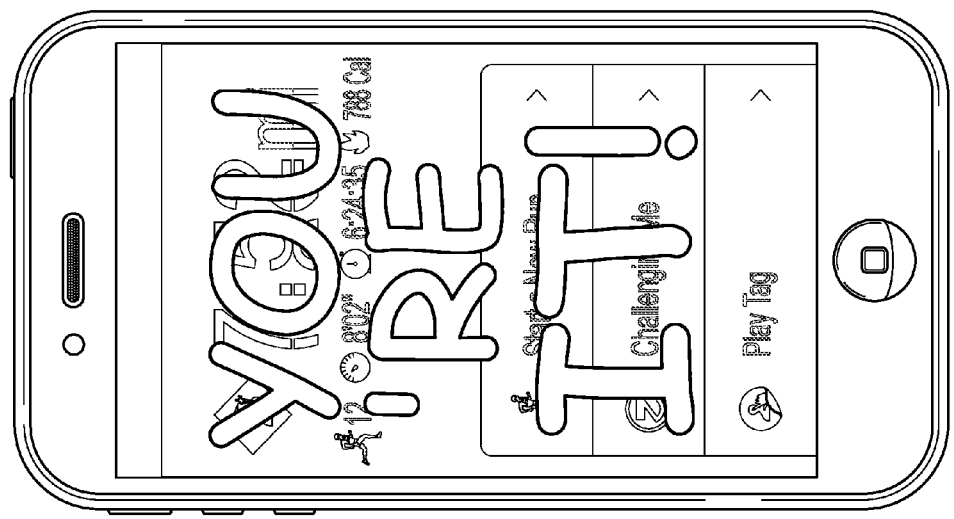
FIGS. 89A-89C illustrate another example interface effect that may be applied upon a user losing a game according to one or more aspects described herein.
Figure 89A:
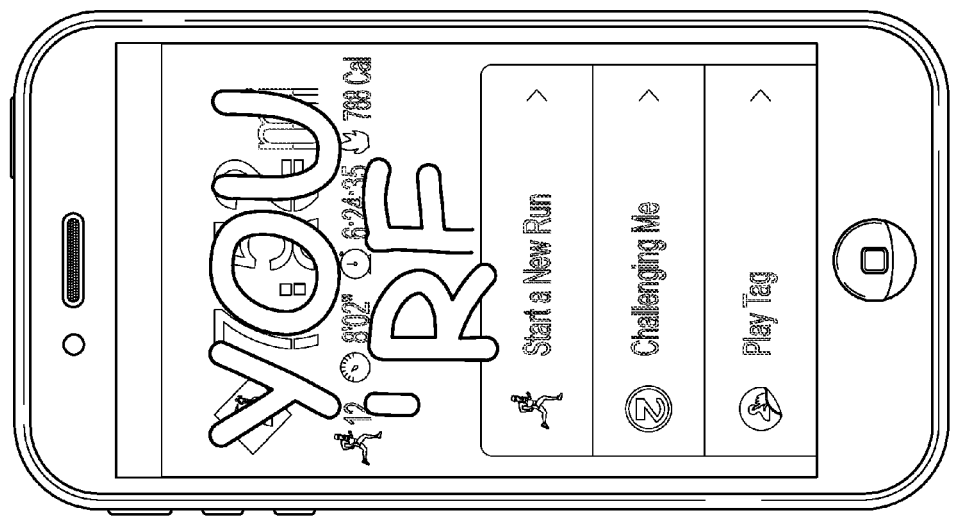
Figure 89C:
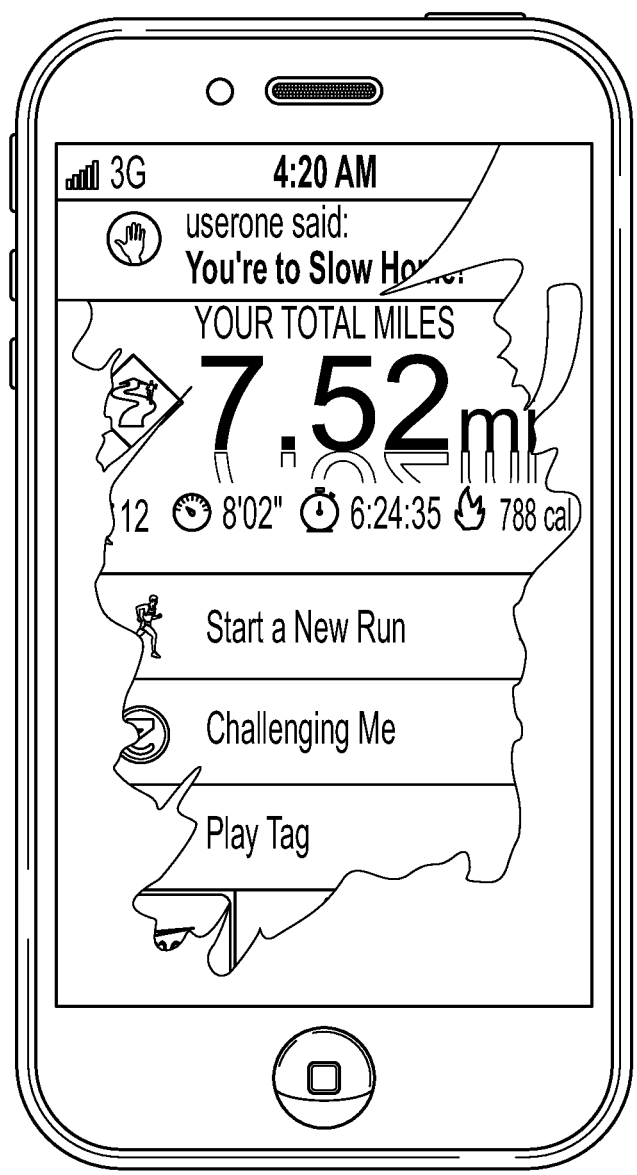

FIGS. 89A-89C illustrate another example set of interfaces exhibiting visual effects that may be applied to a user's device upon the user losing a game. The visual effect, in this example, simulates a foggy screen. The words "YOU'RE IT!" are etched into the fog. The fog effect makes it difficult for the user to view the user interface and thus may further motivate the user to start and complete a new game (without losing) to remove these effects. A user may manually remove the effect each time by clearing the screen as if the user were clearing fog or condensation off of a window or other glass structure. A variety of other visual effects, audio effects, tactile effects and the like may be incorporated into a game losing consequence to provide additional motivation to the user to perform additional athletic activity. In one example, a user may be locked out from all functionality of an athletic activity monitoring application other than starting a new game until the user has cleared himself of a loser status (e.g., by winning or not losing the new game). In another example, the consequences may affect other functionality (beyond the athletic performance monitoring application) of a user's mobile device or other computing device such as restrictions in calling, ability to download content, etc.

Figure 90A:
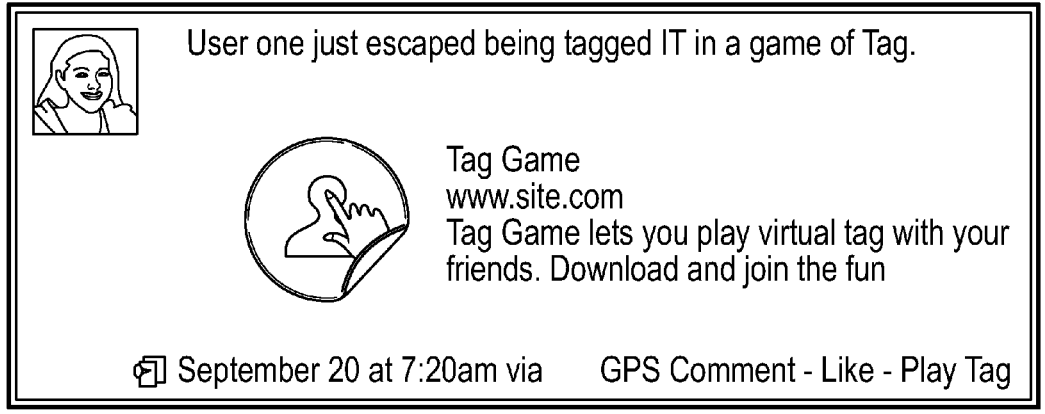
FIGS. 90A and 90B illustrate example social networking messages that may be posted on one or more community sites according to one or more aspects described herein.
Figure 90B:
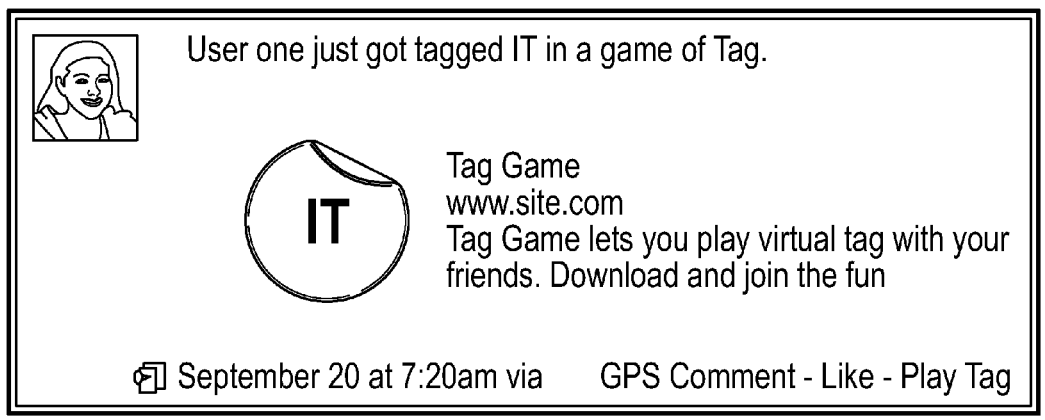

FIGS. 90A and 90B illustrate example social network community posts that may be generated and/or automatically posted to a user's social networking account upon completion of a game. For example, in FIG. 90A, the social networking message may indicate that the user did not lose the game. In FIG. 90B, on the other hand, the social networking message may indicate that the user did loser the game. The messages (FIGS. 90A and 90B) may also invite others to initiate and join new games and offer links to the appropriate sites for downloading the game or downloading data needed for playing the game. Additionally or alternatively, one or more visual attributes of the message may differ depending on whether the user lost the game. For example, in the interface of FIG. 90A, a visual logo may display a logo for the game. In contrast, if the user loses, the logo may be replaced with a loser status logo such as "IT" as shown in FIG. 90B. Various other display or appearance attributes may be modified such as color, patterns, background images, profile pictures, font colors, font size, color intensities, pattern complexity and the like.

During or after a game, a user may view progress or the results thereof through visualizations. For example, FIGS.

Figure 91B:
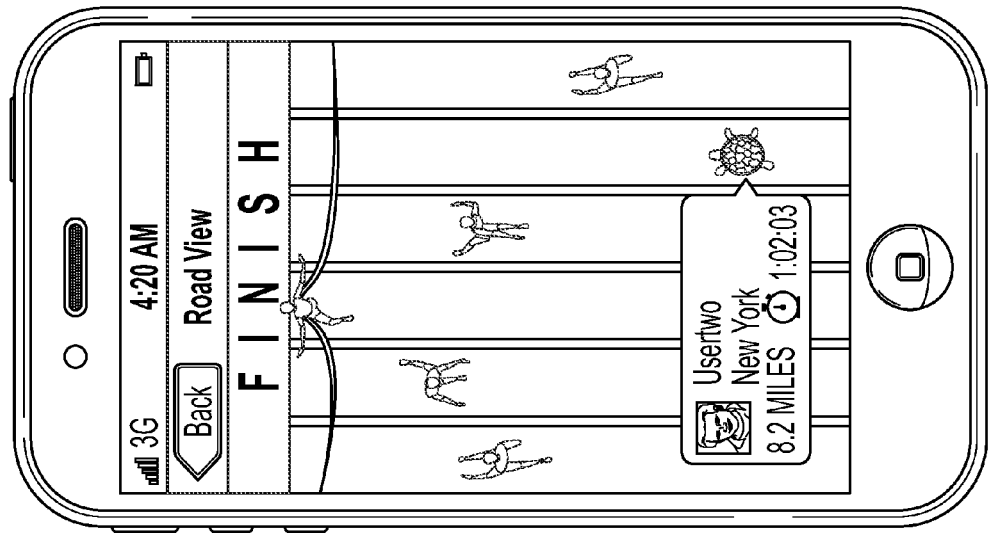
FIGS. 91A-91D illustrate example progress visualization interfaces through which the user may gauge his or her progress relative to other participants of the game according to one or more aspects described herein.
Figure 91A:
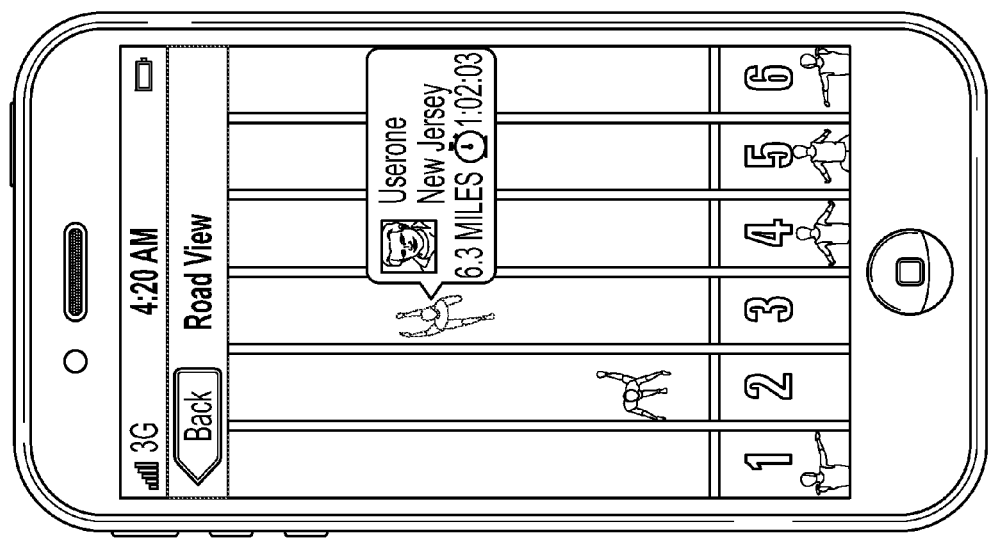

91A-91D illustrate example visualizations in which the participants of the game are displayed as runners along a track. FIG. 91A, for instance, illustrates the progress of participants during a run. Two users are shown as having initiated a run or other type of athletic activity for the game while the remaining four participants are show to have not yet started (e.g., not accepted or not yet begun performing an athletic activity). In FIG. 91B, the game is completed with the winner shown crossing a finishing line. The loser of the game may be converted from a first avatar to a second avatar. The second avatar may be indicative of a losing status, such as a turtle or other animals or inanimate objects.

Figure 91D:
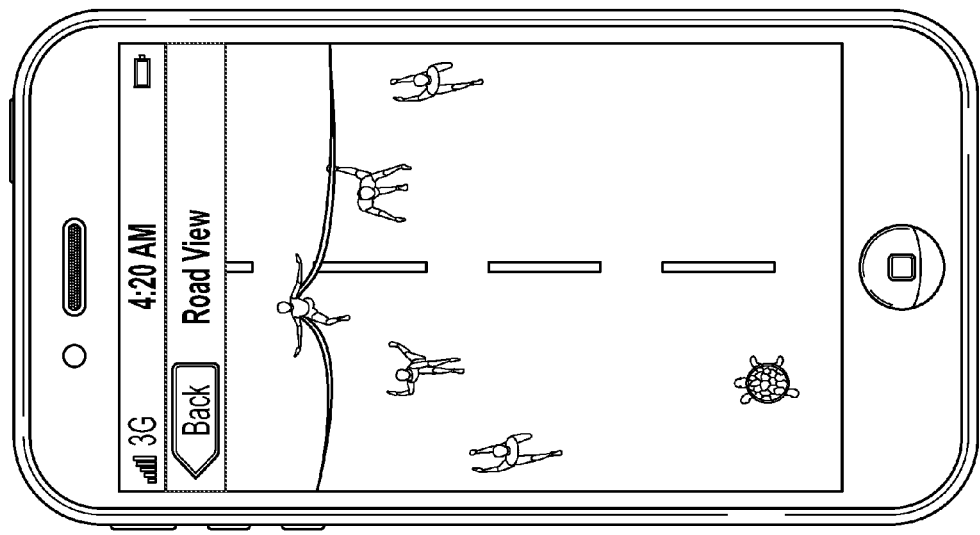
Figure 91C:
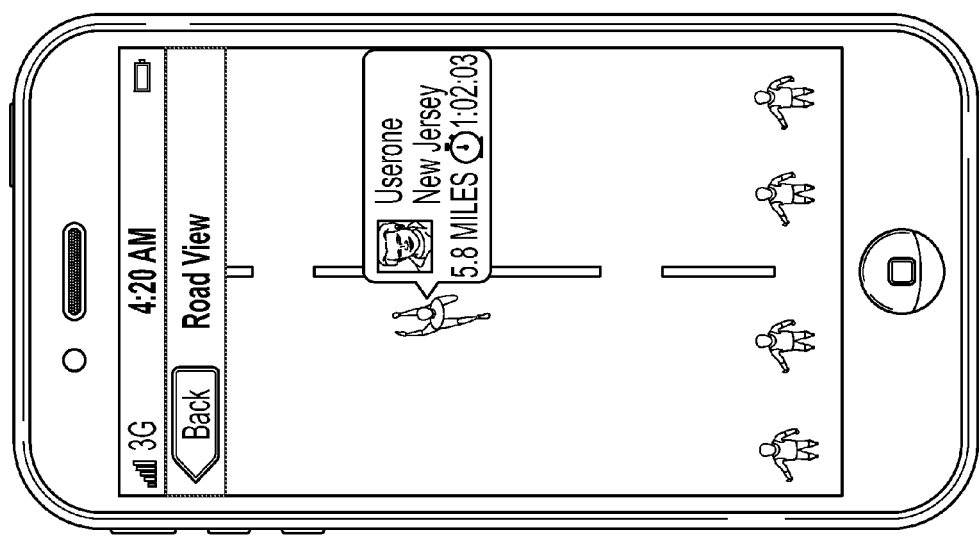

FIGS. 91C and 91D also illustrate example progress visualizations. In these examples, the participants are shown against a road rather than along a track. Various other types of visualizations may also be implemented such as bar graphs, pie charts, other sports-related visualizations (e.g., skiers on a ski slope, swimmers in a pool, etc.) and/or combinations thereof.

Additionally or alternatively, progress and/or scoreboards may be displayed in an athletic activity monitoring site or system and is not limited to display on a user's mobile athletic monitoring device. Accordingly, spectators (e.g., non-participants) and participants may access a progress visualization and/or a user's scoreboard through other devices by accessing a network site (e.g., a website or webpage hosted by an athletic activity monitoring service provider).

In one or more configurations, games might only allow participants to register a single workout session. Accordingly, in a distance-based running game, for example, each participant might only be allowed to attribute one run to the game. In other arrangements, participants may be able to attribute multiple runs to a single game so long as the runs or other type of workout was performed within the effective game period.

Additionally or alternatively, the number of participants required for a game may vary depending on the game type. For example, for games relating to a last-to-perform or complete (e.g., last-to-run, last-to-walk, last-to-swim), the game may require at least 3 participants (the game creator+2 accepted invitees). If the minimum number of participants is not fulfilled within an invitation/acceptance period, the game may be ended, cancelled or otherwise dissolved. In other cases such as distance-based games, only 2 participants may be required.

Conclusion

Providing an activity monitoring system and environment having one or more of the features described herein provides a user with an immersive experience that will encourage and motivate the user to engage in athletic activities and improve his or her fitness. By encouraging the user to exceed previous statistics set in other runs, the user may be motivated by the improvements he or she is able to make. Additionally, users may be able to user a single device for both indoor and outdoor workouts and are thus able to aggregate workout data on a single device. Further, users may be motivated to exercise by being to issue live challenges to other users. Accordingly, the users may feel as if they are working out with other users even though they are physically running by themselves. Games in which a user is adversely affected in real-life (e.g., real-life use of a mobile device) may further motivate the user to complete additional athletic activity and to compete with additional effort so that the user does not lose.

We claim:

1. A method comprising:
receiving, by a computing device having at least one processor, specifications for defining a multi-user athletic activity game executed through an electronic game application, wherein the specifications include identification of at least two potential participants;
transmitting, by the computing device, a game invitation to at least one of the at least two potential participants;
determining, by the computing device, whether a sufficient number of potential participants have accepted the game invitation;
in response to determining that a sufficient number of potential participants have accepted, initiating, by the computing device, monitoring of athletic performance statistics of accepted participants;
determining, by the computing device, a loser of the athletic activity game based on the athletic performance statistics; and
applying, by the computing device, a punishment to the loser of the athletic activity game, wherein the punishment includes a requirement by the electronic game application for the loser to initiate and complete a new athletic activity game without losing.

2. The method of claim 1, wherein the punishment includes one or more effects in an athletic activity game application executing on an athletic performance monitoring device of the loser.

3. The method of claim 2, wherein the one or more effects include a visual effect obscuring one or more functionalities of the athletic activity game application.

4. The method of claim 1, wherein applying the punishment includes applying a loser status to a profile of the loser and removing the loser status only upon:
expiration of a predefined time period; or
completion of a new athletic activity game without losing.

5. The method of claim 1, wherein the invitation includes one or more device setting parameters configured to automatically set one or more settings of an accepted participant's athletic performance monitoring device.

6. The method of claim 1, further comprising cancelling the athletic activity game in response to determining that a sufficient number of potential participants have not accepted within a predefined amount of time.

7. The method of claim 1, wherein the specifications for defining the multi-user athletic activity game includes a game type, wherein the game type includes at least one of: a last person to perform an athletic activity, a shortest distance for an athletic activity and shortest time spent performing an athletic activity.

8. The method of claim 1, wherein the athletic activity game type includes a random start time and wherein a last person to perform the athletic activity after the random start time is determined to be the loser.

9. The method of claim 1, wherein a participant that is not determined to be the loser is further provided with an option to have one or more visual or functional effects activated on a device of the loser.

10. The method of claim 9, wherein the one or more visual or functional effects includes posting a user-generated message to a display of the device of the loser.

11. The method of claim 10, wherein the one or more visual or functional effects includes displaying an image configured to obscure one or more functions of the device of the loser.

12. An apparatus comprising:
at least one processor; and
memory operatively coupled to the at least one processor and storing computer readable instructions that, when executed, cause the apparatus to:
receive a selection from a user to join a multi-user athletic activity game executed through an electronic game application;

initiate recording of one or more athletic activity performance metrics;

transmit the one or more athletic activity performance metrics to a game monitoring system;

determining that the user has lost the game;

in response to determining that the user has lost the game, the electronic game application applying a loser status to the user;

determining whether the user has, through the electronic game application, initiated and completed a new multi-user athletic activity game without losing; and in response to determining that the user has initiated and completed the new multi-user athletic activity game without losing, removing the loser status from the user, otherwise, maintaining the loser status applied to the user through the electronic game application in a subsequent game.

13. The apparatus of claim 12, wherein applying the loser status includes adding a label to a profile of the user.

14. The apparatus of claim 12, wherein applying the loser status includes activating one or more visual or functional effects on a device of a user.

15. The apparatus of claim 14, wherein the one or more visual or functional effects includes an effect configured to obstruct at least one functionality of the device of the user.

16. The apparatus of claim 15, wherein the effect includes an image configured to obstruct the at least one functionality of the device.

17. The apparatus of claim 12, wherein transmitting the one or more athletic activity performance metrics to a game monitoring system includes:

receiving a user selection of one or more multi-user athletic activity games to which the one or more athletic activity performance metrics are to be applied; and transmitting the user selection to the game monitoring system.

18. The apparatus of claim 17, wherein the user selection includes a plurality of multi-user athletic activity games and wherein transmitting the one or more athletic activity performance metrics further includes:

receiving user specifications for dividing the one or more athletic activity performance metrics among the plurality of multi-user athletic activity games.

19. The apparatus of claim 12, wherein receiving a selection from a user to join the multi-user athletic activity game includes:

upon receiving the selection from the user to join the multi-user athletic activity game, automatically applying one or more device settings based on one or more corresponding setting parameters defined in an invitation to join the multi-user athletic activity game.

* * * * *